US007375209B2

(12) United States Patent
Keetman et al.

(10) Patent No.: US 7,375,209 B2
(45) Date of Patent: May 20, 2008

(54) EXPRESSION CASSETTES FOR SEED-PREFERENTIAL EXPRESSION IN PLANTS

(75) Inventors: Ulrich Keetman, Quedlinburg (DE); Elke Duwenig, Ludwigshafen (DE); Linda Patricia Loyall, Mannheim (DE); Karin Herbers, Neustadt (DE); Helke Hillebrand, Mannheim (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 11/266,446

(22) Filed: Nov. 3, 2005

(65) Prior Publication Data

US 2006/0112452 A1 May 25, 2006

(30) Foreign Application Priority Data

| | | |
|---|---|---|
| Nov. 5, 2004 | (EP) | 04026295 |
| Dec. 8, 2004 | (EP) | 04029024 |
| Feb. 3, 2005 | (EP) | 05002262 |
| Feb. 11, 2005 | (EP) | 05002850 |

(51) Int. Cl.
*C12N 15/63* (2006.01)
*C12N 5/04* (2006.01)
*C12N 15/82* (2006.01)

(52) U.S. Cl. .................... 536/24.1; 435/468; 435/419; 435/320

(58) Field of Classification Search .................... None
See application file for complete search history.

(56) References Cited

U.S. PATENT DOCUMENTS 5,623,067 A 4/1997 Vandekerckhove et al.
6,433,252 B1 8/2002 Kriz et al.

FOREIGN PATENT DOCUMENTS

WO WO-97/44465 11/1997
WO WO-99/20775 4/1999

OTHER PUBLICATIONS

Verwoert et al. 1994, Plant Mol. Biol. 26:189-202.*
Oommenn et al 1994, The Plant Cell 6:1789-1803.*
Fourgoux-Nicol et al. 1999, Plant Molecular Biology 40 :857-872.*
Kim et al. 1994, Plant Molecular Biology 24: 105-117.*
Rounsley et al. 2002, Genbank accession: AC004481.*
Xiao et al. 2003, Genbank accession AY247802.*
Padgette et al 1995, Crop Sci. 35:1451-1461.*
An et al 1986, Plant Physiol. 81:301-305.*
"*Arabidopsis thaliana* SCPL20; serine carboxypeptidase AT4G12910 (SCPL20) mRNA, complete cds." Feb. 17, 2004, NM_117360.
"SCPL20; serine carboxypeptidase [*Arabidopsis thaliana*]." May 13, 2003, NP_193027.
"*Arabidopsis thaliana* hydrolase, hydrolyzing O-glycosyl compounds AT1G66250 mRNA, complete cds." Feb. 17, 2004, NM_105296.
"Hydrolase, hydrolyzing O-glycosyl compounds [*Arabidopsis thaliana*]." Feb. 17, 2004, NP_176799.
"*Arabidopsis thaliana* calmodulin binding AT4G00820 mRNA, complete cds." Feb. 17, 2004, NM_116308.
"Calmodulin binding [*Arabidopsis thaliana].*" *Feb. 17, 2004,NP*_567191.
"*Arabidopsis thaliana* ATECP63 (Embryonic Cell Protein 63) AT2G36640 (ATECP63) mRNA, complete cds." Nov. 4, 2005, NM_129219.
"ATECP63 (Embryonic Cell Protein 63) [*Arabidopsis thaliana*]." Nov. 4, 2005, NP_181202.
"*Arabidopsis thaliana* protein binding / ubiquitin-protein ligase/ zinc ion binding AT2G34200 mRNA, complete cds." Feb. 17, 2004 NM_128971.
"Protein binding / ubiquitin-protein ligase/ zinc ion binding [*Arabidopsis thaliana*]." Feb. 17, 2004, NP_180967.
" *Arabidopsis thaliana* iron ion binding / isopenicillin-N synthase AT3G11180 mRNA, complete cds. " May 13, 2003, NM_ 111954.
"Iron ion binding / isopenicillin-N synthase [*Arabidopsis thaliana*]. " Nov. 4, 2005, NP _187728.
"*Arabidopsis thaliana* CYP86A2; oxygen binding AT4G00360 (CYP86A2) mRNA, complete cds." May 13, 2003, NM_116260.
"CPY86A2; oxygen binding [*Arabidopsis thaliana*]." Nov. 4, 2005, NP_191946.
"*Arabidopsis thaliana* hydrolase AT2G48030 mRNA, complete cds." Feb. 17, 2004, NM_130370.
"Hydrolase [*Arabidopsis thaliana*]."Nov. 4, 2005, NP_566121.
"*Arabidopsis thaliana* unknown protein AT2G38590 mRNA, complete cds." May 13, 2003, NM_129416.
"Unknown protein [*Arabidopsis thaliana*]." Nov. 4, 2005, NP_181393.
"*Arabidopsis thaliana* metal ion binding AT1G23000 mRNA, complete cds." Feb. 17, 2004, NM_102148.
"Metal ion binding [*Arabidopsis thaliana*]." Nov. 4, 2005, NP_173713.
"*Arabidopsis thaliana* ATNAC2; transcription factor AT3G15510 (ATNAC2) mRNA, complete cds." May 13, 2003, NM_112419.
"ATNAC2; transcription factor [*Arabidopsis thaliana*]. " Nov. 4, 2005, NP_188170.
"*Arabidopsis thaliana* MNP (MONOPOLE); transcription factor AT3G50870 (MNP) mRNA, complete cds. " May 13, 2003, NM_114947.

(Continued)

*Primary Examiner*—Ashwin Mehta
*Assistant Examiner*—Li Zheng
(74) *Attorney, Agent, or Firm*—Connolly Bove Lodge & Hutz LLP

(57) ABSTRACT

The present invention relates to expression cassettes comprising transcription regulating sequences with seed-preferential or seed-specific expression profiles in plants obtainable from *Arabidopsis thaliana* genes At4g12910, At1g66250, At4g00820, At2g36640, At2g34200, At3g11180, At4g00360, At2g48030, At2g38590, At1g23000, At3g15510, At3g50870, At4g00220, or At4g26320.

18 Claims, No Drawings-

OTHER PUBLICATIONS

"MNP (MONOPOLE); transcription factor [*Arabidopsis thaliana*]. "Nov. 4, 2005, NP_566939.

"*Arabidopsis thaliana* unknown protein AT4G00220 mRNA, complete cds." May 13, 2003, NM_116239.

"*Arabidopsis thaliana* AGP13 (Arabinogalactan Protein 13) AT4G26320 (AGP13) mRNA, complete cds." May 13, 2003, NM_118765.

"AGP13 (Arabinogalastan Protein 13) [*Arabidopsis thaliana*]." Nov. 4, 2005, NP_194362.

Doan, N.P. et al., "The A- and B-chains of Carboxypeptidase I from Germinated Barley Originate from a Single Precursor Polypeptide ", 1988, vol. 263, No. 23, pp. 11106-11110.

"AT4G12910: Serine Carboxypeptidase 1-like Protein", Oct. 1, 2002, GenBank Accession No. Q8L7B2.

"*Arabidopsis thaliana* Serine Carboxypeptidase 1 Precursor-Like Protein (At4g12910), mRNA, complete cds.", Aug. 29, 2002, GenBank Accession No. AY136365.

"*Arabidopsis thaliana* DNA Chromosome 4, Contig Fragment No. 35", Mar. 16, 2000, GenBank Accession No. AL161535.

"Serine carboxypeptidase 1 precursor ", Nov. 1, 1997, Database UniProtKB/Swiss-Prot Accession No. P07519, P07620.

* cited by examiner

SEQUENCE LISTING

```
<160> NUMBER OF SEQ ID NOS: 156

<210> SEQ ID NO 1
<211> LENGTH: 935
<212> TYPE: DNA
<213> ORGANISM: Arabidopsis thaliana

<400> SEQUENCE: 1

ttgttcaagt aaaattgtgt taccagatat tcaactttct atatatacat atatatttga      60

caactattcg actttctata tttaactgaa agagttgtat cattgaaatt tggagtattg     120

ttccctgtaa ataatccgat ttgtttccaa aacgctatgg aacaggcctt gattttgata     180

ctctttcgtg ctgacacttg aaacggcgtc gtatcaataa tagaagaaaa ccttactgtg     240

gaaataatca aattgtgaat ctccaccaac ctcagtgggt cccattgcca cccactaatc     300

tccccacgta caccaactcc ccttcacgtt ttaatctctt aatatacttt tattataagt     360
```

-continued

```
taattaaatg atttcaacct taataatatt aaccattaat tattcatttg taatctccaa    420
cttttttttg aaaaaccttt gtgttcagat attttcgtca attaatcaag atctcattca    480
taaattaaaa aaaaaacaaa attcaagcta aaaatacata cccaacaaaa attccttaaa    540
aaatttactt agggggcatc tggtaattta attttcctat aaaagatggc aatattaatt    600
cagatttttt tttaatttac caacatgata ctttaattat atttcttact tgttagctct    660
actaatgcac acatacttat ttcgacgact aaaagaaaaa tactgaactc aaacaataga    720
gaaaaaaaaa gaaataatcc tactcaacta tgttgaaaaa taacatcaaa ttcagagaaa    780
atgcacaaac accaataata taaataaata gggatattta aaataataat taaaattgcg    840
aaaatatcga gcaccaccag atctacagaa atgacacaga gcccaacgaa gatgtatctc    900
gtttattttc gctataaata aactcacaca gccca                               935
```

<210> SEQ ID NO 2
<211> LENGTH: 1569
<212> TYPE: DNA
<213> ORGANISM: Arabidopsis thaliana
<220> FEATURE:
<221> NAME/KEY: promoter
<222> LOCATION: (1)..(1569)
<223> OTHER INFORMATION: promoter of gene At5g17920

<400> SEQUENCE: 2

```
ttgttcaagt aaaattgtgt taccagatat tcaactttct atatatacat atatatttga     60
caactattcg actttctata tttaactgaa agagttgtat cattgaaatt tggagtattg    120
ttccctgtaa ataatccgat ttgtttccaa aacgctatgg aacaggcctt gattttgata    180
ctctttcgtg ctgacacttg aaacggcgtc gtatcaataa tagaagaaaa ccttactgtg    240
gaaataatca aattgtgaat ctccaccaac ctcagtgggt cccattgcca cccactaatc    300
tccccacgta caccaactcc ccttcacgtt ttaatctctt aatatacttt tattataagt    360
taattaaatg atttcaacct taataatatt aaccattaat tattcatttg taatctccaa    420
cttttttttg aaaaaccttt gtgttcagat attttcgtca attaatcaag atctcattca    480
taaattaaaa aaaaaacaaa attcaagcta aaaatacata cccaacaaaa attccttaaa    540
aaatttactt agggggcatc tggtaattta attttcctat aaaagatggc aatattaatt    600
cagatttttt tttaatttac caacatgata ctttaattat atttcttact tgttagctct    660
actaatgcac acatacttat ttcgacgact aaaagaaaaa tactgaactc aaacaataga    720
gaaaaaaaaa gaaataatcc tactcaacta tgttgaaaaa taacatcaaa ttcagagaaa    780
atgcacaaac accaataata taaataaata gggatattta aaataataat taaaattgcg    840
aaaatatcga gcaccaccag atctacagaa atgacacaga gcccaacgaa gatgtatctc    900
gtttattttc gctataaata aactcacaca gcccactctt cttcctcgct ctctctttcg    960
ccttctctta gcctaccctt tttccttcct cctctccgat tcttcctccg tcaggttcgt   1020
ctccgacttt ctatgtcttc cttacgtctc tcttatttag ctccctttcc ttccttctcc   1080
acgttattat taccacttgt gttagtgtga ttcgtttcat tctcgttttt ttttattcct   1140
cgatctgttt gctcatttgt tgagatctat ccgctaagtg agttcatttg actcagatct   1200
ggatatttcg tgttgttcga tttatagatc tggtttctgg atctgtttac gatctattgt   1260
catcattctt ttggaaatga ttggtgtttc tgtgttcgta ttcgtttaga tctaacgttt   1320
ttgatcgatg aatgtcgcat gtgtttttat ctgaaagttt tcgattacag tatcaagtag   1380
tagtagtaga ctcaaaaagc tgcataaact ttttatacac ttgaatcgta attctatcag   1440
```

```
tttcattgat gctttacggt tttcttggag tttgttaact aaaatcattt aacattacca   1500

attcatttta tatggtttta gatattgatt tttggtttgt gttttaatgc agtaaaagaa   1560

aatcaaacc                                                           1569
```

<210> SEQ ID NO 3
<211> LENGTH: 1591
<212> TYPE: DNA
<213> ORGANISM: Arabidopsis thaliana
<220> FEATURE:
<221> NAME/KEY: promoter
<222> LOCATION: (1)..(1591)
<223> OTHER INFORMATION: promoter of gene At5g17920

<400> SEQUENCE: 3

```
gatccttgtt caagtaaaat tgtgttacca gatattcaac tttctatata tacatataga     60

tttgacaact attcgacttt ctatatttaa ctgaaagagt tgtatcactg aaatttggag    120

tattgttccc tgtaaataat tcgatttgtt tccaaaacgc tatggaacag gccttgattt    180

tgatactctt tcgtgctgac acttgaaacg gcgtcgtatc aataatagaa gaaaacctta    240

ctgtggaaat aatcaaattg tgaatctcca ccaacctcaa tgggtcccat tgccacccac    300

taatctcccc acgtacacca actccccttc acgttttaat ctcttaatat acttttatta    360

taagttaatt aaatgatttc aaccttagta atactaacca ttaattattc atttctaatc    420

tccaatattt tttttgaaaa acctttctgt tcagatattt tcgtcaatta atcaagatct    480

cattcataaa ttaaaaaaaa aaacaaaatt caagctaaaa atacataccc aacaaaaatt    540

ccttaaaaaa attacttatg gggcatctgg taatttaatt ttcctataaa agatggcaat    600

attaattcag tttttttttt taatttacca atatgatact ttaattatat ttcttacttg    660

ttagctctac taatgcacac atacttattt ctacgaatat aagaaaaaaa tactgaactc    720

aaacaataga caaaaaagaa ataatcctac actcaagtgt gttgaaaaat aacatcaaat    780

tcagagaaaa tgcacataca ccaataatat aaataaatag ggatatttaa aataataaat    840

aaaattgcga aaatatcgag caccaccaga tctacagaaa tgacacagag cccaacgatg    900

atgtatctcg tttattttcg ctataaataa actcacacag cccactcttc ttcctcgctc    960

tctctttcgc cttctcttag cctacccttt ttccttcctc ctctccgatt cttcctccgt   1020

caggttcgtc tccgactttc tatgtcttcc ttacgtctct cttatttagc tccctttcct   1080

tccttctcca cgttattatt actacttcgc ttttagtgtg attcgtttca ttctcgtttt   1140

tttatattcc tcgatctgtt tgctcatttg ttgagatcta ttcgctatgt gagttcattt   1200

gactcagatc tggatatttc gtgttgttcg atttatagat ctggtttctg gatctgttta   1260

cgatctatcg tcatctttcc tttgaaaatg attggtgttt ctgtgttcgt attcgtttag   1320

atctaaagtt tttgatcgat gaatgtcgca tgtgttttta tctgaaagtt ttcgattaca   1380

gtatcaagtg gtggtagtag tagtagtaga ctcaaaaagc tgcacaaact ttttatacac   1440

gtgaattgtg attgctttac ggttttcttg gagtttgtta attaaatcat ttaatattaa   1500

gaagtttatg aattaagaga acgttatttt atactatgat tttgattttg atttggtttg   1560

tgtgttttaa tgcagtaaaa gaaaatcaaa c                                  1591
```

<210> SEQ ID NO 4
<211> LENGTH: 2424
<212> TYPE: DNA
<213> ORGANISM: Arabidopsis thaliana
<220> FEATURE:

<221> NAME/KEY: promoter
<222> LOCATION: (1)..(2424)
<223> OTHER INFORMATION: promoter of gene At5g17920

<400> SEQUENCE: 4

```
tgtattggac ctgagaaatg ggaaaggtac tgccgtttgg atttttctat gaaacattgt     60

aaaataatgg actcgatcga agatggtaac accgttaagc ttacaaatag tttctggtgg    120

ttcatattta gttgtaaatc tcgtattaac atgaagcatt gcctctcttt tttttggtaa    180

aagatgaagc attgccttgt gtttgagatt atatgtaaat aaagtatcca agtgtattca    240

tataaatcac caacttttga ttcaaagcat aatgtgtgtg tatagagttt tattgtttca    300

catgtctaaa agcatgcctt tccatagttt aatcataaag ttttataagc cagcaataag    360

aatacttttg gatcttgtga ttcgtgtatc atatgattac caaactcaag atgccaaaaa    420

aggttggtaa acaagtattt tattgatcca ataatttgtt atactaatac acatacgatt    480

tagttcaata attcctaaag aaaagttttt tgtttgtttt tcgtttaatt ggattgataa    540

aagtattcaa ttctttatgt cgtacaacaa gtaaatagaa agaaaaaaag agagtgcgag    600

tttcactttc aataaatgct tgtgtgatta tctttatttg tgtacatact agatctacat    660

ccaccgacaa accagtgtcg aggaagcata tgcaactgtc ctgcagattt aaagtctcat    720

gtaattaaat gttgttcaat ttgtttgttg tgtgattacc agtttggtgt atagttaaag    780

ttaccaagta attatacaaa tcatcaaaca tatagtacta tttttctgt ttatcacata     840

aacattttgt tgagtttttg gttttgtttg caaaagcatc ttcttgataa attcctagtg    900

aactcaaaat tgacctacac cagttcccat acaaatagaa agctactcca aaactagttg    960

tggaagtggt tgaatataat tttatattcc aaacttagaa aattcaccgc aaaagagctt   1020

ataacgtagt ttatgcagat atggttaaac ttcatcagtt gctatagagt taaaaaaatc   1080

aaatattttg aaattggtaa ctagtacgtg aattttttta atgcagactg aaagaacaaa   1140

ataaaactta aaatatgttt acaagaaaat attctttcat gatttacgca aaccaaaagt   1200

tacatttaag tttaggaaag aaaaaatgac ctaggaaatt aaaacaatga ggttcgttga   1260

taaaggtcaa gaatcaaagt ttggtagcca aattatcagc aaacaaaaaa aaagattaag   1320

accatcgatc catgcgtata ctcattgtct tatgaatctt aaacaataat attatattat   1380

acacagtagg tccataattt atgtttcttt acctactcta tttaccaaaa acatacatag   1440

tttttatccg acttacacaa gtgtactaat ggccagacaa gattgttacc tgttcaagta   1500

aaattgtgtt accagatatt caactttcta tatatacata tatatttgac aactattcga   1560

ctttctatat ttaactgaaa gagttgtatc attgaaattt ggagtattgt tccctgtaaa   1620

taatccgatt tgtttccaaa acgctatgga acaggccttg attttgatac tctttcgtgc   1680

tgacacttga aacggcgtcg tatcaataat agaagaaaac cttactgtgg aaataatcaa   1740

attgtgaatc tccaccaacc tcagtgggtc ccattgccac ccactaatct ccccacgtac   1800

accaactccc cttcacgttt taatctctta atatactttt attataagtt aattaaatga   1860

tttcaacctt aataatatta accattaatt attcatttgt aatctccaac ttttttttga   1920

aaaacctttg tgttcagata ttttcgtcaa ttaatcaaga tctcattcat aaattaaaaa   1980

aaaaacaaaa ttcaagctaa aaatacatac ccaacaaaaa ttccttaaaa aatttactta   2040

gggggcatct ggtaatttaa ttttcctata aaagatggca atattaattc agattttttt   2100

ttaatttacc aacatgatac tttaattata tttcttactt gttagctcta ctaatgcaca   2160

catacttatt tcgacgacta aaagaaaaat actgaactca aacaatagag aaaaaaaaag   2220
```

```
aaataatcct actcaactat gttgaaaaat aacatcaaat tcagagaaaa tgcacaaaca   2280

ccaataatat aaataaatag ggatatttaa aataataatt aaaattgcga aaatatcgag   2340

caccaccaga tctacagaaa tgacacagag cccaacgaag atgtatctcg tttattttcg   2400

ctataaataa actcacacag ccca                                          2424


<210> SEQ ID NO 5
<211> LENGTH: 3058
<212> TYPE: DNA
<213> ORGANISM: Arabidopsis thaliana
<220> FEATURE:
<221> NAME/KEY: promoter
<222> LOCATION: (1)..(3058)
<223> OTHER INFORMATION: promoter of gene At5g17920

<400> SEQUENCE: 5

tgtattggac ctgagaaatg ggaaaggtac tgccgtttgg atttttctat gaaacattgt     60

aaaataatgg actcgatcga agatggtaac accgttaagc ttacaaatag tttctggtgg    120

ttcatattta gttgtaaatc tcgtattaac atgaagcatt gcctctcttt tttttggtaa    180

aagatgaagc attgccttgt gtttgagatt atatgtaaat aaagtatcca agtgtattca    240

tataaatcac caacttttga ttcaaagcat aatgtgtgtg tatagagttt tattgtttca    300

catgtctaaa agcatgcctt tccatagttt aatcataaag ttttataagc cagcaataag    360

aatacttttg gatcttgtga ttcgtgtatc atatgattac caaactcaag atgccaaaaa    420

aggttggtaa acaagtattt tattgatcca ataatttgtt atactaatac acatacgatt    480

tagttcaata attcctaaag aaaagttttt tgtttgtttt tcgtttaatt ggattgataa    540

aagtattcaa ttctttatgt cgtacaacaa gtaaatagaa agaaaaaaag agagtgcgag    600

tttcactttc aataaatgct tgtgtgatta tctttattgg tgtacatact agatctacat    660

ccaccgacaa accagtgtcg aggaagcata tgcaactgtc ctgcagattt aaagtctcat    720

gtaattaaat gttgttcaat ttgtttgttg tgtgattacc agtttggtgt atagttaaag    780

ttaccaagta attatacaaa tcatcaaaca tatagtacta ttttttctgt ttatcacata    840

aacattttgt tgagtttttg gttttgtttg caaaagcatc ttcttgataa attcctagtg    900

aactcaaaat tgacctacac cagttcccat acaaatagaa agctactcca aaactagttg    960

tggaagtggt tgaatataat tttatattcc aaacttagaa aattcaccgc aaaagagctt   1020

ataacgtagt ttatgcagat atggttaaac ttcatcagtt gctatagagt taaaaaaatc   1080

aaatattttg aaattggtaa ctagtacgtg aattttttta atgcagactg aaagaacaaa   1140

ataaaactta aaatatgttt acaagaaaat attctttcat gatttacgca aaccaaaagt   1200

tacatttaag tttaggaaag aaaaaatgac ctaggaaatt aaaacaatga ggttcgttga   1260

taaaggtcaa gaatcaaagt ttggtagcca aattatcagc aaacaaaaaa aaagattaag   1320

accatcgatc catgcgtata ctcattgtct tatgaatctt aaacaataat attatattat   1380

acacagtagg tccataattt atgtttcttt acctactcta tttaccaaaa acatacatag   1440

tttttatccg acttacacaa gtgtactaat ggccagacaa gattgttacc tgttcaagta   1500

aaattgtgtt accagatatt caactttcta tatatacata tatatttgac aactattcga   1560

ctttctatat ttaactgaaa gagttgtatc attgaaattt ggagtattgt tccctgtaaa   1620

taatccgatt tgtttccaaa acgctatgga acaggccttg attttgatac tctttcgtgc   1680

tgacacttga aacggcgtcg tatcaataat agaagaaaac cttactgtgg aaataatcaa   1740
```

-continued

```
attgtgaatc tccaccaacc tcagtgggtc ccattgccac ccactaatct ccccacgtac   1800
accaactccc cttcacgttt taatctctta atatactttt attataagtt aattaaatga   1860
tttcaacctt aataatatta accattaatt attcatttgt aatctccaac tttttttga    1920
aaaacctttg tgttcagata ttttcgtcaa ttaatcaaga tctcattcat aaattaaaaa   1980
aaaaacaaaa ttcaagctaa aaatacatac ccaacaaaaa ttccttaaaa aatttactta   2040
gggggcatct ggtaatttaa ttttcctata aaagatggca atattaattc agattttttt   2100
ttaatttacc aacatgatac tttaattata tttcttactt gttagctcta ctaatgcaca   2160
catacttatt tcgacgacta aaagaaaaat actgaactca aacaatagag aaaaaaaaag   2220
aaataatcct actcaactat gttgaaaaat aacatcaaat tcagagaaaa tgcacaaaca   2280
ccaataatat aaataaatag ggatatttaa aataataatt aaaattgcga aaatatcgag   2340
caccaccaga tctacagaaa tgacacagag cccaacgaag atgtatctcg tttattttcg   2400
ctataaataa actcacacag cccactcttc ttcctcgctc tctctttcgc cttctcttag   2460
cctacccttt ttccttcctc ctctccgatt cttcctccgt caggttcgtc tccgactttc   2520
tatgtcttcc ttacgtctct cttatttagc tccctttcct tccttctcca cgttattatt   2580
accacttgtg ttagtgtgat tcgtttcatt ctcgtttttt tttattcctc gatctgtttg   2640
ctcatttgtt gagatctatc cgctaagtga gttcatttga ctcagatctg gatatttcgt   2700
gttgttcgat ttatagatct ggtttctgga tctgtttacg atctattgtc atcattcttt   2760
tggaaatgat tggtgtttct gtgttcgtat tcgtttagat ctaacgtttt tgatcgatga   2820
atgtcgcatg tgtttttatc tgaaagtttt cgattacagt atcaagtagt agtagtagac   2880
tcaaaaagct gcataaactt tttatacact tgaatcgtaa ttctatcagt ttcattgatg   2940
ctttacggtt ttcttggagt ttgttaacta aaatcattta acattaccaa ttcattttat   2000
atggttttag atattgattt ttggtttgtg ttttaatgca gtaaaagaaa atcaaacc     3058

<210> SEQ ID NO 6
<211> LENGTH: 3074
<212> TYPE: DNA
<213> ORGANISM: Arabidopsis thaliana
<220> FEATURE:
<221> NAME/KEY: promoter
<222> LOCATION: (1)..(3074)
<223> OTHER INFORMATION: promoter of gene At5g17920

<400> SEQUENCE: 6

tgtattggac ctgagaaatg ggaaaggtac tgccgtttgg atttttctat gaacattgta     60
atataatgga ctcgatcgaa gatggtaaca ccgttcagat tacaaatagt tttggtggt     120
tcatatttag ttgtaaatct cttattaaca tgaagcattg cctctctttt tttttttggt    180
aaaagatgaa cttgtgtttg agattttatg taaataaagt atccaagtat attcatataa    240
atcaccaact tttgattcaa agcataatgt gtgtgtatac agtttttatt gtttcacatg    300
tctaaaagca tgcctttcca tagtttaatc ataaagtttt ataagccagc aataagaata    360
cttttggatc ttgtgattcg tgtatcatat gattaccaaa ctcaagatgc caaaaaaggt    420
tggtaaacaa gtattttatt gatccaataa tttgttatac taatacacat acgatttagt    480
tcaataattc ctaaagaaaa gtttttttgt ttgtttttca tttggattgt taaagtattc    540
aattctttat gtcgtacaac aagtaaatag aaagaaaaaa atagagtgcg agtttcactt    600
tcaataaatg cttgtgtgat tatctttatt tgtgtacata ctagatctac atccaccgac    660
aaaccagtgt cgaggaagca tatgcaactg tcctgcagat ttaaagtctc atgtaattaa    720
```

-continued

```
atgttgttca atttgtttgt tgtgtgatta ccagtttgat gtatagttaa agttaccaag    780
taataaaatc atcaaacata catatagtac taattttttg tttatcacat aaacattttg    840
ttgacttttt ggtgttgttt gcaatagcat cttcttgata aattcctagt gaactcaaaa    900
ttgacctaca ccagttccat acaaatagaa agatactcca aaactagttg tggaagtggt    960
tgaatataat tttatattcc aaacttagaa aattcatgtt aaattccgca aaagagctta   1020
taacgtagtt tatgcacgat atggttaaac ttcctcagtt gctatagagt taaaaaaaaa   1080
caaatatttt gaaattggta actagtacgt gaaatttttt aatgcagact gaaagaacaa   1140
aataaaactt aaaatatgtt tacaaaaaaa tattctttca tgatttacgc aaaccaaaag   1200
ttacatttaa ggttaggaaa gaaaaaatga cctaggaaat taaaacaatg aggttcgttg   1260
ataaaggtca agaatcaaag tttggtagcc aaattaccag caaacaaaaa aagattaaga   1320
ccattaatcc atcgcgtata ctcattgtct tatgaatctt aaacaataat attatattat   1380
atacagtagg tccataattt atgtttcttt acctactcta tttaccaaaa acatacatag   1440
tttttatctg acttacacaa gtgtactaat ggccagacaa gattgttact tgttcaagta   1500
aaattgtgtt accagatatt caactttcta tatatacata tagatttgac aactattcga   1560
ctttctatat ttaactgaaa gagttgtatc actgaaattt ggagtattgt tccctgtaaa   1620
taattcgatt tgtttccaaa acgctatgga acaggccttg attttgatac tctttcgtgc   1680
tgacacttga aacggcgtcg tatcaataat agaagaaaac cttactgtgg aaataatcaa   1740
attgtgaatc tccaccaacc tcaatgggtc ccattgccac ccactaatct ccccacgtac   1800
accaactccc cttcacgttt taatctctta atatactttt attataagtt aattaaatga   1860
tttcaacctt agtaatacta accattaatt attcatttct aatctccaat attttttttg   1920
aaaaaccttt ctgttcagat attttcgtca attaatcaag atctcattca taaattaaaa   1980
aaaaaaacaa aattcaagct aaaaatacat acccaacaaa aattccttaa aaaaattact   2040
tatggggcat ctggtaattt aattttccta taaaagatgg caatattaat tcagtttttt   2100
tttttaattt accaatatga tactttaatt atatttctta cttgttagct ctactaatgc   2160
acacatactt atttctacga atataagaaa aaaatactga actcaaacaa tagacaaaaa   2220
agaaataatc ctacactcaa gtgtgttgaa aaataacatc aaattcagag aaaatgcaca   2280
tacaccaata atataaataa atagggatat ttaaaataat aaataaaatt gcgaaaatat   2340
cgagcaccac cagatctaca gaaatgacac agagcccaac gatgatgtat ctcgtttatt   2400
ttcgctataa ataaactcac acagcccact cttcttcctc gctctctctt tcgccttctc   2460
ttagcctacc ctttttcctt cctcctctcc gattcttcct ccgtcaggtt cgtctccgac   2520
tttctatgtc ttccttacgt ctctcttatt tagctccctt tccttccttc tccacgttat   2580
tattactact tcgcttttag tgtgattcgt ttcattctcg tttttttata ttcctcgatc   2640
tgtttgctca tttgttgaga tctattcgct atgtgagttc atttgactca gatctggata   2700
tttcgtgttg ttcgatttat agatctggtt tctggatctg tttacgatct atcgtcatct   2760
ttcctttgaa aatgattggt gtttctgtgt tcgtattcgt ttagatctaa agtttttgat   2820
cgatgaatgt cgcatgtgtt tttatctgaa agttttcgat tacagtatca agtggtggta   2880
gtagtagtag tagactcaaa aagctgcaca aactttttat acacgtgaat tgtgattgct   2940
ttacggtttt cttggagttt gttaattaaa tcatttaata ttaagaagtt tatgaattaa   3000
gagaacgtta ttttatacta tgattttgat tttgatttgg tttgtgtgtt ttaatgcagt   3060
```

-continued

```
aaaagaaaat caaa                                                   3074


<210> SEQ ID NO 7
<211> LENGTH: 2682
<212> TYPE: DNA
<213> ORGANISM: Arabidopsis thaliana
<220> FEATURE:
<221> NAME/KEY: CDS
<222> LOCATION: (93)..(2387)
<223> OTHER INFORMATION: coding for 5-methyltetrahydro
      -pteroyltriglutamate homocysteine methyltransferase (At5g17920)

<400> SEQUENCE: 7

cttcttcctc gctctctctt tcgccttctc ttagcctacc ctttttcctt cctcctctcc      60

gattcttcct ccgtcagtaa aagaaaatca aa atg gct tca cac att gtt gga      113
                                    Met Ala Ser His Ile Val Gly
                                    1               5

tac cca cgt atg ggc cct aag aga gag ctc aag ttt gca ttg gaa tct      161
Tyr Pro Arg Met Gly Pro Lys Arg Glu Leu Lys Phe Ala Leu Glu Ser
        10                  15                  20

ttc tgg gat ggt aag agc act gct gag gat ctt cag aag gtg tct gct      209
Phe Trp Asp Gly Lys Ser Thr Ala Glu Asp Leu Gln Lys Val Ser Ala
    25                  30                  35

gat ctc agg tca tcc atc tgg aaa cag atg tct gcc gct ggg act aag      257
Asp Leu Arg Ser Ser Ile Trp Lys Gln Met Ser Ala Ala Gly Thr Lys
40                  45                  50                  55

ttc atc cct agc aac acc ttt gct cac tac gac cag gtt ctt gac acc      305
Phe Ile Pro Ser Asn Thr Phe Ala His Tyr Asp Gln Val Leu Asp Thr
                60                  65                  70

acc gcc atg ctc ggt gct gtt cca cct agg tat gga tac act ggt ggt      353
Thr Ala Met Leu Gly Ala Val Pro Pro Arg Tyr Gly Tyr Thr Gly Gly
            75                  80                  85

gag atc ggc ctt gat gtt tac ttc tcc atg gct aga gga aat gcc tct      401
Glu Ile Gly Leu Asp Val Tyr Phe Ser Met Ala Arg Gly Asn Ala Ser
        90                  95                  100

gtg cct gcc atg gaa atg acc aag tgg ttc gac acc aac tac cat tac      449
Val Pro Ala Met Glu Met Thr Lys Trp Phe Asp Thr Asn Tyr His Tyr
    105                 110                 115

atc gtc cct gag ttg ggc cct gag gtt aac ttc tct tac gca tcc cac      497
Ile Val Pro Glu Leu Gly Pro Glu Val Asn Phe Ser Tyr Ala Ser His
120                 125                 130                 135

aag gcg gtg aat gag tac aag gag gcc aag gct ctt ggt gtt gac acc      545
Lys Ala Val Asn Glu Tyr Lys Glu Ala Lys Ala Leu Gly Val Asp Thr
                140                 145                 150

gtc cct gta ctt gtt ggc cca gtc tct tac ttg ctg ctt tcc aag gct      593
Val Pro Val Leu Val Gly Pro Val Ser Tyr Leu Leu Leu Ser Lys Ala
            155                 160                 165

gcc aag ggt gtt gac aag tca ttc gaa ctt ctt tct ctt ctc cct aag      641
Ala Lys Gly Val Asp Lys Ser Phe Glu Leu Leu Ser Leu Leu Pro Lys
        170                 175                 180

att ctc ccg atc tac aag gaa gtg att acc gag ctt aag gct gct ggt      689
Ile Leu Pro Ile Tyr Lys Glu Val Ile Thr Glu Leu Lys Ala Ala Gly
    185                 190                 195

gcc acc tgg att cag ctt gac gag cct gtc ctt gtt atg gat ctt gag      737
Ala Thr Trp Ile Gln Leu Asp Glu Pro Val Leu Val Met Asp Leu Glu
200                 205                 210                 215

ggt cag aaa ctc cag gcc ttt act ggt gcc tat gct gaa ctt gaa tca      785
Gly Gln Lys Leu Gln Ala Phe Thr Gly Ala Tyr Ala Glu Leu Glu Ser
                220                 225                 230

act ctt tct ggt ttg aat gtt ctt gtc gag acc tac ttc gct gat atc      833
Thr Leu Ser Gly Leu Asn Val Leu Val Glu Thr Tyr Phe Ala Asp Ile
```

-continued

```
            235                 240                 245

cct gct gag gca tac aag acc cta acc tca ttg aag ggt gtg act gcc      881
Pro Ala Glu Ala Tyr Lys Thr Leu Thr Ser Leu Lys Gly Val Thr Ala
        250                 255                 260

ttt gga ttt gat ttg gtt cgt ggc acc aag acc ctt gat ttg gtc aag      929
Phe Gly Phe Asp Leu Val Arg Gly Thr Lys Thr Leu Asp Leu Val Lys
    265                 270                 275

gca ggt ttc cct gag gga aag tac ctc ttt gct ggt gtt gtt gat gga      977
Ala Gly Phe Pro Glu Gly Lys Tyr Leu Phe Ala Gly Val Val Asp Gly
280                 285                 290                 295

agg aac atc tgg gcc aac gac ttt gct gcg tcc cta agc acc ttg cag     1025
Arg Asn Ile Trp Ala Asn Asp Phe Ala Ala Ser Leu Ser Thr Leu Gln
                300                 305                 310

gca ctt gaa ggc att gtt ggt aaa gac aag ctt gtg gtc tca acc tcc     1073
Ala Leu Glu Gly Ile Val Gly Lys Asp Lys Leu Val Val Ser Thr Ser
            315                 320                 325

tgc tct ctt ctc cac acc gct gtt gat ctt atc aat gag act aag ctt     1121
Cys Ser Leu Leu His Thr Ala Val Asp Leu Ile Asn Glu Thr Lys Leu
        330                 335                 340

gat gat gaa atc aag tca tgg ttg gcg ttt gct gcc cag aag gtc gtt     1169
Asp Asp Glu Ile Lys Ser Trp Leu Ala Phe Ala Ala Gln Lys Val Val
    345                 350                 355

gaa gtg aac gct ttg gcc aag gct ttg gct ggt cag aag gac gag gct     1217
Glu Val Asn Ala Leu Ala Lys Ala Leu Ala Gly Gln Lys Asp Glu Ala
360                 365                 370                 375

ctt ttc tct gcc aat gct gcg gct ttg gct tca agg aga tct tcc cca     1265
Leu Phe Ser Ala Asn Ala Ala Ala Leu Ala Ser Arg Arg Ser Ser Pro
                380                 385                 390

aga gtc acc aac gag ggt gtc cag aag gct gct gct gct ttg aag gga     1313
Arg Val Thr Asn Glu Gly Val Gln Lys Ala Ala Ala Ala Leu Lys Gly
            395                 400                 405

tct gac cac cgt cgt gca acc aat gtt agt gct agg cta gat gct cag     1361
Ser Asp His Arg Arg Ala Thr Asn Val Ser Ala Arg Leu Asp Ala Gln
        410                 415                 420

cag aag aag ctc aat ctc cca atc cta cca acc aca acc att gga tcc     1409
Gln Lys Lys Leu Asn Leu Pro Ile Leu Pro Thr Thr Thr Ile Gly Ser
    425                 430                 435

ttc cca cag act gta gag ctc agg aga gtt cgt cgt gag tac aag gcc     1457
Phe Pro Gln Thr Val Glu Leu Arg Arg Val Arg Arg Glu Tyr Lys Ala
440                 445                 450                 455

aaa aag gtc tca gag gag gac tac gtt aaa gcc atc aag gaa gag atc     1505
Lys Lys Val Ser Glu Glu Asp Tyr Val Lys Ala Ile Lys Glu Glu Ile
                460                 465                 470

aag aaa gtt gtt gac ctc caa gag gaa ctt gac atc gat gtt ctt gtc     1553
Lys Lys Val Val Asp Leu Gln Glu Glu Leu Asp Ile Asp Val Leu Val
            475                 480                 485

cac gga gag cca gag aga aac gac atg gtt gag tac ttt ggt gag cag     1601
His Gly Glu Pro Glu Arg Asn Asp Met Val Glu Tyr Phe Gly Glu Gln
        490                 495                 500

ttg tct ggt ttt gcc ttc act gca aac gga tgg gtc caa tct tat gga     1649
Leu Ser Gly Phe Ala Phe Thr Ala Asn Gly Trp Val Gln Ser Tyr Gly
    505                 510                 515

tct cgc tgt gtg aag cca cca gtt atc tat ggt gat gtg agc cgt ccc     1697
Ser Arg Cys Val Lys Pro Pro Val Ile Tyr Gly Asp Val Ser Arg Pro
520                 525                 530                 535

aag gca atg acc gtc ttc tgg tcc gca atg gct cag agc atg acc tct     1745
Lys Ala Met Thr Val Phe Trp Ser Ala Met Ala Gln Ser Met Thr Ser
                540                 545                 550

cgc cca atg aag ggt atg ctt act ggt ccc gtc acc att ctc aac tgg     1793
```

```
Arg Pro Met Lys Gly Met Leu Thr Gly Pro Val Thr Ile Leu Asn Trp
            555                 560                 565

tcc ttt gtc agg aac gac cag ccc agg cac gaa acc tgt tac cag atc     1841
Ser Phe Val Arg Asn Asp Gln Pro Arg His Glu Thr Cys Tyr Gln Ile
        570                 575                 580

gct ttg gcc atc aag gac gaa gtc gag gat ctt gag aaa ggt gga atc     1889
Ala Leu Ala Ile Lys Asp Glu Val Glu Asp Leu Glu Lys Gly Gly Ile
    585                 590                 595

ggt gtc att cag att gat gag gct gca ctt aga gaa gga cta cca ctc     1937
Gly Val Ile Gln Ile Asp Glu Ala Ala Leu Arg Glu Gly Leu Pro Leu
600                 605                 610                 615

agg aaa tcc gag cat gct ttc tac ttg gac tgg gcc gtc cac tcc ttc     1985
Arg Lys Ser Glu His Ala Phe Tyr Leu Asp Trp Ala Val His Ser Phe
                620                 625                 630

aga atc acc aac tgt gga gtc caa gac agc acc cag atc cac act cac     2033
Arg Ile Thr Asn Cys Gly Val Gln Asp Ser Thr Gln Ile His Thr His
            635                 640                 645

atg tgc tac tcc cac ttc aat gac atc ata cac tcc atc atc gac atg     2081
Met Cys Tyr Ser His Phe Asn Asp Ile Ile His Ser Ile Ile Asp Met
        650                 655                 660

gat gct gat gtc atc acc att gag aac tcc agg tct gat gag aag ctt     2129
Asp Ala Asp Val Ile Thr Ile Glu Asn Ser Arg Ser Asp Glu Lys Leu
    665                 670                 675

ctt tcc gtg ttc cgt gaa gga gtg aag tac ggt gct gga atc ggt cca     2177
Leu Ser Val Phe Arg Glu Gly Val Lys Tyr Gly Ala Gly Ile Gly Pro
680                 685                 690                 695

gga gtc tac gac atc cac tct cca aga ata cca tct tct gag gaa atc     2225
Gly Val Tyr Asp Ile His Ser Pro Arg Ile Pro Ser Ser Glu Glu Ile
                700                 705                 710

gca gac agg gtc aac aag atg ctt gct gtc cta gag cag aac atc ctt     2273
Ala Asp Arg Val Asn Lys Met Leu Ala Val Leu Glu Gln Asn Ile Leu
            715                 720                 725

tgg gtt aac cct gac tgt ggt ctc aag acc cgt aag tac acc gag gtc     2321
Trp Val Asn Pro Asp Cys Gly Leu Lys Thr Arg Lys Tyr Thr Glu Val
        730                 735                 740

aag cct gca ctc aag aac atg gtt gat gcg gct aag ctc atc cgc tcc     2369
Lys Pro Ala Leu Lys Asn Met Val Asp Ala Ala Lys Leu Ile Arg Ser
    745                 750                 755

cag ctc gcc agt gcc aag tgaagaaaag cttgatttga acaaggaaac            2417
Gln Leu Ala Ser Ala Lys
760                 765

gttttttttt ctctaaaatg gttgtgtttt atttggttta ataactttct taaaaatatt   2477

tttagtcgaa ggtagatttg atgcatatgg tttctttctt gttgagagag agaaaggcta   2537

tagcatcctt tggatttgat gcaatgtttg tgattttctt tttgtctcca atatatttct   2597

ctgatggaat gtctttttc taaagtatct tgaaaaggaa taagaggatt gattcttata   2657

caaatacttt tgtttgcgtt gtcct                                          2682


<210> SEQ ID NO 8
<211> LENGTH: 765
<212> TYPE: PRT
<213> ORGANISM: Arabidopsis thaliana

<400> SEQUENCE: 8

Met Ala Ser His Ile Val Gly Tyr Pro Arg Met Gly Pro Lys Arg Glu
1               5                   10                  15

Leu Lys Phe Ala Leu Glu Ser Phe Trp Asp Gly Lys Ser Thr Ala Glu
            20                  25                  30
```

-continued

```
Asp Leu Gln Lys Val Ser Ala Asp Leu Arg Ser Ser Ile Trp Lys Gln
        35                  40                  45

Met Ser Ala Ala Gly Thr Lys Phe Ile Pro Ser Asn Thr Phe Ala His
    50                  55                  60

Tyr Asp Gln Val Leu Asp Thr Thr Ala Met Leu Gly Ala Val Pro Pro
65                  70                  75                  80

Arg Tyr Gly Tyr Thr Gly Gly Glu Ile Gly Leu Asp Val Tyr Phe Ser
                85                  90                  95

Met Ala Arg Gly Asn Ala Ser Val Pro Ala Met Glu Met Thr Lys Trp
            100                 105                 110

Phe Asp Thr Asn Tyr His Tyr Ile Val Pro Glu Leu Gly Pro Glu Val
        115                 120                 125

Asn Phe Ser Tyr Ala Ser His Lys Ala Val Asn Glu Tyr Lys Glu Ala
    130                 135                 140

Lys Ala Leu Gly Val Asp Thr Val Pro Val Leu Val Gly Pro Val Ser
145                 150                 155                 160

Tyr Leu Leu Leu Ser Lys Ala Ala Lys Gly Val Asp Lys Ser Phe Glu
                165                 170                 175

Leu Leu Ser Leu Leu Pro Lys Ile Leu Pro Ile Tyr Lys Glu Val Ile
            180                 185                 190

Thr Glu Leu Lys Ala Ala Gly Ala Thr Trp Ile Gln Leu Asp Glu Pro
        195                 200                 205

Val Leu Val Met Asp Leu Glu Gly Gln Lys Leu Gln Ala Phe Thr Gly
    210                 215                 220

Ala Tyr Ala Glu Leu Glu Ser Thr Leu Ser Gly Leu Asn Val Leu Val
225                 230                 235                 240

Glu Thr Tyr Phe Ala Asp Ile Pro Ala Glu Ala Tyr Lys Thr Leu Thr
                245                 250                 255

Ser Leu Lys Gly Val Thr Ala Phe Gly Phe Asp Leu Val Arg Gly Thr
            260                 265                 270

Lys Thr Leu Asp Leu Val Lys Ala Gly Phe Pro Glu Gly Lys Tyr Leu
        275                 280                 285

Phe Ala Gly Val Val Asp Gly Arg Asn Ile Trp Ala Asn Asp Phe Ala
    290                 295                 300

Ala Ser Leu Ser Thr Leu Gln Ala Leu Glu Gly Ile Val Gly Lys Asp
305                 310                 315                 320

Lys Leu Val Val Ser Thr Ser Cys Ser Leu Leu His Thr Ala Val Asp
                325                 330                 335

Leu Ile Asn Glu Thr Lys Leu Asp Asp Glu Ile Lys Ser Trp Leu Ala
            340                 345                 350

Phe Ala Ala Gln Lys Val Val Glu Val Asn Ala Leu Ala Lys Ala Leu
        355                 360                 365

Ala Gly Gln Lys Asp Glu Ala Leu Phe Ser Ala Asn Ala Ala Ala Leu
    370                 375                 380

Ala Ser Arg Arg Ser Ser Pro Arg Val Thr Asn Glu Gly Val Gln Lys
385                 390                 395                 400

Ala Ala Ala Ala Leu Lys Gly Ser Asp His Arg Arg Ala Thr Asn Val
                405                 410                 415

Ser Ala Arg Leu Asp Ala Gln Gln Lys Lys Leu Asn Leu Pro Ile Leu
            420                 425                 430

Pro Thr Thr Thr Ile Gly Ser Phe Pro Gln Thr Val Glu Leu Arg Arg
        435                 440                 445

Val Arg Arg Glu Tyr Lys Ala Lys Lys Val Ser Glu Glu Asp Tyr Val
```

-continued

```
    450                 455                 460

Lys Ala Ile Lys Glu Glu Ile Lys Lys Val Val Asp Leu Gln Glu Glu
465                 470                 475                 480

Leu Asp Ile Asp Val Leu Val His Gly Glu Pro Glu Arg Asn Asp Met
                485                 490                 495

Val Glu Tyr Phe Gly Glu Gln Leu Ser Gly Phe Ala Phe Thr Ala Asn
            500                 505                 510

Gly Trp Val Gln Ser Tyr Gly Ser Arg Cys Val Lys Pro Pro Val Ile
        515                 520                 525

Tyr Gly Asp Val Ser Arg Pro Lys Ala Met Thr Val Phe Trp Ser Ala
    530                 535                 540

Met Ala Gln Ser Met Thr Ser Arg Pro Met Lys Gly Met Leu Thr Gly
545                 550                 555                 560

Pro Val Thr Ile Leu Asn Trp Ser Phe Val Arg Asn Asp Gln Pro Arg
                565                 570                 575

His Glu Thr Cys Tyr Gln Ile Ala Leu Ala Ile Lys Asp Glu Val Glu
            580                 585                 590

Asp Leu Glu Lys Gly Gly Ile Gly Val Ile Gln Ile Asp Glu Ala Ala
        595                 600                 605

Leu Arg Glu Gly Leu Pro Leu Arg Lys Ser Glu His Ala Phe Tyr Leu
    610                 615                 620

Asp Trp Ala Val His Ser Phe Arg Ile Thr Asn Cys Gly Val Gln Asp
625                 630                 635                 640

Ser Thr Gln Ile His Thr His Met Cys Tyr Ser His Phe Asn Asp Ile
                645                 650                 655

Ile His Ser Ile Ile Asp Met Asp Ala Asp Val Ile Thr Ile Glu Asn
            660                 665                 670

Ser Arg Ser Asp Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
    690                 695                 700

Ile Pro Ser Ser Glu Glu Ile Ala Asp Arg Val Asn Lys Met Leu Ala
705                 710                 715                 720

Val Leu Glu Gln Asn Ile Leu Trp Val Asn Pro Asp Cys Gly Leu Lys
                725                 730                 735

Thr Arg Lys Tyr Thr Glu Val Lys Pro Ala Leu Lys Asn Met Val Asp
            740                 745                 750

Ala Ala Lys Leu Ile Arg Ser Gln Leu Ala Ser Ala Lys
        755                 760                 765
```

<210> SEQ ID NO 9
<211> LENGTH: 1599
<212> TYPE: DNA
<213> ORGANISM: Arabidopsis thaliana
<220> FEATURE:
<221> NAME/KEY: promoter
<222> LOCATION: (1)..(1599)
<223> OTHER INFORMATION: promoter of gene At3g03780

<400> SEQUENCE: 9

```
gaattctttt agtttcctta tatattgaat atcatattct cttttcaaag tatggaaact     60

ttatcgtctc ttgcatgtga tctcgccgtt aaaacttata gtatattctg taggattgat    120

gatatgtaaa cgtgtttatt catttaactt tcttacaaaa aaaattgaaa gtaaattagg    180

tatgtaatgt gtaatgcgat atttcaagac gcacaagtat atattagtcg gaacattttg    240
```

```
tcaaattctt ttactttggg aataccgaat acgcatgata cattaggcat tagcgagaaa    300

taagaaaaaa aaaatgtctc attaaatggt cgtgcgtttt tatatctata tcccaccgac    360

agccgacaaa accatagcaa ggcatctact gatctactaa tgcttcggaa tagaccgatg    420

ttggatattg tgaggaaata taaaatttac cggatacaaa tatttctgtg ttttgttttg    480

aaatttgaag ttacttgtta agcgtcttga tggattaaag ttttttgagt ccaaaaacaa    540

aagaacggac tttctcatgt gaaagcatta aaaaaaagag ttcttgctac aaaacaagtt    600

acaagagatg gtagaaatac acttctttat tcgaaacata gaattttcgt attagtcgtc    660

caaacagagc attgaatatt ctttactgaa ctagtttacc atttcatact agacttcttt    720

acatacatta tagacgtata ttcctcatta aggtgaatat tatgacaact tatggttaat    780

aggtttcaaa cttcattgtt gaataaaaaa aattatgtga agatcaaacc ataagaggga    840

cgtggaggat ctcataatca ttcaccaact ttgtttacca aacaaatctc caaatttgtg    900

tggcaagaat tgttggtact gactcccaaa aatgaaatta aaagtgaata tctcaccaac    960

tccctaatgg gctccaccca ccaatcccgc tacctccttc tcctcatgta tactcttcac   1020

aaacaacaca caccaactct cctccccacc ttcacatttt caattccgta attaatcccc   1080

tcttaagctc ttatatctta attaatacta cgctttacaa tacaacatac actaacccct   1140

taattaaccc ttaaacaatt gttttaagct ttaactagcc agtgaggact tgacaaaagt   1200

caactaaaat taccagtaaa ctagtactaa ttcaacggaa ttaagttcta ccagcttata   1260

taattgtaat gtcatgccat gatcgaatac atttttttat tatgtaaacc gtcgttatac   1320

gtataattct cgaaagttgt acataattga ccgtgccctt aaatttgaaa gataaaaatt   1380

agtatcattc tggatacatg gattacacgt atttttattt atcatatagt ataatgttgt   1440

agagagggta aaaacctaaa tatacgtact ttgatgtaca tgtacgtatt attaatttaa   1500

atagaaaaat aatcagccac cacgagtgag tgagagaaac caaggaacga tgtgtaattg   1560

atttgctata aataagctta acacagaaca ctctccatc                          1599

<210> SEQ ID NO 10
<211> LENGTH: 2112
<212> TYPE: DNA
<213> ORGANISM: Arabidopsis thaliana
<220> FEATURE:
<221> NAME/KEY: promoter
<222> LOCATION: (1)..(2112)
<223> OTHER INFORMATION: promoter of gene At3g03780

<400> SEQUENCE: 10

gaattctttt agtttcctta tatattgaat atcatattct cttttcaaag tatggaaact     60

ttatcgtctc ttgcatgtga tctcgccgtt aaaacttata gtatattctg taggattgat    120

gatatgtaaa cgtgtttatt catttaactt tcttacaaaa aaaattgaaa gtaaattagg    180

tatgtaatgt gtaatgcgat atttcaagac gcacaagtat atattagtcg gaacattttg    240

tcaaattctt ttactttggg aataccgaat acgcatgata cattaggcat tagcgagaaa    300

taagaaaaaa aaaatgtctc attaaatggt cgtgcgtttt tatatctata tcccaccgac    360

agccgacaaa accatagcaa ggcatctact gatctactaa tgcttcggaa tagaccgatg    420

ttggatattg tgaggaaata taaaatttac cggatacaaa tatttctgtg ttttgttttg    480

aaatttgaag ttacttgtta agcgtcttga tggattaaag ttttttgagt ccaaaaacaa    540

aagaacggac tttctcatgt gaaagcatta aaaaaaagag ttcttgctac aaaacaagtt    600

acaagagatg gtagaaatac acttctttat tcgaaacata gaattttcgt attagtcgtc    660
```

-continued

```
caaacagagc attgaatatt ctttactgaa ctagtttacc atttcatact agacttcttt     720
acatacatta tagacgtata ttcctcatta aggtgaatat tatgacaact tatggttaat     780
aggtttcaaa cttcattgtt gaataaaaaa aattatgtga agatcaaacc ataagaggga     840
cgtggaggat ctcataatca ttcaccaact ttgtttacca aacaaatctc caaatttgtg     900
tggcaagaat tgttggtact gactcccaaa aatgaaatta aaagtgaata tctcaccaac     960
tccctaatgg gctccaccca ccaatcccgc tacctccttc tcctcatgta tactcttcac    1020
aaacaacaca caccaactct cctccccacc ttcacatttt caattccgta attaatcccc    1080
tcttaagctc ttatatctta attaatacta cgctttacaa tacaacatac actaacccct    1140
taattaaccc ttaaacaatt gttttaagct ttaactagcc agtgaggact tgacaaaagt    1200
caactaaaat taccagtaaa ctagtactaa ttcaacggaa ttaagttcta ccagcttata    1260
taattgtaat gtcatgccat gatcgaatac atttttttat tatgtaaacc gtcgttatac    1320
gtataattct cgaaagttgt acataattga ccgtgccctt aaatttgaaa gataaaaatt    1380
agtatcattc tggatacatg gattacacgt atttttattt atcatatagt ataatgttgt    1440
agagagggta aaaacctaaa tatacgtact ttgatgtaca tgtacgtatt attaatttaa    1500
atagaaaaat aatcagccac cacgagtgag tgagagaaac caaggaacga tgtgtaattg    1560
atttgctata aataagctta acacagaaca ctctccatcg tcgctctctt tgcccatctc    1620
tcatttccac tcttctcatt ccgtaaggta cgcttccgag tttccatggc ttccgcatga    1680
ctattcttgc tctctccctt cccactctct tatttagctt ccgtctcttc gttttcttct    1740
caattcaatt ttcgtttgat tccgtttctt cttcgttcgt taatacttag atctaattcc    1800
ggtgagtgaa attctacgaa gcacagatct ggctttttat acgatcagat tcgtaaaatc    1860
tctgttttgc gatctttctc tgcgttagat ctctgttttc cctagttgtg attcgttttg    1920
atctttaaac tctctcatac tctgttttca ataaatacga caaaaaaaac tgcaaaagtt    1980
ttttactttt ttaacgattg gtggctttta ccatatgaca agaagtacat tttaggattg    2040
tgtttggttt actgactgat tttggttttg tttgtggttc aaatgtagta aaaaaacaaa    2100
aaacaaacaa aa                                                        2112
```

```
<210> SEQ ID NO 11
<211> LENGTH: 2112
<212> TYPE: DNA
<213> ORGANISM: Arabidopsis thaliana
<220> FEATURE:
<221> NAME/KEY: promoter
<222> LOCATION: (1)..(2112)
<223> OTHER INFORMATION: promoter of gene At3g03780

<400> SEQUENCE: 11
```

```
aattctttta gtttccttat atattgaata tcatattctc ttttcaaagt atggaaactt      60
tatcgtctct tgcatgtgat ctcgccgtta aaacttatag tatattctgt aggattgatg     120
atatgtaaac gtgtttattc atttaacttt cttacaaaaa aaattgaaag taaattaggt     180
atgtaatgtg taatgcgata tttcaagacg cacaagtata tattagtcgg aacattttgt     240
caaattcttt tactttggga ataccgaata cgcatgatac attaggcatt agcgagaaat     300
aagaaaaaaa aaatgtctca ttaaatggtc gtgcgttttt atatctatat cccaccgaca     360
gccgacaaaa ccatagcaag gcatctactg atctactaat gcttcggaat agaccgatgt     420
tggatattgt gaggaaatat aaaatttacc ggatacaaat atttctgtgt tttgttttga     480
```

-continued

```
aatttgaagt tacttgttaa gcgtcttgat ggattaaagt tttttgagtc gaaaaacaaa    540

agaacggact ttctcatgtg aaagcattaa aaaaaagagt tcttgctaca aaacaagtta    600

caagagatgg tagaaataca cttctttatt cgaaacatag aattttcgta ttagtcgtcc    660

aaacagagca ttgaatattc tttactgaac tagtttacca tttcatacta gacttcttta    720

catacattat agacgtatat tcctcattaa ggtgaatatt atgacaactt atggttaata    780

ggtttcaaac gtcattgttg aataaaaaaa attatgtgaa gatcaaacca taagagggac    840

gtggaggatc tcataatcat tcaccaactt tgtttaccaa acaaatctcc aaatttgtgt    900

ggcaagaatt gttggtactg actcccaaaa atgaaattaa aagtgaatat ctcaccaact    960

ccctaatggg ctccacccac caatcccgct acctccttct cctcatgtat actcttcaca   1020

aacaacacac accaactctc ctccccacct tcacattttc aattccataa ttaatcccct   1080

cttaagctct tatatcttaa ttaatactac gctttacaat acaacataca ctaacccctt   1140

aattaaccct taaacaattg ttttaagctt taactagcca gtgaggactt gacaaaagtc   1200

aactaaaatt accagtaaac tagtactaat tcaacggaat taagttctac cagcttatat   1260

aattgtaatg tcatgccatg atcaaataca ttttttttatt atgtaaaccg tcgttatacg   1320

tataattctc gaaagttgta tataattgac cgtgccctta aatttgaaag ataaaaatta   1380

gtatcattct ggatacatgg attacacgta tttttattta tcatatagta taatgttgta   1440

gagagggtaa aaacctaaat atacgtattt tgatgtacat gtacgtatta ttaatttaaa   1500

tagaaaaata atcagccacc acgagtgagt gagagaaacc aaggaacgat gtgtaattga   1560

tttgctataa ataagcttaa cacagaacac tctccatcgt cgctctcttt gcccatctct   1620

catctccact cttctcattc cgtaaggtac gcttccgagt ttccatggct tccgcatgac   1680

tattcttgct ctctcccttc ccactctctt atttaccttc cgtctcttcg ttttcttctc   1740

aattcaattt tcgtttgatt ccgtttcttc ttcgttcgtt aatacttaga tcttaatccg   1800

gtgagtgaaa ttctatgaaa cacagatctg gattttttat acgatcagat tcgtaaaatc   1860

tctgttttgc gatctttctc tgcgttagat ctctgttttc cctagttgtg attcgttttg   1920

atctttaaac tctctcatac tctgttttca ataaatacga caaaaaaaac tgcaaaagtt   1980

ttttactttt ttaacgattg gtggctttta ccatatgaca agaagtacat tttaggattg   2040

tgtttggttt actgactgat tttggttttg tttgtggttc aaatgtagta aaaaaacaaa   2100

aaacaaacaa aa                                                        2112
```

<210> SEQ ID NO 12
<211> LENGTH: 2482
<212> TYPE: DNA
<213> ORGANISM: Arabidopsis thaliana
<220> FEATURE:
<221> NAME/KEY: promoter
<222> LOCATION: (1)..(2482)
<223> OTHER INFORMATION: promoter of gene At3g03780

<400> SEQUENCE: 12

```
gtcgatcatg aaactcacat ctgtaaacaa acaaaagaga agggaagaat tatgaaaata     60

tattcttgca tttcatatta aaaagagtcc aatattaaca aactggctac aataacgatt    120

tgttagataa agcgaagaga ttgaaactga aacatgttta tagtactatc atctctagac    180

tacacaaaac tatccgaaag attaattcga tggtcatggt tatattccgg agatgataca    240

caacaattgt tttaaataat tgggttttgt aagtgcaaac gatacacata agttaaatct    300

tgaaaattat gtatgtataa atacaaaaga ataacattat gaattcagaa aaagaagtga    360
```

-continued

```
aaacaaagca agaaatgaaa tgataaaatt aagataatta aatgagaaaa gtgatagatt    420
aagaaaccat taattgtctt gagtaatttt tccaaggatt tcttccattc cggcgtagga    480
gattctatct tcaagagaca tgtctgcgtt taaaaacata agatttatac acactttcaa    540
ataaacataa aatatataca caaatcttac aatctattat gcgtttacgc ataccatgtg    600
attggaagat gattccatcg atctagatta gatatgtttt gttatttgtt cctgctcttg    660
agaaacctta ggaaaacaaa aaatttggga ggttttgggt ggtgaagaaa agtttcttct    720
tttattatat tttggaaata tggatatatg atgataagag atatcaatct atgaattttt    780
tattttcctt aattagtaaa aaatttcgat ctatggatat cagtatatcg tctatgaatt    840
ttttattttc cttatgataa gagatatcaa tctatggata tatgaattct tttagtttcc    900
ttatatattg aatatcatat tctcttttca aagtatggaa actttatcgt ctcttgcatg    960
tgatctcgcc gttaaaactt atagtatatt ctgtaggatt gatgatatgt aaacgtgttt   1020
attcatttaa ctttcttaca aaaaaaattg aaagtaaatt aggtatgtaa tgtgtaatgc   1080
gatatttcaa gacgcacaag tatatattag tcggaacatt ttgtcaaatt cttttacttt   1140
gggaataccg aatacgcatg atacattagg cattagcgag aaataagaaa aaaaaaatgt   1200
ctcattaaat ggtcgtgcgt ttttatatct atatcccacc gacagccgac aaaaccatag   1260
caaggcatct actgatctac taatgcttcg gaatagaccg atgttggata ttgtgaggaa   1320
atataaaatt taccggatac aaatatttct gtgttttgtt ttgaaatttg aagttacttg   1380
ttaagcgtct tgatggatta aagttttttg agtccaaaaa caaaagaacg gactttctca   1440
tgtgaaagca ttaaaaaaaa gagttcttgc tacaaaacaa gttacaagag atggtagaaa   1500
tacacttctt tattcgaaac atagaatttt cgtattagtc gtccaaacag agcattgaat   1560
attctttact gaactagttt accatttcat actagacttc tttacataca ttatagacgt   1620
atattcctca ttaaggtgaa tattatgaca acttatggtt aataggtttc aaacttcatt   1680
gttgaataaa aaaaattatg tgaagatcaa accataagag ggacgtggag gatctcataa   1740
tcattcacca actttgttta ccaaacaaat ctccaaattt gtgtggcaag aattgttggt   1800
actgactccc aaaaatgaaa ttaaaagtga atatctcacc aactccctaa tgggctccac   1860
ccaccaatcc cgctacctcc ttctcctcat gtatactctt cacaaacaac acacaccaac   1920
tctcctcccc accttcacat tttcaattcc gtaattaatc ccctcttaag ctcttatatc   1980
ttaattaata ctacgcttta caatacaaca tacactaacc ccttaattaa cccttaaaca   2040
attgttttaa gctttaacta gccagtgagg acttgacaaa agtcaactaa aattaccagt   2100
aaactagtac taattcaacg gaattaagtt ctaccagctt atataattgt aatgtcatgc   2160
catgatcgaa tacatttttt tattatgtaa accgtcgtta tacgtataat tctcgaaagt   2220
tgtacataat tgaccgtgcc cttaaatttg aaagataaaa attagtatca ttctggatac   2280
atggattaca cgtattttta tttatcatat agtataatgt tgtagagagg gtaaaaacct   2340
aaatatacgt actttgatgt acatgtacgt attattaatt taaatagaaa aataatcagc   2400
caccacgagt gagtgagaga aaccaaggaa cgatgtgtaa ttgatttgct ataaataagc   2460
ttaacacaga acactctcca tc                                            2482
```

<210> SEQ ID NO 13
<211> LENGTH: 2995
<212> TYPE: DNA
<213> ORGANISM: Arabidopsis thaliana
<220> FEATURE:

<221> NAME/KEY: promoter
<222> LOCATION: (1)..(2995)
<223> OTHER INFORMATION: promoter of gene At3g03780

<400> SEQUENCE: 13

```
gtcgatcatg aaactcacat ctgtaaacaa acaaaagaga agggaagaat tatgaaaata     60
tattcttgca tttcatatta aaaagagtcc aatattaaca aactggctac aataacgatt    120
tgttagataa agcgaagaga ttgaaactga aacatgttta tagtactatc atctctagac    180
tacacaaaac tatccgaaag attaattcga tggtcatggt tatattccgg agatgataca    240
caacaattgt tttaaataat tgggttttgt aagtgcaaac gatacacata agttaaatct    300
tgaaaattat gtatgtataa atacaaaaga ataacattat gaattcagaa aaagaagtga    360
aaacaaagca agaaatgaaa tgataaaatt aagataatta aatgagaaaa gtgatagatt    420
aagaaaccat taattgtctt gagtaatttt tccaaggatt tcttccattc cggcgtagga    480
gattctatct tcaagagaca tgtctgcgtt taaaaacata agatttatac acactttcaa    540
ataaacataa aatatataca caaatcttac aatctattat gcgtttacgc ataccatgtg    600
attggaagat gattccatcg atctagatta gatatgtttt gttatttgtt cctgctcttg    660
agaaacctta ggaaaacaaa aaatttggga ggttttgggt ggtgaagaaa agtttcttct    720
tttattatat tttggaaata tggatatatg atgataagag atatcaatct atgaattttt    780
tattttcctt aattagtaaa aaatttcgat ctatggatat cagtatatcg tctatgaatt    840
ttttattttc cttatgataa gagatatcaa tctatggata tatgaattct tttagtttcc    900
ttatatattg aatatcatat tctcttttca aagtatggaa actttatcgt ctcttgcatg    960
tgatctcgcc gttaaaactt atagtatatt ctgtaggatt gatgatatgt aaacgtgttt   1020
attcatttaa ctttcttaca aaaaaaattg aaagtaaatt aggtatgtaa tgtgtaatgc   1080
gatatttcaa gacgcacaag tatatattag tcggaacatt ttgtcaaatt cttttacttt   1140
gggaataccg aatacgcatg atacattagg cattagcgag aaataagaaa aaaaaaatgt   1200
ctcattaaat ggtcgtgcgt ttttatatct atatcccacc gacagccgac aaaaccatag   1260
caaggcatct actgatctac taatgcttcg gaatagaccg atgttggata ttgtgaggaa   1320
atataaaatt taccggatac aaatatttct gtgttttgtt ttgaaatttg aagttacttg   1380
ttaagcgtct tgatggatta aagtttttttg agtccaaaaa caaaagaacg gactttctca   1440
tgtgaaagca ttaaaaaaaa gagttcttgc tacaaaacaa gttacaagag atggtagaaa   1500
tacacttctt tattcgaaac atagaatttt cgtattagtc gtccaaacag agcattgaat   1560
attctttact gaactagttt accatttcat actagacttc tttacataca ttatagacgt   1620
atattcctca ttaaggtgaa tattatgaca acttatggtt aataggtttc aaacttcatt   1680
gttgaataaa aaaaattatg tgaagatcaa accataagag ggacgtggag gatctcataa   1740
tcattcacca actttgttta ccaaacaaat ctccaaattt gtgtggcaag aattgttggt   1800
actgactccc aaaaatgaaa ttaaaagtga atatctcacc aactccctaa tgggctccac   1860
ccaccaatcc cgctacctcc ttctcctcat gtatactctt cacaaacaac acacaccaac   1920
tctcctcccc accttcacat tttcaattcc gtaattaatc ccctcttaag ctcttatatc   1980
ttaattaata ctacgcttta caatacaaca tacactaacc ccttaattaa cccttaaaca   2040
attgttttaa gctttaacta gccagtgagg acttgacaaa agtcaactaa aattaccagt   2100
aaactagtac taattcaacg gaattaagtt ctaccagctt atataattgt aatgtcatgc   2160
catgatcgaa tacatttttt tattatgtaa accgtcgtta tacgtataat tctcgaaagt   2220
```

```
tgtacataat tgaccgtgcc cttaaatttg aaagataaaa attagtatca ttctggatac   2280

atggattaca cgtattttta tttatcatat agtataatgt tgtagagagg gtaaaaacct   2340

aaatatacgt actttgatgt acatgtacgt attattaatt taaatagaaa aataatcagc   2400

caccacgagt gagtgagaga aaccaaggaa cgatgtgtaa ttgatttgct ataaataagc   2460

ttaacacaga acactctcca tcgtcgctct ctttgcccat ctctcatttc cactcttctc   2520

attccgtaag gtacgcttcc gagtttccat ggcttccgca tgactattct tgctctctcc   2580

cttcccactc tcttatttag cttccgtctc ttcgttttct tctcaattca attttcgttt   2640

gattccgttt cttcttcgtt cgttaatact tagatctaat tccggtgagt gaaattctac   2700

gaagcacaga tctggctttt tatacgatca gattcgtaaa atctctgttt tgcgatcttt   2760

ctctgcgtta gatctctgtt ttccctagtt gtgattcgtt ttgatcttta aactctctca   2820

tactctgttt tcaataaata cgacaaaaaa aactgcaaaa gtttttttact tttttaacga   2880

ttggtggctt ttaccatatg acaagaagta cattttagga ttgtgtttgg tttactgact   2940

gattttggtt ttgtttgtgg ttcaaatgta gtaaaaaaac aaaaaacaaa caaaa        2995
```

```
<210> SEQ ID NO 14
<211> LENGTH: 2996
<212> TYPE: DNA
<213> ORGANISM: Arabidopsis thaliana
<220> FEATURE:
<221> NAME/KEY: promoter
<222> LOCATION: (1)..(2996)
<223> OTHER INFORMATION: promoter of gene At3g03780

<400> SEQUENCE: 14

gtcgatcatg aaactcacat ctgtaaacaa acaaaagaga agggaagaat tatgaaaata     60

tattcttgca tttcatatta aaaagagtcc aatattaaca aactggctac aataacgatt    120

tgttcgataa agcgaagaga ttgaaacgga aacatgttta tagtactatc atctctagac    180

tacacaaaac tatccgaaag attaattcga tggtcatggt tatattccgg agatgataca    240

caacaattgt tttaaataat tgggttttgt aagtgcaaac gatacacata agttaaatct    300

tgaaaattat gtatgtataa atacaaaaga aaaacattat gcattcagaa aaagaagtga    360

agacaaagta agaaatgaaa tgataaaatt aagataatta aacgagaaaa gtgatagatt    420

aagaaaccat taattgtctt gagtaatttt tccaaggatt tcttccatcc cggcgtagga    480

gattctatct tcaaaagaca tatctgcgct taaaaacata agatttatac acactttcaa    540

ataaacataa aatatataca caaatcttac aatctattat gcgtttacgc ataccatgtg    600

attggaagat gattccatcg atctagatta gatatgtttt gttatttgtt cctgctcttg    660

agaaacctta ggaaaacaaa aaatttggga ggttttgggt ggtgaagaaa agtttcttct    720

tttattatat tttggaaata tggatatatg atgataagag atatcaatct atgaattttt    780

tattttcctt aattagtaaa aaatttcgat ctatggatat cagtatatcg tctatgaatt    840

ttttattttc cttatgataa gagatatcaa tctatggata tatgaattct tttagtttcc    900

ttatatattg aatatcatat tctcttttca aagtatggaa actttatcgt ctcttgcatg    960

tgatctcgcc gttaaaactt atagtatatt ctgtaggatt gatgatatgt aaacgtgttt   1020

attcatttaa ctttcttaca aaaaaaattg aaagtaaatt aggtatgtaa tgtgtaatgc   1080

gatatttcaa gacgcacaag tatatattag tcggaacatt ttgtcaaatt cttttacttt   1140

gggaataccg aatacgcatg atacattagg cattagcgag aaataagaaa aaaaaaatgt   1200
```

-continued

```
ctcattaaat ggtcgtgcgt ttttatatct atatcccacc gacagccgac aaaaccatag   1260

caaggcatct actgatctac taatgcttcg gaatagaccg atgttggata ttgtgaggaa   1320

atataaaatt taccggatac aaatatttct gtgttttgtt ttgaaatttg aagttacttg   1380

ttaagcgtct tgatggatta aagtttttttg agtcgaaaaa caaaagaacg gactttctca   1440

tgtgaaagca ttaaaaaaaa gagttcttgc tacaaaacaa gttacaagag atggtagaaa   1500

tacacttctt tattcgaaac atagaatttt cgtattagtc gtccaaacag agcattgaat   1560

attctttact gaactagttt accatttcat actagacttc tttacataca ttatagacgt   1620

atattcctca ttaaggtgaa tattatgaca acttatggtt aataggtttc aaacgtcatt   1680

gttgaataaa aaaaattatg tgaagatcaa accataagag ggacgtggag gatctcataa   1740

tcattcacca actttgttta ccaaacaaat ctccaaattt gtgtggcaag aattgttggt   1800

actgactccc aaaaatgaaa ttaaaagtga atatctcacc aactccctaa tgggctccac   1860

ccaccaatcc cgctacctcc ttctcctcat gtatactctt cacaaacaac acacaccaac   1920

tctcctcccc accttcacat tttcaattcc ataattaatc ccctcttaag ctcttatatc   1980

ttaattaata ctacgcttta caatacaaca tacactaacc ccttaattaa cccttaaaca   2040

attgttttaa gctttaacta gccagtgagg acttgacaaa agtcaactaa aattaccagt   2100

aaactagtac taattcaacg gaattaagtt ctaccagctt atataattgt aatgtcatgc   2160

catgatcaaa tacatttttt tattatgtaa accgtcgtta tacgtataat tctcgaaagt   2220

tgtatataat tgaccgtgcc cttaaatttg aaagataaaa attagtatca ttctggatac   2280

atggattaca cgtattttta tttatcatat agtataatgt tgtagagagg gtaaaaacct   2340

aaatatacgt attttgatgt acatgtacgt attattaatt taaatagaaa aataatcagc   2400

caccacgagt gagtgagaga aaccaaggaa cgatgtgtaa ttgatttgct ataaataagc   2460

ttaacacaga acactctcca tcgtcgctct ctttgcccat ctctcatctc cactcttctc   2520

attccgtaag gtacgcttcc gagtttccat ggcttccgca tgactattct tgctctctcc   2580

cttcccactc tcttatttac cttccgtctc ttcgttttct tctcaattca attttcgttt   2640

gattccgttt cttcttcgtt cgttaatact tagatcttaa tccggtgagt gaaattctat   2700

gaaacacaga tctggatttt ttatacgatc agattcgtaa aatctctgtt ttgcgatctt   2760

tctctgcgtt agatctctgt tttccctagt tgtgattcgt tttgatcttt aaactctctc   2820

atactctgtt ttcaataaat acgacaaaaa aaactgcaaa agttttttac tttttttaacg   2880

attggtggct tttaccatat gacaagaagt acattttagg attgtgtttg gtttactgac   2940

tgattttggt tttgtttgtg gttcaaatgt agtaaaaaaa caaaaaaacaa acaaaa      2996
```

```
<210> SEQ ID NO 15
<211> LENGTH: 2608
<212> TYPE: DNA
<213> ORGANISM: Arabidopsis thaliana
<220> FEATURE:
<221> NAME/KEY: CDS
<222> LOCATION: (73)..(2367)
<223> OTHER INFORMATION: coding for putative
      5-methyltetrahydropteroyltriglutamate-homocysteine
      methyltransferase (At3g03780)

<400> SEQUENCE: 15

gtcgctctct ttgcccatct ctcatctcca ctcttctcat tccgtaagta aaaaaacaaa     60

aaacaaacaa aa atg gct tcc cac att gtt gga tat cca cgt atg gga cct    111
              Met Ala Ser His Ile Val Gly Tyr Pro Arg Met Gly Pro
              1               5                   10
```

-continued

```
aag aga gag ctc aag ttt gca ttg gag tct ttc tgg gat ggc aag agc      159
Lys Arg Glu Leu Lys Phe Ala Leu Glu Ser Phe Trp Asp Gly Lys Ser
    15                  20                  25

agt gcc gat gat ttg cag aag gtg tct gct gat ctc agg tct gat atc      207
Ser Ala Asp Asp Leu Gln Lys Val Ser Ala Asp Leu Arg Ser Asp Ile
30                  35                  40                  45

tgg aaa cag atg tct gct gct ggg att aag tat atc cca agc aac acc      255
Trp Lys Gln Met Ser Ala Ala Gly Ile Lys Tyr Ile Pro Ser Asn Thr
                50                  55                  60

ttt tct cat tat gac cag gtg ctt gac acc acc gcc atg ctt ggt gct      303
Phe Ser His Tyr Asp Gln Val Leu Asp Thr Thr Ala Met Leu Gly Ala
            65                  70                  75

gtt cca tct aga tat gga ttt acc agt ggt gag atc ggt ctc gat gtt      351
Val Pro Ser Arg Tyr Gly Phe Thr Ser Gly Glu Ile Gly Leu Asp Val
        80                  85                  90

tac ttc tcc atg gct aga gga aat gcc tct gtt cca gct atg gag atg      399
Tyr Phe Ser Met Ala Arg Gly Asn Ala Ser Val Pro Ala Met Glu Met
    95                  100                 105

acc aag tgg ttt gac acc aac tac cat tac atc gtc cca gag ttg ggc      447
Thr Lys Trp Phe Asp Thr Asn Tyr His Tyr Ile Val Pro Glu Leu Gly
110                 115                 120                 125

cct gaa gtg aaa ttt tct tac gca tct cac aag gct gtc aat gag tac      495
Pro Glu Val Lys Phe Ser Tyr Ala Ser His Lys Ala Val Asn Glu Tyr
                130                 135                 140

aag gag gcc aag gct ctt ggt gtt gag acc gtc cct gta ctt gtt ggc      543
Lys Glu Ala Lys Ala Leu Gly Val Glu Thr Val Pro Val Leu Val Gly
            145                 150                 155

cct gtc tct tac ttg ctt ctt tcc aag ctt gct aag ggt gtt gac aag      591
Pro Val Ser Tyr Leu Leu Leu Ser Lys Leu Ala Lys Gly Val Asp Lys
        160                 165                 170

tca ttt gat ctt ctc tcc ctt ctc ccc aaa atc ctc cca gtt tac aag      639
Ser Phe Asp Leu Leu Ser Leu Leu Pro Lys Ile Leu Pro Val Tyr Lys
    175                 180                 185

gaa gtc att gca gag ctt aag gca gct ggt gcc tcc tgg att cag ctt      687
Glu Val Ile Ala Glu Leu Lys Ala Ala Gly Ala Ser Trp Ile Gln Leu
190                 195                 200                 205

gat gag cct ctc ttt gtc atg gat ctc gag ggt cac aaa ctc cag gct      735
Asp Glu Pro Leu Phe Val Met Asp Leu Glu Gly His Lys Leu Gln Ala
                210                 215                 220

ttt agc ggt gcc tat gct gag ctt gaa tca act ctc tct ggt ctg aat      783
Phe Ser Gly Ala Tyr Ala Glu Leu Glu Ser Thr Leu Ser Gly Leu Asn
            225                 230                 235

gtt ctt gtg gag acc tac ttc gct gat atc cct gct gaa gca tac aag      831
Val Leu Val Glu Thr Tyr Phe Ala Asp Ile Pro Ala Glu Ala Tyr Lys
        240                 245                 250

acc ctt act tcc ttg aag ggt gtg act gcc ttc gga ttt gat ttg gtt      879
Thr Leu Thr Ser Leu Lys Gly Val Thr Ala Phe Gly Phe Asp Leu Val
    255                 260                 265

cgt ggc acc aag acc att gac ttg atc aag tca ggt ttc cca cag ggc      927
Arg Gly Thr Lys Thr Ile Asp Leu Ile Lys Ser Gly Phe Pro Gln Gly
270                 275                 280                 285

aag tac ctc ttt gct ggt gtt gtt gac gga agg aac atc tgg gcc aat      975
Lys Tyr Leu Phe Ala Gly Val Val Asp Gly Arg Asn Ile Trp Ala Asn
                290                 295                 300

gac ctc gct gcc tct ctc atc acc ttg cag tca ctt gag ggt gtt gtt     1023
Asp Leu Ala Ala Ser Leu Ile Thr Leu Gln Ser Leu Glu Gly Val Val
            305                 310                 315

ggt aaa gac aag ctt gtg gtc tca acc tct tgc tct ctt ctc cac act     1071
Gly Lys Asp Lys Leu Val Val Ser Thr Ser Cys Ser Leu Leu His Thr
```

-continued

```
        320                 325                 330

gcc gtt gac ctt att aac gag act aag ctt gat gct gaa atc aag tcg     1119
Ala Val Asp Leu Ile Asn Glu Thr Lys Leu Asp Ala Glu Ile Lys Ser
    335                 340                 345

tgg cta gct ttt gct gcc cag aag gtt gtt gaa gtt gac gca ttg gcc     1167
Trp Leu Ala Phe Ala Ala Gln Lys Val Val Glu Val Asp Ala Leu Ala
350                 355                 360                 365

aag gct ttg gcc ggt cag aca aat gag agt ttc ttc act gcc aac gct     1215
Lys Ala Leu Ala Gly Gln Thr Asn Glu Ser Phe Phe Thr Ala Asn Ala
                370                 375                 380

gac gca ttg tct tcg agg agg tct tcc cca aga gtc acc aat gag tct     1263
Asp Ala Leu Ser Ser Arg Arg Ser Ser Pro Arg Val Thr Asn Glu Ser
            385                 390                 395

gtc cag aag gct gct gct gct ttg aag gga tct gac cac cgc cgt aca     1311
Val Gln Lys Ala Ala Ala Ala Leu Lys Gly Ser Asp His Arg Arg Thr
        400                 405                 410

act gaa gtt agc gca agg cta gat gct cag cag aag aag ctt aac ctt     1359
Thr Glu Val Ser Ala Arg Leu Asp Ala Gln Gln Lys Lys Leu Asn Leu
    415                 420                 425

cca atc ctc cca acc aca acc att gga tcc ttc cca cag acc gtg gaa     1407
Pro Ile Leu Pro Thr Thr Thr Ile Gly Ser Phe Pro Gln Thr Val Glu
430                 435                 440                 445

ctc agg aga gtt cgc cgt gaa tac aag gcc aag aaa atc tct gaa gag     1455
Leu Arg Arg Val Arg Arg Glu Tyr Lys Ala Lys Lys Ile Ser Glu Glu
                450                 455                 460

gat tac gtc aag gcc atc aag gaa gag atc aag aaa gtt gtt gac atc     1503
Asp Tyr Val Lys Ala Ile Lys Glu Glu Ile Lys Lys Val Val Asp Ile
            465                 470                 475

caa gag gac ctt gac att gat gtt ctt gtt cac gga gag cct gag aga     1551
Gln Glu Asp Leu Asp Ile Asp Val Leu Val His Gly Glu Pro Glu Arg
        480                 485                 490

aac gac atg gtt gag tac ttt gga gag caa ttg tca ggt ttc gca ttc     1599
Asn Asp Met Val Glu Tyr Phe Gly Glu Gln Leu Ser Gly Phe Ala Phe
    495                 500                 505

aca gca aac gga tgg gtg caa tcc tat gga tct cgc tgt gtg aag cca     1647
Thr Ala Asn Gly Trp Val Gln Ser Tyr Gly Ser Arg Cys Val Lys Pro
510                 515                 520                 525

cca gtt atc tat ggt gac gtg agc cgc ccc aag cca atg aca gtc ttc     1695
Pro Val Ile Tyr Gly Asp Val Ser Arg Pro Lys Pro Met Thr Val Phe
                530                 535                 540

tgg tcc tca aca gct cag agc atg acc aaa cgt cca atg aag ggt atg     1743
Trp Ser Ser Thr Ala Gln Ser Met Thr Lys Arg Pro Met Lys Gly Met
            545                 550                 555

ctt aca ggt cca gtc aca att ctc aac tgg tct ttt gtc aga aac gac     1791
Leu Thr Gly Pro Val Thr Ile Leu Asn Trp Ser Phe Val Arg Asn Asp
        560                 565                 570

cag ccc agg cac gaa acc tgt tac cag atc gct ttg gcc atc aaa gat     1839
Gln Pro Arg His Glu Thr Cys Tyr Gln Ile Ala Leu Ala Ile Lys Asp
    575                 580                 585

gaa gtg gaa gac ctc gag aaa ggc ggt att gga gtc att cag atc gat     1887
Glu Val Glu Asp Leu Glu Lys Gly Gly Ile Gly Val Ile Gln Ile Asp
590                 595                 600                 605

gaa gcc gca ctt aga gaa gga ttg cct ctt agg aaa gcc gaa cac tct     1935
Glu Ala Ala Leu Arg Glu Gly Leu Pro Leu Arg Lys Ala Glu His Ser
                610                 615                 620

ttc tac ttg gac tgg gct gtt cac tct ttc aga atc acc aac tgt ggc     1983
Phe Tyr Leu Asp Trp Ala Val His Ser Phe Arg Ile Thr Asn Cys Gly
            625                 630                 635

gtc caa gac agc act cag att cac act cac atg tgt tac tca aac ttc     2031
```

```
Val Gln Asp Ser Thr Gln Ile His Thr His Met Cys Tyr Ser Asn Phe
        640                 645                 650

aac gac atc atc cac tca atc att gac atg gac gct gat gtc atc acc      2079
Asn Asp Ile Ile His Ser Ile Ile Asp Met Asp Ala Asp Val Ile Thr
    655                 660                 665

att gag aac tct cgt tca gac gag aag ctt ctc tca gtg ttc cgt gaa      2127
Ile Glu Asn Ser Arg Ser Asp Glu Lys Leu Leu Ser Val Phe Arg Glu
670                 675                 680                 685

gga gtg aag tac ggt gca gga atc ggt cct ggt gtt tac gac att cac      2175
Gly Val Lys Tyr Gly Ala Gly Ile Gly Pro Gly Val Tyr Asp Ile His
                690                 695                 700

tct ccg aga ata cca tcc aca gat gaa att gca gac agg atc aac aag      2223
Ser Pro Arg Ile Pro Ser Thr Asp Glu Ile Ala Asp Arg Ile Asn Lys
            705                 710                 715

atg ctt gcg gtt ctt gag cag aac atc ttg tgg gtt aac cct gac tgt      2271
Met Leu Ala Val Leu Glu Gln Asn Ile Leu Trp Val Asn Pro Asp Cys
        720                 725                 730

ggt ctg aag aca agg aag tac act gag gtt aaa cca gca ctt aaa gcc      2319
Gly Leu Lys Thr Arg Lys Tyr Thr Glu Val Lys Pro Ala Leu Lys Ala
    735                 740                 745

atg gtt gac gcg gct aag ctt atc cgc tcc cag ctc ggt agt gcc aag      2367
Met Val Asp Ala Ala Lys Leu Ile Arg Ser Gln Leu Gly Ser Ala Lys
750                 755                 760                 765

tgaagagctt gaagatatta tttctatatt ccgggatttt tctacgtggt ttgtgtttgt    2427

tcagtttcaa taacttttct tccaagaaaa atattttagc caaagttagg ttttgaggga    2487

atggagtcac actctctcgc tttcgttgaa gagagtttac ggctttatac tatatgtttc    2547

tcttgttgca atgttatatg tatctttgtt ttctctaatg aaatatatgc ttctttgatc    2607

t                                                                    2608


<210> SEQ ID NO 16
<211> LENGTH: 765
<212> TYPE: PRT
<213> ORGANISM: Arabidopsis thaliana

<400> SEQUENCE: 16

Met Ala Ser His Ile Val Gly Tyr Pro Arg Met Gly Pro Lys Arg Glu
1               5                   10                  15

Leu Lys Phe Ala Leu Glu Ser Phe Trp Asp Gly Lys Ser Ser Ala Asp
            20                  25                  30

Asp Leu Gln Lys Val Ser Ala Asp Leu Arg Ser Asp Ile Trp Lys Gln
        35                  40                  45

Met Ser Ala Ala Gly Ile Lys Tyr Ile Pro Ser Asn Thr Phe Ser His
    50                  55                  60

Tyr Asp Gln Val Leu Asp Thr Thr Ala Met Leu Gly Ala Val Pro Ser
65                  70                  75                  80

Arg Tyr Gly Phe Thr Ser Gly Glu Ile Gly Leu Asp Val Tyr Phe Ser
                85                  90                  95

Met Ala Arg Gly Asn Ala Ser Val Pro Ala Met Glu Met Thr Lys Trp
            100                 105                 110

Phe Asp Thr Asn Tyr His Tyr Ile Val Pro Glu Leu Gly Pro Glu Val
        115                 120                 125

Lys Phe Ser Tyr Ala Ser His Lys Ala Val Asn Glu Tyr Lys Glu Ala
    130                 135                 140

Lys Ala Leu Gly Val Glu Thr Val Pro Val Leu Val Gly Pro Val Ser
145                 150                 155                 160
```

-continued

```
Tyr Leu Leu Leu Ser Lys Leu Ala Lys Gly Val Asp Lys Ser Phe Asp
                165                 170                 175

Leu Leu Ser Leu Leu Pro Lys Ile Leu Pro Val Tyr Lys Glu Val Ile
            180                 185                 190

Ala Glu Leu Lys Ala Ala Gly Ala Ser Trp Ile Gln Leu Asp Glu Pro
        195                 200                 205

Leu Phe Val Met Asp Leu Glu Gly His Lys Leu Gln Ala Phe Ser Gly
    210                 215                 220

Ala Tyr Ala Glu Leu Glu Ser Thr Leu Ser Gly Leu Asn Val Leu Val
225                 230                 235                 240

Glu Thr Tyr Phe Ala Asp Ile Pro Ala Glu Ala Tyr Lys Thr Leu Thr
                245                 250                 255

Ser Leu Lys Gly Val Thr Ala Phe Gly Phe Asp Leu Val Arg Gly Thr
            260                 265                 270

Lys Thr Ile Asp Leu Ile Lys Ser Gly Phe Pro Gln Gly Lys Tyr Leu
        275                 280                 285

Phe Ala Gly Val Val Asp Gly Arg Asn Ile Trp Ala Asn Asp Leu Ala
    290                 295                 300

Ala Ser Leu Ile Thr Leu Gln Ser Leu Glu Gly Val Val Gly Lys Asp
305                 310                 315                 320

Lys Leu Val Val Ser Thr Ser Cys Ser Leu Leu His Thr Ala Val Asp
                325                 330                 335

Leu Ile Asn Glu Thr Lys Leu Asp Ala Glu Ile Lys Ser Trp Leu Ala
            340                 345                 350

Phe Ala Ala Gln Lys Val Val Glu Val Asp Ala Leu Ala Lys Ala Leu
        355                 360                 365

Ala Gly Gln Thr Asn Glu Ser Phe Phe Thr Ala Asn Ala Asp Ala Leu
    370                 375                 380

Ser Ser Arg Arg Ser Ser Pro Arg Val Thr Asn Glu Ser Val Gln Lys
385                 390                 395                 400

Ala Ala Ala Ala Leu Lys Gly Ser Asp His Arg Arg Thr Thr Glu Val
                405                 410                 415

Ser Ala Arg Leu Asp Ala Gln Gln Lys Lys Leu Asn Leu Pro Ile Leu
            420                 425                 430

Pro Thr Thr Thr Ile Gly Ser Phe Pro Gln Thr Val Glu Leu Arg Arg
        435                 440                 445

Val Arg Arg Glu Tyr Lys Ala Lys Lys Ile Ser Glu Glu Asp Tyr Val
    450                 455                 460

Lys Ala Ile Lys Glu Glu Ile Lys Lys Val Val Asp Ile Gln Glu Asp
465                 470                 475                 480

Leu Asp Ile Asp Val Leu Val His Gly Glu Pro Glu Arg Asn Asp Met
                485                 490                 495

Val Glu Tyr Phe Gly Glu Gln Leu Ser Gly Phe Ala Phe Thr Ala Asn
            500                 505                 510

Gly Trp Val Gln Ser Tyr Gly Ser Arg Cys Val Lys Pro Pro Val Ile
        515                 520                 525

Tyr Gly Asp Val Ser Arg Pro Lys Pro Met Thr Val Phe Trp Ser Ser
    530                 535                 540

Thr Ala Gln Ser Met Thr Lys Arg Pro Met Lys Gly Met Leu Thr Gly
545                 550                 555                 560

Pro Val Thr Ile Leu Asn Trp Ser Phe Val Arg Asn Asp Gln Pro Arg
                565                 570                 575

His Glu Thr Cys Tyr Gln Ile Ala Leu Ala Ile Lys Asp Glu Val Glu
```

-continued

```
            580                 585                 590

Asp Leu Glu Lys Gly Gly Ile Gly Val Ile Gln Ile Asp Glu Ala Ala
        595                 600                 605

Leu Arg Glu Gly Leu Pro Leu Arg Lys Ala Glu His Ser Phe Tyr Leu
    610                 615                 620

Asp Trp Ala Val His Ser Phe Arg Ile Thr Asn Cys Gly Val Gln Asp
625                 630                 635                 640

Ser Thr Gln Ile His Thr His Met Cys Tyr Ser Asn Phe Asn Asp Ile
                645                 650                 655

Ile His Ser Ile Ile Asp Met Asp Ala Asp Val Ile Thr Ile Glu Asn
            660                 665                 670

Ser Arg Ser Asp Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
    690                 695                 700

Ile Pro Ser Thr Asp Glu Ile Ala Asp Arg Ile Asn Lys Met Leu Ala
705                 710                 715                 720

Val Leu Glu Gln Asn Ile Leu Trp Val Asn Pro Asp Cys Gly Leu Lys
                725                 730                 735

Thr Arg Lys Tyr Thr Glu Val Lys Pro Ala Leu Lys Ala Met Val Asp
            740                 745                 750

Ala Ala Lys Leu Ile Arg Ser Gln Leu Gly Ser Ala Lys
        755                 760                 765


<210> SEQ ID NO 17
<211> LENGTH: 1169
<212> TYPE: DNA
<213> ORGANISM: Arabidopsis thaliana
<220> FEATURE:
<221> NAME/KEY: promoter
<222> LOCATION: (1)..(1169)
<223> OTHER INFORMATION: promoter of gene At2g01100

<400> SEQUENCE: 17

ctactgcaaa ccataactaa cacgggctcc gtccgtgtgg gttttgtttc tctggcaaac     60

tgcgattgct ttgttttcgt actgagtttg tgatacgtcc attaatgttt aatgataagt    120

ggagtaataa aaaggaagaa tccgattcta tcttagctta ggtccatttt attcaactgt    180

ttggtatgaa atcattgaat taattcaaag cacgttggtg ttaaacgtct ccagtttcaa    240

agtgcaaaca tattaacaag gcacgatgac aaaacggcac gctgtgcttt ggttttgtgc    300

ataaacggca cgctaaccaa atgtgtactg tatataaata cataaatact aataattaca    360

agtcttcaga acagaaaggc aaatttctca aaggaagcga agccctagcg tcctctctct    420

gtcttctcgt ttctgcgccg gtaagctctc tctcagattt tagatctcat caagatctaa    480

cccttatatc tctcacggat catcatcgat ctttcagatc tgttttccaa ttttccctgc    540

tgatagcgtc ttggtttctc taaatccgtt gatttgtttt cgtctctagt ttttttttt     600

tttttcgttt ttacatgcct gagtctagcg tagactttct ctgacttgac cctcttttgc    660

agattcgtag tctgttgtgc gcttgcctct cctcttttgg attagcatac ctctcactcg    720

catcaggtaa gaagtttggt tcagatttag tgaatctcat tgctttagtt tcaaagctta    780

ttagctctct gtgtttttgc gttggttatt acgttggaat acttaaccct tatagcaact    840

actggaattt tgctgaaaca tagttagtct ctatgctttg tttggattga attgattatg    900

atggaatgca acatagttat cgctgtgcct tgtttggatg gaatgtgtta ccctaatagc    960
```

```
aacaactggg atttagctga aagtgttttt tttattcctt ctgtattagc attgtgtagt   1020

gttctgtatt accatcatgt agatactctc tgtgctttgg ctggactgat tgatggaaga   1080

gctaacattg ttttttcttc tcttttgtga gatgcacttt tggttatcct cataccaaaa   1140

tgcagatttt cagttgcttt ttctatcca                                      1169
```

<210> SEQ ID NO 18
<211> LENGTH: 1171
<212> TYPE: DNA
<213> ORGANISM: Arabidopsis thaliana
<220> FEATURE:
<221> NAME/KEY: promoter
<222> LOCATION: (1)..(1171)
<223> OTHER INFORMATION: promoter of gene At2g01100

<400> SEQUENCE: 18

```
ctactgcaaa ccataactaa cacgggctcc gtccgtgtgg gttttgtttc tctggcaaac     60

tgcgattgct ttgttttcgt actgagtttg tgatgcgtcc attaatgttt aatgataagt    120

ggagtaataa aaaggaagaa tccgattcta tcttagctta ggtccatttt attcaactgt    180

ttggtatgaa atcattgaat taattcaaag cacgttggtg ttaaacgtct ccagtttcaa    240

agtgcaaaca tattaacaag gcacgatgac aaaacggcac gctgtgcttt ggttttgtgc    300

ataaacggca cgctaaccaa atgtgtactg tatataaata cataaatact aataattaca    360

agtcttcaga acagaaaggc aaatttctca aaggaagcga agccctagcg tcctctctct    420

gtcttctcgt ttctgcgccg gtaagctctc tctcagattt tagatctcat caagatctaa    480

cccttatatc tctcacggat catcatcgat ctttcagatc tgttttccaa ttttccctgc    540

tgatagcgtc ttggtttctc taaatccgtt gatttgtttt cgtctctagt ttttttttt     600

tttttttcgt ttttacatgc ctgagtctag cgtagacttt ctctgacttg accctctttt    660

gcagattcgt agtctgttgt gcgcttgcct ctcctctttt ggattagcat acctctcact    720

cgcatcaggt aagaagtttg gttcagattt agtgaatctc attgctttag tttcaaagct    780

tattagctct ctgtgttttt gcgttggtta ttacgttgga atacttaacc cttatagcaa    840

ctactggaat tttgctgaaa catagttagt ctctatgctt tgtttggatt gaattgatta    900

tgatggaatg caacatagtt atcgctgtgc cttgtttgga tggaatgttt taccctaata    960

gcaacaactg tgatttagct gaaagtgttt tttttattcc ttctgtatta gcattgtgta   1020

gtgttctgta ttaccatcat gtagatactc tctgtgcttt ggctggactg attgatggaa   1080

gagctaacat tgttttttct tctcttttgt gagatgcact tttggttatc ctcataccaa   1140

aatgcagatt ttcagttgct ttttctatcc a                                  1171
```

<210> SEQ ID NO 19
<211> LENGTH: 1110
<212> TYPE: DNA
<213> ORGANISM: Arabidopsis thaliana
<220> FEATURE:
<221> NAME/KEY: promoter
<222> LOCATION: (1)..(1110)
<223> OTHER INFORMATION: promoter of gene At2g01100

<400> SEQUENCE: 19

```
ctgcgattgc tttgttttcg tactgagttt gtgatacgtc cattaatgtt taatgataag     60

tggagtaata aaaaggaaga atccgattct atcttagctt aggtccattt tattcaactg    120

tttggtatga aatcattgaa ttaattcaaa gcacgttggt gttaaacgtc tccagtttca    180

aagtgcaaac atattaacaa ggcacgatga caaaacggca cgctgtgctt tggttttgtg    240
```

```
cataaacggc acgctaacca aatgtgtact gtatataaat acataaatac taataattac    300

aagtcttcag aacagaaagg caaatttctc aaaggaagcg aagccctagc gtcctctctc    360

tgtcttctcg tttctgcgcc ggtaagctct ctctcagatt ttagatctca tcaagatcta    420

acccttatat ctctcacgga tcatcatcga tctttcagat ctgttttcca attttccctg    480

ctgatagcgt cttggtttct ctaaatccgt tgatttgttt tcgtctctag ttttttttt     540

tttttttcg tttttacatg cctgagtcta gcgtagactt tctctgactt gaccctcttt     600

tgcagattcg tagtctgttg tgcgcttgcc tctcctcttt tggattagca tacctctcac    660

tcgcatcagg taagaagttt ggttcagatt tagtgaatct cattgcttta gtttcaaagc    720

ttattagctc tctgtgtttt tgcgttggtt attacgttgg aatacttaac ccttatagca    780

actactggaa ttttgctgaa acatagttag tctctatgct ttgtttggat tgaattgatt    840

atgatggaat gcaacatagt tatcgctgtg ccttgtttgg atggaatgtg ttaccctaat    900

agcaacaact gggatttagc tgaaagtgtt tttttattc cttctgtatt agcattgtgt     960

agtgttctgt attaccatca tgtagatact ctctgtgctt tggctggact gattgatgga   1020

agagctaaca ttgtttttc ttctcttttg tgagatgcac ttttggttat cctcatacca    1080

aaatgcagat tttcagttgc tttttcttcc                                    1110
```

<210> SEQ ID NO 20
<211> LENGTH: 1115
<212> TYPE: DNA
<213> ORGANISM: Arabidopsis thaliana
<220> FEATURE:
<221> NAME/KEY: promoter
<222> LOCATION: (1)..(1115)
<223> OTHER INFORMATION: promoter of gene At2g01100

<400> SEQUENCE: 20

```
gatccctgcg attgctttgt tttcgtactg agtttgtgat gcgtccatta atgtttaatg     60

ataagtggag taataaaaag gaagaatccg attctatctt agcttaggtc cattttattc    120

aactgtttgg tatgaaatca ttgaattaat tcaaagcacg ttggtgttaa acgtctccag    180

tttcaaagtg caaacatatt aacaaggcac gatgacaaaa cggcacgctg tgctttggtt    240

ttgtgcataa acggcacgct aaccaaatgt gtactgtata taaatacata aatactaata    300

attacaagtc ttcagaacag aaaggcaaat ttctcaaagg aagcgaagcc ctagcgtcct    360

ctctctgtct tctcgtttct gcgccggtaa gctctctctc agattttaga tctcatcaag    420

atctaaccct tatatctctc acggatcatc atcgatcttt cagatctgtt ttccaatttt    480

ccctgctgat agcgtcttgg tttctctaaa tccgttgatt tgttttcgtc tctagttttt    540

ttttttttt tttcgtttt acatgcctga gtctagcgta gactttctct gacttgaccc      600

tcttttgcag attcgtagtc tgttgtgcgc ttgcctctcc tcttttggat tagcatacct    660

ctcactcgca tcaggtaaga agtttggttc agatttagtg aatctcattg ctttagtttc    720

aaagcttatt agctctctgt gtttttgcgt tggttattac gttggaatac ttaaccctta    780

tagcaactac tggaattttg ctgaaacata gttagtctct atgctttgtt tggattgaat    840

tgattatgat ggaatgcaac atagttatcg ctgtgccttg tttggatgga atgttttacc    900

ctaatagcaa caactgtgat ttagctgaaa gtgttttttt tattccttct gtattagcat    960

tgtgtagtgt tctgtattac catcatgtag atactctctg tgctttggct ggactgattg   1020

atggaagagc taacattgtt ttttcttctc ttttgtgaga tgcacttttg gttatcctca   1080
```

-continued taccaaaatg cagattttca gttgcttttt ctatc 1115

<210> SEQ ID NO 21
<211> LENGTH: 484
<212> TYPE: DNA
<213> ORGANISM: Arabidopsis thaliana
<220> FEATURE:
<221> NAME/KEY: promoter
<222> LOCATION: (1)..(484)
<223> OTHER INFORMATION: promoter of gene At2g01100

<400> SEQUENCE: 21
ctgtttttct gtatacacct aaagtttcgc gaaactaaaa tgacaaagac agctacttgg 60
agtctatttt tctttccagg gttatataaa atgatgtgga tgcttaacat tactactgca 120
aaccataact aacacgggct ccgtccgtgt gggttttgtt tctctggcaa actgcgattg 180
ctttgttttc gtactgagtt tgtgatgcgt tcattaatgt ttaatgataa gtggagtaat 240
aaaaaggaag aatccgattc tatcttagct taggtccatt ttattcaact gtttggtatg 300
aaatcattga attaattcaa agcacgttgg tgttaaacgt ctccagtttc aaagtgcaaa 360
catattaaca aggcacgatg acaaaacggc acgctgtgct ttggttttgt gcataaacgg 420
cacgctaacc aaatgtgtac tgtatataaa tacataaata ctaataatta caagtcttca 480
gaac 484

<210> SEQ ID NO 22
<211> LENGTH: 484
<212> TYPE: DNA
<213> ORGANISM: Arabidopsis thaliana
<220> FEATURE:
<221> NAME/KEY: promoter
<222> LOCATION: (1)..(484)
<223> OTHER INFORMATION: promoter of gene At2g01100

<400> SEQUENCE: 22
ctgtttttct gtatacacct aaagtttcgc gaaactaaaa tgacaaagac agctacttgg 60
agtctatttt tctttccagg gttatataaa atgatgtgga tgcttaacat tactactgca 120
aaccataact aacacgggct ccgtccgtgt gggttttgtt tctctggcaa actgcgattg 180
ctttgttttc gtactgagtt tgtgatgcgt ccattaatgt ttaatgataa gtggagtaat 240
aaaaaggaag aatccgattc tatcttagct taggtccatt ttattcaact gtttggtatg 300
aaatcattga attaattcaa agcacgttgg tgttaaacgt ctccagtttc aaagtgcaaa 360
catattaaca aggcacgatg acaaaacggc acgctgtgct ttggttttgt gcataaacgg 420
cacgctaacc aaatgtgtac tgtatataaa tacataaata ctaataatta caagtcttca 480
gaac 484

<210> SEQ ID NO 23
<211> LENGTH: 1281
<212> TYPE: DNA
<213> ORGANISM: Arabidopsis thaliana
<220> FEATURE:
<221> NAME/KEY: promoter
<222> LOCATION: (1)..(1281)
<223> OTHER INFORMATION: promoter of gene At2g01100

<400> SEQUENCE: 23
ctgtttttct gtatacacct aaagtttcgc gaaactaaaa tgacaaagac agctacttgg 60
agtctatttt tctttccagg gttatataaa atgatgtgga tgcttaacat tactactgca 120
aaccataact aacacgggct ccgtccgtgt gggttttgtt tctctggcaa actgcgattg 180

```
ctttgttttc gtactgagtt tgtgatgcgt tcattaatgt ttaatgataa gtggagtaat    240

aaaaaggaag aatccgattc tatcttagct taggtccatt ttattcaact gtttggtatg    300

aaatcattga attaattcaa agcacgttgg tgttaaacgt ctccagtttc aaagtgcaaa    360

catattaaca aggcacgatg acaaaacggc acgctgtgct ttggttttgt gcataaacgg    420

cacgctaacc aaatgtgtac tgtatataaa tacataaata ctaataatta caagtcttca    480

gaacagaaag gcaaatttct caaaggaagc gaagccctag cgtcctctct ctgtcttctc    540

gtttctgcgc cggtaagctc tctctcagat tttagatctc atcaagatct aacccttata    600

tctctcacgg atcatcatcg atctttcaga tctgttttcc aattttccct gctgatagcg    660

tcttggtttc tctaaatccg ttgatttgtt ttcgtctcta gttttttttt ttttttttcg    720

tttttacatg cctgagtcta gcgtagactt tctctgactt gaccctcttt tgcagattcg    780

tagtctgttg tgcgcttgcc tctcctcttt tggattagca tacctctcac tcgcatcagg    840

taagaagttt ggttcaaatt tagtgaatct cattgcttta gtttcaaagc ttattagctc    900

tctgtgtttt tgcgttggtt attacgttgg aatacttaac ccttatagca actactggaa    960

ttttgctgaa acatagttag tctctatgct ttgtttggat tgaattgatt atgatggaat   1020

gcaacatagt tatcgctgtg ccttgtttgg atggaatgtt ttaccctaat agcaacaact   1080

gtgatttagc tgaaagtgtt ttttttattc cttctgtatt agcattgtgt agtgttctgt   1140

attaccatca tgtagatact ctctgtgctt tggctggact gattgatgga agagctaaca   1200

ttgttttttc ttctcttttg tgagatgcac ttttggttat cctcatacca aaatgcagat   1260

tttcagttgc tttttctatc c                                             1281
```

```
<210> SEQ ID NO 24
<211> LENGTH: 1282
<212> TYPE: DNA
<213> ORGANISM: Arabidopsis thaliana
<220> FEATURE:
<221> NAME/KEY: promoter
<222> LOCATION: (1)..(1282)
<223> OTHER INFORMATION: promoter of gene At2g01100

<400> SEQUENCE: 24

ctgtttttct gtatacacct aaagtttcgc gaaactaaaa tgacaaagac agctacttgg     60

agtctatttt tctttccagg gttatataaa atgatgtgga tgcttaacat tactactgca    120

aaccataact aacacgggct ccgtccgtgt gggttttgtt tctctggcaa actgcgattg    180

ctttgttttc gtactgagtt tgtgatgcgt ccattaatgt ttaatgataa gtggagtaat    240

aaaaaggaag aatccgattc tatcttagct taggtccatt ttattcaact gtttggtatg    300

aaatcattga attaattcaa agcacgttgg tgttaaacgt ctccagtttc aaagtgcaaa    360

catattaaca aggcacgatg acaaaacggc acgctgtgct ttggttttgt gcataaacgg    420

cacgctaacc aaatgtgtac tgtatataaa tacataaata ctaataatta caagtcttca    480

gaacagaaag gcaaatttct caaaggaagc gaagccctag cgtcctctct ctgtcttctc    540

gtttctgcgc cggtaagctc tctctcagat tttagatctc atcaagatct aacccttata    600

tctctcacgg atcatcatcg atctttcaga tctgttttcc aattttccct gctgatagcg    660

tcttggtttc tctaaatccg ttgatttgtt ttcgtctcta gttttttttt ttttttttc    720

gtttttacat gcctgagtct agcgtagact ttctctgact tgaccctctt ttgcagattc    780

gtagtctgtt gtgcgcttgc ctctcctctt ttggattagc atacctctca ctcgcatcag    840
```

-continued

```
gtaagaagtt tggttcagat ttagtgaatc tcattgcttt agtttcaaag cttattagct    900

ctctgtgttt ttgcgttggt tattacgttg gaatacttaa cccttatagc aactactgga    960

attttgctga aacatagtta gtctctatgc tttgtttgga ttgaattgat tatgatggaa   1020

tgcaacatag ttatcgctgt gccttgtttg gatggaatgt tttaccctaa tagcaacaac   1080

tgtgatttag ctgaaagtgt ttttttttatt ccttctgtat tagcattgtg tagtgttctg   1140

tattaccatc atgtagatac tctctgtgct ttggctggac tgattgatgg aagagctaac   1200

attgtttttt cttctctttt gtgagatgca cttttggtta tcctcatacc aaaatgcaga   1260

ttttcagttg ctttttctat cc                                            1282


<210> SEQ ID NO 25
<211> LENGTH: 1539
<212> TYPE: DNA
<213> ORGANISM: Arabidopsis thaliana
<220> FEATURE:
<221> NAME/KEY: CDS
<222> LOCATION: (567)..(1307)
<223> OTHER INFORMATION: coding for protein with unknown function
      (At2g01100)

<400> SEQUENCE: 25

atttctcaaa ggaagcgaag ccctagcgtc ctctctctgt cttctcgttt ctgcgccgat     60

tcgtagtctg ttgtgcgctt gcctctcctc ttttggatta gcatacctct cactcgcatc    120

aggtaagaag tttggttcag atttagtgaa tctcattgct ttagtttcaa agcttattag    180

ctctctgtgt ttttgcgttg gttattacgt tggaatactt aacccttata gcaactactg    240

gaattttgct gaaacatagt tagtctctat gctttgtttg gattgaattg attatgatgg    300

aatgcaacat agttatcgct gtgccttgtt tggatggaat gttttaccct aatagcaaca    360

actgtgattt agctgaaagt gttttttttta ttccttctgt attagcattg tgtagtgttc    420

tgtattacca tcatgtagat actctctgtg ctttggctgg actgattgat ggaagagcta    480

acattgtttt ttcttctctt ttgtgagatg cacttttggt tatcctcata ccaaaatgca    540

gattttcagt tgctttttct atccaa atg gac tgc aag aag ttc atc cag atg     593
                             Met Asp Cys Lys Lys Phe Ile Gln Met
                             1               5

gtc gag gag aag aaa cga aga gtt ctt gag aag caa gaa gct cct ttg      641
Val Glu Glu Lys Lys Arg Arg Val Leu Glu Lys Gln Glu Ala Pro Leu
10                  15                  20                  25

aaa tgg gag cag aag cta gag gcg gct gcg aat gcc aaa gca gac aca      689
Lys Trp Glu Gln Lys Leu Glu Ala Ala Ala Asn Ala Lys Ala Asp Thr
                30                  35                  40

gaa act aaa gtg aag aga tca aag ggc cct aag aga aaa caa agg gct      737
Glu Thr Lys Val Lys Arg Ser Lys Gly Pro Lys Arg Lys Gln Arg Ala
            45                  50                  55

gcg tct gaa tct agc tca gaa agt gat agt agc tct gag gtg aga aga      785
Ala Ser Glu Ser Ser Ser Glu Ser Asp Ser Ser Ser Glu Val Arg Arg
        60                  65                  70

aag tct aga aga tct cac aat aag cac cga aga cat gca cac tct gat      833
Lys Ser Arg Arg Ser His Asn Lys His Arg Arg His Ala His Ser Asp
    75                  80                  85

tca gat gac agt gat agg agg aaa gag aag aaa tcc agg agg cag aaa      881
Ser Asp Asp Ser Asp Arg Arg Lys Glu Lys Lys Ser Arg Arg Gln Lys
90                  95                  100                 105

aga agg tcc ttg agt cca agc gat gat agc act ggt gat tat gaa agt      929
Arg Arg Ser Leu Ser Pro Ser Asp Asp Ser Thr Gly Asp Tyr Glu Ser
                110                 115                 120
```

-continued

```
ggg tca gag gat gag ctg agg atg aag ata aag cac cat cgg agg cac      977
Gly Ser Glu Asp Glu Leu Arg Met Lys Ile Lys His His Arg Arg His
            125                 130                 135

aag tgg cat agc tca aga aag act tgc gat gat gac agt acc gaa gat     1025
Lys Trp His Ser Ser Arg Lys Thr Cys Asp Asp Asp Ser Thr Glu Asp
        140                 145                 150

gtg aga aga aaa cat tta aag cat cac agg cgc agt gag gtg gtc act     1073
Val Arg Arg Lys His Leu Lys His His Arg Arg Ser Glu Val Val Thr
    155                 160                 165

tca agt gat agt gag gaa gag agt gga aga aga agg cga ggc aaa tat     1121
Ser Ser Asp Ser Glu Glu Glu Ser Gly Arg Arg Arg Arg Gly Lys Tyr
170                 175                 180                 185

cac agg cac aac aga ggt tca gcc tcc tcg agt ggc tcg gaa gaa gat     1169
His Arg His Asn Arg Gly Ser Ala Ser Ser Ser Gly Ser Glu Glu Asp
                190                 195                 200

agt ggg aaa agt atg aag aga agg caa cat aaa agg cat cgt ttg gct     1217
Ser Gly Lys Ser Met Lys Arg Arg Gln His Lys Arg His Arg Leu Ala
            205                 210                 215

gag tct tca agt gag gaa gat ggg gca atg aga agg act agg cat cat     1265
Glu Ser Ser Ser Glu Glu Asp Gly Ala Met Arg Arg Thr Arg His His
        220                 225                 230

aaa cat ggc aga gat tca gca tct gag tct gat gga aga agg             1307
Lys His Gly Arg Asp Ser Ala Ser Glu Ser Asp Gly Arg Arg
    235                 240                 245

taatcagatg agaaaagaga gcactacttc gacaaatgaa aatggaaaat gtctttgttt   1367

aattcacatc ataagaactg aatcttgtgg taaaccatca gcacatgatt actacccaga   1427

tgttgggacc caaatacgat gaatattgtg ttgaattact atggtggcac tctgttctta   1487

gattttcatt tttacatttg tagcaagaat ggtacacaac caattgaact ct           1539


<210> SEQ ID NO 26
<211> LENGTH: 247
<212> TYPE: PRT
<213> ORGANISM: Arabidopsis thaliana

<400> SEQUENCE: 26

Met Asp Cys Lys Lys Phe Ile Gln Met Val Glu Glu Lys Lys Arg Arg
1               5                   10                  15

Val Leu Glu Lys Gln Glu Ala Pro Leu Lys Trp Glu Gln Lys Leu Glu
            20                  25                  30

Ala Ala Ala Asn Ala Lys Ala Asp Thr Glu Thr Lys Val Lys Arg Ser
        35                  40                  45

Lys Gly Pro Lys Arg Lys Gln Arg Ala Ala Ser Glu Ser Ser Ser Glu
    50                  55                  60

Ser Asp Ser Ser Ser Glu Val Arg Arg Lys Ser Arg Arg Ser His Asn
65                  70                  75                  80

Lys His Arg Arg His Ala His Ser Asp Ser Asp Asp Ser Asp Arg Arg
                85                  90                  95

Lys Glu Lys Lys Ser Arg Arg Gln Lys Arg Arg Ser Leu Ser Pro Ser
            100                 105                 110

Asp Asp Ser Thr Gly Asp Tyr Glu Ser Gly Ser Glu Asp Glu Leu Arg
        115                 120                 125

Met Lys Ile Lys His His Arg Arg His Lys Trp His Ser Ser Arg Lys
    130                 135                 140

Thr Cys Asp Asp Asp Ser Thr Glu Asp Val Arg Arg Lys His Leu Lys
145                 150                 155                 160

His His Arg Arg Ser Glu Val Val Thr Ser Ser Asp Ser Glu Glu Glu
```

-continued

```
                165                 170                 175

Ser Gly Arg Arg Arg Arg Gly Lys Tyr His Arg His Asn Arg Gly Ser
            180                 185                 190

Ala Ser Ser Ser Gly Ser Glu Glu Asp Ser Gly Lys Ser Met Lys Arg
        195                 200                 205

Arg Gln His Lys Arg His Arg Leu Ala Glu Ser Ser Ser Glu Glu Asp
    210                 215                 220

Gly Ala Met Arg Arg Thr Arg His His Lys His Gly Arg Asp Ser Ala
225                 230                 235                 240

Ser Glu Ser Asp Gly Arg Arg
                245
```

<210> SEQ ID NO 27
<211> LENGTH: 1850
<212> TYPE: DNA
<213> ORGANISM: Arabidopsis thaliana
<220> FEATURE:
<221> NAME/KEY: promoter
<222> LOCATION: (1)..(1850)
<223> OTHER INFORMATION: promoter of gene At2g34770

<400> SEQUENCE: 27

```
atagggaaag gagagctata agaatcgacg taaccaagta aaatctccat tgattacaga     60

ttttacaaga gaaaactagt ataaagacac aaaatacgac ggtgagagaa ctcacgagga    120

tgaataattg aatgggtccg tcagctcagg gaaacccttg tcactgtccc gttctgataa    180

ttccggcctt cgttttttac tccttcgcta tggtttttc ttggagaaga aaaatagaga    240

aggagcagat tctgatgaaa gacggcgata atcgataaat aataggagac gtttagggtt    300

cacacttact ttttcctatt tctttaattc catctttttt tttcttcact attgtcgtca    360

ttacatcaaa ttttgttttc tatgtttctg tcgtgtgaca aacacaaatt tttacttaat    420

ttaagtaagt gaactataga cattattttt ggttaactgg tctactttga ttgctcacat    480

aaccataact aaataagacc aaaccagata tatataaacc aaaacgagaa aagattaggg    540

gcaacacaca tacaaattag tttctcatta caatttttac acccaaaaca acagacaaaa    600

gagcaatcaa agccagcgga tacgaaaaga aaacaactcc atttaaagat ctaaaaatct    660

caagcatcga gctcagcatc ttcatccatc tcctctttat actcctcttc atcagctgta    720

gcatcttgat attgctgata ctcagccaca agatcgttca tgttactctc tgcttcatta    780

aactccatct cgtccattcc ttcttctgtg taccaatgca agaaagctta tctcaacatc    840

aggctgatat aaccaatatc ttacttcttt tacatttgtg aaatggaacc aacccatttt    900

tctggaaaaa gtgctaacca aacatttgat taaccgtatc actactactt tcatttctat    960

cttctgtttc attatgctga ctatttaagc tccgttgtca aatctctaag ttagacataa   1020

aagacaaaga ctaatcaatt gtcatcacac cagcgtcgtc gagtgagcta ttaatcgtgg   1080

attttaagca ttaaagaaac attctatagt actaatttct taagcaaata aaataattat   1140

aatcaaacac tatgcttgac actggtcacg tatactggta gtgaatgatt ctacatcata   1200

agaggccgca tcaaaatcct aaaaataagc ataatgaatt aatcatttac aaattttatt   1260

ttactcaata agaaaatcga aagtatgatt attatctagc tgccacaatc ttcgaattta   1320

atatttactc aagaagagac cgactttaat ccttgacttt ctcattgctc tatggaaaat   1380

gattaaagca gtcaataaaa tcttttgaca ttgttggcag aagaccaata attcgaagtc   1440

taaaatgtaa tcgtccacac agtgtatgag tatcctagta ttttttttct tttccatata   1500
```

```
agttgaattt gtaatatata tagtgtaatg ttgtttattt gtggcaacgt acaaaattgg   1560

gaatcctata agtgcgacga caagtgacaa gacgaggcta tgaacagcta atgtatgaag   1620

agagccaaaa gagcaacaac ctggcacagc cgttggtttt tttgaatata ttgacgattc   1680

gttggcctcc gagatctaag gcatctctta caatcaacgg tccagattcc atctagaaga   1740

tatattacac cgaccttgtt ttctctatct aattctcaca cacacaccaa cgcaaacctc   1800

caaaacaggg ccggggcgat tcattcacaa tctcggcgat tctctcttcc              1850
```

<210> SEQ ID NO 28
<211> LENGTH: 1849
<212> TYPE: DNA
<213> ORGANISM: Arabidopsis thaliana
<220> FEATURE:
<221> NAME/KEY: promoter
<222> LOCATION: (1)..(1849)
<223> OTHER INFORMATION: promoter of gene At2g34770

<400> SEQUENCE: 28

```
gatccatagg gaaaggagag ctataagaat cgatgtaacc aagtaaaatc tccattgatt     60

acagatttta caagagaaaa ctagtataaa gacacaaaat acgacggtga gagaactcac    120

gaggatgaat aattgaaagg gtccgtcagc tcagggaaac ccttgtcact gtcccgttct    180

gataattccg gccttcgttt tttactcctt cgctatggtt ttttcttgga gaagaaaaat    240

agagaaggag cagattctga tgaaagacgg cgataatcga taaataatag gagacgttta    300

gggttcacac ttactttttc ctatttcttt aattccatct tttttttct tcactattgt    360

cgtcattaca tcaaattttg ttttctatgt ttctgtcgtg tgacaaacac aaatttttac    420

ttaatttaag taagtgaact atagacatta tttttggtta attggtctac tttgattgct    480

cacataacca taactaaata agaccaaacc agatatatat aaaccaaaac gagaaaagat    540

tagggccaac acacatacaa attagtttct cattacaatt tttacaccca aaacaacaga    600

caaaagagca atcaaagcca gcggatacga aaagaaaaca actccattta aagatctaaa    660

aatctcaagc atcgaggtca gcatcttcat ccatctcctc tttatactcc tcttcatcag    720

ctgtagcatc ttgatattgc tgatactcag ccacaagatc gttcatgtta ctctctgctt    780

cattaaactc catctcgtcc attccttctt ctgtgtacca atgcaagaaa gcttatctca    840

acatcaggct gatataacca atatcttact tcttttacat ttgtgaaatg gaaccaaccc    900

atttttctgg aaaaagtgct aaccaaacat ttgattaacc gtatcactac tactttcatt    960

tctatcttct gtttcattat gctgactatt taagctccgt tgtcaaatct ctaagttaga   1020

cataaaagac aaagactaat caattgtcat cacaccagcg tcgtcgagtg agctatatta   1080

atcgtggatt ttaagcatta aagaaacatt ctatagtact aaagcaaata aaataattat   1140

aatcaaacac tatgcttgac actggtcacg tgtactggta gtgaatgatt ctacatcata   1200

agaggccgca tcaaaatcct aaaaataagc ataatgaatt aatcatttac aaattttatt   1260

ttactcaata agaaaatcga aagtatgatt attatctagc tgccacaatc ttcgaattta   1320

atatttactc aagaagagac cgactttaat ccttgacttt ctcattgctc tatggaaaat   1380

gattaaagca gtcaataaaa tcttttgaca ttgttggcag aagaccaata attcgaagtc   1440

taaaatgtaa tcgtccacac agtgtatgag tatcctagta ttttttttct tttccatata   1500

agttgaattt gtaatatata tagtgtaatg ttgtttattt gtggcaacgt acaaaattgg   1560

gaatcctata agtgcgacga caagtgacaa gacgaggcta tgaacagcta atgtatgaag   1620

agagccaaaa gagcaacaac ctggcacagc cgttgttttt tttgaatata ttgacgattc   1680
```

```
gttggcctcc gagatctaag gcatctctca caatcaacgg tccagattcc atctagaaga   1740

tatattacac cgaccttgtt ttctctatct aattctcaca cacacaccaa cgcaaacctc   1800

caaaacaggg ccggggcgat tcattcacaa tctcggcgat tctctcttc               1849
```

<210> SEQ ID NO 29
<211> LENGTH: 2792
<212> TYPE: DNA
<213> ORGANISM: Arabidopsis thaliana
<220> FEATURE:
<221> NAME/KEY: promoter
<222> LOCATION: (1)..(2792)
<223> OTHER INFORMATION: promoter of gene At2g34770

<400> SEQUENCE: 29

```
atagggaaag gagagctata agaatcagta aaaggtctgc aaaccatggc ggatccatag     60

ggaaaggaga gctataagaa tcgacgtaac caagtaaaat ctccattgat tacagatttt    120

acaagagaaa actagtataa agacacaaaa tacgacggtg agagaactca cgaggatgaa    180

taattgaatg ggtccgtcag ctcagggaaa cccttgtcac tgtcccgttc tgataattcc    240

ggccttcgtt ttttactcct tcgctatggt tttttcttgg agaagaaaaa tagagaagga    300

gcagattctg atgaaagacg gcgataatcg ataaataata ggagacgttt agggttcaca    360

cttacttttt cctatttctt taattccatc tttttttttc ttcactattg tcgtcattac    420

atcaaatttt gttttctatg tttctgtcgt gtgacaaaca caaattttta cttaatttaa    480

gtaagtgaac tatagacatt atttttggtt aactggtcta ctttgattgc tcacataacc    540

ataactaaat aagaccaaac cagatatata taaaccaaaa cgagaaaaga ttaggggcaa    600

cacacataca aattagtttc tcattacaat ttttacaccc aaaacaacag acaaaagagc    660

aatcaaagcc agcggatacg aaaagaaaac aactccattt aaagatctaa aaatctcaag    720

catcgagctc agcatcttca tccatctcct ctttatactc ctcttcatca gctgtagcat    780

cttgatattg ctgatactca gccacaagat cgttcatgtt actctctgct tcattaaact    840

ccatctcgtc cattccttct tctgtgtacc aatgcaagaa agcttatctc aacatcaggc    900

tgatataacc aatatcttac ttcttttaca tttgtgaaat ggaaccaacc catttttctg    960

gaaaaagtgc taaccaaaca tttgattaac cgtatcacta ctactttcat ttctatcttc   1020

tgtttcatta tgctgactat ttaagctccg ttgtcaaatc tctaagttag acataaaaga   1080

caaagactaa tcaattgtca tcacaccagc gtcgtcgagt gagctattaa tcgtggattt   1140

taagcattaa agaaacattc tatagtacta atttcttaag caaataaaat aattataatc   1200

aaacactatg cttgacactg gtcacgtata ctggtagtga atgattctac atcataagag   1260

gccgcatcaa aatcctaaaa ataagcataa tgaattaatc atttacaaat tttattttac   1320

tcaataagaa aatcgaaagt atgattatta tctagctgcc acaatcttcg aatttaatat   1380

ttactcaaga agagaccgac tttaatcctt gactttctca ttgctctatg gaaaatgatt   1440

aaagcagtca ataaaatctt ttgacattgt tggcagaaga ccaataattc gaagtctaaa   1500

atgtaatcgt ccacacagtg tatgagtatc ctagtatttt ttttcttttc catataagtt   1560

gaatttgtaa tatatatagt gtaatgttgt ttatttgtgg caacgtacaa aattgggaat   1620

cctataagtg cgacgacaag tgacaagacg aggctatgaa cagctaatgt atgaagagag   1680

ccaaaagagc aacaacctgg cacagccgtt ggttttttttg aatatattga cgattcgttg   1740

gcctccgaga tctaaggcat ctcttacaat caacggtcca gattccatct agaagatata   1800
```

```
ttacaccgac cttgttttct ctatctaatt ctcacacaca caccaacgca aacctccaaa   1860

acagggccgg ggcgattcat tcacaatctc ggcgattctc tcttccgtct cgagtcgctg   1920

agatccatca ggttcgtttc tattcgaatc tattctcttg aatccgtatt tgtttccttt   1980

cctccctaga tagatttcat ttttctggaa acattgagat ttccattgat ttgatgttta   2040

gtggtttaga tcggataatt tttgttgttg actctcaaaa aacgaatcat aactatctta   2100

aaactttgtt tacgcattgt tattgaaggc taaataaaaa atgctcaatt gttgctagaa   2160

aggaaggtgt ctcgaaaaca tgtgaattta tttcttgagc ctcattgttt ctcactgcaa   2220

caatagtgaa tgattcaatt gaaaagaact tttggttaag ccattttctc aactcaatta   2280

ggaactgtgt gtttttttttg tttccttgat gttaacttgt gagttgattt atttgggtag   2340

ttaacttgta tatttggtgg tgggtcctgg agggaaatga gtgagaggga gctctgttca   2400

tacattctat gtttttaaat gattagtttt tttctttcat ctaatacttg ctttttgtgc   2460

taggaatttc gatttttggg actaatttat cgagtatata taattggata agtgagtttg   2520

gtattaatat taagagcaat taggttggtt atcttgccaa acagtagacc cctgtcgttt   2580

tcttagtcat ttaagaagta atgcttaaga ttcaggcctc taatctggtt atgatagtga   2640

agaggatctg taaatttacc tatacgacct gttgaaaagg acctctggtg tttgttacta   2700

tgcgtttctg atcaatatag acatagttgg atcatattct tctcttgatc gtctgtttca   2760

ttttttttca aaatcagtaa aaggtctgca aa                                 2792
```

<210> SEQ ID NO 30
<211> LENGTH: 2761
<212> TYPE: DNA
<213> ORGANISM: Arabidopsis thaliana
<220> FEATURE:
<221> NAME/KEY: promoter
<222> LOCATION: (1)..(2761)
<223> OTHER INFORMATION: promoter of gene At2g34770

<400> SEQUENCE: 30

```
gatccatagg gaaaggagag ctataagaat cgatgtaacc aagtaaaatc tccattgatt     60

acagatttta caagagaaaa ctagtataaa gacacaaaat acgacggtga gagaactcac    120

gaggatgaat aattgaaagg gtccgtcagc tcagggaaac ccttgtcact gtcccgttct    180

gataattccg gccttcgttt tttactcctt cgctatggtt ttttcttgga gaagaaaaat    240

agagaaggag cagattctga tgaaagacgg cgataatcga taaataatag gagacgttta    300

gggttcacac ttactttttc ctatttcttt aattccatct tttttttttct tcactattgt    360

cgtcattaca tcaaattttg ttttctatgt ttctgtcgtg tgacaaacac aaatttttac    420

ttaatttaag taagtgaact atagacatta tttttggtta attggtctac tttgattgct    480

cacataacca taactaaata agaccaaacc agatatatat aaaccaaaac gagaaaagat    540

tagggccaac acacatacaa attagtttct cattacaatt tttacaccca aaacaacaga    600

caaaagagca atcaaagcca gcggatacga aaagaaaaca actccattta aagatctaaa    660

aatctcaagc atcgaggtca gcatcttcat ccatctcctc tttatactcc tcttcatcag    720

ctgtagcatc ttgatattgc tgatactcag ccacaagatc gttcatgtta ctctctgctt    780

cattaaactc catctcgtcc attccttctt ctgtgtacca atgcaagaaa gcttatctca    840

acatcaggct gatataacca atatcttact tcttttacat ttgtgaaatg gaaccaaccc    900

atttttctgg aaaaagtgct aaccaaacat ttgattaacc gtatcactac tactttcatt    960

tctatcttct gtttcattat gctgactatt taagctccgt tgtcaaatct ctaagttaga   1020
```

-continued

```
cataaaagac aaagactaat caattgtcat cacaccagcg tcgtcgagtg agctatatta   1080

atcgtggatt ttaagcatta aagaaacatt ctatagtact aaagcaaata aaataattat   1140

aatcaaacac tatgcttgac actggtcacg tgtactggta gtgaatgatt ctacatcata   1200

agaggccgca tcaaaatcct aaaaataagc ataatgaatt aatcatttac aaattttatt   1260

ttactcaata agaaaatcga aagtatgatt attatctagc tgccacaatc ttcgaattta   1320

atatttactc aagaagagac cgactttaat ccttgacttt ctcattgctc tatggaaaat   1380

gattaaagca gtcaataaaa tcttttgaca ttgttggcag aagaccaata attcgaagtc   1440

taaaatgtaa tcgtccacac agtgtatgag tatcctagta tttttttct tttccatata   1500

agttgaattt gtaatatata tagtgtaatg ttgtttattt gtggcaacgt acaaaattgg   1560

gaatcctata agtgcgacga caagtgacaa gacgaggcta tgaacagcta atgtatgaag   1620

agagccaaaa gagcaacaac ctggcacagc cgttgttttt tttgaatata ttgacgattc   1680

gttggcctcc gagatctaag gcatctctca caatcaacgg tccagattcc atctagaaga   1740

tatattacac cgaccttgtt ttctctatct aattctcaca cacacaccaa cgcaaacctc   1800

caaaacaggg ccggggcgat tcattcacaa tctcggcgat tctctcttcc gtctcgagtc   1860

gctgagatcc atcaggttcg tttctattcg aatctattct cttgaatccg tatttgtttc   1920

ctttcctctc tagatagatt tcatttttct ggaaacattg agatttccat tgatttgatg   1980

tttagtggtt tagatcggat aatttttgtt attgactctc aaaaaacgaa tcataactat   2040

cttaaaactt tgtttacgca ttgttattga aggctaaata aaaaatgctc aattgttgct   2100

agaaaggaag gtgtctcgaa aacatgtgaa tttattttt gagcctcatt gtttctcact   2160

gcaacaatag tgaatgattc aattgaaaag aacttttggt taagccattt ttctctttaa   2220

tagattatgt gtctcaactc aattaggaac tgtgtgtttt tttgtttcct tgatgttaac   2280

ttgtgagttg atttatttgg gtagtttact tgtatatata tttggtggtg ggtcctggag   2340

ggaaatgagt gagagggagc tctgttcata cattctatgt ttttaaatga ttagtatttt   2400

tctttcatct aatacttgct ttttgtgcta ggaatttcga tttttgggac taatttatcg   2460

agtatatata attggataag tgagtttggt attaatatta agagcaatta ggttggttat   2520

cttgccaaac agtagacccc tgtcgttttc ttagtcattt aagaagtaat gcttaagatt   2580

caggcctcta atctggttat gatagtgaag aggatctgta aatttaccta tacgacctgt   2640

tgaaaaggac ctctggtgtt tgttactatg cgtttctgat caatatagac atagttggat   2700

catattcttc tcttgatcgt ctgtttcatt tttttcaaa atcagtaaaa ggtctgcaaa   2760

c                                                                   2761
```

<210> SEQ ID NO 31
<211> LENGTH: 1142
<212> TYPE: DNA
<213> ORGANISM: Arabidopsis thaliana
<220> FEATURE:
<221> NAME/KEY: CDS
<222> LOCATION: (240)..(950)
<223> OTHER INFORMATION: coding for fatty acid hydroxylase (FAH1) (At2g34770)

<400> SEQUENCE: 31

```
gttgtttttt ttgaatatat tgacgattcg ttggcctccg agatctaagg catctctcac     60

aatcaacggt ccagattcca tctagaagat atattacacc gaccttgttt tctctatcta    120

attctcacac acacaccaac gcaaacctcc aaaacagggc cggggcgatt cattcacaat    180
```

-continued

```
ctcggcgatt ctctcttccg tctcgagtcg ctgagatcca tcagtaaaag gtctgcaaa     239

atg gtt gct cag gga ttc act gtg gat ctt aaa aag ccc ctt gta ttt      287
Met Val Ala Gln Gly Phe Thr Val Asp Leu Lys Lys Pro Leu Val Phe
1               5                   10                  15

cag gtt ggt cat ctt gga gaa gat tat gag gaa tgg gtt cac caa cct      335
Gln Val Gly His Leu Gly Glu Asp Tyr Glu Glu Trp Val His Gln Pro
            20                  25                  30

atc gcg acc aag gaa ggc cct cgg ttt ttt cag agt gac ttt tgg gag      383
Ile Ala Thr Lys Glu Gly Pro Arg Phe Phe Gln Ser Asp Phe Trp Glu
        35                  40                  45

ttc ttg aca ctt aca gtt tgg tgg gca gtt cct gtc att tgg ttg cca      431
Phe Leu Thr Leu Thr Val Trp Trp Ala Val Pro Val Ile Trp Leu Pro
    50                  55                  60

gtt gta gtc tgg tgc ata tca agg tca gta agt atg gga tgt tca ctt      479
Val Val Val Trp Cys Ile Ser Arg Ser Val Ser Met Gly Cys Ser Leu
65                  70                  75                  80

cca gaa atc gtc cca att gtt gtc atg gga ata ttc atc tgg aca ttt      527
Pro Glu Ile Val Pro Ile Val Val Met Gly Ile Phe Ile Trp Thr Phe
                85                  90                  95

ttt gaa tac gtt ctt cac cgg ttc gtt ttc cac ata aaa acg aag agt      575
Phe Glu Tyr Val Leu His Arg Phe Val Phe His Ile Lys Thr Lys Ser
            100                 105                 110

tac tgg gga aac act gca cac tat ctt att cac gga tgc cat cat aag      623
Tyr Trp Gly Asn Thr Ala His Tyr Leu Ile His Gly Cys His His Lys
        115                 120                 125

cac ccg atg gac cac ctt cgg ctc gtc ttt cct cct act gca aca gcg      671
His Pro Met Asp His Leu Arg Leu Val Phe Pro Pro Thr Ala Thr Ala
    130                 135                 140

att tta tgc ttt ccg ttc tgg aac att gcg aag gct atc tca act cct      719
Ile Leu Cys Phe Pro Phe Trp Asn Ile Ala Lys Ala Ile Ser Thr Pro
145                 150                 155                 160

tca acc gca cct gca ttg ttt ggt gga ggc atg ctc gga tat gtg atg      767
Ser Thr Ala Pro Ala Leu Phe Gly Gly Gly Met Leu Gly Tyr Val Met
                165                 170                 175

tac gat gtc act cat tat tac ctt cac cat gcc caa cct act aga cca      815
Tyr Asp Val Thr His Tyr Tyr Leu His His Ala Gln Pro Thr Arg Pro
            180                 185                 190

gtg acc aaa aat ctc aag aag tac cat ttg aat cat cac ttc agg att      863
Val Thr Lys Asn Leu Lys Lys Tyr His Leu Asn His His Phe Arg Ile
        195                 200                 205

cag gac aaa gga ttt ggt ata act tcg tcg tta tgg gac ata gtc ttt      911
Gln Asp Lys Gly Phe Gly Ile Thr Ser Ser Leu Trp Asp Ile Val Phe
    210                 215                 220

ggg aca ctt ccc acc aca aaa gcc ccc aga aaa gag caa tagtagtaaa       960
Gly Thr Leu Pro Thr Thr Lys Ala Pro Arg Lys Glu Gln
225                 230                 235

aggcaaaaac taaaaagatg tttgtaatac atttaattta atcttaagtt attaatcatc   1020

cttctgaatt ttgagatgtt taatctgagg tttcatttgg atcactgtct tttgtagttt   1080

gtaaatcaat acttcacaat cctaatataa tatttttctg cgaaagcaat aaaaaatcta   1140

ct                                                                  1142


<210> SEQ ID NO 32
<211> LENGTH: 237
<212> TYPE: PRT
<213> ORGANISM: Arabidopsis thaliana

<400> SEQUENCE: 32
```

-continued

```
Met Val Ala Gln Gly Phe Thr Val Asp Leu Lys Lys Pro Leu Val Phe
1               5                   10                  15

Gln Val Gly His Leu Gly Glu Asp Tyr Glu Glu Trp Val His Gln Pro
            20                  25                  30

Ile Ala Thr Lys Glu Gly Pro Arg Phe Phe Gln Ser Asp Phe Trp Glu
        35                  40                  45

Phe Leu Thr Leu Thr Val Trp Trp Ala Val Pro Val Ile Trp Leu Pro
    50                  55                  60

Val Val Val Trp Cys Ile Ser Arg Ser Val Ser Met Gly Cys Ser Leu
65                  70                  75                  80

Pro Glu Ile Val Pro Ile Val Val Met Gly Ile Phe Ile Trp Thr Phe
                85                  90                  95

Phe Glu Tyr Val Leu His Arg Phe Val Phe His Ile Lys Thr Lys Ser
            100                 105                 110

Tyr Trp Gly Asn Thr Ala His Tyr Leu Ile His Gly Cys His His Lys
        115                 120                 125

His Pro Met Asp His Leu Arg Leu Val Phe Pro Pro Thr Ala Thr Ala
    130                 135                 140

Ile Leu Cys Phe Pro Phe Trp Asn Ile Ala Lys Ala Ile Ser Thr Pro
145                 150                 155                 160

Ser Thr Ala Pro Ala Leu Phe Gly Gly Gly Met Leu Gly Tyr Val Met
                165                 170                 175

Tyr Asp Val Thr His Tyr Tyr Leu His His Ala Gln Pro Thr Arg Pro
            180                 185                 190

Val Thr Lys Asn Leu Lys Lys Tyr His Leu Asn His His Phe Arg Ile
        195                 200                 205

Gln Asp Lys Gly Phe Gly Ile Thr Ser Ser Leu Trp Asp Ile Val Phe
    210                 215                 220

Gly Thr Leu Pro Thr Thr Lys Ala Pro Arg Lys Glu Gln
225                 230                 235
```

<210> SEQ ID NO 33
<211> LENGTH: 1843
<212> TYPE: DNA
<213> ORGANISM: Arabidopsis thaliana
<220> FEATURE:
<221> NAME/KEY: promoter
<222> LOCATION: (1)..(1843)
<223> OTHER INFORMATION: promoter of gene At5g61560

<400> SEQUENCE: 33

```
aaaaattaca atcggttcta tcaatgtgtt tactctaata tgttttttt ttgtgtgttt      60

ttctctgttc cgaggattcc tcatttgtct gatgacatgc acaattacaa caatatatat    120

agagagaaat gtctttcgat ataagtttat tttgtttcta ttggtaaaaa tgtaacttta    180

gtttgaactt ccccaaagaa aaattcttgg cttatcatcc aatccagtaa ttgatttgtc    240

attctatata gtccaaatat aattattaat ctctagaatg aatgtagatt ttggaccatc    300

cattagataa aatccttacc tattgtcaat ttgtcatgtc tcaaacacgt ccacaagtta    360

aggccaataa gttccacata caaatcaatg ataaagttaa tactgtactt atcaaaggca    420

taatttgtgt gttttcttct caataacatc cgcatctcag agataactat cacctgttat    480

tttgtccaaa cattaaatga cctctactct caacccattt aatgcacata ataaatgcta    540

aaaagtacac ctgtgtgatc caataaatta ataatatttc tctgtttcat aatactagta    600

tttcataact ttaaagaaat ttacataagt taatacaagt atgaacaatg aagtatgtca    660
```

-continued

```
atgttaaaac agtgaacata tccatccgta cttgttgagt tacaaaagct tgatgcttaa    720
agtaccacaa ggtcaaggtt taatttgtct tgtctagttg tctatagagc ttcgagtatt    780
gttgttgcgg agagatccaa gctgaaagtg accgggaggt gccgatgtag agaggtctaa    840
aatagaagct ttcatatcga tagtttcttc cacttatcga aaagagaaat cctctcctgt    900
aaatcgaaaa gaatctttag agttgactaa acttttgttt actttaccta ttcacataac    960
ttgaaattta ttagtcaaaa gtttagaaga aaaaacaaaa aaattcgcaa aagaaaaaca   1020
cgataatata gctgaacaag aaaatcaaaa acaaaattgt attttggcag aaaatgaaac   1080
ctatattcat tcataaggga agggaaacag cccaaaaatt gaaaagtcaa caaaattgaa   1140
taaagaacaa gttggtagtc cgacaaaagc ccagttgttc tgactttcaa cgtcatcaaa   1200
actaaggaaa ctaccggaaa agacatcaca tattcacacg aactcttcta gacttttttg   1260
acattttcat ttctctcatc gttttctttt ttatcattac ttctttgaat ctttggttat   1320
aaccattaaa gaattcaact ggtatgcgca taaatttccg cataactcca ttaatataat   1380
caggagacca attcactgga ctcaaatttg attcgtcttc ttcttctctc tctctctcca   1440
tttgtcaaga agctgttgaa tcatcgtccc ccacgagttt tggaaaaagc ttgcaagtca   1500
aatatcaata ggtactctat cttcaactct gatgattgat catagccgtt caattggcta   1560
acaagatctt ttatcttttg agtattttgt tatctaaatt ataatattat ccattaaggt   1620
ttcaacttgt tttgttttgt tttgcccaga aaatgtctct gtaacttaca tttaattaaa   1680
cttaaaaacc agaccaattc atgactctct ctctcttctt ctctctgttt tgtctcttta   1740
agcacgacta gagattaagg aaacaaaagc ttgaaccttt gtagtcaaaa tcatcaggta   1800
tatatatctt caaaaatctc tctatagttt caacaaaacc ctg                     1843
```

<210> SEQ ID NO 34
<211> LENGTH: 1842
<212> TYPE: DNA
<213> ORGANISM: Arabidopsis thaliana
<220> FEATURE:
<221> NAME/KEY: promoter
<222> LOCATION: (1)..(1842)
<223> OTHER INFORMATION: promoter of gene At5g61560

<400> SEQUENCE: 34

```
aaaattacaa tcggttctat caatgtgttt actctaatat gttttttttt tgtgtgtttt     60
tctctgttcc gaggattcct catttgtctg atgacatgca caattacaac aatatatata    120
gagagaaatg tctttcgata taagtttatt ttgtttctat tggtaaaaat gtaactttag    180
tttgaacttc cccaaagaaa aattcttggc ttatcatcca atccagtaat tgatttgtca    240
ttctatatag tccaaatata attattaatc tctagaatga atgtagattt tggaccatcc    300
attagataaa atccttacct attgtcaatt tgtcatgtct caaacacgtc cacaagttaa    360
ggccaataag ttccacatac aaatcaatga taaagttaat actgtactta tcaaaggcat    420
aatttgtgtg ttttcttctc aataacatcc gcatctcaga gataactatc acctgttatt    480
ttgtccaaac attaaatgac ctctactctc aacccattta atgcacataa taaatgctaa    540
aaagtacacc tgtgtgatcc aataaattaa taatatttct ctgtttcata atactagtat    600
ttcataactt taaagaaatt tacataagtt aatacaagta tgaacaatga agtatgtcaa    660
tgttaaaaca gtgaacatat ccatccgtac ttgttgagtt acaaaagctt gatgcttaaa    720
gtaccacaag gtcaaggttt aatttgtctt gtctagttgt ctatagagct tcgagtattg    780
ttgttgcgga gagatccaag ctgaaagtga ccgggaggtg ccgatgtaga gaggtctaaa    840
```

-continued

```
atagaagctt tcatatcgat agtttcttcc acttatcgaa aagagaaatc ctctcctgta    900
aatcgaaaag aatctttaga gttgactaaa cttttgttta ctttacctat tcacataact    960
tgaaatttat tagtcaaaag tttagaagaa aaaacaaaaa aattcgcaaa agaaaaacac   1020
gataatatag ctgaacaaga aaatcaaaaa caaaattgta ttttggcaga aaatgaaacc   1080
tatattcatt cataagggaa gggaaacagc ccaaaaattg aaaagtcaac aaaattgaat   1140
aaagaacaag ttggtagtcc gacaaaagcc cagttgttct gactttcaac gtcatcaaaa   1200
ctaaggaaac taccggaaaa gacatcacat attcacacga actcttctag actttttga    1260
cattttcatt tctctcatcg ttttcttttt tatcattact tctttgaatc tttggttata   1320
accattaaag aattcaactg gtatgcgcat aaatttccgc ataactccat taatataatc   1380
aggagaccaa ttcactggac tcaaatttga ttcgtcttct tcttctctct ctctctccat   1440
ttgtcaagaa gctgttgaat catcgtcccc cacgagtttt ggaaaaagct tgcaagtcaa   1500
atatcaatag gtactctatc ttcaactctg atgattgatc atagccgttc aattggctaa   1560
caagatcttt tatcttttga gtattttgtt atctaaatta taatattatc cattaaggtt   1620
tcaacttgtt ttgttttgtt ttgcccagaa aatgtctctg taacttacat ttaattaaac   1680
ttaaaaacca gaccaattca tgactctctc tctcttcttc tctctgtttt gtctctttaa   1740
gcacgactag agattaagga aacaaaagct tgaacctttg tagtcaaaat catcaggtat   1800
atatatcttc aaaaatctct ctatagtttc aacaaaaccc tg                      1842
```

<210> SEQ ID NO 35
<211> LENGTH: 2901
<212> TYPE: DNA
<213> ORGANISM: Arabidopsis thaliana
<220> FEATURE:
<221> NAME/KEY: CDS
<222> LOCATION: (299)..(2686)
<223> OTHER INFORMATION: coding for protein kinase family protein (At5g61560)

<400> SEQUENCE: 35

```
atcattactt ctttgaatct ttggttataa ccattaaaga attcaactgg tatgcgcata     60
aatttccgca taactccatt aatataatca ggagaccaat tcactggact caaatttgat    120
tcgtcttctt cttctctctc tctctccatt tgtcaagaag ctgttgaatc atcgtccccc    180
acgagttttg gaaaaagctt gcaagtcaaa tatcaatagc acgactagag attaaggaaa    240
caaaagcttg aacctttgta gtcaaaatca tcagatctta gccgttggaa atccagag      298

atg gga gac gga gct tta atc gta gcg gtg gct atc aaa ggg aac aat      346
Met Gly Asp Gly Ala Leu Ile Val Ala Val Ala Ile Lys Gly Asn Asn
1               5                   10                  15

agc aaa acc aaa ggc gtt gtt cga tgg gca ctt caa gaa ttt gct tct      394
Ser Lys Thr Lys Gly Val Val Arg Trp Ala Leu Gln Glu Phe Ala Ser
            20                  25                  30

caa gaa cat gtc gtc ttc aag ctc tta cat gtc caa cca aga gat tcg      442
Gln Glu His Val Val Phe Lys Leu Leu His Val Gln Pro Arg Asp Ser
        35                  40                  45

aat tcg gtt tca act aca aga aaa gat ttg acc aca agt gtt tac aaa      490
Asn Ser Val Ser Thr Thr Arg Lys Asp Leu Thr Thr Ser Val Tyr Lys
    50                  55                  60

aaa gat gtt gat aga aaa acc aga gag atg ctt ctt cca agc aga gac      538
Lys Asp Val Asp Arg Lys Thr Arg Glu Met Leu Leu Pro Ser Arg Asp
65                  70                  75                  80

atg ttt gtt cat aga gag gtt caa ttg gat ata atg gtg ctt gaa tca      586
```

-continued

```
Met Phe Val His Arg Glu Val Gln Leu Asp Ile Met Val Leu Glu Ser
                85                  90                  95

gac gat ata gct gat gca atc tct aaa gca gtt caa gat cat gga att      634
Asp Asp Ile Ala Asp Ala Ile Ser Lys Ala Val Gln Asp His Gly Ile
            100                 105                 110

agt gag cta gtc att gga gct tcc tct tca atc atc ttc tca tgg aag      682
Ser Glu Leu Val Ile Gly Ala Ser Ser Ser Ile Ile Phe Ser Trp Lys
        115                 120                 125

ttg aag aga agc aac ttg tct tca aga att gca gat gct aca cca aga      730
Leu Lys Arg Ser Asn Leu Ser Ser Arg Ile Ala Asp Ala Thr Pro Arg
    130                 135                 140

ttt tgc tca gtt cat gtt atc tct aaa gga aag ctt ctc aat gtt cgt      778
Phe Cys Ser Val His Val Ile Ser Lys Gly Lys Leu Leu Asn Val Arg
145                 150                 155                 160

aaa tcc gat atg gac acc gaa acg agc att gca gac gat aga agc gaa      826
Lys Ser Asp Met Asp Thr Glu Thr Ser Ile Ala Asp Asp Arg Ser Glu
                165                 170                 175

agc cgg ttc tct tca gat agc cat tca gga aca gta agt tcg aca tcg      874
Ser Arg Phe Ser Ser Asp Ser His Ser Gly Thr Val Ser Ser Thr Ser
            180                 185                 190

agt cat caa ttc tca tca aca cct tta ctc ttc caa cga atc caa gcc      922
Ser His Gln Phe Ser Ser Thr Pro Leu Leu Phe Gln Arg Ile Gln Ala
        195                 200                 205

cta aca acc gtg aac cag aag gtt gga aca aac att gga aaa cag aac      970
Leu Thr Thr Val Asn Gln Lys Val Gly Thr Asn Ile Gly Lys Gln Asn
    210                 215                 220

aat gaa ccg cat cat cat cat cat aac aga gct ggg tct cta gac gtg     1018
Asn Glu Pro His His His His His Asn Arg Ala Gly Ser Leu Asp Val
225                 230                 235                 240

gat gaa tca aag tta ctg aac cag aag ggc ttt tat cga aca agc agc     1066
Asp Glu Ser Lys Leu Leu Asn Gln Lys Gly Phe Tyr Arg Thr Ser Ser
                245                 250                 255

tcc gga atc ggg tat gga gga agt gat atc agt agc tgg aga agc tct     1114
Ser Gly Ile Gly Tyr Gly Gly Ser Asp Ile Ser Ser Trp Arg Ser Ser
            260                 265                 270

cag atg gaa gag gct tca agc tca agt acc tac agt gac cct act tca     1162
Gln Met Glu Glu Ala Ser Ser Ser Ser Thr Tyr Ser Asp Pro Thr Ser
        275                 280                 285

tct agt agc cag ata cat aaa gac ttt gag tta gag aag ctg aag att     1210
Ser Ser Ser Gln Ile His Lys Asp Phe Glu Leu Glu Lys Leu Lys Ile
    290                 295                 300

gaa ctc cgt cac att aaa gga atg tat gca gtt gct caa agc gaa gtc     1258
Glu Leu Arg His Ile Lys Gly Met Tyr Ala Val Ala Gln Ser Glu Val
305                 310                 315                 320

atc gat gct tct aaa aag atg caa gat ctg aac cag cgg cga tca gag     1306
Ile Asp Ala Ser Lys Lys Met Gln Asp Leu Asn Gln Arg Arg Ser Glu
                325                 330                 335

gaa gct aca agg ctc aag aac tta acg ata aga gaa gaa gaa gcg gat     1354
Glu Ala Thr Arg Leu Lys Asn Leu Thr Ile Arg Glu Glu Glu Ala Asp
            340                 345                 350

gaa gtg gtg gaa atg gag agg gag aga caa gag gat gcg gaa aac gaa     1402
Glu Val Val Glu Met Glu Arg Glu Arg Gln Glu Asp Ala Glu Asn Glu
        355                 360                 365

gct gag ctc gtg aga gaa tgc att gag aga gaa acc gaa gag aga ctt     1450
Ala Glu Leu Val Arg Glu Cys Ile Glu Arg Glu Thr Glu Glu Arg Leu
    370                 375                 380

gag gcg gaa gca aga gcg gaa gag gtt aga aaa gag aag cag agg tta     1498
Glu Ala Glu Ala Arg Ala Glu Glu Val Arg Lys Glu Lys Gln Arg Leu
385                 390                 395                 400
```

-continued

```
gag gat gca ctt gaa ggt gga ccg ctt caa cgc caa caa tac atg aaa      1546
Glu Asp Ala Leu Glu Gly Gly Pro Leu Gln Arg Gln Gln Tyr Met Lys
                405                 410                 415

ttt gag tgg gaa gag atc gtc gag gcg acg tca tct ttc tcg gat gaa      1594
Phe Glu Trp Glu Glu Ile Val Glu Ala Thr Ser Ser Phe Ser Asp Glu
            420                 425                 430

ctt aag atc gga gtc ggt ggt tac gga agc gta tat agg tgt aac ttg      1642
Leu Lys Ile Gly Val Gly Gly Tyr Gly Ser Val Tyr Arg Cys Asn Leu
        435                 440                 445

cat cac acg aca gta gct gtc aag gtt ctt cat tca gac aaa agt agt      1690
His His Thr Thr Val Ala Val Lys Val Leu His Ser Asp Lys Ser Ser
    450                 455                 460

tta acc aaa cag ttt cac caa gag ctt gag att ctt agc aag att cgt      1738
Leu Thr Lys Gln Phe His Gln Glu Leu Glu Ile Leu Ser Lys Ile Arg
465                 470                 475                 480

cat cca cac ttg ctt ctc ctc cta ggc gcg tgt cct gaa cgc gga agc      1786
His Pro His Leu Leu Leu Leu Leu Gly Ala Cys Pro Glu Arg Gly Ser
                485                 490                 495

tta gtt tac gag tat atg cac aac gga agc ctt gag gaa aga ctc atg      1834
Leu Val Tyr Glu Tyr Met His Asn Gly Ser Leu Glu Glu Arg Leu Met
            500                 505                 510

aaa cgc cga cca aac gtt gac aca ccg caa ccg ccg cca tta cgg tgg      1882
Lys Arg Arg Pro Asn Val Asp Thr Pro Gln Pro Pro Pro Leu Arg Trp
        515                 520                 525

ttc gag cgg ttc cga atc gct tgg gag atc gct tca gca ctc tac ttt      1930
Phe Glu Arg Phe Arg Ile Ala Trp Glu Ile Ala Ser Ala Leu Tyr Phe
    530                 535                 540

ctc cac aca aac gaa cca aga cca atc gtt cac cgc gat ctt aaa cca      1978
Leu His Thr Asn Glu Pro Arg Pro Ile Val His Arg Asp Leu Lys Pro
545                 550                 555                 560

gcc aat atc ctc cta gac cgg aac aat gtg agc aaa atc gga gac gta      2026
Ala Asn Ile Leu Leu Asp Arg Asn Asn Val Ser Lys Ile Gly Asp Val
                565                 570                 575

ggc ctt tcc aaa atg gtt aat ctt gat cct tct cat gcc tca acg gtt      2074
Gly Leu Ser Lys Met Val Asn Leu Asp Pro Ser His Ala Ser Thr Val
            580                 585                 590

ttc aac gaa acc ggt cca gtt gga aca ttc ttc tac ata gat cct gaa      2122
Phe Asn Glu Thr Gly Pro Val Gly Thr Phe Phe Tyr Ile Asp Pro Glu
        595                 600                 605

tac caa aga acc gga gtg gta act ccc gaa tct gat atc tac gcg ttt      2170
Tyr Gln Arg Thr Gly Val Val Thr Pro Glu Ser Asp Ile Tyr Ala Phe
    610                 615                 620

gga atc ata ctt ctt cag cta gtc aca gct aga tcc gcg atg ggt ttg      2218
Gly Ile Ile Leu Leu Gln Leu Val Thr Ala Arg Ser Ala Met Gly Leu
625                 630                 635                 640

gct cat tcg ata gag aaa gcg ttg aga gat caa acc ggg aaa ttt aca      2266
Ala His Ser Ile Glu Lys Ala Leu Arg Asp Gln Thr Gly Lys Phe Thr
                645                 650                 655

gag atc ttg gat aaa act gct gga gat tgg ccg gtt aag gaa gct aaa      2314
Glu Ile Leu Asp Lys Thr Ala Gly Asp Trp Pro Val Lys Glu Ala Lys
            660                 665                 670

gag atg gtt atg ata ggg ctt aga tgt gca gag atg aga aag cgt gat      2362
Glu Met Val Met Ile Gly Leu Arg Cys Ala Glu Met Arg Lys Arg Asp
        675                 680                 685

cgt cct gat tta ggg aaa gag att ttg ccg gtt ctt gaa cgg tta aag      2410
Arg Pro Asp Leu Gly Lys Glu Ile Leu Pro Val Leu Glu Arg Leu Lys
    690                 695                 700

gaa gtt gcg tct atc gca agg aac atg ttt gct gat aac cta att gat      2458
Glu Val Ala Ser Ile Ala Arg Asn Met Phe Ala Asp Asn Leu Ile Asp
705                 710                 715                 720
```

-continued

```
cat cac cat aac gct ccg acc cat ttc tac tgt cca ata aca aag gat     2506
His His His Asn Ala Pro Thr His Phe Tyr Cys Pro Ile Thr Lys Asp
                725                 730                 735

gtg atg gag aat cca tgt gtt gct tcg gat gga tat acg tat gag aag     2554
Val Met Glu Asn Pro Cys Val Ala Ser Asp Gly Tyr Thr Tyr Glu Lys
            740                 745                 750

aga gcg att aag gaa tgg ctt cag aag aat cat aaa tct cca atg acg     2602
Arg Ala Ile Lys Glu Trp Leu Gln Lys Asn His Lys Ser Pro Met Thr
        755                 760                 765

gat ttg ccc ttt cct agt gat tct ctt ctt cct aat cat tct ctt ctt     2650
Asp Leu Pro Phe Pro Ser Asp Ser Leu Leu Pro Asn His Ser Leu Leu
    770                 775                 780

tct gca atc aag gag tgg aga tca caa cta att aaa taaattaatt          2696
Ser Ala Ile Lys Glu Trp Arg Ser Gln Leu Ile Lys
785                 790                 795

aaaggttctt aaatttatac ggctaaattc gtcaattaac atgaatcgtt gtggtttttg   2756

ttttgtcata ccattcttgc gcacaaacgt tgatgaaata ttcgagcttt tgtgtgtaaa   2816

tttttttac cttatttgtt tgattgtatt ataggttttg actgcatatt tgcaagaaga    2876

atataatagt gttgattttt gttgt                                         2901


<210> SEQ ID NO 36
<211> LENGTH: 796
<212> TYPE: PRT
<213> ORGANISM: Arabidopsis thaliana

<400> SEQUENCE: 36

Met Gly Asp Gly Ala Leu Ile Val Ala Val Ala Ile Lys Gly Asn Asn
1               5                   10                  15

Ser Lys Thr Lys Gly Val Val Arg Trp Ala Leu Gln Glu Phe Ala Ser
            20                  25                  30

Gln Glu His Val Val Phe Lys Leu Leu His Val Gln Pro Arg Asp Ser
        35                  40                  45

Asn Ser Val Ser Thr Thr Arg Lys Asp Leu Thr Thr Ser Val Tyr Lys
    50                  55                  60

Lys Asp Val Asp Arg Lys Thr Arg Glu Met Leu Leu Pro Ser Arg Asp
65                  70                  75                  80

Met Phe Val His Arg Glu Val Gln Leu Asp Ile Met Val Leu Glu Ser
                85                  90                  95

Asp Asp Ile Ala Asp Ala Ile Ser Lys Ala Val Gln Asp His Gly Ile
            100                 105                 110

Ser Glu Leu Val Ile Gly Ala Ser Ser Ser Ile Ile Phe Ser Trp Lys
        115                 120                 125

Leu Lys Arg Ser Asn Leu Ser Ser Arg Ile Ala Asp Ala Thr Pro Arg
    130                 135                 140

Phe Cys Ser Val His Val Ile Ser Lys Gly Lys Leu Leu Asn Val Arg
145                 150                 155                 160

Lys Ser Asp Met Asp Thr Glu Thr Ser Ile Ala Asp Asp Arg Ser Glu
                165                 170                 175

Ser Arg Phe Ser Ser Asp Ser His Ser Gly Thr Val Ser Ser Thr Ser
            180                 185                 190

Ser His Gln Phe Ser Ser Thr Pro Leu Leu Phe Gln Arg Ile Gln Ala
        195                 200                 205

Leu Thr Thr Val Asn Gln Lys Val Gly Thr Asn Ile Gly Lys Gln Asn
    210                 215                 220
```

```
Asn Glu Pro His His His His His Asn Arg Ala Gly Ser Leu Asp Val
225                 230                 235                 240

Asp Glu Ser Lys Leu Leu Asn Gln Lys Gly Phe Tyr Arg Thr Ser Ser
                245                 250                 255

Ser Gly Ile Gly Tyr Gly Gly Ser Asp Ile Ser Ser Trp Arg Ser Ser
            260                 265                 270

Gln Met Glu Glu Ala Ser Ser Ser Ser Thr Tyr Ser Asp Pro Thr Ser
        275                 280                 285

Ser Ser Ser Gln Ile His Lys Asp Phe Glu Leu Glu Lys Leu Lys Ile
    290                 295                 300

Glu Leu Arg His Ile Lys Gly Met Tyr Ala Val Ala Gln Ser Glu Val
305                 310                 315                 320

Ile Asp Ala Ser Lys Lys Met Gln Asp Leu Asn Gln Arg Arg Ser Glu
                325                 330                 335

Glu Ala Thr Arg Leu Lys Asn Leu Thr Ile Arg Glu Glu Glu Ala Asp
            340                 345                 350

Glu Val Val Glu Met Glu Arg Glu Arg Gln Glu Asp Ala Glu Asn Glu
        355                 360                 365

Ala Glu Leu Val Arg Glu Cys Ile Glu Arg Glu Thr Glu Glu Arg Leu
    370                 375                 380

Glu Ala Glu Ala Arg Ala Glu Glu Val Arg Lys Glu Lys Gln Arg Leu
385                 390                 395                 400

Glu Asp Ala Leu Glu Gly Gly Pro Leu Gln Arg Gln Gln Tyr Met Lys
                405                 410                 415

Phe Glu Trp Glu Glu Ile Val Glu Ala Thr Ser Ser Phe Ser Asp Glu
            420                 425                 430

Leu Lys Ile Gly Val Gly Gly Tyr Gly Ser Val Tyr Arg Cys Asn Leu
        435                 440                 445

His His Thr Thr Val Ala Val Lys Val Leu His Ser Asp Lys Ser Ser
    450                 455                 460

Leu Thr Lys Gln Phe His Gln Glu Leu Glu Ile Leu Ser Lys Ile Arg
465                 470                 475                 480

His Pro His Leu Leu Leu Leu Leu Gly Ala Cys Pro Glu Arg Gly Ser
                485                 490                 495

Leu Val Tyr Glu Tyr Met His Asn Gly Ser Leu Glu Glu Arg Leu Met
            500                 505                 510

Lys Arg Arg Pro Asn Val Asp Thr Pro Gln Pro Pro Pro Leu Arg Trp
        515                 520                 525

Phe Glu Arg Phe Arg Ile Ala Trp Glu Ile Ala Ser Ala Leu Tyr Phe
    530                 535                 540

Leu His Thr Asn Glu Pro Arg Pro Ile Val His Arg Asp Leu Lys Pro
545                 550                 555                 560

Ala Asn Ile Leu Leu Asp Arg Asn Asn Val Ser Lys Ile Gly Asp Val
                565                 570                 575

Gly Leu Ser Lys Met Val Asn Leu Asp Pro Ser His Ala Ser Thr Val
            580                 585                 590

Phe Asn Glu Thr Gly Pro Val Gly Thr Phe Phe Tyr Ile Asp Pro Glu
        595                 600                 605

Tyr Gln Arg Thr Gly Val Val Thr Pro Glu Ser Asp Ile Tyr Ala Phe
    610                 615                 620

Gly Ile Ile Leu Leu Gln Leu Val Thr Ala Arg Ser Ala Met Gly Leu
625                 630                 635                 640

Ala His Ser Ile Glu Lys Ala Leu Arg Asp Gln Thr Gly Lys Phe Thr
```

-continued

```
                645                 650                 655

Glu Ile Leu Asp Lys Thr Ala Gly Asp Trp Pro Val Lys Glu Ala Lys
            660                 665                 670

Glu Met Val Met Ile Gly Leu Arg Cys Ala Glu Met Arg Lys Arg Asp
        675                 680                 685

Arg Pro Asp Leu Gly Lys Glu Ile Leu Pro Val Leu Glu Arg Leu Lys
    690                 695                 700

Glu Val Ala Ser Ile Ala Arg Asn Met Phe Ala Asp Asn Leu Ile Asp
705                 710                 715                 720

His His His Asn Ala Pro Thr His Phe Tyr Cys Pro Ile Thr Lys Asp
                725                 730                 735

Val Met Glu Asn Pro Cys Val Ala Ser Asp Gly Tyr Thr Tyr Glu Lys
            740                 745                 750

Arg Ala Ile Lys Glu Trp Leu Gln Lys Asn His Lys Ser Pro Met Thr
        755                 760                 765

Asp Leu Pro Phe Pro Ser Asp Ser Leu Leu Pro Asn His Ser Leu Leu
    770                 775                 780

Ser Ala Ile Lys Glu Trp Arg Ser Gln Leu Ile Lys
785                 790                 795
```

<210> SEQ ID NO 37
<211> LENGTH: 624
<212> TYPE: DNA
<213> ORGANISM: Arabidopsis thaliana
<220> FEATURE:
<221> NAME/KEY: promoter
<222> LOCATION: (1)..(624)
<223> OTHER INFORMATION: promoter of gene At4g00830

<400> SEQUENCE: 37

```
atctttgaga ttggtgtgta attttgtttg tgtttatgtt tgtgtgtgtg aatttgtagc      60

ttataattgg aagtgtttac taactaatct ctatataaat atgtatgctc atatttttat     120

ctataaatgt tgcaattagg atgtgaacaa tagtttatca atctgtcatg gtatctttgt     180

taattatatg gaatcgtttt agtataaaat aacgaaaatt ttcactggcc ttatttgttt     240

ttacatgcaa agtgaagttg ttaagaaaac cataaaaaaa gctgcaattt tgcaacttga     300

gatccacgag caaggaacat tacccatgtg acatgattcc tacatgatca gtcttgtctt     360

ctacgttata cactactact ctatatccac ctaaatataa attaaatgct tctgaaatgg     420

aataatttta aaacagcacg tagttttcat atcaccgaag aaaacggcag ggctggcaaa     480

atcacgaatt ttttaaacag gtataataaa gaactagaaa acactaggcc caataaaaac     540

agtgggctta aaaagcgttt tgatttaggg ttaatgtgtg cgtaacatgt gatcatagcc     600

cacgagtggg taaggagtgt cttc                                            624
```

<210> SEQ ID NO 38
<211> LENGTH: 1353
<212> TYPE: DNA
<213> ORGANISM: Arabidopsis thaliana
<220> FEATURE:
<221> NAME/KEY: promoter
<222> LOCATION: (1)..(1353)
<223> OTHER INFORMATION: promoter of gene At4g00830

<400> SEQUENCE: 38

```
atctttgaga ttggtgtgta attttgtttg tgtttatgtt tgtgtgtgtg aatttgtagc      60

ttataattgg aagtgtttac taactaatct ctatataaat atgtatgctc atatttttat     120
```

-continued

```
ctataaatgt tgcaattagg atgtgaacaa tagtttatca atctgtcatg gtatctttgt    180

taattatatg gaatcgtttt agtataaaat aacgaaaatt ttcactggcc ttatttgttt    240

ttacatgcaa agtgaagttg ttaagaaaac cataaaaaaa gctgcaattt tgcaacttga    300

gatccacgag caaggaacat tacccatgtg acatgattcc tacatgatca gtcttgtctt    360

ctacgttata cactactact ctatatccac ctaaatataa attaaatgct tctgaaatgg    420

aataatttta aaacagcacg tagttttcat atcaccgaag aaaacggcag ggctggcaaa    480

atcacgaatt ttttaaacag gtataataaa gaactagaaa acactaggcc caataaaaac    540

agtgggctta aaaagcgttt tgatttaggg ttaatgtgtg cgtaacatgt gatcatagcc    600

cacgagtggg taaggagtgt cttcatcttc ttctaccgga gatcgagaaa tagccgacga    660

agttttgttt tttgagtaaa acagtattcg tcggacaacc gaagcgaaat ccctaatttc    720

ccacaacacg aaataccaat ttccccaatt cgaaaacaaa cacggtctgg tatgccgaga    780

aaattctcca tttctacttt tcttatacat ttgttttggt tgtttcatat aaatacttct    840

catcttcttc gattttgtta ccctccccca aacaatataa aaaaaaagga taaaccctag    900

tttctttctc agactgtttc aagttcagat ttttatttct gagcttaact ggtgagtaat    960

ttgctttctg gagagatgtg tgagttacga tctctaattt cattggttgc ttcggttatg   1020

gcttgattct tctctctgtt atcaatttgg atctggaatc atatatatac atacacaaaa   1080

actctgctct ttttcaaagt tttgattttt atctcattg acgcttgttt cgtgatagca   1140

atgaactaca attcttctgt atctctgcca ctaaaagaac ctgaatttag tttgaaccat   1200

cctttcttct ccacttgaca ttaaacgaaa aagagcagtt ctcttatcac ccattataag   1260

cttttttttt tggtgtatgg tcctatagca tttttttcac agtgattacc tgagcttcgt   1320

ggttaaaaaa gagtatggtt attggtagac cag                                  1353
```

```
<210> SEQ ID NO 39
<211> LENGTH: 1355
<212> TYPE: DNA
<213> ORGANISM: Arabidopsis thaliana
<220> FEATURE:
<221> NAME/KEY: promoter
<222> LOCATION: (1)..(1355)
<223> OTHER INFORMATION: promoter of gene At4g00830

<400> SEQUENCE: 39

atctttgaga ttggtgtgta attttgtttg tgtttatgtt tgtgtgtgtg aatttgtagc     60

ttataattgg aagtgtttac taactaatct ctatataaat atgtatgctc atatttttat    120

ctataaatgt tgcaattagg atgtgaacaa tagtttatca atctgtcatg gtatctttgt    180

taattatatg gaatcttttt agtataaaat aacgaaaatt ttcactggcc ttatttgttt    240

ttacatgcaa agtgaagttg ttaagaaaac cataaaaaaa agctgcaact ttgcaacttg    300

agatccacga gcaaggaaca ttacccatgt gacatgattc ctacatgatc agtcttgtct    360

tctacgttat acactactac tctatatcca cctaaatata aattaaatgc ttctgaaatg    420

gaataatttt aaaacagcac gtagttttca tatcaccaaa gaaaacggca gggctggcaa    480

aatcacgaat tttttaaaca ggtataataa agaactagaa aacactaggc ccaataaaaa    540

cagtgggctt aaaaagcgtt ttgatttagg gttaatgtgt gcgtaacatg tgatcatagc    600

ccacgagtgg gtaaggagtg tcttcatctt cttctaccgg agatcgagaa atagccgacg    660

aagttttgtt ttttgagtaa aacagtattc gtcggacaac cgaagcgaaa tccctaattt    720

cccacaacac gaaataccaa tttccccaat tcgaaaacaa acacggtctg gtatgccgag    780
```

```
aaaattctcc atttctactt ttcttataca tttgttttgg ttgtttcata taaatacttc    840

tcatcttctt cgattttgtt accctccccc aaacaatata aaaaaaaaag gataaaccct    900

agtttctttc tcagactgtt tcaagttcag atttttattt ctgagcttaa ctggtgagta    960

atttgctttc tggagagatg tgtgagttac gatctctaat ttcattggtt gcttcggtta   1020

tggcttgatt cttctctctg ttatcaattt ggatctggaa tcatatatat acatacacaa   1080

aaactctgct ctttttcaaa gttttgattt ttatctcatt tgacgcttgt ttcgtgatag   1140

caatgaacta caattcttct gtatctctgc cactaaaaga acctgaattt agtttgaacc   1200

atcctttctt ctccacattt ttttaaacga aaaagagcag ttctcatatc acccattata   1260

agcttttttt tttggtgtat ggtcctatag catttttttta acagtgatta cctgagcttc   1320

gtggttaaaa aagagtatgg ttattggatg accag                             1355


<210> SEQ ID NO 40
<211> LENGTH: 2267
<212> TYPE: DNA
<213> ORGANISM: Arabidopsis thaliana
<220> FEATURE:
<221> NAME/KEY: CDS
<222> LOCATION: (147)..(1631)
<223> OTHER INFORMATION: coding for protein similar to nucleolin protein
      (At4g00830)

<400> SEQUENCE: 40

catcttcttc taccggagat cgagaaatag ccgacgaagt tttgtttttt gagtaaaaca     60

gtattcgtcg gacaaccgaa gcgaaatccc taatttccca caacacgaaa taccaatttc    120

cccaattcga aaacaaacac ggtctg atg tca gac gca aga gat aat gat gac     173
                             Met Ser Asp Ala Arg Asp Asn Asp Asp
                             1               5

cgt gtg gat ttc gag gag ggt agc tac agt gag atg gag gat gaa gtg      221
Arg Val Asp Phe Glu Glu Gly Ser Tyr Ser Glu Met Glu Asp Glu Val
10                  15                  20                  25

gag gag gaa caa gta gaa gag tat gaa gag gag gaa gaa gaa gat gat      269
Glu Glu Glu Gln Val Glu Glu Tyr Glu Glu Glu Glu Glu Glu Asp Asp
                30                  35                  40

gat gat gat gac gtt ggc aat cag aat gcc gaa gaa cgt gag gtg gag      317
Asp Asp Asp Asp Val Gly Asn Gln Asn Ala Glu Glu Arg Glu Val Glu
            45                  50                  55

gat tat ggt gat aca aaa ggt ggg gat atg gaa gat gtt cag gag gaa      365
Asp Tyr Gly Asp Thr Lys Gly Gly Asp Met Glu Asp Val Gln Glu Glu
        60                  65                  70

ata gct gaa gat gac gac aac cat att gat att gag aca gca gat gat      413
Ile Ala Glu Asp Asp Asp Asn His Ile Asp Ile Glu Thr Ala Asp Asp
    75                  80                  85

gat gag aaa cca cca tct cct att gat gat gaa gat agg gaa aag tat      461
Asp Glu Lys Pro Pro Ser Pro Ile Asp Asp Glu Asp Arg Glu Lys Tyr
90                  95                  100                 105

tcc cac ctt ctt tca ctt cct cct cat ggt tct gaa gtt ttt att ggt      509
Ser His Leu Leu Ser Leu Pro Pro His Gly Ser Glu Val Phe Ile Gly
                110                 115                 120

ggg ctc cca agg gat gtt gga gaa gag gac ctg agg gat cta tgt gaa      557
Gly Leu Pro Arg Asp Val Gly Glu Glu Asp Leu Arg Asp Leu Cys Glu
            125                 130                 135

gag ata ggc gag atc ttt gag gtg aga ctg atg aaa gat agg gac tct      605
Glu Ile Gly Glu Ile Phe Glu Val Arg Leu Met Lys Asp Arg Asp Ser
        140                 145                 150

ggt gat agc aaa ggc tat gct ttt gta gct ttc aaa acc aaa gac gtt      653
```

-continued

```
Gly Asp Ser Lys Gly Tyr Ala Phe Val Ala Phe Lys Thr Lys Asp Val
    155                 160                 165

gca caa aag gcc att gag gag ttg cac agt aaa gag ttt aag gga aaa      701
Ala Gln Lys Ala Ile Glu Glu Leu His Ser Lys Glu Phe Lys Gly Lys
170                 175                 180                 185

acc ata agg tgc tct ctt tcc gaa acg aag aat agg ttg ttc att ggt      749
Thr Ile Arg Cys Ser Leu Ser Glu Thr Lys Asn Arg Leu Phe Ile Gly
                190                 195                 200

aac ata cca aag aac tgg act gag gat gag ttt aga aaa gtc ata gag      797
Asn Ile Pro Lys Asn Trp Thr Glu Asp Glu Phe Arg Lys Val Ile Glu
            205                 210                 215

gat gtt ggt cct gga gtg gag aac atc gag ctc ata aaa gac cca aca      845
Asp Val Gly Pro Gly Val Glu Asn Ile Glu Leu Ile Lys Asp Pro Thr
        220                 225                 230

aat acc act cgt aac cgt ggt ttt gca ttt gtt ttg tac tat aac aat      893
Asn Thr Thr Arg Asn Arg Gly Phe Ala Phe Val Leu Tyr Tyr Asn Asn
    235                 240                 245

gca tgt gct gat tat tca aga cag aaa atg ata gat tct aat ttt aag      941
Ala Cys Ala Asp Tyr Ser Arg Gln Lys Met Ile Asp Ser Asn Phe Lys
250                 255                 260                 265

ctt gag ggt aac gct cca act gtg act tgg gca gac cca aaa agc tct      989
Leu Glu Gly Asn Ala Pro Thr Val Thr Trp Ala Asp Pro Lys Ser Ser
                270                 275                 280

cct gag cat tct gct gct gct gct cag gtg aaa gcc ctt tat gtc aag     1037
Pro Glu His Ser Ala Ala Ala Ala Gln Val Lys Ala Leu Tyr Val Lys
            285                 290                 295

aat att cca gag aat acc tca aca gag cag cta aag gaa ctc ttt cag     1085
Asn Ile Pro Glu Asn Thr Ser Thr Glu Gln Leu Lys Glu Leu Phe Gln
        300                 305                 310

agg cat gga gaa gtg acc aaa atc gtt aca cct cct gga aag ggt gga     1133
Arg His Gly Glu Val Thr Lys Ile Val Thr Pro Pro Gly Lys Gly Gly
    315                 320                 325

aaa cgt gat ttt ggg ttt gtc cac tat gct gaa aga tct agt gca ttg     1181
Lys Arg Asp Phe Gly Phe Val His Tyr Ala Glu Arg Ser Ser Ala Leu
330                 335                 340                 345

aag gct gtc aaa gat acc gag aga tat gaa gtc aat ggt caa cca cta     1229
Lys Ala Val Lys Asp Thr Glu Arg Tyr Glu Val Asn Gly Gln Pro Leu
                350                 355                 360

gaa gtt gtg ctt gct aaa ccc cag gct gaa agg aag cat gac cct tct     1277
Glu Val Val Leu Ala Lys Pro Gln Ala Glu Arg Lys His Asp Pro Ser
            365                 370                 375

tct tat tct tac ggg gct gca cct act cct gcc ccc ttt gtg cat ccc     1325
Ser Tyr Ser Tyr Gly Ala Ala Pro Thr Pro Ala Pro Phe Val His Pro
        380                 385                 390

acg ttt ggt ggt ttt gct gcg gct cct tac ggt gct atg ggt gcc ggt     1373
Thr Phe Gly Gly Phe Ala Ala Ala Pro Tyr Gly Ala Met Gly Ala Gly
    395                 400                 405

ttg ggt att gcc ggt agt ttt agt cag cca atg atc tat ggt aga gga     1421
Leu Gly Ile Ala Gly Ser Phe Ser Gln Pro Met Ile Tyr Gly Arg Gly
410                 415                 420                 425

gca atg cca aca ggg atg caa atg gtt cca atg ctt ctt ccc gat ggc     1469
Ala Met Pro Thr Gly Met Gln Met Val Pro Met Leu Leu Pro Asp Gly
                430                 435                 440

cga gtt ggc tat gtt ctg caa cag cct ggt atg ccg atg gca gca gca     1517
Arg Val Gly Tyr Val Leu Gln Gln Pro Gly Met Pro Met Ala Ala Ala
            445                 450                 455

cca cca caa cga cca aga aga aat gac cgg aat aac ggc tca agc gga     1565
Pro Pro Gln Arg Pro Arg Arg Asn Asp Arg Asn Asn Gly Ser Ser Gly
        460                 465                 470
```

-continued

```
ggg tca ggc aga gat aac agt cat gaa cat gat ggt aac cga gga ggc      1613
Gly Ser Gly Arg Asp Asn Ser His Glu His Asp Gly Asn Arg Gly Gly
    475                 480                 485

cga agg tac cga ccc tac tagtaaccat agagaaaaat aagcaagtag             1661
Arg Arg Tyr Arg Pro Tyr
490                 495

aaaaagaaaa ggagaagtgt attgggattt gtttgtagtt tgtttttgga gaactttaaa    1721

aagctctctc tcatgtgtta taaaatatga aatcgaaacc ttatggtttc tggtttgata    1781

tggagactgc tggggggata ggattgagtg attcgatctt taaattatga gactttttag    1841

tttttctct tctgaataat actcttatca attatccatc agatttggtg tttttgcttt     1901

ccctagccct tgtgcaacgt tgtttactta tacaacaagt tatcactggg tctcatcaca    1961

taacattaca gtctgaagat gtcaaacgaa cttagacttt caacaagaag caaagaaatg    2021

aatcaaatca attacaataa tacaacaaca attggcaatg agaattcttt ttgagtagag    2081

agttatctac attggagtgc agttgaaggc tgtttcgaat atgattgatt gattttgttt    2141

caactttcaa tcaagggtcg atgtcagaac aagttggaaa ttcaaggcct tcaagggaag    2201

ttatgttatc gatatcgtct ttagagtaca atgggaggag ccaaaacgcc ttcttcttcc    2261

caaaaa                                                               2267


<210> SEQ ID NO 41
<211> LENGTH: 495
<212> TYPE: PRT
<213> ORGANISM: Arabidopsis thaliana

<400> SEQUENCE: 41

Met Ser Asp Ala Arg Asp Asn Asp Asp Arg Val Asp Phe Glu Glu Gly
1               5                   10                  15

Ser Tyr Ser Glu Met Glu Asp Glu Val Glu Glu Glu Gln Val Glu Glu
            20                  25                  30

Tyr Glu Glu Glu Glu Glu Glu Asp Asp Asp Asp Asp Asp Val Gly Asn
        35                  40                  45

Gln Asn Ala Glu Glu Arg Glu Val Glu Asp Tyr Gly Asp Thr Lys Gly
    50                  55                  60

Gly Asp Met Glu Asp Val Gln Glu Glu Ile Ala Glu Asp Asp Asp Asn
65                  70                  75                  80

His Ile Asp Ile Glu Thr Ala Asp Asp Asp Glu Lys Pro Pro Ser Pro
                85                  90                  95

Ile Asp Asp Glu Asp Arg Glu Lys Tyr Ser His Leu Leu Ser Leu Pro
            100                 105                 110

Pro His Gly Ser Glu Val Phe Ile Gly Gly Leu Pro Arg Asp Val Gly
        115                 120                 125

Glu Glu Asp Leu Arg Asp Leu Cys Glu Glu Ile Gly Glu Ile Phe Glu
    130                 135                 140

Val Arg Leu Met Lys Asp Arg Asp Ser Gly Asp Ser Lys Gly Tyr Ala
145                 150                 155                 160

Phe Val Ala Phe Lys Thr Lys Asp Val Ala Gln Lys Ala Ile Glu Glu
                165                 170                 175

Leu His Ser Lys Glu Phe Lys Gly Lys Thr Ile Arg Cys Ser Leu Ser
            180                 185                 190

Glu Thr Lys Asn Arg Leu Phe Ile Gly Asn Ile Pro Lys Asn Trp Thr
        195                 200                 205

Glu Asp Glu Phe Arg Lys Val Ile Glu Asp Val Gly Pro Gly Val Glu
    210                 215                 220
```

```
Asn Ile Glu Leu Ile Lys Asp Pro Thr Asn Thr Thr Arg Asn Arg Gly
225                 230                 235                 240

Phe Ala Phe Val Leu Tyr Tyr Asn Asn Ala Cys Ala Asp Tyr Ser Arg
                245                 250                 255

Gln Lys Met Ile Asp Ser Asn Phe Lys Leu Glu Gly Asn Ala Pro Thr
            260                 265                 270

Val Thr Trp Ala Asp Pro Lys Ser Ser Pro Glu His Ser Ala Ala Ala
        275                 280                 285

Ala Gln Val Lys Ala Leu Tyr Val Lys Asn Ile Pro Glu Asn Thr Ser
    290                 295                 300

Thr Glu Gln Leu Lys Glu Leu Phe Gln Arg His Gly Glu Val Thr Lys
305                 310                 315                 320

Ile Val Thr Pro Pro Gly Lys Gly Gly Lys Arg Asp Phe Gly Phe Val
                325                 330                 335

His Tyr Ala Glu Arg Ser Ser Ala Leu Lys Ala Val Lys Asp Thr Glu
            340                 345                 350

Arg Tyr Glu Val Asn Gly Gln Pro Leu Glu Val Val Leu Ala Lys Pro
        355                 360                 365

Gln Ala Glu Arg Lys His Asp Pro Ser Ser Tyr Ser Tyr Gly Ala Ala
    370                 375                 380

Pro Thr Pro Ala Pro Phe Val His Pro Thr Phe Gly Gly Phe Ala Ala
385                 390                 395                 400

Ala Pro Tyr Gly Ala Met Gly Ala Gly Leu Gly Ile Ala Gly Ser Phe
                405                 410                 415

Ser Gln Pro Met Ile Tyr Gly Arg Gly Ala Met Pro Thr Gly Met Gln
            420                 425                 430

Met Val Pro Met Leu Leu Pro Asp Gly Arg Val Gly Tyr Val Leu Gln
        435                 440                 445

Gln Pro Gly Met Pro Met Ala Ala Ala Pro Pro Gln Arg Pro Arg Arg
    450                 455                 460

Asn Asp Arg Asn Asn Gly Ser Ser Gly Gly Ser Gly Arg Asp Asn Ser
465                 470                 475                 480

His Glu His Asp Gly Asn Arg Gly Gly Arg Arg Tyr Arg Pro Tyr
                485                 490                 495
```

<210> SEQ ID NO 42
<211> LENGTH: 396
<212> TYPE: DNA
<213> ORGANISM: Arabidopsis thaliana
<220> FEATURE:
<221> NAME/KEY: promoter
<222> LOCATION: (1)..(396)
<223> OTHER INFORMATION: promoter of gene At3g10220

<400> SEQUENCE: 42

```
caccggaata ttcctcctcc tcacggattc tctcgtgtcc tttttgttta gaccagggat     60

tagaggattt atactaacct gcgggtgagt acacagagtt taacgtgcga ctatacacgt    120

ggctaaatct aacgagtcta atgacctttt gaacactaga gaaaactacg tcgttttatt    180

aatcgtctct ctcgtttctc agctacattc tcagcggtgc gtctccgatc cggcgagatt    240

cgattcgatt tctgctgaca agtcaaactc tttgcccaga aatagctaag aaggtaagcg    300

tcttttgtta cccaattcga gaaagtcgaa ttttttttg gatttcattg agataagtga    360

tttaacagag ctttttgtc aggtctagag gtgaaa                               396
```

```
<210> SEQ ID NO 43
<211> LENGTH: 395
<212> TYPE: DNA
<213> ORGANISM: Arabidopsis thaliana
<220> FEATURE:
<221> NAME/KEY: promoter
<222> LOCATION: (1)..(395)
<223> OTHER INFORMATION: promoter of gene At3g10220

<400> SEQUENCE: 43

caccggaata ttcctcctcc tcacggattc tctcgtgtcc tttttgttta gaccagggat      60

tagaggattt atactaacct gcgggtgagt acacagtgtt taacgtgcga ctatacacgt     120

gcctaaatct aacgagtcta atgacctttt gaacactaga gaaaactacg tcgttttatt     180

aatcgtctct ctcgtttctc agctacattc tcagcggtgc gtctccgatc cggcgagatt     240

cgattcgatt tctgctgaca agtcaaactc tttgcccaga aatagctaag aaggtaagcg     300

tcttttgtta cccaattcga gaaagtcgaa tttttttttg atttcattga gataagtgat     360

ttaacagagc ttttttgtca ggtctagagg tgaaa                                395


<210> SEQ ID NO 44
<211> LENGTH: 1443
<212> TYPE: DNA
<213> ORGANISM: Arabidopsis thaliana
<220> FEATURE:
<221> NAME/KEY: CDS
<222> LOCATION: (80)..(808)
<223> OTHER INFORMATION: coding for tubulin folding cofactor B
      (At3g10220)

<400> SEQUENCE: 44

cggcgagatt cgattcgatt tctgctgaca agtcaaactc tttgcccaga aatagctaag      60

aaggtctaga ggtgaaaaa atg gca act tcg cgt tta cag ttg gaa gga gat     112
                     Met Ala Thr Ser Arg Leu Gln Leu Glu Gly Asp
                     1               5                   10

gac tct gta cat cta cac att act cac gcc aac ctt aaa agc ttc tct      160
Asp Ser Val His Leu His Ile Thr His Ala Asn Leu Lys Ser Phe Ser
            15                  20                  25

gcg gac gct cgt ttc tct ccg caa atg agt gta gaa gct gtg aaa gaa      208
Ala Asp Ala Arg Phe Ser Pro Gln Met Ser Val Glu Ala Val Lys Glu
        30                  35                  40

aag cta tgg aag aaa tgt ggt aca tct gtt aat tcc atg gct tta gag      256
Lys Leu Trp Lys Lys Cys Gly Thr Ser Val Asn Ser Met Ala Leu Glu
    45                  50                  55

ctc tat gat gac tct ggc tca aag gtt gca gtt ctc agt gat gat tct      304
Leu Tyr Asp Asp Ser Gly Ser Lys Val Ala Val Leu Ser Asp Asp Ser
60                  65                  70                  75

aga cct ctt ggt ttc ttc tct cct ttt gat ggg ttt cgg tta cac atc      352
Arg Pro Leu Gly Phe Phe Ser Pro Phe Asp Gly Phe Arg Leu His Ile
                80                  85                  90

ata gat ctt gac ccc tcc tcg gtc aca act gga ggc tgg ctt gaa gat      400
Ile Asp Leu Asp Pro Ser Ser Val Thr Thr Gly Gly Trp Leu Glu Asp
            95                  100                 105

acg tca ctg gtt gag aag tat aac atc tca gag gag gat tat gct aaa      448
Thr Ser Leu Val Glu Lys Tyr Asn Ile Ser Glu Glu Asp Tyr Ala Lys
        110                 115                 120

cga act gac agt ttt agg aaa ttc aaa gaa aag aga gtt tct caa aat      496
Arg Thr Asp Ser Phe Arg Lys Phe Lys Glu Lys Arg Val Ser Gln Asn
    125                 130                 135

ccg gtt gct gct gag gct aag acg aaa gag aac tat atg gaa gat ctc      544
Pro Val Ala Ala Glu Ala Lys Thr Lys Glu Asn Tyr Met Glu Asp Leu
140                 145                 150                 155
```

```
tgc gca aat atc aag gtg gga gat aga tgc caa gtt gag cct ggg gag      592
Cys Ala Asn Ile Lys Val Gly Asp Arg Cys Gln Val Glu Pro Gly Glu
                160                 165                 170

aaa aga gga atg gtc aaa tat gtt gga cga gca gag tcg ttg ggt cct      640
Lys Arg Gly Met Val Lys Tyr Val Gly Arg Ala Glu Ser Leu Gly Pro
            175                 180                 185

ggc tat tgg gtt gga att cag tat gat gag ccc ctt gga aaa cat gat      688
Gly Tyr Trp Val Gly Ile Gln Tyr Asp Glu Pro Leu Gly Lys His Asp
        190                 195                 200

ggc atg gtg aaa gga aca aga ttc ttt gag tgc cct cgg ctt caa ggt      736
Gly Met Val Lys Gly Thr Arg Phe Phe Glu Cys Pro Arg Leu Gln Gly
    205                 210                 215

ggt atg gtc agg cct gac aaa gta aag gtt ggt gat tat ccg gaa aga      784
Gly Met Val Arg Pro Asp Lys Val Lys Val Gly Asp Tyr Pro Glu Arg
220                 225                 230                 235

gac cct ttc gag gaa gat gaa ata taagactttc acgaaagcat caaatattaa     838
Asp Pro Phe Glu Glu Asp Glu Ile
                240

ggagcggaag gagtttgaaa gatttgcttt tgtgttcaaa atccactctt ttatcttatt    898

acattttgcc tctagttttg gatttacaag agttggtgaa acacaatgca gcacaaagta    958

ttaattttaa tgaactagta gtaacaattt gatttcacaa ggattcaggt tatgatctgt   1018

ggtttataca caattatcca acgacttgca atgcggatat actactggtc aagaaccaaa   1078

gaacagatgt acttatatgt ctaagtttct ggtccttagt ctctatcttg taccaaattg   1138

ttgatcatct tagcaagagg aacagtcccc tttgtcatga tctccaatct tgaggtattg   1198

gaagcgtgtg agaagagcga caacccgaag accaacagtt ccgggagaaa cagcctggaa   1258

gacaagaatc cgtgccagta atgaggttgc agatcaaaga atgcatcaaa gaaccttcta   1318

gtagcgtcta aatcgagttt cagcagaata tccattccaa aacagaagaa ctccctctgt   1378

ctacgccgtt cgataggcca caagtctctc caaacctcag cagagagttg atctcctctc   1438

aggct                                                               1443
```

```
<210> SEQ ID NO 45
<211> LENGTH: 243
<212> TYPE: PRT
<213> ORGANISM: Arabidopsis thaliana

<400> SEQUENCE: 45

Met Ala Thr Ser Arg Leu Gln Leu Glu Gly Asp Asp Ser Val His Leu
1               5                   10                  15

His Ile Thr His Ala Asn Leu Lys Ser Phe Ser Ala Asp Ala Arg Phe
            20                  25                  30

Ser Pro Gln Met Ser Val Glu Ala Val Lys Glu Lys Leu Trp Lys Lys
        35                  40                  45

Cys Gly Thr Ser Val Asn Ser Met Ala Leu Glu Leu Tyr Asp Asp Ser
    50                  55                  60

Gly Ser Lys Val Ala Val Leu Ser Asp Asp Ser Arg Pro Leu Gly Phe
65                  70                  75                  80

Phe Ser Pro Phe Asp Gly Phe Arg Leu His Ile Ile Asp Leu Asp Pro
                85                  90                  95

Ser Ser Val Thr Thr Gly Gly Trp Leu Glu Asp Thr Ser Leu Val Glu
            100                 105                 110

Lys Tyr Asn Ile Ser Glu Glu Asp Tyr Ala Lys Arg Thr Asp Ser Phe
        115                 120                 125
```

-continued

```
Arg Lys Phe Lys Glu Lys Arg Val Ser Gln Asn Pro Val Ala Ala Glu
    130                 135                 140

Ala Lys Thr Lys Glu Asn Tyr Met Glu Asp Leu Cys Ala Asn Ile Lys
145                 150                 155                 160

Val Gly Asp Arg Cys Gln Val Glu Pro Gly Glu Lys Arg Gly Met Val
                165                 170                 175

Lys Tyr Val Gly Arg Ala Glu Ser Leu Gly Pro Gly Tyr Trp Val Gly
            180                 185                 190

Ile Gln Tyr Asp Glu Pro Leu Gly Lys His Asp Gly Met Val Lys Gly
        195                 200                 205

Thr Arg Phe Phe Glu Cys Pro Arg Leu Gln Gly Gly Met Val Arg Pro
    210                 215                 220

Asp Lys Val Lys Val Gly Asp Tyr Pro Glu Arg Asp Pro Phe Glu Glu
225                 230                 235                 240

Asp Glu Ile


<210> SEQ ID NO 46
<211> LENGTH: 1796
<212> TYPE: DNA
<213> ORGANISM: Arabidopsis thaliana
<220> FEATURE:
<221> NAME/KEY: promoter
<222> LOCATION: (1)..(1796)
<223> OTHER INFORMATION: promoter of gene At4g38520

<400> SEQUENCE: 46

ggatccatgt atcatgaatg attgacgtat acctaaacct aataactaaa ttttacttca     60

acatatatat cctcaacatg attttttttt attttttttt aacattctta tcgttatttt    120

taattaaaag atagtattcg tacataactt tgcattatat tttaagttct actatttaag    180

aaacctatat aatttgttta taattaccgt agtagtaaat ttactaaaaa aattctagct    240

tagtagttgt gattatgatc ttttttttaaa agatattttt gtgaagtaaa tgtgaagggt    300

ttatatatac acgttcatat ataagtgaaa gtattggcat attgggagat gattggataa    360

cgaagttggt cctgaagtga aaggttcaga gtggttggat ttttgtgtga ttgatggaag    420

ctatgttctg taagtaggga ccttctccac agtccacacc accctttttct ctatttttag    480

gtcgccctta ttattgttat ctttataaat caatttttgg ttatgtaagt tcacatatat    540

tgacactcgg cgagatacca tgggagcatg catgatggga agtatataca tttgttggtg    600

aaaaaagtat gaaaaagttc gcatatacat caatttggtc ccgcaaaatt agattatcta    660

gaactttgtg ataattatcg tggacgtatt catgttttag aagcaggctt ttagtttctc    720

atttaattca tagttctgtt tttctttatt gagctgaaat ttttatagtt gattcttcta    780

ttattggtac tacaaaagta taaataacta caaagagtcg atggggagaa aagggccaaa    840

tttagtggta catacattaa tataaaatta aataatgtta ggtaaagtga catatctcac    900

tttatcccaa tcactttcgg gtcccaaatt ttttaaaata tttcttattc aatttttcat    960

tcttcaagcc caagcctctt ctctatatat tttttttaaaa ttttaatctc agggtcctgg   1020

accaccactt ttatgggcat taaacgtttg atacaaattg tgtggggaaa ttaaaaatga   1080

aagattcatg aatccacata tattatttct agactgtaca tgtattttat tttatatgca   1140

cactgcttaa aatcttgatt ataatttacg aggagtagtt ttaacgaaga aagaaaaaaa   1200

cacatggagt aagtaaaaga aataaatctt ggtgacataa aaacaaaagt actcgtgtag   1260

ttttatcagt cgtagtcatg taacaccgcc acataaccaa attttatcga aaccgtatat   1320
```

-continued

```
ttttactctt ctttgatttg tgttaagaga ttttattaaa cgttgaagaa aaatcttccg   1380

tttgacccca gtttatgata atgtctaaag taaaagagtt gaatattttt aaaataaaga   1440

ggagacttga atgaattatt atatcaataa tatcaactat tttattttct tccctaaaaa   1500

aactgtaata ttattctttg ccactgtttg gtgttgtcca tctaatgagg caaaaaagga   1560

cgagagggaa gtggagcccg aaagctggga cctttgatgt gctggctccg acctcgccat   1620

cgttggtctt ttatgggtct tgtctggtaa gaatcactct tagtcttaag actatagaga   1680

gagataaaga gagaagataa aaaaaacaac tccaactttc tttctttttt ttacataaaa   1740

acgtcaaagg aggatgtctc gttcggcgac ttgacctctc tctctctctc ttttac       1796
```

```
<210> SEQ ID NO 47
<211> LENGTH: 2581
<212> TYPE: DNA
<213> ORGANISM: Arabidopsis thaliana
<220> FEATURE:
<221> NAME/KEY: promoter
<222> LOCATION: (1)..(2581)
<223> OTHER INFORMATION: promoter of gene At4g38520

<400> SEQUENCE: 47

ggatccatgt atcatgaatg attgacgtat acctaaacct aataactaaa ttttacttca     60

acatatatat cctcaacatg attttttttt attttttttt aacattctta tcgttatttt    120

taattaaaag atagtattcg tacataactt tgcattatat tttaagttct actatttaag    180

aaacctatat aatttgttta taattaccgt agtagtaaat ttactaaaaa aattctagct    240

tagtagttgt gattatgatc ttttttttaaa agatattttt gtgaagtaaa tgtgaagggt    300

ttatatatac acgttcatat ataagtgaaa gtattggcat attgggagat gattggataa    360

cgaagttggt cctgaagtga aaggttcaga gtggttggat ttttgtgtga ttgatggaag    420

ctatgttctg taagtaggga ccttctccac agtccacacc accctttct ctatttttag    480

gtcgccctta ttattgttat ctttataaat caatttttgg ttatgtaagt tcacatatat    540

tgacactcgg cgagatacca tgggagcatg catgatggga agtatataca tttgttggtg    600

aaaaaagtat gaaaaagttc gcatatacat caatttggtc ccgcaaaatt agattatcta    660

gaactttgtg ataattatcg tggacgtatt catgttttag aagcaggctt ttagtttctc    720

atttaattca tagttctgtt tttctttatt gagctgaaat ttttatagtt gattcttcta    780

ttattggtac tacaaaagta taaataacta caaagagtcg atggggagaa aagggccaaa    840

tttagtggta catacattaa tataaaatta aataatgtta ggtaaagtga catatctcac    900

tttatcccaa tcactttcgg gtcccaaatt ttttaaaata tttcttattc aatttttcat    960

tcttcaagcc caagcctctt ctctatatat ttttttaaaa ttttaatctc agggtcctgg   1020

accaccactt ttatgggcat taaacgtttg atacaaattg tgtggggaaa ttaaaaatga   1080

aagattcatg aatccacata tattatttct agactgtaca tgtattttat tttatatgca   1140

cactgcttaa aatcttgatt ataatttacg aggagtagtt ttaacgaaga aagaaaaaaa   1200

cacatggagt aagtaaaaga aataaatctt ggtgacataa aaacaaaagt actcgtgtag   1260

ttttatcagt cgtagtcatg taacaccgcc acataaccaa attttatcga aaccgtatat   1320

ttttactctt ctttgatttg tgttaagaga ttttattaaa cgttgaagaa aaatcttccg   1380

tttgacccca gtttatgata atgtctaaag taaaagagtt gaatattttt aaaataaaga   1440

ggagacttga atgaattatt atatcaataa tatcaactat tttattttct tccctaaaaa   1500

aactgtaata ttattctttg ccactgtttg gtgttgtcca tctaatgagg caaaaaagga   1560
```

-continued

```
cgagagggaa gtggagcccg aaagctggga cctttgatgt gctggctccg acctcgccat   1620

cgttggtctt ttatgggtct tgtctggtaa gaatcactct tagtcttaag actatagaga   1680

gagataaaga gagaagataa aaaaaacaac tccaactttc tttctttttt ttacataaaa   1740

acgtcaaagg aggatgtctc gttcggcgac ttgacctctc tctctctctc ttttaccttc   1800

attgttcact gtttccagac attgaaagaa agatcattag tttctgaggg gataaccatt   1860

tttttttctt cttaaaaaag ttttttttt ttgtcaattg gtcttctttc cttcttcttc   1920

ttcctcatcc gcccgcttat atttaattta ataataataa aaatcggtgt tcatttttat   1980

ataaaagtat aaattttgtg tttggttgat ccatccgtag tcgtagtaga tctacaaact   2040

ctgaaattcc acgcccacat ctcctccgtc ctcttgagat ccttctcttc attcattttc   2100

ttgctcaact tgagttgctt ccaacatctt gcaaggtaaa gtttcctttt ttttggtagc   2160

gaatacgaac cagttcgaat ctgccgcata aatccttttg ttttttttc ttgcttgccg    2220

catcactaat tttgctttct tccgatggtt tccttactta aagatgttaa cttttcaatg   2280

ttgcatcaag tttcttagat tgttcaatca ctagactaat cagtctcact ataatctcct   2340

acagattcat ttctattgcc actcataaca attgagtttt ctcacttttt tgctctttag   2400

attgtctttg agttcattca ggtcttgaag aagagcactc ttttaagctg tgtgaaactt   2460

gcgccgttcc tgtgaagaac tacttttggc attggagatt tcagagagct gtgatttgtg   2520

ctatcttaaa aacggacaag ttctatgttg tggcggatga gatgagggat gctatctggg   2580

t                                                                   2581
```

<210> SEQ ID NO 48
<211> LENGTH: 2569
<212> TYPE: DNA
<213> ORGANISM: Arabidopsis thaliana
<220> FEATURE:
<221> NAME/KEY: promoter
<222> LOCATION: (1)..(2569)
<223> OTHER INFORMATION: promoter of gene At4g38520

<400> SEQUENCE: 48

```
gatccatgta tcatgaatga ttgacgtata cctaaaccta ataactaaat tttacttcaa     60

catatatatc atcaacatga ttttttttt ttctttttta acattcttat cgttattttt    120

aattaaaaga tagtattcgt acataacttt gcattatatt ttaagttcta ctatttaaga    180

aacctatata atttgtttat aattaccgta gtagtaaatt tactaaaaaa ttctagctta    240

gtagttgtga ttatgatctt tttttaaaag atatttttgt gaagtaaatg tgaagggttt    300

atatatacac gttcatatat aagtgaaagt attggcatat tgggagatga ttggataacg    360

aagttggtcc tgaagtgaaa ggttcagagt ggttggattt ttgtgtgatt gatggaagct    420

atgttctgta agtagggacc ttctccacag tccacaccac ccttttctct atttttaggt    480

ctcccttatt attgttatct ttataaatca atttttggtt atgtaagttc acatatattg    540

acactcggcg agataccatg ggagcatgca tgatgggaag tatatacatt tgttggtgaa    600

aaaagtatga aaaagttcgc atatacatca atttggtccc gcaaaattag attatctaga    660

acttagtgat aattatcgtg gacgtattca tgttttagaa gcaggctttt gagtttctca    720

cttaattcat agttctgttt ttctttattg agctgaaatt tttatagttg attcttctat    780

tattggtact acaaaagtat aaataactac aaagagtcga tggggagaaa agggccaaat    840

ttagtggtac atacattaat ataaaattaa ataatgttag gtaaagtgac atatctcact    900
```

-continued

```
ttatcccaat cactttcggg tcccaaattt ttttaaatat ttgttattca atttttcatt    960

cttcaagccc aagcctcttc tctatatatt tttttaaaat tttaatctca gggtcctgga   1020

ccaccacttt tatgggcatt aaacgtttga tacaaattgt gtggggaaat taaaaatgaa   1080

agattcatga atccacatat attatttcta gactgtacat gtattttatt ttatatgcac   1140

actgcttaaa atcttgatta taatttacga ggagtagttt taacgaagaa agaaaaaaac   1200

acatggagta agtaaaagaa ataaatcttg gtgacagaaa aacaaaagta ctcgtgtagt   1260

tttatcagtc gtagtcatgt aacaccgcca cataaccaaa ttttatcgaa accgtatatt   1320

tttactcttc tttgatttgt gttaagagat tttattaaac gttgaagaaa aatcttccgt   1380

ttgaccccag tttatgataa tgtctaaagt aaaagagttg aatattttta aaataaagag   1440

gagacttgaa tgaattatta tatcaataat atcaactatt ttattttctt ccctaaaaaa   1500

actgtaatat tattctttgc cactgtttgg tgttgtccat ctaatgaggc aaaaaaggac   1560

gagagggaag tggagcccga aagctgggac ctttgatgtg ctggctccga cctcgccatc   1620

gttggtcttt tatgggtctt gtctggtaag aatcactctt agtcttaaga ctatagagag   1680

agataaagag agaagataaa aaaaacaact ccaactttct ttcttttttt tacataaaaa   1740

cgtcgaagga ggatgtctcg ttcggcgact tgacctctct ctctctctct cttttacctt   1800

cattgttcac tgtttccaga cattgaaaga aagatcatta gtttctgagg ggataaccat   1860

tttttttttct tcttaaaaag ttttttttttt tgtcaattgg tcttcttctt cctcatccgc   1920

tcgcttatat ttaatttaat aataataaaa atcggtgttc atttttatat aaaagtataa   1980

attttgtgtt tggttgatcc atccgtagtc gtagtagatc tacaagctct gaaattccac   2040

gcccacatct cctccgtcct cttgagatcc ttctcttcat tcattttctt gctcaacttg   2100

agttgcttcc aacatcttgc aaggtaaagt ttccttttttt ttggtagcga atacgaacca   2160

gttggaatct gccgcataaa tccttttgtt tttttttcttt gcttgccgca tcactaattt   2220

tgctttcttc cgatggtttc cttacttaaa gatgttaact tttcaatgtt gcatcaagtt   2280

tcttagattg ttcaatcact agactaatca gtctcactat aatctcctac agattcattt   2340

ctattgccac tcataacaat tgagttttct cactttttttg ctctttagat tgtctttgag   2400

ttcattcagg tcttgaagaa gagcactctt ttaagctgtg tgaaacttgc gccgttcctg   2460

tgaagaacta cttttggcat tgcagatttc agagagctgt gatttgtgct atcttaaaaa   2520

cggacaagtt ctatgttgtg gcggatgaga tgagggatgc tatctgggt              2569
```

```
<210> SEQ ID NO 49
<211> LENGTH: 2225
<212> TYPE: DNA
<213> ORGANISM: Arabidopsis thaliana
<220> FEATURE:
<221> NAME/KEY: CDS
<222> LOCATION: (760)..(1959)
<223> OTHER INFORMATION: coding for protein phosphatase 2C family
      protein / PP2C family protein (At4g38520)

<400> SEQUENCE: 49
```

```
cttcattgtt cactgtttcc agacattgaa agaaagatca ttagtttctg aggggataac     60

cattttttttt tcttcttaaa aagtttttttt ttttgtcaat tggtcttctt cttcctcatc   120

cgctcgctta tatttaattt aataataata aaaatcggtg ttcattttta tataaaagta   180

taaattttgt gtttggttga tccatccgta gtcgtagtag atctacaagc tctgaaattc   240

cacgcccaca tctcctccgt cctcttgaga tccttctctt cattcatttt cttgctcaac   300
```

-continued

```
ttgagttgct tccaacatct tgcaaggtaa agtttccttt tttttggtag cgaatacgaa    360

ccagttggaa tctgccgcat aaatcctttt gttttttttt cttgcttgcc gcatcactaa    420

ttttgctttc ttccgatggt ttccttactt aaagatgtta acttttcaat gttgcatcaa    480

gtttcttaga ttgttcaatc actagactaa tcagtctcac tataatctcc tacagattca    540

tttctattgc cactcataac aattgagttt tctcactttt ttgctcttta gattgtcttt    600

gagttcattc aggtcttgaa gaagagcact cttttaagct gtgtgaaact tgcgccgttc    660

ctgtgaagaa ctacttttgg cattgcagat ttcagagagc tgtgatttgt gctatcttaa    720

aaacggacaa gttctatgtt gtggcggatg agatgaggg atg cta tct ggg ttg      774
                                          Met Leu Ser Gly Leu
                                          1               5

atg aat ttt ctg aat gcc tgt ctc tgg cca cgg tca gat cag cag gct      822
Met Asn Phe Leu Asn Ala Cys Leu Trp Pro Arg Ser Asp Gln Gln Ala
                10                  15                  20

cgt tct gcc tca gat tct ggt ggc cgc caa gag ggt ttg ctc tgg ttc      870
Arg Ser Ala Ser Asp Ser Gly Gly Arg Gln Glu Gly Leu Leu Trp Phe
            25                  30                  35

aga gac tcc ggc cag cac gtc ttt ggt gac ttc tcc atg gcc gtc gtt      918
Arg Asp Ser Gly Gln His Val Phe Gly Asp Phe Ser Met Ala Val Val
        40                  45                  50

caa gcc aac agc ttg cta gag gac cag agc cag ctc gag tct ggc tct      966
Gln Ala Asn Ser Leu Leu Glu Asp Gln Ser Gln Leu Glu Ser Gly Ser
    55                  60                  65

ctt agc tcc cac gac tct ggt ccc ttt ggc acc ttt gtt ggc gtc tac     1014
Leu Ser Ser His Asp Ser Gly Pro Phe Gly Thr Phe Val Gly Val Tyr
70                  75                  80                  85

gac ggc cac ggt ggg cct gag aca tct cgc ttc atc aat gat cat atg     1062
Asp Gly His Gly Gly Pro Glu Thr Ser Arg Phe Ile Asn Asp His Met
                90                  95                  100

ttc cac cac ctc aag agg ttt act gca gag caa cag tgt atg tca tca     1110
Phe His His Leu Lys Arg Phe Thr Ala Glu Gln Gln Cys Met Ser Ser
            105                 110                 115

gag gtg ata aaa aaa gcg ttc caa gcc act gaa gaa ggc ttc tta tcc     1158
Glu Val Ile Lys Lys Ala Phe Gln Ala Thr Glu Glu Gly Phe Leu Ser
        120                 125                 130

ata gtt aca aat caa ttt caa act aga cct cag ata gcc aca gtg gga     1206
Ile Val Thr Asn Gln Phe Gln Thr Arg Pro Gln Ile Ala Thr Val Gly
    135                 140                 145

tca tgc tgt ctt gta agt gtc atc tgc gat ggg aag cta tac gtg gcc     1254
Ser Cys Cys Leu Val Ser Val Ile Cys Asp Gly Lys Leu Tyr Val Ala
150                 155                 160                 165

aac gca ggg gac tca cgg gcc gtt ctg gga caa gtc atg agg gta aca     1302
Asn Ala Gly Asp Ser Arg Ala Val Leu Gly Gln Val Met Arg Val Thr
                170                 175                 180

ggt gaa gct cat gcc act cag ctc tca gca gag cac aac gca tct ata     1350
Gly Glu Ala His Ala Thr Gln Leu Ser Ala Glu His Asn Ala Ser Ile
            185                 190                 195

gag tca gtg aga cgg gaa ctt cag gcc ctg cat ccg gat cat cca gat     1398
Glu Ser Val Arg Arg Glu Leu Gln Ala Leu His Pro Asp His Pro Asp
        200                 205                 210

att gtg gtt ctg aaa cat aac gtc tgg cga gta aaa ggc atc att cag     1446
Ile Val Val Leu Lys His Asn Val Trp Arg Val Lys Gly Ile Ile Gln
    215                 220                 225

gtt tca aga tcc att ggt gat gtg tat ttg aaa agg tca gag ttc aac     1494
Val Ser Arg Ser Ile Gly Asp Val Tyr Leu Lys Arg Ser Glu Phe Asn
230                 235                 240                 245

agg gaa cca ctg tat gca aaa ttc cgg ctg agg tca ccg ttc agc aag     1542
```

```
Arg Glu Pro Leu Tyr Ala Lys Phe Arg Leu Arg Ser Pro Phe Ser Lys
                250                 255                 260

cca tta ctg agt gca gag ccg gcg atc acg gtg cat aca ctg gag ccg      1590
Pro Leu Leu Ser Ala Glu Pro Ala Ile Thr Val His Thr Leu Glu Pro
            265                 270                 275

cac gat cag ttc att ata tgt gca tca gat gga ctg tgg gaa cat atg      1638
His Asp Gln Phe Ile Ile Cys Ala Ser Asp Gly Leu Trp Glu His Met
        280                 285                 290

agc aac caa gaa gca gta gac ata gtc cag aat cat ccg cga aac ggg      1686
Ser Asn Gln Glu Ala Val Asp Ile Val Gln Asn His Pro Arg Asn Gly
    295                 300                 305

ata gca aag cgg ctg gtg aaa gta gcg cta caa gaa gcg gca aag aag      1734
Ile Ala Lys Arg Leu Val Lys Val Ala Leu Gln Glu Ala Ala Lys Lys
310                 315                 320                 325

aga gag atg aga tac tca gac ctg aaa aag ata gac aga gga gtg agg      1782
Arg Glu Met Arg Tyr Ser Asp Leu Lys Lys Ile Asp Arg Gly Val Arg
                330                 335                 340

aga cat ttc cac gat gac ata aca gtg att gtt gtc ttc ttt gat aca      1830
Arg His Phe His Asp Asp Ile Thr Val Ile Val Val Phe Phe Asp Thr
            345                 350                 355

aac cta gtg agc aga gga agt atg ttg aga gga cca gcc gtg tca gtg      1878
Asn Leu Val Ser Arg Gly Ser Met Leu Arg Gly Pro Ala Val Ser Val
        360                 365                 370

aga gga gcg ggt gtg aat cta cct cac aac acc ctg gcg cct tgc acc      1926
Arg Gly Ala Gly Val Asn Leu Pro His Asn Thr Leu Ala Pro Cys Thr
    375                 380                 385

acg ccc act caa gct gct gct gct ggc gcc tcc tgactattga atttttacgg    1979
Thr Pro Thr Gln Ala Ala Ala Ala Gly Ala Ser
390                 395                 400

tgtccttaaa attctttcca agatccttcc tgtaactata tataaatata tatatttgat    2039

tattattatc attgactggg aaaggatata tcatcatcaa gtgggaaagg atatatcata    2099

atcaagtggt tagttttgtt tgttcccttt gttagctgtg tactggagaa agaaaggtga    2159

caagaattct tcttcttctt cattaatttt cattgcttgc tttttaaggt attactgatt    2219

cagact                                                               2225


<210> SEQ ID NO 50
<211> LENGTH: 400
<212> TYPE: PRT
<213> ORGANISM: Arabidopsis thaliana

<400> SEQUENCE: 50

Met Leu Ser Gly Leu Met Asn Phe Leu Asn Ala Cys Leu Trp Pro Arg
1               5                   10                  15

Ser Asp Gln Gln Ala Arg Ser Ala Ser Asp Ser Gly Gly Arg Gln Glu
            20                  25                  30

Gly Leu Leu Trp Phe Arg Asp Ser Gly Gln His Val Phe Gly Asp Phe
        35                  40                  45

Ser Met Ala Val Val Gln Ala Asn Ser Leu Leu Glu Asp Gln Ser Gln
    50                  55                  60

Leu Glu Ser Gly Ser Leu Ser Ser His Asp Ser Gly Pro Phe Gly Thr
65                  70                  75                  80

Phe Val Gly Val Tyr Asp Gly His Gly Gly Pro Glu Thr Ser Arg Phe
                85                  90                  95

Ile Asn Asp His Met Phe His His Leu Lys Arg Phe Thr Ala Glu Gln
            100                 105                 110

Gln Cys Met Ser Ser Glu Val Ile Lys Lys Ala Phe Gln Ala Thr Glu
```

-continued

```
        115                 120                 125

Glu Gly Phe Leu Ser Ile Val Thr Asn Gln Phe Gln Thr Arg Pro Gln
    130                 135                 140

Ile Ala Thr Val Gly Ser Cys Cys Leu Val Ser Val Ile Cys Asp Gly
145                 150                 155                 160

Lys Leu Tyr Val Ala Asn Ala Gly Asp Ser Arg Ala Val Leu Gly Gln
                165                 170                 175

Val Met Arg Val Thr Gly Glu Ala His Ala Thr Gln Leu Ser Ala Glu
            180                 185                 190

His Asn Ala Ser Ile Glu Ser Val Arg Arg Glu Leu Gln Ala Leu His
        195                 200                 205

Pro Asp His Pro Asp Ile Val Val Leu Lys His Asn Val Trp Arg Val
    210                 215                 220

Lys Gly Ile Ile Gln Val Ser Arg Ser Ile Gly Asp Val Tyr Leu Lys
225                 230                 235                 240

Arg Ser Glu Phe Asn Arg Glu Pro Leu Tyr Ala Lys Phe Arg Leu Arg
                245                 250                 255

Ser Pro Phe Ser Lys Pro Leu Leu Ser Ala Glu Pro Ala Ile Thr Val
            260                 265                 270

His Thr Leu Glu Pro His Asp Gln Phe Ile Ile Cys Ala Ser Asp Gly
        275                 280                 285

Leu Trp Glu His Met Ser Asn Gln Glu Ala Val Asp Ile Val Gln Asn
    290                 295                 300

His Pro Arg Asn Gly Ile Ala Lys Arg Leu Val Lys Val Ala Leu Gln
305                 310                 315                 320

Glu Ala Ala Lys Lys Arg Glu Met Arg Tyr Ser Asp Leu Lys Lys Ile
                325                 330                 335

Asp Arg Gly Val Arg Arg His Phe His Asp Asp Ile Thr Val Ile Val
            340                 345                 350

Val Phe Phe Asp Thr Asn Leu Val Ser Arg Gly Ser Met Leu Arg Gly
        355                 360                 365

Pro Ala Val Ser Val Arg Gly Ala Gly Val Asn Leu Pro His Asn Thr
    370                 375                 380

Leu Ala Pro Cys Thr Thr Pro Thr Gln Ala Ala Ala Ala Gly Ala Ser
385                 390                 395                 400
```

<210> SEQ ID NO 51
<211> LENGTH: 1021
<212> TYPE: DNA
<213> ORGANISM: Arabidopsis thaliana
<220> FEATURE:
<221> NAME/KEY: promoter
<222> LOCATION: (1)..(1021)
<223> OTHER INFORMATION: promoter of gene At3g11110

<400> SEQUENCE: 51

```
ggaagtgaaa aatggtggga tgtaattaat taggaaatag gtaaggaagc gaattgttag     60

gtaagagaga gcatcgcaaa cgtgtaggtc gtagactcta tgtctataat gtatgtttcg    120

tgccgtggtc tcgtctaatt gtctttttgc tgtctcgcca attgatatgt tagtccatgc    180

ctaactacta ctgtttcctc ataactacta aaatgtcgct gaaatatttg aaaaaagagc    240

tgaggtgttt tttctgtcga tcaaagtttc cacgatggta ttggtgaaga gctagtataa    300

ataatcatat agttttctaa actaaatatg tcattatcat catttactgg tttacatgca    360

tcttttattc atttcaaact ttcttatgaa aacgcagatg tgaaaagata aatcatgatt    420
```

```
tacaggttat atcaaagtga tgtgagttgg aacatttaaa acaatttagt ttgtcaactg    480

aatcttagac gcaatcgatt attgttactc ttaaatcact ttacaataat atcaaatatc    540

acatcctgca gccaagtaat cgagctaatc catgatcaag tataggtggt gaagcaacta    600

aaaatgtggc caatttcgtt tgtacgcata atttaacgat gctggttatt ttagtatgtt    660

gctacttgcc agttgctacc attgggatct cgaaaacaca caaacgtacg tgcatgctgc    720

ctaatatagt ctttattatt gttcctaaac taattaagac aaattaaaac aatctataaa    780

gttacaaaaa aaatcccact ttcctccaaa cttgagtctt gcttgtacag acagttgtac    840

tacttgtgga agctgtttaa ctcaaattaa tattctcttt ctgttatttt atttaaggaa    900

atacaatcac gtgactgaga ttagcactag tatactatat atatacatca cgacgctttt    960

tttatacata ctatatatca acggccagaa ttaagtaagt aaccatccat cgccaaccgg   1020

a                                                                   1021
```

```
<210> SEQ ID NO 52
<211> LENGTH: 1067
<212> TYPE: DNA
<213> ORGANISM: Arabidopsis thaliana
<220> FEATURE:
<221> NAME/KEY: promoter
<222> LOCATION: (1)..(1067)
<223> OTHER INFORMATION: promoter of gene At3g11110

<400> SEQUENCE: 52

aaatcaagtt ttcccgccaa aatcacaaaa aaaaatattt tttgccaaat ttgaaaatat     60

tattatcatt atatgttatt gaaatctata ttttagtaaa ttataaatat ttcagattta    120

gctaatgttt atggactgtt gttatttatc tattaagttt atgaattaat taataaaagg    180

caatatctca cttaattggt ttaaatgggt tcacatggat ttactaaatt taaatgggta    240

gggttaaatg ggtttcaaaa ataaatggat ttatatgagt ttaaagttaa atggagtggg    300

tttaaatggg atgggtttaa ttggggtggg ttagcccata ttaacatcac tacatatagt    360

tttctaaact aaatatgtca ttatcatcat ttactggttt acatgcatct tttatacatt    420

tcaaactttc ttatgaaaac gcagatgtga aaagataaat catgatttac aggttatcaa    480

agtgatgtga gttggaacgt aaaacaattt agtttgtcaa ctgaatctta gacgcaatcg    540

attattgtta ctcttaaatc actttacaat aatatcaaat atcacatcct gcagccaagt    600

aatcgagcta atccatgatc aagtataggt ggtgaagcaa ctaaaaatgt agccaatttc    660

gtttgtacgc ataattaaac aatgctattt attttagtat gttgctactt gccagttgct    720

accattggga tctcgaaaac acacaaacgt acgtgcatgt tgcctaatat agtctttatt    780

attgttccta aactaattaa gacaaattaa aacaatatat aaagtaacaa aaaaaaatcc    840

cactttcctt caaacttgag tcttgcttgt acagacagtt gtactacttg tggaagctgt    900

ttaactcaaa ttaatattct ctttctgtta ttttatttaa ggaaatacaa tcacgtgact    960

gagattagca ctagtatact atatatatac atcacgacgc tgtttttata catactatat   1020

atcaacggcc agaattaagt aagtaaccat ccatcgccaa ccggaaa                 1067
```

```
<210> SEQ ID NO 53
<211> LENGTH: 477
<212> TYPE: DNA
<213> ORGANISM: Arabidopsis thaliana
<220> FEATURE:
<221> NAME/KEY: CDS
<222> LOCATION: (1)..(474)
<223> OTHER INFORMATION: coding for zinc finger (C3HC4-type RINGfinger)
```

```
     family protein (At3g11110)

<400> SEQUENCE: 53

atg acg tca tct tca ccg tct cca caa gcc tcg atg ctt ttg tac tgg       48
Met Thr Ser Ser Ser Pro Ser Pro Gln Ala Ser Met Leu Leu Tyr Trp
1               5                   10                  15

cac gag aat caa tac gac gac cgg aac ttc cag att cat ggc cgg aca       96
His Glu Asn Gln Tyr Asp Asp Arg Asn Phe Gln Ile His Gly Arg Thr
            20                  25                  30

ctc ttc ttc gcc tta gct tta ttc tcc gtc gtg ctc ttc ttc gca cta      144
Leu Phe Phe Ala Leu Ala Leu Phe Ser Val Val Leu Phe Phe Ala Leu
        35                  40                  45

ctc act ctc tac atc cac cgg aac tgc ctc ccc cgg gat tct atc aat      192
Leu Thr Leu Tyr Ile His Arg Asn Cys Leu Pro Arg Asp Ser Ile Asn
    50                  55                  60

ctc cac gcg tcc tct ccc gat cga ctc acg cgt tgc cgt agc gga ggg      240
Leu His Ala Ser Ser Pro Asp Arg Leu Thr Arg Cys Arg Ser Gly Gly
65                  70                  75                  80

ctt gat ccg gcg gag att cgg agc ttg ccg gtg gtg ctt tgc cgg aga      288
Leu Asp Pro Ala Glu Ile Arg Ser Leu Pro Val Val Leu Cys Arg Arg
                85                  90                  95

gaa agg gcg gag gag gag gag gag aag gag tgt tgt ata tgt cta ggt      336
Glu Arg Ala Glu Glu Glu Glu Glu Lys Glu Cys Cys Ile Cys Leu Gly
            100                 105                 110

ggt ttc gaa gaa gga gag aag atg aaa gtg ctt cct ccg tgt agc cat      384
Gly Phe Glu Glu Gly Glu Lys Met Lys Val Leu Pro Pro Cys Ser His
        115                 120                 125

tgt tac cac tgc gaa tgt gtg gat cgg tgg ctt aaa acc gag tcg agt      432
Cys Tyr His Cys Glu Cys Val Asp Arg Trp Leu Lys Thr Glu Ser Ser
    130                 135                 140

tgt ccg ctc tgc cga gtc tcc atc cgt gtc gac tcg tca agc taa          477
Cys Pro Leu Cys Arg Val Ser Ile Arg Val Asp Ser Ser Ser
145                 150                 155


<210> SEQ ID NO 54
<211> LENGTH: 158
<212> TYPE: PRT
<213> ORGANISM: Arabidopsis thaliana

<400> SEQUENCE: 54

Met Thr Ser Ser Ser Pro Ser Pro Gln Ala Ser Met Leu Leu Tyr Trp
1               5                   10                  15

His Glu Asn Gln Tyr Asp Asp Arg Asn Phe Gln Ile His Gly Arg Thr
            20                  25                  30

Leu Phe Phe Ala Leu Ala Leu Phe Ser Val Val Leu Phe Phe Ala Leu
        35                  40                  45

Leu Thr Leu Tyr Ile His Arg Asn Cys Leu Pro Arg Asp Ser Ile Asn
    50                  55                  60

Leu His Ala Ser Ser Pro Asp Arg Leu Thr Arg Cys Arg Ser Gly Gly
65                  70                  75                  80

Leu Asp Pro Ala Glu Ile Arg Ser Leu Pro Val Val Leu Cys Arg Arg
                85                  90                  95

Glu Arg Ala Glu Glu Glu Glu Glu Lys Glu Cys Cys Ile Cys Leu Gly
            100                 105                 110

Gly Phe Glu Glu Gly Glu Lys Met Lys Val Leu Pro Pro Cys Ser His
        115                 120                 125

Cys Tyr His Cys Glu Cys Val Asp Arg Trp Leu Lys Thr Glu Ser Ser
    130                 135                 140
```

```
Cys Pro Leu Cys Arg Val Ser Ile Arg Val Asp Ser Ser Ser
145                 150                 155


<210> SEQ ID NO 55
<211> LENGTH: 1963
<212> TYPE: DNA
<213> ORGANISM: Arabidopsis thaliana
<220> FEATURE:
<221> NAME/KEY: promoter
<222> LOCATION: (1)..(1963)
<223> OTHER INFORMATION: promoter of gene At2g47170

<400> SEQUENCE: 55

ctcgagataa ttgagagatc gaggaaaaca aaaaatatta taaacatatc tattaagcaa     60

aaaaaacttt aagtgagaaa agacaaaaac caactgtgta taaagccgaa acagatgatg    120

ggtccataaa aggccgaacc tccacttcta ttttctgtat ataactacga tttattccca    180

taataacaaa aaattaaacc atctctcaaa gtggtaggtc agtttccttc atcatttcac    240

attttcttct atttgacacc cttcacttca acaacacttc acattgttgt tatatgacct    300

ttctgtcacc acatcattgg tagagagagt tactgctata tatcatgtac tatatagttt    360

ctaattaaaa ccaattaaca gttaatatgt agatttactc gtcccgtatg ttatttttaa    420

gttttatcac actttcgcct taacatttga ttaagtaatg atatcataaa ggatttctga    480

ttgaattcag taacaagacg gatccttcat tatgcatgta tatttatcag atatcaagaa    540

tattattcaa cgttataagt atatcgaaat tcagagtcag aatatggtat ttaattagcg    600

atctcaagta catgtacgac tataattcca tacaagtaca ttagatgaaa cggctacata    660

tgcaacaagc gtcgagcgag atcagcactc gtgtaaactt taaggagtaa aatgtcatgt    720

gcaacctttg accggtttaa ttctacaatt ttaataaata tttaaaatgt ttaaatatat    780

atgcaaacta aaaaaaaaaa agtaattgat tagcttaatt tgaaacgacg tctccataac    840

gtttgtgctt tgtttgttaa tgcgtctgaa tctctttacg cataatgcat tacggatata    900

aggaattctg acattatttg atatccgaaa gtttcatata aattccatat atgattgtta    960

gcttttattt ccatgaaata gaaagataga ctacatacct ttcaaactac tgtatttgaa   1020

gcttatgtaa aaaatattta attaaaatat atgtaattta tatgttgatt gagttatgag   1080

tatcaagtaa aaaccctaat ccgttgctaa aatatcaatg attataacgt atttataaac   1140

gaaagaaaaa agaacatcta gaattttcga tatttgatcc tcaagttaaa cttggaaaaa   1200

tttggatgta tgaaatattt tgtcgtccac ttatacaata aagtatgaaa catggatgca   1260

tgaaggctag acatccaatg tctaaaaata ctatatataa tgcttttggt agggtctttt   1320

ctttatcatg tctcacttct gtttctatcc ctcattttaa atagccaata taatttcact   1380

ctttactata aaattattat ataaacatca ttttgattga actacctaaa aggaagaaac   1440

gtataggaat ttttggagcc tcaagattgt aataatgtct catagtttga cttgcaaaac   1500

ctaaattaaa cgcctaaatc attaccatta aataaatgaa cttttgtacg caattgattc   1560

agacacaagg accgaccaat tcgaaaacaa tgaatggata tgattcatcc ttatgaaagc   1620

ttgacaacag actcggtttt ggctggttaa cctagactcg gtttatttaa accagacaat   1680

aatttctttc gtcgtcgttt tatttgaata ggtgcgtcaa aaataaaagc tgaaattctt   1740

ggttgcaaaa gcccaacagg cctgtggaga tagcttttta gattgattaa atgggccgaa   1800

ttgggctgac acatgacgag aatgtggcta tagaaattgt tagtgagagg gtccgggtcc   1860

aaaaatgttg cagaagtgat atagtattta tttaattaaa aacatattat tcgacgtatt   1920
```

tttaacgctc actggattta taagtagaga ttttttgtgt ctc 1963

<210> SEQ ID NO 56
<211> LENGTH: 2556
<212> TYPE: DNA
<213> ORGANISM: Arabidopsis thaliana
<220> FEATURE:
<221> NAME/KEY: promoter
<222> LOCATION: (1)..(2556)
<223> OTHER INFORMATION: promoter of gene At2g47170

<400> SEQUENCE: 56

```
ctcgagataa ttgagagatc gaggaaaaca aaaaatatta taaacatatc tattaagcaa     60
aaaaaacttt aagtgagaaa agacaaaaac caactgtgta taaagccgaa acagatgatg    120
ggtccataaa aggccgaacc tccacttcta ttttctgtat ataactacga tttattccca    180
taataacaaa aaattaaacc atctctcaaa gtggtaggtc agtttccttc atcatttcac    240
attttcttct atttgacacc cttcacttca acaacacttc acattgttgt tatatgacct    300
ttctgtcacc acatcattgg tagagagagt tactgctata tatcatgtac tatatagttt    360
ctaattaaaa ccaattaaca gttaatatgt agatttactc gtcccgtatg ttatttttaa    420
gttttatcac actttcgcct taacatttga ttaagtaatg atatcataaa ggatttctga    480
ttgaattcag taacaagacg gatccttcat tatgcatgta tatttatcag atatcaagaa    540
tattattcaa cgttataagt atatcgaaat tcagagtcag aatatggtat ttaattagcg    600
atctcaagta catgtacgac tataattcca tacaagtaca ttagatgaaa cggctacata    660
tgcaacaagc gtcgagcgag atcagcactc gtgtaaactt taaggagtaa aatgtcatgt    720
gcaacctttg accggtttaa ttctacaatt ttaataaata tttaaaatgt ttaaatatat    780
atgcaaacta aaaaaaaaaa agtaattgat tagcttaatt tgaaacgacg tctccataac    840
gtttgtgctt tgtttgttaa tgcgtctgaa tctctttacg cataatgcat tacggatata    900
aggaattctg acattatttg atatccgaaa gtttcatata aattccatat atgattgtta    960
gcttttattt ccatgaaata gaaagataga ctacatacct ttcaaactac tgtatttgaa   1020
gcttatgtaa aaaatattta attaaaatat atgtaattta tatgttgatt gagttatgag   1080
tatcaagtaa aaaccctaat ccgttgctaa aatatcaatg attataacgt atttataaac   1140
gaaagaaaaa agaacatcta gaattttcga tatttgatcc tcaagttaaa cttggaaaaa   1200
tttggatgta tgaaatattt tgtcgtccac ttatacaata aagtatgaaa catggatgca   1260
tgaaggctag acatccaatg tctaaaaata ctatatataa tgcttttggt agggtctttt   1320
ctttatcatg tctcacttct gtttctatcc ctcattttaa atagccaata taatttcact   1380
ctttactata aaattattat ataaacatca ttttgattga actacctaaa aggaagaaac   1440
gtataggaat ttttggagcc tcaagattgt aataatgtct catagtttga cttgcaaaac   1500
ctaaattaaa cgcctaaatc attaccatta aataaatgaa cttttgtacg caattgattc   1560
agacacaagg accgaccaat tcgaaaacaa tgaatggata tgattcatcc ttatgaaagc   1620
ttgacaacag actcggtttt ggctggttaa cctagactcg gtttatttaa accagacaat   1680
aatttctttc gtcgtcgttt tatttgaata ggtgcgtcaa aaataaaagc tgaaattctt   1740
ggttgcaaaa gcccaacagg cctgtggaga tagcttttta gattgattaa atgggccgaa   1800
ttgggctgac acatgacgag aatgtggcta tagaaattgt tagtgagagg gtccgggtcc   1860
aaaaatgttg cagaagtgat atagtattta tttaattaaa aacatattat tcgacgtatt   1920
tttaacgctc actggattta taagtagaga ttttttgtgt ctcacaaaaa caaaaaaatc   1980
```

```
atcgtgaaac gttcgaaggc cattttcttt ggacgaccat cggcgttaag gagagagctt   2040

agatctcgtg ccgtcgtgcg acgttgtttt ccggtacgtt tattcctgtt gattccttct   2100

ctgtctctct cgattcactg ctacttctgt ttggattcct ttcgcgcgat ctctggatcc   2160

atgcgttatt cattggctcg tcgttttcag atctgttgcg tttcttctgt tttctgttat   2220

gagtggatgc gttttcttgt gattcgcttg tttgtaatgc tggatctgta tctgcgtcgt   2280

gggaattcaa agtgatagta gttgatattt tttccagatc gggcatgttc tcgtataatc   2340

aggtctaatg gttgatgatt ctgcggaatt atagatctaa gatcttgatt gatttagatt   2400

tgaggatatg aatgagattc gtaggtccac aaaggtcttg ttatctctgc tgctagatag   2460

atgattatcc aattgcgttt cgtagttatt tttagggatt caaggaattg cgtgtaattg   2520

agagttttac tctttttgtg aacaggcttg atcaaa                             2556
```

```
<210> SEQ ID NO 57
<211> LENGTH: 2557
<212> TYPE: DNA
<213> ORGANISM: Arabidopsis thaliana
<220> FEATURE:
<221> NAME/KEY: promoter
<222> LOCATION: (1)..(2557)
<223> OTHER INFORMATION: promoter of gene At2g47170

<400> SEQUENCE: 57
```

```
tcgagataat tgagagatcg aggaaaacaa aaaatattat aaacatatct attaagcaaa     60

aaaaacttta agtgagaaaa gacaaaaacc aactgtgtat aaagccgaaa cagatgatgg    120

gtccataaaa ggccgaacct ccacttctat tttctgtata taactacgat ttattcccat    180

aataacaaaa aattaaacca tctctcaaag tggtaggtca gtttccttca tcatttcaca    240

ttttcttcta tttgacaccc ttcacttcaa caacacttca cattgttgtt atatgacctt    300

tctgtcacca catcattggt agagagagtt actgctatat atcatgtact atatagattt    360

ctaattaaaa ccaattaaca gttaatatgt agatttactc gtcccgtatg ttatttttaa    420

gttttatcac actttcgcct taacatttga ttaagtaatg atatcataaa ggatttctga    480

ttgaattcag taacaagacg gatccttcat tatgcatgta tatttatcag atatcaagaa    540

tattattcaa cgttataagt atatcgaaat tcagagtcag aatatggtat ttaattagcg    600

atctcaagta catgtacgac tataattcca tacaagtaca ttagatgaaa cggctacata    660

tgcaacaagc gtcgagcgag atcagcactc gtgtaaactt taaggagtaa aatgtcatgt    720

gcaacctttg accggtttaa ttctacaatt ttaataaata tttaaaatgt ttaaatatat    780

atgcaaacta aaaaaaaaaa agtaattgat tagcttaatt tgaaacgacg tctccttaac    840

gtttgtgctt tgtttgttaa tgcgtctgaa tctctttacg cataatgcat tacggatata    900

aggaattctg acattatttg atatccgaaa gtttcatata aattccatat atgattgtta    960

gcttttattt ccatgaaata gaaagatgga ctacatacct ttcaaactac tgtatttgaa   1020

gcttatgtca aaaatattta attaaaatat atgtaattta tatgttgatt gagttatgag   1080

tatcaagtaa aaaccctaat ccgttattaa aatatcaatg attataacgt atttataaac   1140

gaaaaaaaaa agaacatcta gaattttcga tatttgatcc tcaagttaaa cttggaaaaa   1200

tttggatgta tgaaatattt tgtcgtccac ttatacaata aagtatgaaa catggatgca   1260

tgaaggctag acatccaatg tctaaaaata ctatatataa tgcttttggt agggtctttt   1320

ctttatcatg tctcacttct gtttctatcc ctcattttaa atagccaata taatttcact   1380
```

-continued

```
ctttactata aaattattat ataaacatca ttttgattga actacctaaa aggaagaaac   1440

gtataggaat ttttggagcc tcaagattgt aataatgtct catagtttga cttgcaaaag   1500

ctaaattaaa cgcctaaatc attaccatta aataaatgaa cttttgtacg caattgattc   1560

agacacaagg accgaccaat tcgaaaacaa tgaatggata tgattcatcc ttatgaaagc   1620

ttgacaacaa actcggtttt ggctggttaa cctagactcg gtttatttaa accagacaat   1680

aatttctttc gtcgtcgttt tatttgaata ggtgcgtcaa aaataaaagc tgaaattctt   1740

ggttgcaaaa gcccaacagg cctgtggaga tagcttttta gattgattaa atgggccgaa   1800

ttgggctgac acatgacgag aatgtggcta tagaaattgt tagtgagagg gtccgggtcc   1860

aaaaatgttg cagaagtgat atagtattta tttaattaaa aacatattat tcgacgtatt   1920

tttaacgctc actggattta taagtagaga tttttttgtgt ctcacaaaaa caaaaaaatc   1980

atcgtgaaac gttcgaaggc cattttcttt ggacgaccat cggcgttaag gagagagctt   2040

agatctcgtg ccgtcgtgcg acgttgtttt ccggtacgtt tattcctgtt gattccttct   2100

ctgtctctct cgattcactg ctacttctgt ttggattcct ttcgcgcgat ctctggatcc   2160

gtgcgttatt cattggctcg tcgttttcag atctgttgcg tttcttctgt tttctgttat   2220

gagtggatgc gttttcttgt gattcgcttg tttgtaatgc tggatctgta tctgcgtcgt   2280

gggaattcaa agtgatagta gttgatattt tttccagatc aggcatgttc tcgtataatc   2340

aggtctaatg gttgatgatt ctgcggaatt atagatctaa gatcttgatt gatttagatt   2400

tgaggatatg aatgagattc gtaggtccac aaaggtcttg ttatctctgc tgctagatag   2460

atgattatcc aattgcgttt cgtagttatt tttatggatt caaggaattg cgtgtaattg   2520

agagttttac tctgttttgt gaacaggctt gatcaaa                            2557
```

<210> SEQ ID NO 58
<211> LENGTH: 995
<212> TYPE: DNA
<213> ORGANISM: Arabidopsis thaliana
<220> FEATURE:
<221> NAME/KEY: CDS
<222> LOCATION: (168)..(710)
<223> OTHER INFORMATION: coding for ADP-ribosylation factor 1 (ARF1)
(At2g47170)

<400> SEQUENCE: 58

```
atttttaacg ctcactggat ttataagtag agattttttg tgtctcacaa aaacaaaaaa     60

atcatcgtga aacgttcgaa ggccattttc tttggacgac catcggcgtt aaggagagag    120

cttagatctc gtgccgtcgt gcgacgttgt tttccggctt gatcaaa atg ggg ttg      176
                                                    Met Gly Leu
                                                    1

tca ttc gga aag ttg ttc agc agg ctc ttt gcg aag aaa gag atg cgt      224
Ser Phe Gly Lys Leu Phe Ser Arg Leu Phe Ala Lys Lys Glu Met Arg
    5                   10                  15

att ctg atg gtt ggt ctc gat gct gct ggt aag acg act atc ctc tac      272
Ile Leu Met Val Gly Leu Asp Ala Ala Gly Lys Thr Thr Ile Leu Tyr
20                  25                  30                  35

aag ctc aaa ctt gga gag atc gtc acc act att cca acc att ggg ttc      320
Lys Leu Lys Leu Gly Glu Ile Val Thr Thr Ile Pro Thr Ile Gly Phe
                40                  45                  50

aac gtt gag act gtt gaa tac aag aac atc agc ttc acc gtg tgg gat      368
Asn Val Glu Thr Val Glu Tyr Lys Asn Ile Ser Phe Thr Val Trp Asp
            55                  60                  65

gtt ggg ggt caa gac aag atc cgt cca ttg tgg aga cat tac ttc cag      416
Val Gly Gly Gln Asp Lys Ile Arg Pro Leu Trp Arg His Tyr Phe Gln
```

-continued

```
        70                  75                  80

aac aca cag gga ctt atc ttt gtt gtg gac agc aat gat cgt gac cgt      464
Asn Thr Gln Gly Leu Ile Phe Val Val Asp Ser Asn Asp Arg Asp Arg
    85                  90                  95

gtt gtt gaa gcc agg gac gag ctt cac agg atg ctg aat gag gat gaa      512
Val Val Glu Ala Arg Asp Glu Leu His Arg Met Leu Asn Glu Asp Glu
100                 105                 110                 115

ttg agg gat gca gtt ctg ctt gta ttt gct aac aag caa gat ctt ccc      560
Leu Arg Asp Ala Val Leu Leu Val Phe Ala Asn Lys Gln Asp Leu Pro
                120                 125                 130

aac gcg atg aac gct gct gag ata act gac aag ctt ggg ctt cat tct      608
Asn Ala Met Asn Ala Ala Glu Ile Thr Asp Lys Leu Gly Leu His Ser
            135                 140                 145

ctt cgt caa cga cac tgg tac att cag agc aca tgt gcc acc tct gga      656
Leu Arg Gln Arg His Trp Tyr Ile Gln Ser Thr Cys Ala Thr Ser Gly
        150                 155                 160

gaa gga ctc tat gag gga ctt gac tgg ctc tcc aac aac atc gca agc      704
Glu Gly Leu Tyr Glu Gly Leu Asp Trp Leu Ser Asn Asn Ile Ala Ser
    165                 170                 175

aag gca tagatggaat gttagccaga ttcctcttct gcttgtttgg tttacaaatc       760
Lys Ala
180

aaagacagag gtctgtttct ctagtactaa aagatttatt attatattct tcttcgtcac    820

ttatctcaaa cgcagatcat tttacacttt gtacttcccc ttcaataact tgttacttct    880

ctcgtttgct tcctgaattt gagtatatca tttttacatc tgcttttcat caaagcataa    940

agcatctttc gaaacaaaaa ttgaaccgaa tttttctgta aactgatcaa atgtg         995


<210> SEQ ID NO 59
<211> LENGTH: 181
<212> TYPE: PRT
<213> ORGANISM: Arabidopsis thaliana

<400> SEQUENCE: 59

Met Gly Leu Ser Phe Gly Lys Leu Phe Ser Arg Leu Phe Ala Lys Lys
1               5                   10                  15

Glu Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Ser Phe Thr
    50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                85                  90                  95

Arg Asp Arg Val Val Glu Ala Arg Asp Glu Leu His Arg Met Leu Asn
            100                 105                 110

Glu Asp Glu Leu Arg Asp Ala Val Leu Leu Val Phe Ala Asn Lys Gln
        115                 120                 125

Asp Leu Pro Asn Ala Met Asn Ala Ala Glu Ile Thr Asp Lys Leu Gly
    130                 135                 140

Leu His Ser Leu Arg Gln Arg His Trp Tyr Ile Gln Ser Thr Cys Ala
145                 150                 155                 160

Thr Ser Gly Glu Gly Leu Tyr Glu Gly Leu Asp Trp Leu Ser Asn Asn
                165                 170                 175
```

```
Ile Ala Ser Lys Ala
            180


<210> SEQ ID NO 60
<211> LENGTH: 2224
<212> TYPE: DNA
<213> ORGANISM: Arabidopsis thaliana
<220> FEATURE:
<221> NAME/KEY: promoter
<222> LOCATION: (1)..(2224)
<223> OTHER INFORMATION: promoter of gene At1g64090

<400> SEQUENCE: 60

cgttttacaa acaaagctat gctgaaagaa aataaaccac aaccaccaaa agaaaaaaaa     60

aagctttgga tactgttttt gtatgtattt aaaaattgaa gttattcaca ataaaacaaa    120

ttttattttg ttataaattt gtatataatt ttgtaaattc attttgtttt gccttgtttt    180

aacaaagaag cagaggcaaa taagaaaaaa cgtggcaaac agtcgcgttg cgttgctaag    240

cgtagggagc agctgagtca cgtgactttc agacggagac agtcagacca aaaggtcaga    300

gatcattaaa gtatttatat acgtactctt ttattttcta catagtacac ataaataata    360

gtgatacttt ttggcactac tttgaaccaa agaaaatctt gcatttgaaa cacaaataag    420

tgcaattttg ttttatgttt acgagattat gttacataat attatactac taagtagtaa    480

tatattaatc atatgggaat cgacaaaatt gatggtgtcg cctacaaagc atttaaaaaa    540

actaaactga ttctgaaaga atctggataa tgtttaatat tactactact tgtaaaaaat    600

atgcacaata tatgtgtaaa gtttgtagtt ccgagacgta ttattaacat catcattatt    660

tgccaaaaaa tttcagaccg taagattcaa tggatgtaga ccccaaagtc ccattatcac    720

ccttctttaa tgggcctcat caagttccca aaatcagtaa agatgatggg ccctttacac    780

tgtacatgtg tacgtgattt cgtatgatcc atttatttat ttattaatcc tttttttcta    840

ttccatttaa tttcttaatc caattcatgg attcatactg caatcatgta taattcttat    900

attagtgttt ctgaaaataa gtttatagag cttgagttgg taaacaaatg aatgggacac    960

actctcgtca aaataaaaca aaaatttctt tctttctcct cattaattcg ctttatctaa   1020

aattcaaaag ggcaaagcac tttcaaaagc aagtcaaaga agctagtcac tcgttgtttg   1080

ataggcttcc ccgaaattca gctttagtgg acttcctcca aaatataaag aagctattac   1140

gtttttggtt gagattgata cactaatagc ataatgtata agttttaaaa tgaatttgga   1200

tgagagtgat cccatatttt gactccaacg aatttaacaa atcttataat ttactggtaa   1260

aagaaaaacg cttcattgca tttgcagctt agctatttcc gtcaaactca atgattaagt   1320

taattatata ttttaactaa atgtcgatcc caaatcattt cagatagtta tacaatatgt   1380

tctctttatc ctattgatca cgagaagaat attactaccc taagaaaatc tgatcttgtc   1440

gggctaattg tttggcatga tggcgcaata gtaagcccta gagatttgat ttggctaggt   1500

ggtagctaca tactttttta gttaaattcg aatgtgtata taatatcgtt tcaaatgata   1560

tggattatgg tccgaaaaca cacatttaaa tgcacagtgg gttatagaaa aatcaaggaa   1620

acaaccagcc aatgtgatta gaccaataac cagaatatga ttttgtctta catgactaac   1680

aataaatatg atgagtatgc caggcagaaa gcataaatat atagcatcac aaaataaata   1740

acatattgtg ttctagtgac aaaattaata ctaaatctat attactttta tattttagac   1800

ttaaatctat atttgtcaaa aaaaaaaaaa aaaaaaagct gttattttta taacttcact   1860

taacctattg ggctttccct caagtttctt attggcccaa ataaaatctc atcatagtat   1920
```

-continued

```
cgtctattct atgatcccta taaacaaatt tcccttaaat ttcatacgac gtcgtagtca   1980

agcatctacc ttctcgacga cgacgacgtg ctgaccccat tgaacgctac actaacggag   2040

acgttaatta agaattcgtc gtctgtcttc cgtctcaaag atgttactgt tatttaatga   2100

ttttcttaga aagtaagcta ttaattccca acggccaaga ttgagttaaa taaatcgacg   2160

ggtgagattg aatctgtatc aaacgctctt atttagagag aggtatgact gaaagagact   2220

tttc                                                                 2224
```

<210> SEQ ID NO 61
<211> LENGTH: 2303
<212> TYPE: DNA
<213> ORGANISM: Arabidopsis thaliana
<220> FEATURE:
<221> NAME/KEY: promoter
<222> LOCATION: (1)..(2303)
<223> OTHER INFORMATION: promoter of gene At1g64090

<400> SEQUENCE: 61

```
cgttttacaa acaaagctat gctgaaagaa aataaaccac aaccaccaaa agaaaaaaaa     60

aagctttgga tactgttttt gtatgtattt aaaaattgaa gttattcaca ataaaacaaa    120

ttttattttg ttataaattt gtatataatt ttgtaaattc attttgtttt gccttgtttt    180

aacaaagaag cagaggcaaa taagaaaaaa cgtggcaaac agtcgcgttg cgttgctaag    240

cgtagggagc agctgagtca cgtgactttc agacggagac agtcagacca aaaggtcaga    300

gatcattaaa gtatttatat acgtactctt ttattttcta catagtacac ataaataata    360

gtgatacttt ttggcactac tttgaaccaa agaaaatctt gcatttgaaa cacaaataag    420

tgcaattttg ttttatgttt acgagattat gttacataat attatactac taagtagtaa    480

tatattaatc atatgggaat cgacaaaatt gatggtgtcg cctacaaagc atttaaaaaa    540

actaaactga ttctgaaaga atctggataa tgtttaatat tactactact tgtaaaaaat    600

atgcacaata tatgtgtaaa gtttgtagtt ccgagacgta ttattaacat catcattatt    660

tgccaaaaaa tttcagaccg taagattcaa tggatgtaga ccccaaagtc ccattatcac    720

ccttctttaa tgggcctcat caagttccca aaatcagtaa agatgatggg ccctttacac    780

tgtacatgtg tacgtgattt cgtatgatcc atttatttat ttattaatcc tttttttcta    840

ttccatttaa tttcttaatc caattcatgg attcatactg caatcatgta taattcttat    900

attagtgttt ctgaaaataa gtttatagag cttgagttgg taaacaaatg aatgggacac    960

actctcgtca aaataaaaca aaaatttctt tctttctcct cattaattcg ctttatctaa   1020

aattcaaaag ggcaaagcac tttcaaaagc aagtcaaaga agctagtcac tcgttgtttg   1080

ataggcttcc ccgaaattca gctttagtgg acttcctcca aaatataaag aagctattac   1140

gtttttggtt gagattgata cactaatagc ataatgtata agttttaaaa tgaatttgga   1200

tgagagtgat cccatatttt gactccaacg aatttaacaa atcttataat ttactggtaa   1260

aagaaaaacg cttcattgca tttgcagctt agctatttcc gtcaaactca atgattaagt   1320

taattatata ttttaactaa atgtcgatcc caaatcattt cagatagtta tacaatatgt   1380

tctctttatc ctattgatca cgagaagaat attactaccc taagaaaatc tgatcttgtc   1440

gggctaattg tttggcatga tggcgcaata gtaagcccta gagatttgat ttggctaggt   1500

ggtagctaca tactttttta gttaaattcg aatgtgtata taatatcgtt tcaaatgata   1560

tggattatgg tccgaaaaca cacatttaaa tgcacagtgg gttatagaaa aatcaaggaa   1620

acaaccagcc aatgtgatta gaccaataac cagaatatga ttttgtctta catgactaac   1680
```

```
aataaatatg atgagtatgc caggcagaaa gcataaatat atagcatcac aaaataaata   1740

acatattgtg ttctagtgac aaaattaata ctaaatctat attactttta tattttagac   1800

ttaaatctat atttgtcaaa aaaaaaaaaa aaaaaaagct gttattttta taacttcact   1860

taacctattg ggctttccct caagtttctt attggcccaa ataaaatctc atcatagtat   1920

cgtctattct atgatcccta taaacaaatt tcccttaaat ttcatacgac gtcgtagtca   1980

agcatctacc ttctcgacga cgacgacgtg ctgaccccat tgaacgctac actaacggag   2040

acgttaatta agaattcgtc gtctgtcttc cgtctcaaag atgttactgt tatttaatga   2100

ttttcttaga aagtaagcta ttaattccca acggccaaga ttgagttaaa taaatcgacg   2160

ggtgagattg aatctgtatc aaacgctctt atttagagag aggtatgact gaaagagact   2220

tttcgttttc ttctccgttt ctcgctcatc gcttactgaa atcagaaaca agtttagggt   2280

ttttgcggag gtttcaaagt taa                                           2303
```

<210> SEQ ID NO 62
<211> LENGTH: 2297
<212> TYPE: DNA
<213> ORGANISM: Arabidopsis thaliana
<220> FEATURE:
<221> NAME/KEY: promoter
<222> LOCATION: (1)..(2297)
<223> OTHER INFORMATION: promoter of gene At1g64090

<400> SEQUENCE: 62

```
cgttttacaa acaaagctat ggctgaaaga aaataaacca caaccacaaa aagaaaaaaa     60

aaagctttgg atactgtttt tgtatgtatt taaaaattga aattattcac aataaaacaa    120

attttatttt gttataaatt tgtaaattca ttttgttttg ccatgtttta acaaaagaag    180

cagaggcaaa taagaaaaaa cgtggcaaag agttgcgttg cgttgcgttg ctaagcgtag    240

ggagcagctg agtcacgtga ctttcagact gagacagtca gaccaaaagg tcagagatca    300

ttaaagtatt tatatacgta ctcttttatt ttctacatag tacacataaa taatagtgat    360

actttttggc actactttga accaaagaaa atcttgcatt tgaaacacaa attagtgcaa    420

ttttgtttta tgtttacgag attatgttac ataatattat actactaagt agtaatatat    480

taatcatatg ggaatcgaca aaattgatgg tgtcgcctac aaagcattta aaaaaactaa    540

actgattctg aaagaatctg gataatgttt aatattacta ctacttgtaa aaaatatgca    600

caatatatgt gtaaagtttg tagttccgag acgtattatt aacatcatca ttatttgcca    660

aaaaatttca ggccgtcaga ttcaatggat gtagacccca aagtcccatt atcacccttc    720

tttaatgggc ctcatcaagt tcccaaaatc agtaaagatg atgggccctt tacactgtac    780

atgtgtacgt gatttcgtat gatccattta tttatttatt aatccttttt ttctattcca    840

tttaatttct taatccaatt catggattca tactgcaatc atgtataatt cttatattag    900

tgtttctgaa aataagttta tagagcttga gttggtaaac aaatgaatgg gacacactct    960

cgtcaaaata aaacaaaaat ttctttcttt ctcctcatta attcgcttta tctaaaattc   1020

aaaagggcaa agcactttca aaagcaagtc aaagaagcta gtcactcgtt gtttgatagg   1080

cttccccgaa attcagcttt agtggacttc ctccaaaata taaagaagct attacgtttt   1140

tggttgagat tgatacacta atagcataat gtataagttt taaaatgaat ttggatgaga   1200

gtgatccata ttttgactcc aacgaattta acaaatctta taatttactg gtaaaagaaa   1260

aacgcttcat tgcatttgca gcttagctat ttccgtcaaa ctcaatgatt aagttaatta   1320
```

-continued

```
tatattttaa ctaaacgtcg atcccaaatc atttcagata gttatacaat atgttctctt   1380

tatcctattg atcacgagaa gaatattact accctaagaa aatctgatct tgtcgggcta   1440

attgtttggc atgatggcgc aatagtaagc cctagagatt tgatttggct aggtggtagc   1500

tacatacttt tttagttaaa ttcgaatgtg tatataatat cgtttcaaat gatatggatt   1560

atggtccgaa aacacacatt taaatgcaca gtgggttata gaaaaatcaa ggaaacaacc   1620

agccaatgtg attagaccaa taaccagaat atgattttgt cttacatgac taacaataaa   1680

tatgatgagt atgccaggca gaaagcataa atatatagca tcacaaaata aataacatat   1740

tgtgttctag tgacaaaatt aatactaaat ctatattatt tttatatttt agacttaaat   1800

ctatatttgt caaaaaaaaa aaaaaaaaaa agctgttatt tttataactt cacttaacct   1860

attgggcttt ccctcaagtt tcttattggc ccaaataaaa tctcatcata gcatcgtcta   1920

ttctatgatc cctataaaca aatttccctt aaatttcata cgacgtcgta gtcaagcatc   1980

taccttctcg acgacgacga cgtgctgacc ccattgaacg ctacactaac ggagacgtta   2040

attaagaatt cgtcgtctgt cttccgtctc aaagatgtta ctgttattta atgattttct   2100

tagaaagtaa gctattaatt cccaacggcc aagattgagt taaataaatc gacgggtgag   2160

attgaatctg tatcaaacgc tcttatttag agagaggtat gactgaaaga gacttttcgt   2220

tttcttctcc gtttctcgct catcgcttac tgaaaccaga aacaagttta gggtttttgc   2280

ggaggtttca aagttaa                                                  2297


<210> SEQ ID NO 63
<211> LENGTH: 1102
<212> TYPE: DNA
<213> ORGANISM: Arabidopsis thaliana
<220> FEATURE:
<221> NAME/KEY: CDS
<222> LOCATION: (82)..(846)
<223> OTHER INFORMATION: coding for reticulon family protein (RTNLB3)
      (At1g64090)

<400> SEQUENCE: 63

gttttcttct ccgtttctcg ctcatcgctt actgaaacca gaaacaagtt tagggttttt     60

gcggaggttt caaagttaac a atg gcg gaa gag cac aag cac gag gaa tcg      111
                        Met Ala Glu Glu His Lys His Glu Glu Ser
                        1               5                   10

atc atg gag aag atc tct gag aag atc cat ggt cac gat gac tct tct      159
Ile Met Glu Lys Ile Ser Glu Lys Ile His Gly His Asp Asp Ser Ser
                15                  20                  25

tct tct tct tcc gat tcg gat gac gat aag aac tct gcg tct ctc aaa      207
Ser Ser Ser Ser Asp Ser Asp Asp Asp Lys Asn Ser Ala Ser Leu Lys
            30                  35                  40

acc aag att tat cgt ctt ttc gga aga gaa cag cct ctt cac aag ctt      255
Thr Lys Ile Tyr Arg Leu Phe Gly Arg Glu Gln Pro Leu His Lys Leu
        45                  50                  55

ttc ggt ggc gga aaa cct gcc gac att ttc ctg tgg agg aac aag aag      303
Phe Gly Gly Gly Lys Pro Ala Asp Ile Phe Leu Trp Arg Asn Lys Lys
    60                  65                  70

gta tca gga gga gta ttg ggt gct gca act gtt tcc tgg atc tta ttc      351
Val Ser Gly Gly Val Leu Gly Ala Ala Thr Val Ser Trp Ile Leu Phe
75                  80                  85                  90

gag tta ctt gag tac aat ctt ctc aca ctc ttc ggc cac att tca att      399
Glu Leu Leu Glu Tyr Asn Leu Leu Thr Leu Phe Gly His Ile Ser Ile
                95                  100                 105

ctt gct ctc gca gta ttg ttc ttg tgg tct agt gct agt acc ttc att      447
Leu Ala Leu Ala Val Leu Phe Leu Trp Ser Ser Ala Ser Thr Phe Ile
```

-continued

```
            110                 115                 120

cac aag tca cct ctt cat atc cct gaa gtt cac atc ccc gag gat gtt      495
His Lys Ser Pro Leu His Ile Pro Glu Val His Ile Pro Glu Asp Val
        125                 130                 135

gtt ctt cag ctt gct tct gga tta agg att gaa atc aat cgt gga ttt      543
Val Leu Gln Leu Ala Ser Gly Leu Arg Ile Glu Ile Asn Arg Gly Phe
    140                 145                 150

act gtt ctt agg gac att gca tca gga aga gat ctt aag aag ttt ctg      591
Thr Val Leu Arg Asp Ile Ala Ser Gly Arg Asp Leu Lys Lys Phe Leu
155                 160                 165                 170

ttg gtg att gct ggt tta tgg gtt ttg tcc aaa gtt ggt agc tcc tgc      639
Leu Val Ile Ala Gly Leu Trp Val Leu Ser Lys Val Gly Ser Ser Cys
                175                 180                 185

aac ttc ttg acc tta atc tac atc gca act gta ctt ctc ttc acg att      687
Asn Phe Leu Thr Leu Ile Tyr Ile Ala Thr Val Leu Leu Phe Thr Ile
            190                 195                 200

ccc gtg ctt tac gag aag tat gaa gat aaa gta gat gac ttt ggt gaa      735
Pro Val Leu Tyr Glu Lys Tyr Glu Asp Lys Val Asp Asp Phe Gly Glu
        205                 210                 215

aag gcg atg agg gag atc aag aag caa tac gtg gag ttc gac gtg aag      783
Lys Ala Met Arg Glu Ile Lys Lys Gln Tyr Val Glu Phe Asp Val Lys
    220                 225                 230

gtt ttg agt aag gtg atg agc aaa att cct aaa gga gcc ttt gcc ttt      831
Val Leu Ser Lys Val Met Ser Lys Ile Pro Lys Gly Ala Phe Ala Phe
235                 240                 245                 250

atc aag aag aaa gat tagagagtgt gtaagtttct ctcatcatca ttatccgaga      886
Ile Lys Lys Lys Asp
                255

ttattcaaga ttgatatata aatctcgaag cattgttttt ttggctgttg gttaataacc    946

ctttattctc tcaaatatct gctatatgga ttttattcgg gttttaacca aattttatag   1006

caatattgaa tctgattgaa atttgaattg atccttttt cggataccat ggtcgtcatg   1066

aatgttatta tgataaatct ttaaatattc cgaact                             1102


<210> SEQ ID NO 64
<211> LENGTH: 255
<212> TYPE: PRT
<213> ORGANISM: Arabidopsis thaliana

<400> SEQUENCE: 64

Met Ala Glu Glu His Lys His Glu Glu Ser Ile Met Glu Lys Ile Ser
1               5                   10                  15

Glu Lys Ile His Gly His Asp Asp Ser Ser Ser Ser Ser Ser Asp Ser
            20                  25                  30

Asp Asp Asp Lys Asn Ser Ala Ser Leu Lys Thr Lys Ile Tyr Arg Leu
        35                  40                  45

Phe Gly Arg Glu Gln Pro Leu His Lys Leu Phe Gly Gly Gly Lys Pro
    50                  55                  60

Ala Asp Ile Phe Leu Trp Arg Asn Lys Lys Val Ser Gly Gly Val Leu
65                  70                  75                  80

Gly Ala Ala Thr Val Ser Trp Ile Leu Phe Glu Leu Leu Glu Tyr Asn
                85                  90                  95

Leu Leu Thr Leu Phe Gly His Ile Ser Ile Leu Ala Leu Ala Val Leu
            100                 105                 110

Phe Leu Trp Ser Ser Ala Ser Thr Phe Ile His Lys Ser Pro Leu His
        115                 120                 125

Ile Pro Glu Val His Ile Pro Glu Asp Val Val Leu Gln Leu Ala Ser
```

```
    130                 135                 140

Gly Leu Arg Ile Glu Ile Asn Arg Gly Phe Thr Val Leu Arg Asp Ile
145                 150                 155                 160

Ala Ser Gly Arg Asp Leu Lys Lys Phe Leu Leu Val Ile Ala Gly Leu
                165                 170                 175

Trp Val Leu Ser Lys Val Gly Ser Ser Cys Asn Phe Leu Thr Leu Ile
            180                 185                 190

Tyr Ile Ala Thr Val Leu Leu Phe Thr Ile Pro Val Leu Tyr Glu Lys
        195                 200                 205

Tyr Glu Asp Lys Val Asp Asp Phe Gly Glu Lys Ala Met Arg Glu Ile
    210                 215                 220

Lys Lys Gln Tyr Val Glu Phe Asp Val Lys Val Leu Ser Lys Val Met
225                 230                 235                 240

Ser Lys Ile Pro Lys Gly Ala Phe Ala Phe Ile Lys Lys Lys Asp
                245                 250                 255


<210> SEQ ID NO 65
<211> LENGTH: 2671
<212> TYPE: DNA
<213> ORGANISM: Arabidopsis thaliana
<220> FEATURE:
<221> NAME/KEY: promoter
<222> LOCATION: (1)..(2671)
<223> OTHER INFORMATION: promoter of gene At5g60690

<400> SEQUENCE: 65

gagcaaccat cttcctttgt aaatttgacc cttttgtgta tcatttatat cgagtgtttg      60

taattgttgg ttgattttgt gttatttgag aggctagtca tttacgcaat ttctaaattt     120

atcttttagt acgtatcaag atgttggagc aactgtgtcc aacatacatg acatgtgaaa     180

ttataattgt taaaacaaaa ggacatgtga aattactatc tacttaaaga aaaaaaccag     240

aaagaaaaaa aggtattaaa tttggaacta aaagaaggtt aaaaagtttt tttacagaaa     300

gtaattacac ttgcagatga aagaaaaagg cagcatcatg atatgtaaaa aattgtcgaa     360

gaggtttagt cgtatcactt tgtttgactg atcactgtct tctgattcat ttttcagttt     420

ttctttttga aattgtagct cacaacatta aagttattca ctgctttaat cagatagttt     480

aatactagta actagctcat ttaggcttta aacacctctt tctgattact agcccactct     540

ttggtggttc ttacatatca cacctaacta aactgtgtat ccttgaagtg aaaatcaaat     600

ttaccattcg tatcttactt acatacacta ttatttttcc tttttttttc actcaaggtc     660

ctactctttg ataccatagc tataatttgg aaataactat ttacagtgta ttaattatac     720

ctaaacagtt taatctggac taaatattta gatagatgtt acaaatttgg ttcgtctaat     780

aaatgaagac aagacatgct aacaaataaa acactaccac aaagggatag tgagagaatg     840

tgttttgcaa caagacataa ctttgattgc ttgatgtgtt aaaatgatta tgtcagagac     900

agagagcgat cataggcttt ctttatttct aataacgtcg attttcttct tcttttctgg     960

cgttcaataa tgtcgaattt taattcttga tttttgcaac tctaaatatc cttaacgaca    1020

ttgaagcatg gtgcatgtcg atcgttaata ataaagttga acaaaaatct tgttgaatta    1080

attacaagca cagcttcaat agcataactt tacgagacga ccagatctta tagacgagtt    1140

tcgcttttac ttttttaatg attaaaactt tcatcggaga acataagtct tcctcttaat    1200

taaaattact acccgtgcat aacttcattt tttaaaacat caataattaa tatacgatta    1260

caaccctaaa aattagtcac cctatagtac ataacaatga tgatagtttt ttctttttgg    1320
```

-continued

```
tgtaatgtta aaataaaatg ttaaccatat taaacgatag ttcttataac ttagccattg   1380

taagatattt cttactttag ttttttctat ccattgtaag atatttctta ctttagtttt   1440

tccgtagaag atattcatta tggtatggat agtatatacc ttaactgagt ttaaatattg   1500

gatcaatacc atctaataac acatatctga tgttcaatac ttaataattt tgcataaatg   1560

ttaagcgtga caacttaaaa aaaaacacat caacagagta aaaacatatc cgttaaatta   1620

gaaaaatgac atttttataa cacttaaaaa aaaatgcatg aaacgtttca tagttttttt   1680

tttttcaaag taatgtaggc gttagatatt tcttacaatt tttgattttt tttttctatg   1740

ttgtgattgg ctgatatcag gtaactaaaa cttatttaaa gaaatgaaga aaatttacaa   1800

agtaaataaa tggattccta tattgtcatt tcagaaaaac agtagggaca acttcgtaaa   1860

tgatagccgt attattaaac aaataaattt aaattagaaa aaaggaaaaa aacgcaccac   1920

ttttcttttt cgctgatgca cagcttgtcg gtttgcgtgc aaatcctctg tttcacaatt   1980

ttttcttctt ctctttctct ctcttcctct tttattcctc tgttccaaag ttcagcagaa   2040

gcaaacacac acatcactta ctatctctct ctccttcttc actttctcac ataaccaaac   2100

tctctctttc tctcttttttt ttgaagtctc ctttgaaact ataattgccc tttagtgttg   2160

tttgttcaga gtcttcaaaa cttttgcagc ttcaattgta cctgggtttc ttcttcattg   2220

ttcctaaggt ttctgtgtcc ttcaattctt ctgatataat gcttctttaa gagagttgac   2280

atcatcactt tcttggggta ctcttctctg tttctcccca gaaaatccaa ctctgtaatt   2340

ttgggtcttt attctgtttt tctctttgaa gaatctttaa aattctcaga tcttctgaat   2400

ctctcttctt taaaactttt tttaacttta ttttttgtac tcgcttcttt gccttcattt   2460

ttctcgtatc cacatgtcgt tggtctttcg ctacaagcca cgaccgtaga atcttctttt   2520

gtctgaaaag aattacaatt tacgtttctc ttacgatacg acggactttc cgaagaaatt   2580

aatttaaaga gaaaagaaga agaagccaaa gaagaagaag aagctagaag aaacagtaaa   2640

gtttgagact ttttttgagg gtcgagctaa a                                  2671


<210> SEQ ID NO 66
<211> LENGTH: 2644
<212> TYPE: DNA
<213> ORGANISM: Arabidopsis thaliana
<220> FEATURE:
<221> NAME/KEY: promoter
<222> LOCATION: (1)..(2644)
<223> OTHER INFORMATION: promoter of gene At5g60690

<400> SEQUENCE: 66

catgggagca accatcttcc tttgtaaatt tgaccctttt gtgtatcatt tatatcgagt     60

gtttgtaatt gttggttgat tttgtgttat ttgagaggct agtcatttac gcaatttcta    120

aatttatctt ttagtacgta tcaagatgtt ggagcaactg tgtccaacat acatgacatg    180

tgaaattata attgttaaaa caaaaggaca tgtgaaatta ctatctactt aaagaaaaaa    240

accagaaaga aaaaaaggta ttaaatttgg aactaaaaga aggttaaaaa gttttttaca    300

gaaagtaatt acacttgcag atgaaagaaa aaaggcagca tcatgatatg taaaaaattg    360

tcgaagaggt ttagtcgtat cactttgttt gactgatcac tgtcttctga ttcatttttc    420

agtttttctt tttcaaattg tagctcacaa cattaaagtt attcactgct ttaatcagat    480

agtttaatac tagtaactag ctcatttagg ctttaaacac ctctttctga ttactagccc    540

actctttggt ggttcttaca tatcacacct aactatactg tgtatccttg aagtgaaaat    600

caaatttacc attcgtatct tacttacata cactattatt tttcctttttt tttttcactc    660
```

-continued

```
aaggtcctac tctttgatac catagctata atttggaaat aactatttac agtgtattaa    720
ttatacctaa acagtttaat ctggactaaa tatttagata gatgttacaa atttggttcg    780
tctaataaat gaagacaaga catgctaaca aataaaacac taccacaaag ggatagtgag    840
agaatgtgtt ttgcaacaag acataacttt gattgcttga tgtgttaaaa tgattatgtc    900
agagacagag agcgatcata ggctttcttt atttctaata acgtcgattt tcttcttctt    960
ttctggcgtt caataatgtc gaattttaat tcttgatttt tgcaactcta aatatcctta   1020
acgacattga agcatggtgc atgtcgatcg ttaataataa agttgaacaa aaatcttgtt   1080
gaattaatta caagcacagc ttcaatagca taactttacg agacgaccag atcttataga   1140
cgagtttcgc ttttactttt ttaatgatta aaactttcat cggagaacat aagtcttcct   1200
cttaattaaa attactaccc gtgcataact tcattttta aaacatcaat aattaatata   1260
cgattacaac cctaaaaatt agtcacccta tagtacataa caatgatgat agttttttct   1320
ttttggtgta atgttaaaat aaaatgttag ccatattaaa cgatagttct tttaacttag   1380
ccattgtaag atatttctta ctttagtttt tccgtagaag atattcatta tggtatggat   1440
agtatatacc ttaactgagt ttaaatattg gatcaatacc atctaataac acatatctga   1500
tgttcaatac ttaataattt tgcataaatg ttaagcgtga caacttaaaa aaaaacacat   1560
caacagagta aaaacatatc tgttaaataa gaaaaatgtc atttttataa cacttaaaaa   1620
aaaatgcatg aagcgtttca tagttttttt ttttttcaaa gtaatgtagg cgttagatat   1680
ttcttacaat tttttgaaaa atattttta tgttgtgatt ggctgatatc aggtaactaa   1740
aacttcttta aagaattgaa gaaaatttga aaagtaaata gatggattcc tatattgtca   1800
tttcagaaaa acagtaggga caacttcgta aatgatagcc gtattattaa acaaataaat   1860
ttaaattaga aaaaaggaaa aaaacgcacc acttttcttt ttcgctgatg cacagcttgt   1920
cggtttgcgt gcaaatcctc tgtttcacaa ttttttcttc ttctctttct ctctcttcct   1980
cttttattcc tctgttccaa agttcagcag aagcaaacac acacatcact tactatctct   2040
ctctccttct tcactttctc acataaccaa actctctctt tctctctttt ttttgaagtc   2100
tcctttgaaa ctataattgc cctttagtgt tgttcgttca gagtcttcaa aacttttgca   2160
gcttcaattg tacctgggtt tcttcttcat tgttcctaag gtttctgtgt ccttcaattc   2220
ttctgatata atgcttcttt aagagagttg acatcatcac tttcttgggg tactcttctc   2280
tgtttctccc cagaaaatcc aactctgtaa ttttgggtct ttattctgtt tttctctttg   2340
aagaatcttt aaaattctca gatcttctga atctctcttc tttaaaactt tttttaactt   2400
tattttttgt actcgcttct ttgccttcat ttttctcgta tccacatgtc gttggtcttt   2460
cgctacaagc cacgaccgta gaatcttctt ttgtctgaaa agaattacaa tttacgtttc   2520
tcttacgata cgacggactt tccgaagaaa ttaatttaaa gagaaaagaa gaagaagcca   2580
aagaagaaga agaagctaga agaaacagta aagtttgaga cttttttttga gggtcgagct   2640
aaac                                                                2644
```

```
<210> SEQ ID NO 67
<211> LENGTH: 3860
<212> TYPE: DNA
<213> ORGANISM: Arabidopsis thaliana
<220> FEATURE:
<221> NAME/KEY: CDS
<222> LOCATION: (712)..(3237)
<223> OTHER INFORMATION: coding for homeodomain-leucine zipper prote-in
      Revoluta (REV) / fascicular fiberless 1 (IFL1) (At5g60690)
```

```
<400> SEQUENCE: 67

aaatcctctg tttcacaatt ttttcttctt ctctttctct ctcttcctct tttattcctc      60

tgttccaaag ttcagcagaa gcaaacacac acatcactta ctatctctct ctccttcttc     120

actttctcac ataaccaaac tctctctttc tctctttttt ttgaagtctc ctttgaaact     180

ataattgccc tttagtgttg ttcgttcaga gtcttcaaaa cttttgcagc ttcaattgta     240

cctgggtttc ttcttcattg ttcctaaggt ttctgtgtcc ttcaattctt ctgatataat     300

gcttctttaa gagagttgac atcatcactt tcttggggta ctcttctctg tttctcccca     360

gaaaatccaa ctctgtaatt ttgggtcttt attctgtttt tctctttgaa gaatctttaa     420

aattctcaga tcttctgaat ctctcttctt taaaactttt tttaacttta ttttttgtac     480

tcgcttcttt gccttcattt ttctcgtatc cacatgtcgt tggtctttcg ctacaagcca     540

cgaccgtaga atcttctttt gtctgaaaag aattacaatt tacgtttctc ttacgatacg     600

acggactttc cgaagaaatt aatttaaaga gaaaagaaga agaagccaaa gaagaagaag     660

aagctagaag aaacagtaaa gtttgagact ttttttgagg gtcgagctaa a atg gag      717
                                                         Met Glu
                                                         1

atg gcg gtg gct aac cac cgt gag aga agc agt gac agt atg aat aga      765
Met Ala Val Ala Asn His Arg Glu Arg Ser Ser Asp Ser Met Asn Arg
        5                   10                  15

cat tta gat agt agc ggt aag tac gtt agg tac aca gct gag caa gtc      813
His Leu Asp Ser Ser Gly Lys Tyr Val Arg Tyr Thr Ala Glu Gln Val
    20                  25                  30

gag gct ctt gag cgt gtc tac gct gag tgt cct aag cct agc tct ctc      861
Glu Ala Leu Glu Arg Val Tyr Ala Glu Cys Pro Lys Pro Ser Ser Leu
35                  40                  45                  50

cgt cga caa caa ttg atc cgt gaa tgt tcc att ttg gcc aat att gag      909
Arg Arg Gln Gln Leu Ile Arg Glu Cys Ser Ile Leu Ala Asn Ile Glu
                55                  60                  65

cct aag cag atc aaa gtc tgg ttt cag aac cgc agg tgt cga gat aag      957
Pro Lys Gln Ile Lys Val Trp Phe Gln Asn Arg Arg Cys Arg Asp Lys
            70                  75                  80

cag agg aaa gag gcg tcg agg ctc cag agc gta aac cgg aag ctc tct     1005
Gln Arg Lys Glu Ala Ser Arg Leu Gln Ser Val Asn Arg Lys Leu Ser
        85                  90                  95

gcg atg aat aaa ctg ttg atg gag gag aat gat agg ttg cag aag cag     1053
Ala Met Asn Lys Leu Leu Met Glu Glu Asn Asp Arg Leu Gln Lys Gln
    100                 105                 110

gtt tct cag ctt gtc tgc gaa aat gga tat atg aaa cag cag cta act     1101
Val Ser Gln Leu Val Cys Glu Asn Gly Tyr Met Lys Gln Gln Leu Thr
115                 120                 125                 130

act gtt gtt aac gat cca agc tgt gaa tct gtg gtc aca act cct cag     1149
Thr Val Val Asn Asp Pro Ser Cys Glu Ser Val Val Thr Thr Pro Gln
                135                 140                 145

cat tcg ctt aga gat gcg aat agt cct gct gga ttg ctc tca atc gca     1197
His Ser Leu Arg Asp Ala Asn Ser Pro Ala Gly Leu Leu Ser Ile Ala
            150                 155                 160

gag gag act ttg gca gag ttc cta tcc aag gct aca gga act gct gtt     1245
Glu Glu Thr Leu Ala Glu Phe Leu Ser Lys Ala Thr Gly Thr Ala Val
        165                 170                 175

gat tgg gtt cag atg cct ggg atg aag cct ggt ccg gat tcg gtt ggc     1293
Asp Trp Val Gln Met Pro Gly Met Lys Pro Gly Pro Asp Ser Val Gly
    180                 185                 190

atc ttt gcc att tcg caa aga tgc aat gga gtg gca gct cga gcc tgt     1341
Ile Phe Ala Ile Ser Gln Arg Cys Asn Gly Val Ala Ala Arg Ala Cys
```

-continued

```
195                 200                 205                 210

ggt ctt gtt agc tta gaa cct atg aag att gca gag atc ctc aaa gat     1389
Gly Leu Val Ser Leu Glu Pro Met Lys Ile Ala Glu Ile Leu Lys Asp
                215                 220                 225

cgg cca tct tgg ttc cgt gac tgt agg agc ctt gaa gtt ttc act atg     1437
Arg Pro Ser Trp Phe Arg Asp Cys Arg Ser Leu Glu Val Phe Thr Met
            230                 235                 240

ttc ccg gct ggt aat ggt ggc aca atc gag ctt gtt tat atg cag acg     1485
Phe Pro Ala Gly Asn Gly Gly Thr Ile Glu Leu Val Tyr Met Gln Thr
        245                 250                 255

tat gca cca acg act ctg gct cct gcc cgc gat ttc tgg acc ctg aga     1533
Tyr Ala Pro Thr Thr Leu Ala Pro Ala Arg Asp Phe Trp Thr Leu Arg
    260                 265                 270

tac aca acg agc ctc gac aat ggg agt ttt gtg gtt tgt gag agg tcg     1581
Tyr Thr Thr Ser Leu Asp Asn Gly Ser Phe Val Val Cys Glu Arg Ser
275                 280                 285                 290

cta tct ggc tct gga gct ggg cct aat gct gct tca gct tct cag ttt     1629
Leu Ser Gly Ser Gly Ala Gly Pro Asn Ala Ala Ser Ala Ser Gln Phe
                295                 300                 305

gtg aga gca gaa atg ctt tct agt ggg tat tta ata agg cct tgt gat     1677
Val Arg Ala Glu Met Leu Ser Ser Gly Tyr Leu Ile Arg Pro Cys Asp
            310                 315                 320

ggt ggt ggt tct att att cac att gtc gat cac ctt aat ctt gag gct     1725
Gly Gly Gly Ser Ile Ile His Ile Val Asp His Leu Asn Leu Glu Ala
        325                 330                 335

tgg agt gtt ccg gat gtg ctt cga ccc ctt tat gag tca tcc aaa gtc     1773
Trp Ser Val Pro Asp Val Leu Arg Pro Leu Tyr Glu Ser Ser Lys Val
    340                 345                 350

gtt gca caa aaa atg acc att tcc gcg ttg cgg tat atc agg caa tta     1821
Val Ala Gln Lys Met Thr Ile Ser Ala Leu Arg Tyr Ile Arg Gln Leu
355                 360                 365                 370

gcc caa gag tct aat ggt gaa gta gtg tat gga tta gga agg cag cct     1869
Ala Gln Glu Ser Asn Gly Glu Val Val Tyr Gly Leu Gly Arg Gln Pro
                375                 380                 385

gct gtt ctt aga acc ttt agc caa aga tta agc agg ggc ttc aat gat     1917
Ala Val Leu Arg Thr Phe Ser Gln Arg Leu Ser Arg Gly Phe Asn Asp
            390                 395                 400

gcg gtt aat ggg ttt ggt gac gac ggg tgg tct acg atg cat tgt gat     1965
Ala Val Asn Gly Phe Gly Asp Asp Gly Trp Ser Thr Met His Cys Asp
        405                 410                 415

gga gcg gaa gat att atc gtt gct att aac tct aca aag cat ttg aat     2013
Gly Ala Glu Asp Ile Ile Val Ala Ile Asn Ser Thr Lys His Leu Asn
    420                 425                 430

aat att tct aat tct ctt tcg ttc ctt gga ggc gtg ctc tgt gcc aag     2061
Asn Ile Ser Asn Ser Leu Ser Phe Leu Gly Gly Val Leu Cys Ala Lys
435                 440                 445                 450

gct tca atg ctt ctc caa aat gtt cct cct gcg gtt ttg atc cgg ttc     2109
Ala Ser Met Leu Leu Gln Asn Val Pro Pro Ala Val Leu Ile Arg Phe
                455                 460                 465

ctt aga gag cat cga tct gag tgg gct gat ttc aat gtt gat gca tat     2157
Leu Arg Glu His Arg Ser Glu Trp Ala Asp Phe Asn Val Asp Ala Tyr
            470                 475                 480

tcc gct gct aca ctt aaa gct ggt agc ttt gct tat ccg gga atg aga     2205
Ser Ala Ala Thr Leu Lys Ala Gly Ser Phe Ala Tyr Pro Gly Met Arg
        485                 490                 495

cca aca aga ttc act ggg agt cag atc ata atg cca cta gga cat aca     2253
Pro Thr Arg Phe Thr Gly Ser Gln Ile Ile Met Pro Leu Gly His Thr
    500                 505                 510

att gaa cac gaa gaa atg cta gaa gtt gtt aga ctg gaa ggt cat tct     2301
```

-continued

```
Ile Glu His Glu Glu Met Leu Glu Val Val Arg Leu Glu Gly His Ser
515                 520                 525                 530

ctt gct caa gaa gat gca ttt atg tca cgg gat gtc cat ctc ctt cag      2349
Leu Ala Gln Glu Asp Ala Phe Met Ser Arg Asp Val His Leu Leu Gln
                535                 540                 545

att tgt acc ggg att gac gag aat gcc gtt gga gct tgt tct gaa ctg      2397
Ile Cys Thr Gly Ile Asp Glu Asn Ala Val Gly Ala Cys Ser Glu Leu
            550                 555                 560

ata ttt gct ccg att aat gag atg ttc ccg gat gat gct cca ctt gtt      2445
Ile Phe Ala Pro Ile Asn Glu Met Phe Pro Asp Asp Ala Pro Leu Val
        565                 570                 575

ccc tct gga ttc cga gtc ata ccc gtt gat gct aaa acg gga gat gta      2493
Pro Ser Gly Phe Arg Val Ile Pro Val Asp Ala Lys Thr Gly Asp Val
    580                 585                 590

caa gat ctg tta acc gct aat cac cgt aca cta gac tta act tct agc      2541
Gln Asp Leu Leu Thr Ala Asn His Arg Thr Leu Asp Leu Thr Ser Ser
595                 600                 605                 610

ctt gaa gtc ggt cca tca cct gag aat gct tct gga aac tct ttt tct      2589
Leu Glu Val Gly Pro Ser Pro Glu Asn Ala Ser Gly Asn Ser Phe Ser
                615                 620                 625

agc tca agc tcg aga tgt att ctc act atc gcg ttt caa ttc cct ttt      2637
Ser Ser Ser Ser Arg Cys Ile Leu Thr Ile Ala Phe Gln Phe Pro Phe
            630                 635                 640

gaa aac aac ttg caa gaa aat gtt gct ggt atg gct tgt cag tat gtg      2685
Glu Asn Asn Leu Gln Glu Asn Val Ala Gly Met Ala Cys Gln Tyr Val
        645                 650                 655

agg agc gtg atc tca tca gtt caa cgt gtt gca atg gcg atc tca ccg      2733
Arg Ser Val Ile Ser Ser Val Gln Arg Val Ala Met Ala Ile Ser Pro
    660                 665                 670

tct ggg ata agc ccg agt ctg ggc tcc aaa ttg tcc cca gga tct cct      2781
Ser Gly Ile Ser Pro Ser Leu Gly Ser Lys Leu Ser Pro Gly Ser Pro
675                 680                 685                 690

gaa gct gtt act ctt gct cag tgg atc tct caa agt tac agt cat cac      2829
Glu Ala Val Thr Leu Ala Gln Trp Ile Ser Gln Ser Tyr Ser His His
                695                 700                 705

tta ggc tcg gag ttg ctg acg att gat tca ctt gga agc gac gac tcg      2877
Leu Gly Ser Glu Leu Leu Thr Ile Asp Ser Leu Gly Ser Asp Asp Ser
            710                 715                 720

gta cta aaa ctt cta tgg gat cac caa gat gcc atc ctg tgt tgc tca      2925
Val Leu Lys Leu Leu Trp Asp His Gln Asp Ala Ile Leu Cys Cys Ser
        725                 730                 735

tta aag cca cag cca gtg ttc atg ttt gcg aac caa gct ggt cta gac      2973
Leu Lys Pro Gln Pro Val Phe Met Phe Ala Asn Gln Ala Gly Leu Asp
    740                 745                 750

atg cta gag aca aca ctt gta gcc tta caa gat ata aca ctc gaa aag      3021
Met Leu Glu Thr Thr Leu Val Ala Leu Gln Asp Ile Thr Leu Glu Lys
755                 760                 765                 770

ata ttc gat gaa tcg ggt cgt aag gct atc tgt tcg gac ttc gcc aag      3069
Ile Phe Asp Glu Ser Gly Arg Lys Ala Ile Cys Ser Asp Phe Ala Lys
                775                 780                 785

cta atg caa cag gga ttt gct tgc ttg cct tca gga atc tgt gtg tca      3117
Leu Met Gln Gln Gly Phe Ala Cys Leu Pro Ser Gly Ile Cys Val Ser
            790                 795                 800

acg atg gga aga cat gtg agt tat gaa caa gct gtt gct tgg aaa gtg      3165
Thr Met Gly Arg His Val Ser Tyr Glu Gln Ala Val Ala Trp Lys Val
        805                 810                 815

ttt gct gca tct gaa gaa aac aac aac aat ctg cat tgt ctt gcc ttc      3213
Phe Ala Ala Ser Glu Glu Asn Asn Asn Asn Leu His Cys Leu Ala Phe
    820                 825                 830
```

```
tcc ttt gta aac tgg tct ttt gtg tgattcgatt gacagaaaaa gactaattta    3267
Ser Phe Val Asn Trp Ser Phe Val
835                840

aatttacgtt agagaactca aatttttggt tgttgtttag gtgtctctgt tttgtttttt   3327

aaaattattt tgatcaaatg ttactcactt tcttctttca caacgtattt ggttttaatg   3387

ttttggggaa aaaagcagag ttgatcaatc tctatatata aagggaatga tgtgataatt   3447

ttgttaaaac taagcttaca acatttttttc tatcgcattt gacagtttca ttttcacatc  3507

tctcgctata tattagtaat ataaactatt tcaaaaaaca aagaatcaac aagaatccac   3567

agatgtaaga aagaaaaatc acagccaaat aactttttta tttatttggc cgttagataa   3627

aactaccttc agaatttcat gcatctagcc ggtaaacctg tctgatgatt gacggcgaca   3687

atctcagaga cattgttgca acgaagaaca tcttgaccaa gcttagctcc tgcagcttta   3747

agacctttaa gcgaaaccgg catgttgaag agattgagtg atggaagctt agaaagcgga   3807

gggagtttct ggttcggtaa gaagtttctg aaatcatcca taagcaatgg aac          3860


<210> SEQ ID NO 68
<211> LENGTH: 842
<212> TYPE: PRT
<213> ORGANISM: Arabidopsis thaliana

<400> SEQUENCE: 68

Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Ser Ile Leu Ala Asn
    50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190

Val Gly Ile Phe Ala Ile Ser Gln Arg Cys Asn Gly Val Ala Ala Arg
        195                 200                 205

Ala Cys Gly Leu Val Ser Leu Glu Pro Met Lys Ile Ala Glu Ile Leu
    210                 215                 220

Lys Asp Arg Pro Ser Trp Phe Arg Asp Cys Arg Ser Leu Glu Val Phe
225                 230                 235                 240

Thr Met Phe Pro Ala Gly Asn Gly Gly Thr Ile Glu Leu Val Tyr Met
                245                 250                 255
```

-continued

```
Gln Thr Tyr Ala Pro Thr Thr Leu Ala Pro Ala Arg Asp Phe Trp Thr
            260                 265                 270

Leu Arg Tyr Thr Thr Ser Leu Asp Asn Gly Ser Phe Val Val Cys Glu
        275                 280                 285

Arg Ser Leu Ser Gly Ser Gly Ala Gly Pro Asn Ala Ala Ser Ala Ser
    290                 295                 300

Gln Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Leu Asn Leu
                325                 330                 335

Glu Ala Trp Ser Val Pro Asp Val Leu Arg Pro Leu Tyr Glu Ser Ser
            340                 345                 350

Lys Val Val Ala Gln Lys Met Thr Ile Ser Ala Leu Arg Tyr Ile Arg
        355                 360                 365

Gln Leu Ala Gln Glu Ser Asn Gly Glu Val Val Tyr Gly Leu Gly Arg
    370                 375                 380

Gln Pro Ala Val Leu Arg Thr Phe Ser Gln Arg Leu Ser Arg Gly Phe
385                 390                 395                 400

Asn Asp Ala Val Asn Gly Phe Gly Asp Asp Gly Trp Ser Thr Met His
                405                 410                 415

Cys Asp Gly Ala Glu Asp Ile Ile Val Ala Ile Asn Ser Thr Lys His
            420                 425                 430

Leu Asn Asn Ile Ser Asn Ser Leu Ser Phe Leu Gly Gly Val Leu Cys
        435                 440                 445

Ala Lys Ala Ser Met Leu Leu Gln Asn Val Pro Pro Ala Val Leu Ile
    450                 455                 460

Arg Phe Leu Arg Glu His Arg Ser Glu Trp Ala Asp Phe Asn Val Asp
465                 470                 475                 480

Ala Tyr Ser Ala Ala Thr Leu Lys Ala Gly Ser Phe Ala Tyr Pro Gly
                485                 490                 495

Met Arg Pro Thr Arg Phe Thr Gly Ser Gln Ile Ile Met Pro Leu Gly
            500                 505                 510

His Thr Ile Glu His Glu Glu Met Leu Glu Val Val Arg Leu Glu Gly
        515                 520                 525

His Ser Leu Ala Gln Glu Asp Ala Phe Met Ser Arg Asp Val His Leu
    530                 535                 540

Leu Gln Ile Cys Thr Gly Ile Asp Glu Asn Ala Val Gly Ala Cys Ser
545                 550                 555                 560

Glu Leu Ile Phe Ala Pro Ile Asn Glu Met Phe Pro Asp Asp Ala Pro
                565                 570                 575

Leu Val Pro Ser Gly Phe Arg Val Ile Pro Val Asp Ala Lys Thr Gly
            580                 585                 590

Asp Val Gln Asp Leu Leu Thr Ala Asn His Arg Thr Leu Asp Leu Thr
        595                 600                 605

Ser Ser Leu Glu Val Gly Pro Ser Pro Glu Asn Ala Ser Gly Asn Ser
    610                 615                 620

Phe Ser Ser Ser Ser Ser Arg Cys Ile Leu Thr Ile Ala Phe Gln Phe
625                 630                 635                 640

Pro Phe Glu Asn Asn Leu Gln Glu Asn Val Ala Gly Met Ala Cys Gln
                645                 650                 655

Tyr Val Arg Ser Val Ile Ser Ser Val Gln Arg Val Ala Met Ala Ile
            660                 665                 670
```

-continued

```
Ser Pro Ser Gly Ile Ser Pro Ser Leu Gly Ser Lys Leu Ser Pro Gly
        675                 680                 685

Ser Pro Glu Ala Val Thr Leu Ala Gln Trp Ile Ser Gln Ser Tyr Ser
    690                 695                 700

His His Leu Gly Ser Glu Leu Leu Thr Ile Asp Ser Leu Gly Ser Asp
705                 710                 715                 720

Asp Ser Val Leu Lys Leu Leu Trp Asp His Gln Asp Ala Ile Leu Cys
                725                 730                 735

Cys Ser Leu Lys Pro Gln Pro Val Phe Met Phe Ala Asn Gln Ala Gly
            740                 745                 750

Leu Asp Met Leu Glu Thr Thr Leu Val Ala Leu Gln Asp Ile Thr Leu
        755                 760                 765

Glu Lys Ile Phe Asp Glu Ser Gly Arg Lys Ala Ile Cys Ser Asp Phe
    770                 775                 780

Ala Lys Leu Met Gln Gln Gly Phe Ala Cys Leu Pro Ser Gly Ile Cys
785                 790                 795                 800

Val Ser Thr Met Gly Arg His Val Ser Tyr Glu Gln Ala Val Ala Trp
                805                 810                 815

Lys Val Phe Ala Ala Ser Glu Glu Asn Asn Asn Asn Leu His Cys Leu
            820                 825                 830

Ala Phe Ser Phe Val Asn Trp Ser Phe Val
        835                 840
```

<210> SEQ ID NO 69
<211> LENGTH: 2067
<212> TYPE: DNA
<213> ORGANISM: Arabidopsis thaliana
<220> FEATURE:
<221> NAME/KEY: promoter
<222> LOCATION: (1)..(2067)
<223> OTHER INFORMATION: promoter of gene At1g76350

<400> SEQUENCE: 69

```
agtcttcttc catacatgtt atgtcaaagt ttattgttcc tttcaatatt caatcataaa      60

cttacttacg tctgctattt attgctaaaa aaaaaggttt ttctaaattc agttcatcta     120

aataaacaaa tagtaagatg gtaacaattg aaaaaaaaag attgtctagg gggaagaaca     180

aaaactaaga cgagttgcat tttgcttctt cgcaaatgca agttgcaaca ataaaaaatc     240

atcttaacct ctcacaaacc acatttttag aggctaaaga tttgacaggt aagattcata     300

tgtcatttgg cttgttataa aatggtgaac actaagccct tttttcttca actctttatg     360

tttttctaga cagtgaccaa aacctcaaaa cattgtagac cactacgaaa cggattaatc     420

agttttgaca cttcttctac tacatatacg tgaatgattt tacaagtttc ttgaagatga     480

ctaaaagagt cacacatctc cacggggctg agtgggacac acattgccca ccatttctat     540

tacaaagtat cttttaatcc aataggacaa acgctgacca aaaacaaaaa aaaccaatag     600

ggacaaacaa aaaaattgaa ctcctattga tttttatttt accaatgggg gaaaagcaaa     660

acctactccc caacttgctc catcaattat taattttctc ttaaaacttt tttctttagc     720

aactttttaag ttaagtaatt attacttgac atcttctctt taactatgcg tttagaatct     780

ttctttgtat ttaacaacta tcaaatagtt ctcctttcga gggtgtacac atggaggact     840

aatcagatca ttttatgtaa acaatgggag aaaatacacc ctctctttcc aatatcgttg     900

ggtttacaat gtaacgtatc aaattaaaaa caagtaatta acaaagtcag cggcgaaaat     960

tcaactttta tattcatttt ttttataacc cttattaatt tgtcaactct acttggtccc    1020
```

```
tttattattg gctccaaaac tctgcctaat aaattatatt gattccaaat caaaggcatt   1080

ttttaataat gattagtgct aattgctgat attttctgac ttcttacata gaaatatctt   1140

ttttttaaag actacatgtt gagaaattcg ctgcccaaaa ttctcaaaaa aaaaagaaat   1200

ggaaaaaata ataaaatctc tttttctctt actctagaat atgggaatct ccgtcctcca   1260

acacccacgc agcctggaac agagacagtc tttgttctgt tgtgaagaaa tactctaaag   1320

aaaccaaaca atttattagt tttacaaata aaaaaaaagt aataattgaa gggttctttt   1380

tttcccgatg catatatgag ataacgatgc ctcaaaatat gattttttttt tcttcctctt   1440

ggtgtatggt aatttatgag gaagagaggt acacattacc ttacttgttc accaggaaca   1500

tacccatcaa agagacatat ctttacagct ttattttccc tcagatttgg ggttcttctt   1560

tcaactgttt ctcctgtctc tcacaagaca agtggtcttt tgggaatctt caattaaaaa   1620

ggataaaacc atttaaaacc tacttcaaga atcttccgag aatctgacgt cttttttttgt   1680

gagttttcgt ttctattttt ttttttcccc atttctgaac ttcaaaagtc tcatcttttt   1740

tgttaatcag gaatcagatt agtgttaaaa aatattcctt ctttgattgg tgttaaatca   1800

gtatctctta acccacaaga gattagggta tatttaacca acttgtaaga atcaacctta   1860

aaaagaaaag ttagggcttt tcactaatct tgattctcag tttcttttct attacaagat   1920

ttttgctttg atttgattct cttcctgaaa tgtgtggttc tttttctgtt ctgttctgct   1980

ctgttctgtt tcatcttaat ttgtttgggg tttggtgaaa aatggatact ttgttttttc   2040

agatgtggct tcattgattt gagtgag                                        2067
```

```
<210> SEQ ID NO 70
<211> LENGTH: 2056
<212> TYPE: DNA
<213> ORGANISM: Arabidopsis thaliana
<220> FEATURE:
<221> NAME/KEY: promoter
<222> LOCATION: (1)..(2056)
<223> OTHER INFORMATION: promoter of gene At1g76350

<400> SEQUENCE: 70
```

```
agtcttcttc catacatgtt atgtcaaagt ttattgttcc tttcaatatt caatcataaa     60

cttacttacg tctgctattt attgctaaaa aaaaaggttt ttctaaattc agttcatcta    120

aataaacaaa tagtaagatg gtaacaattg aaaaaaaaag attgtctagg gggaagaaca    180

aaaactaaga cgagttgcat tttgcttctt cgcaaatgca agttgcaaca ataaaaaatc    240

atcttaacct ctcgcaaacc acatttttag aggctaaaga tttgacaggt aagattcata    300

tgtcatttgg cttgttataa aatggtgaac actaagccct tttttcttca actctttatg    360

tttttctaga cagtgaccaa aacctcaaaa cattgtagac cactacgaaa cggattaatc    420

agttttgaca cttcttctac tacatatacg tgaatgattt tacaagtttc ttgaagatga    480

ctaaaagagt cacacatctc cacggggctg agtgggacac acattgccca ccatttctat    540

tacaaagtat cttttaatcc aataggacaa acgctgacca aaaaaaaaaa aaaccaatag    600

ggacaaacaa aaaaattgaa ctcctattga tttttatttt accaatgggg gaaaagcaaa    660

acctactccc caacttgctc catcaattat taattttctc ttaaaacttt tttctttagc    720

aactttttaag ttaagtaatt attacttgac atcttctctt taactatgcg tttagaatct    780

ttctttgtat ttaacaacta tcaaatagtt ctcctttcga gggtgtacac atggaggact    840

aatcagatca ttttatgtaa acaatgggag aaaatacacc ctctctttcc aatatcgttg    900

ggtttacaat gtaacgtatc aaattaaaag caagtaatta acaaagtcag cggcgaaaat    960
```

```
tcaactttta tattcatttt ttttataacc cttattaatt tgtcaactct acttggtccc   1020

tttattattg gctccaaaac tctgcctaat aaattatatt gattccaaat caaaggcatt   1080

ttttaataat gattagtgct aattgctgat attttctgac ttcttacata gaaatatctt   1140

ttttttaaag actacatgtt gagaaattcg ctgcccaaaa ttctcaaaaa aaaaagaaat   1200

ggaaaaaata ataaaatctc tttttctctt actctagaat atgggaatct ccgtcctcca   1260

acacccacgc agcctggaac agagacagtc tttgttctgt tgtgaagaaa tactctaaag   1320

aaaccaaaca atttattagt tttacaaata aaaaaaagta ataattgaag ggttcttttt   1380

ttcccgatgc atatatgaga taacgatgcc tcaaaatatg attttttttt cttcctcttg   1440

gtgtatggta atttatgagg aagagaggta cacattacct tacttgttca ccaggaacat   1500

acccatcaaa gagacatatc tttacagctt tattttccct cagatttggg gttcttcttt   1560

caactgtttc tcctgtctct cacaagacaa gtggtctttt gggaatcttc aattaaaaag   1620

gataaaacca tttaaaacct acttcaagaa tcttccgaga atctgacgtc tttttttgtg   1680

agttttcgtt tctatttttt tttttcccca tttctgaact tcaaaagtct catctttttt   1740

gttaatcagg aatcagatta gtgttaaaaa atattccttc tttgattggt gttaaatcag   1800

tatctcttaa cccacaagag attagggtat atttaaccaa cttgtaagaa tcaaccttaa   1860

aaagaaaagt tagggctttt cactaatctt gattctcagt ttcttttcta ttacaagatt   1920

tttgctttga tttgattctc ttcctgaaat gtgtggttct ttttctgttc tgttctgttt   1980

catcttaatt tgtttggggt ttggtgaaaa atggatactt tgttttttca gatgtggctt   2040

cattgatttg agtgag                                                   2056
```

<210> SEQ ID NO 71
<211> LENGTH: 3178
<212> TYPE: DNA
<213> ORGANISM: Arabidopsis thaliana
<220> FEATURE:
<221> NAME/KEY: CDS
<222> LOCATION: (28)..(2451)
<223> OTHER INFORMATION: coding for RWP-RK domain-containing protein
(At1g76350)

<400> SEQUENCE: 71

```
atgtggcttc attgatttga gtgagct atg gaa aac aat tct ctt cct atg gat      54
                              Met Glu Asn Asn Ser Leu Pro Met Asp
                              1               5

cca gct atg gat tct tca ttc atg gac gga tta ctt cta gaa ggt tgc      102
Pro Ala Met Asp Ser Ser Phe Met Asp Gly Leu Leu Leu Glu Gly Cys
10                  15                  20                  25

tgg tta gag aca aca gat gca tcc gag ttc ctt aat ttt agt cct tca      150
Trp Leu Glu Thr Thr Asp Ala Ser Glu Phe Leu Asn Phe Ser Pro Ser
                30                  35                  40

act tct gta gcc cct ttt gat cct tct tcc ttc atg tgg tct cca acg      198
Thr Ser Val Ala Pro Phe Asp Pro Ser Ser Phe Met Trp Ser Pro Thr
            45                  50                  55

caa gac aca tct aat agc tta tct cag atg tat ggt caa gat tgt cca      246
Gln Asp Thr Ser Asn Ser Leu Ser Gln Met Tyr Gly Gln Asp Cys Pro
        60                  65                  70

gaa aga tca agt ctt gag gat caa aac caa ggg aga gat ctc tct acc      294
Glu Arg Ser Ser Leu Glu Asp Gln Asn Gln Gly Arg Asp Leu Ser Thr
    75                  80                  85

ttt aac aga cgt tgg tgg att gga cca agt ggt cat cat ggc ttt tct      342
Phe Asn Arg Arg Trp Trp Ile Gly Pro Ser Gly His His Gly Phe Ser
90                  95                  100                 105
```

-continued

```
gtt atg gaa aga ttg gtt caa gca gtg aca cac att aaa gat ttc act      390
Val Met Glu Arg Leu Val Gln Ala Val Thr His Ile Lys Asp Phe Thr
                110                 115                 120

agt gag aga ggc tct ctt ata cag ttg tgg gtg cct gtg gat aga ggt      438
Ser Glu Arg Gly Ser Leu Ile Gln Leu Trp Val Pro Val Asp Arg Gly
            125                 130                 135

ggt aag cga gtt ttg acc aca aag gaa caa cct ttt agt cat gat cca      486
Gly Lys Arg Val Leu Thr Thr Lys Glu Gln Pro Phe Ser His Asp Pro
        140                 145                 150

atg tgt caa agg ctt gct cat tac aga gag atc tct gag aat tat cag      534
Met Cys Gln Arg Leu Ala His Tyr Arg Glu Ile Ser Glu Asn Tyr Gln
    155                 160                 165

ttc tct act gaa cag gag gat tca gat tct agt tcc agg gac ttg gtt      582
Phe Ser Thr Glu Gln Glu Asp Ser Asp Ser Ser Ser Arg Asp Leu Val
170                 175                 180                 185

ggt ttg cct gga aga gtt ttc ttg ggg aag gtt cct gaa tgg act cct      630
Gly Leu Pro Gly Arg Val Phe Leu Gly Lys Val Pro Glu Trp Thr Pro
                190                 195                 200

gat gtg agg ttt ttc aag aat gag gag tat ccg aga gtt caa cat gct      678
Asp Val Arg Phe Phe Lys Asn Glu Glu Tyr Pro Arg Val Gln His Ala
            205                 210                 215

caa gac tgt gat gtt cga ggc acg tta gct att cct gtg ttt gaa caa      726
Gln Asp Cys Asp Val Arg Gly Thr Leu Ala Ile Pro Val Phe Glu Gln
        220                 225                 230

ggt agt cag att tgc tta ggt gtt att gag gtt gtg atg act aca caa      774
Gly Ser Gln Ile Cys Leu Gly Val Ile Glu Val Val Met Thr Thr Gln
    235                 240                 245

atg gtt aaa cta agt cct gac ctt gaa agc atc tgc aga gca ctt cag      822
Met Val Lys Leu Ser Pro Asp Leu Glu Ser Ile Cys Arg Ala Leu Gln
250                 255                 260                 265

gca gtt gat ctt aga agc aca gag att cca ata ccg cct tct cta aag      870
Ala Val Asp Leu Arg Ser Thr Glu Ile Pro Ile Pro Pro Ser Leu Lys
                270                 275                 280

gga cca gat ttc tct tac caa gct gca tta cct gaa atc aga aac ctc      918
Gly Pro Asp Phe Ser Tyr Gln Ala Ala Leu Pro Glu Ile Arg Asn Leu
            285                 290                 295

ttg aga tgt gct tgc gag acg cat aaa cta cca tta gct caa aca tgg      966
Leu Arg Cys Ala Cys Glu Thr His Lys Leu Pro Leu Ala Gln Thr Trp
        300                 305                 310

gtc tca tgt ctc aaa caa agc aaa act ggt tgc cgt cac aat gat gag     1014
Val Ser Cys Leu Lys Gln Ser Lys Thr Gly Cys Arg His Asn Asp Glu
    315                 320                 325

aac tat atc cat tgt gta tcc aca atc gat gat gct tgc tat gtt ggt     1062
Asn Tyr Ile His Cys Val Ser Thr Ile Asp Asp Ala Cys Tyr Val Gly
330                 335                 340                 345

gat cct aca gtc cgt gaa ttc cac gaa gct tgc tct gag cac cat ctc     1110
Asp Pro Thr Val Arg Glu Phe His Glu Ala Cys Ser Glu His His Leu
                350                 355                 360

ttg aaa ggt caa gga gtt gtt gga gaa gcc ttt ttg acc aat ggc cct     1158
Leu Lys Gly Gln Gly Val Val Gly Glu Ala Phe Leu Thr Asn Gly Pro
            365                 370                 375

tgc ttt tca tct gat gtt tct agc tac aag aaa tct gag tac cct ctc     1206
Cys Phe Ser Ser Asp Val Ser Ser Tyr Lys Lys Ser Glu Tyr Pro Leu
        380                 385                 390

tct cac cac gcg act atg ttt ggc tta cat ggt aca gtc gcg ata cgc     1254
Ser His His Ala Thr Met Phe Gly Leu His Gly Thr Val Ala Ile Arg
    395                 400                 405

tta cgc tgt atc cac act ggc tca gtt gat ttc gtc ttg gag ttc ttt     1302
Leu Arg Cys Ile His Thr Gly Ser Val Asp Phe Val Leu Glu Phe Phe
```

-continued

```
410                 415                 420                 425

ttg cct aaa aat tgt cgg gat ata gag gaa cag agg aaa atg ttg aat     1350
Leu Pro Lys Asn Cys Arg Asp Ile Glu Glu Gln Arg Lys Met Leu Asn
                430                 435                 440

gct ctt tcg act ata atg gcg cat gta cct aga agc tta agg aca gtc     1398
Ala Leu Ser Thr Ile Met Ala His Val Pro Arg Ser Leu Arg Thr Val
            445                 450                 455

acg cag aag gaa cta gaa gaa gag gga gat tca atg gtg agc gag gtc     1446
Thr Gln Lys Glu Leu Glu Glu Glu Gly Asp Ser Met Val Ser Glu Val
        460                 465                 470

ata gag aaa gga gtg aca ttg cca aag ata gag aat aca aca gaa gta     1494
Ile Glu Lys Gly Val Thr Leu Pro Lys Ile Glu Asn Thr Thr Glu Val
    475                 480                 485

cat cag agt att agc act cct caa aat gta gga tta gta ttc gat gga     1542
His Gln Ser Ile Ser Thr Pro Gln Asn Val Gly Leu Val Phe Asp Gly
490                 495                 500                 505

gga aca acg gag atg ggc gag tta ggt tct gaa tat ggc aaa ggt gtg     1590
Gly Thr Thr Glu Met Gly Glu Leu Gly Ser Glu Tyr Gly Lys Gly Val
                510                 515                 520

agt gtg aat gag aac aac act ttc tct agt gct agt ggt ttc aat aga     1638
Ser Val Asn Glu Asn Asn Thr Phe Ser Ser Ala Ser Gly Phe Asn Arg
            525                 530                 535

gtg act gag aaa aag cga acg aag gcc gaa aaa aac ata act ttg gat     1686
Val Thr Glu Lys Lys Arg Thr Lys Ala Glu Lys Asn Ile Thr Leu Asp
        540                 545                 550

gtt ctt cgc caa tat ttc gca ggg agt ctc aaa gat gct gcc aag agt     1734
Val Leu Arg Gln Tyr Phe Ala Gly Ser Leu Lys Asp Ala Ala Lys Ser
    555                 560                 565

att ggt gtt tgt cca acg aca ttg aag agg ata tgc aga cag cat ggg     1782
Ile Gly Val Cys Pro Thr Thr Leu Lys Arg Ile Cys Arg Gln His Gly
570                 575                 580                 585

ata cag aga tgg cct tca aga aaa atc aag aaa gtt ggt cat tcg ctt     1830
Ile Gln Arg Trp Pro Ser Arg Lys Ile Lys Lys Val Gly His Ser Leu
                590                 595                 600

cag aaa atc caa agg gtc atc gac tcg gtt gaa ggt gtt tcg ggt cat     1878
Gln Lys Ile Gln Arg Val Ile Asp Ser Val Glu Gly Val Ser Gly His
            605                 610                 615

cat ctt cct ata ggc tcc ttc tac gcg agt ttc cca aat cta gct gct     1926
His Leu Pro Ile Gly Ser Phe Tyr Ala Ser Phe Pro Asn Leu Ala Ala
        620                 625                 630

tca cca gaa gca tca tcc cta caa cag caa tcc aag att act aca ttc     1974
Ser Pro Glu Ala Ser Ser Leu Gln Gln Gln Ser Lys Ile Thr Thr Phe
    635                 640                 645

ttg tcc tat tca cat tca cca cct gca aag tcc cct ggt tcc tcg tgt     2022
Leu Ser Tyr Ser His Ser Pro Pro Ala Lys Ser Pro Gly Ser Ser Cys
650                 655                 660                 665

agt cac agc tca agc tgt tcc agt gaa aca caa gta atc aag gaa gat     2070
Ser His Ser Ser Ser Cys Ser Ser Glu Thr Gln Val Ile Lys Glu Asp
                670                 675                 680

ccc acg gat aag act aga cta gtc tca aga tct ttt aaa gaa acg caa     2118
Pro Thr Asp Lys Thr Arg Leu Val Ser Arg Ser Phe Lys Glu Thr Gln
            685                 690                 695

acc aca cac tta tca cca tca tca caa gag gat gat ttt ctg agg gta     2166
Thr Thr His Leu Ser Pro Ser Ser Gln Glu Asp Asp Phe Leu Arg Val
        700                 705                 710

aag gta agc tat gag gag gag aag atc cgg ttt aag atg aga aac tcg     2214
Lys Val Ser Tyr Glu Glu Glu Lys Ile Arg Phe Lys Met Arg Asn Ser
    715                 720                 725

cat agg tta aaa gat tta ctg tgg gaa ata gca aaa cga ttt agt ata     2262
```

```
His Arg Leu Lys Asp Leu Leu Trp Glu Ile Ala Lys Arg Phe Ser Ile
730                 735                 740                 745

gaa gat gtg agc aga tac gat ctg aaa tac tta gat gaa gac aat gaa      2310
Glu Asp Val Ser Arg Tyr Asp Leu Lys Tyr Leu Asp Glu Asp Asn Glu
                750                 755                 760

tgg gtt ttg ttg aga tgt gac gat gat gta gaa gag tgt gta gat gtt      2358
Trp Val Leu Leu Arg Cys Asp Asp Asp Val Glu Glu Cys Val Asp Val
            765                 770                 775

tgc aga tct ttt cca gga caa acg att aag ctt ttg ctt cag ctc tct      2406
Cys Arg Ser Phe Pro Gly Gln Thr Ile Lys Leu Leu Leu Gln Leu Ser
        780                 785                 790

tct tct tat ctt cca gaa cgt tct tct gtc agt gga tgt ctt tca          2451
Ser Ser Tyr Leu Pro Glu Arg Ser Ser Val Ser Gly Cys Leu Ser
    795                 800                 805

tgacatgaag attaagagac aaagactaca tatagtttgt gttgtgtaag cattgttcat    2511

agtttttctt cactattttc aagattatta ggtggtgctt tatttggctt ttgttttaaa    2571

acgtatcaaa gaaagagaaa acgtgtaaag agcctttctt ctagaaaaaa tgattcaagt    2631

tttctttgtt tactactttt gtaatgtgta gttggtttgc taatgtagat acacaatttt    2691

tatttacatg tcttccaata aattatggct ttattttgaa gtgtacaaca aatatttcac    2751

taggtctaga aattaataac atatattcac taccagagaa aaagtattac attttttttt    2811

ctttaaaggt tgttcgtctg tatatactgt gtaatatacg tatgactgat ccaaaagaac    2871

tctttgacta tccggttcga ccggttctac ggccatatgg tgaatcattt ccacgaaccc    2931

ggttagtatc tggaccactg ctccttttac gcctctcttc ttggggttgg tctctgatag    2991

tccttacgac ttctaattct ctaagcacat catccattgg cggtcggttt ttcgggtcag    3051

cctccagaca ccgaagaatg agctccgcgg ttttggtcac cgccaaaagt ggatacttct    3111

gctcgagccg tggatccatc attttctgaa ccttcttctt ctggttcaac cccggtttag    3171

cccattc                                                              3178
```

```
<210> SEQ ID NO 72
<211> LENGTH: 808
<212> TYPE: PRT
<213> ORGANISM: Arabidopsis thaliana

<400> SEQUENCE: 72

Met Glu Asn Asn Ser Leu Pro Met Asp Pro Ala Met Asp Ser Ser Phe
1               5                   10                  15

Met Asp Gly Leu Leu Leu Glu Gly Cys Trp Leu Glu Thr Thr Asp Ala
            20                  25                  30

Ser Glu Phe Leu Asn Phe Ser Pro Ser Thr Ser Val Ala Pro Phe Asp
        35                  40                  45

Pro Ser Ser Phe Met Trp Ser Pro Thr Gln Asp Thr Ser Asn Ser Leu
    50                  55                  60

Ser Gln Met Tyr Gly Gln Asp Cys Pro Glu Arg Ser Ser Leu Glu Asp
65                  70                  75                  80

Gln Asn Gln Gly Arg Asp Leu Ser Thr Phe Asn Arg Arg Trp Trp Ile
                85                  90                  95

Gly Pro Ser Gly His His Gly Phe Ser Val Met Glu Arg Leu Val Gln
            100                 105                 110

Ala Val Thr His Ile Lys Asp Phe Thr Ser Glu Arg Gly Ser Leu Ile
        115                 120                 125

Gln Leu Trp Val Pro Val Asp Arg Gly Gly Lys Arg Val Leu Thr Thr
    130                 135                 140
```

```
Lys Glu Gln Pro Phe Ser His Asp Pro Met Cys Gln Arg Leu Ala His
145                 150                 155                 160

Tyr Arg Glu Ile Ser Glu Asn Tyr Gln Phe Ser Thr Glu Gln Glu Asp
                165                 170                 175

Ser Asp Ser Ser Ser Arg Asp Leu Val Gly Leu Pro Gly Arg Val Phe
            180                 185                 190

Leu Gly Lys Val Pro Glu Trp Thr Pro Asp Val Arg Phe Phe Lys Asn
        195                 200                 205

Glu Glu Tyr Pro Arg Val Gln His Ala Gln Asp Cys Asp Val Arg Gly
    210                 215                 220

Thr Leu Ala Ile Pro Val Phe Glu Gln Gly Ser Gln Ile Cys Leu Gly
225                 230                 235                 240

Val Ile Glu Val Val Met Thr Thr Gln Met Val Lys Leu Ser Pro Asp
                245                 250                 255

Leu Glu Ser Ile Cys Arg Ala Leu Gln Ala Val Asp Leu Arg Ser Thr
            260                 265                 270

Glu Ile Pro Ile Pro Pro Ser Leu Lys Gly Pro Asp Phe Ser Tyr Gln
        275                 280                 285

Ala Ala Leu Pro Glu Ile Arg Asn Leu Leu Arg Cys Ala Cys Glu Thr
    290                 295                 300

His Lys Leu Pro Leu Ala Gln Thr Trp Val Ser Cys Leu Lys Gln Ser
305                 310                 315                 320

Lys Thr Gly Cys Arg His Asn Asp Glu Asn Tyr Ile His Cys Val Ser
                325                 330                 335

Thr Ile Asp Asp Ala Cys Tyr Val Gly Asp Pro Thr Val Arg Glu Phe
            340                 345                 350

His Glu Ala Cys Ser Glu His His Leu Leu Lys Gly Gln Gly Val Val
        355                 360                 365

Gly Glu Ala Phe Leu Thr Asn Gly Pro Cys Phe Ser Ser Asp Val Ser
    370                 375                 380

Ser Tyr Lys Lys Ser Glu Tyr Pro Leu Ser His His Ala Thr Met Phe
385                 390                 395                 400

Gly Leu His Gly Thr Val Ala Ile Arg Leu Arg Cys Ile His Thr Gly
                405                 410                 415

Ser Val Asp Phe Val Leu Glu Phe Phe Leu Pro Lys Asn Cys Arg Asp
            420                 425                 430

Ile Glu Glu Gln Arg Lys Met Leu Asn Ala Leu Ser Thr Ile Met Ala
        435                 440                 445

His Val Pro Arg Ser Leu Arg Thr Val Thr Gln Lys Glu Leu Glu Glu
    450                 455                 460

Glu Gly Asp Ser Met Val Ser Glu Val Ile Glu Lys Gly Val Thr Leu
465                 470                 475                 480

Pro Lys Ile Glu Asn Thr Thr Glu Val His Gln Ser Ile Ser Thr Pro
                485                 490                 495

Gln Asn Val Gly Leu Val Phe Asp Gly Gly Thr Thr Glu Met Gly Glu
            500                 505                 510

Leu Gly Ser Glu Tyr Gly Lys Gly Val Ser Val Asn Glu Asn Asn Thr
        515                 520                 525

Phe Ser Ser Ala Ser Gly Phe Asn Arg Val Thr Glu Lys Lys Arg Thr
    530                 535                 540

Lys Ala Glu Lys Asn Ile Thr Leu Asp Val Leu Arg Gln Tyr Phe Ala
545                 550                 555                 560
```

-continued

```
Gly Ser Leu Lys Asp Ala Ala Lys Ser Ile Gly Val Cys Pro Thr Thr
                565                 570                 575

Leu Lys Arg Ile Cys Arg Gln His Gly Ile Gln Arg Trp Pro Ser Arg
            580                 585                 590

Lys Ile Lys Lys Val Gly His Ser Leu Gln Lys Ile Gln Arg Val Ile
        595                 600                 605

Asp Ser Val Glu Gly Val Ser Gly His His Leu Pro Ile Gly Ser Phe
    610                 615                 620

Tyr Ala Ser Phe Pro Asn Leu Ala Ala Ser Pro Glu Ala Ser Ser Leu
625                 630                 635                 640

Gln Gln Gln Ser Lys Ile Thr Thr Phe Leu Ser Tyr Ser His Ser Pro
                645                 650                 655

Pro Ala Lys Ser Pro Gly Ser Ser Cys Ser His Ser Ser Ser Cys Ser
            660                 665                 670

Ser Glu Thr Gln Val Ile Lys Glu Asp Pro Thr Asp Lys Thr Arg Leu
        675                 680                 685

Val Ser Arg Ser Phe Lys Glu Thr Gln Thr Thr His Leu Ser Pro Ser
    690                 695                 700

Ser Gln Glu Asp Asp Phe Leu Arg Val Lys Val Ser Tyr Glu Glu Glu
705                 710                 715                 720

Lys Ile Arg Phe Lys Met Arg Asn Ser His Arg Leu Lys Asp Leu Leu
                725                 730                 735

Trp Glu Ile Ala Lys Arg Phe Ser Ile Glu Asp Val Ser Arg Tyr Asp
            740                 745                 750

Leu Lys Tyr Leu Asp Glu Asp Asn Glu Trp Val Leu Leu Arg Cys Asp
        755                 760                 765

Asp Asp Val Glu Glu Cys Val Asp Val Cys Arg Ser Phe Pro Gly Gln
    770                 775                 780

Thr Ile Lys Leu Leu Leu Gln Leu Ser Ser Ser Tyr Leu Pro Glu Arg
785                 790                 795                 800

Ser Ser Val Ser Gly Cys Leu Ser
                805
```

<210> SEQ ID NO 73
<211> LENGTH: 967
<212> TYPE: DNA
<213> ORGANISM: Arabidopsis thaliana
<220> FEATURE:
<221> NAME/KEY: promoter
<222> LOCATION: (1)..(967)
<223> OTHER INFORMATION: promoter of gene At1g76580

<400> SEQUENCE: 73

```
ataatatagg tgattcgcgt taccgaatgt aatttgactt gtggtatact aattgtgact      60

ttgtttttat ttctttgaca ttacgtaaaa tttgtttcta ccaattttga taagtgcacg     120

gtcaaatcaa aagaggaaaa tgaaaacttg ggttgaatt ctcaacttga acatatatga     180

tagtcaacac gacaatacgt tgtattcctt atattgaaat gaagctaatt aaggtctata     240

tggaaacaaa tatgttattt atttatcaat gacgtatcac attttgacga ataaagagat     300

taatgttatc ctttacaaaa taatgaaata agaaagaaac agaagtttat gtttgtccaa     360

ttatcctcaa tgtttgttga tatacgaatt ttgagaattc aaactgaata caagaaataa     420

aaatgtagtg agataataat acaaatttgc attatttctt ccaagattgt tttctttaag     480

taaatgaaaa gtatcttgga ttattacaga aatgacccta aatctttttg aatttacagt     540

ttgtaccacc accgaataaa ataagaaaaa gtttcgttaa atgttacgag tgctcgttga     600
```

```
agacgaagtt tcgaagacga ccaacaaaga gaaagatcaa aatttgagag ggaaacaaaa    660

aaagaggaag agagaagaag aagaagaaaa cacccttgat taataaagtc tcagactttt    720

tgattcgatt cgaaaaaagt gagtttatgc ttgaagctgg gaattccaaa actcggaatt    780

cgtgtaaaac tagttcgatt tatcagagtt atgctaaggt aacatagtcg attcatttca    840

aatttacgaa ctttatgttc atctgatctc tctctctttc tcttctattt ttggtaacga    900

atctcgaaat ttcttgtgtt gaattttgta gttagtgaag gtgaatgaaa aagagttgat    960

ttttgag                                                              967
```

```
<210> SEQ ID NO 74
<211> LENGTH: 968
<212> TYPE: DNA
<213> ORGANISM: Arabidopsis thaliana
<220> FEATURE:
<221> NAME/KEY: promoter
<222> LOCATION: (1)..(968)
<223> OTHER INFORMATION: promoter of gene At1g76580

<400> SEQUENCE: 74

ataatatagc gtgattcgcg ttaccgaatg taatttgact tgtggtatac taattgtgac     60

tttgttttta tttctttgac attacgtaaa atttgtttct accaattttg ataagtgcac    120

ggtcaaatca aaagaggaaa atgaaaactt ggggttgaat tctcaacttg aacatatatg    180

atagtcaaca cgacaatacg ttgtattcct tatattgaaa tgaagctaat taaggtctat    240

atggaaacaa atatgttatt tatttatcaa tgacgtatca cattttgacg aataaagaga    300

ttaatgttat cctttacaaa ataatgaaat aagaaagaaa cagaagttta tgtttgtcca    360

attatcctca atgtttgttg atatacgaat tttgagaatt caaactgaat acaagaaata    420

aaaatgtagt gagataataa tacaaatttg cattatttct tccaagattg ttttctttaa    480

gtaaatgaaa agtatcttgg attattacag aaatgaccct aaatcttttt gaatttacag    540

tttgtaccac caccgaataa aataagaaaa agtttcgtta aatgttacga gtgctcgttg    600

aagacgaagt ttcgaagacg accaacaaag agaaagatca aaatttgaga gggaaacaaa    660

aaaagaggaa gagagaagaa gaagaagaaa acacccttga ttaataaagt ctcagacttt    720

ttgattcgat tcgaaaaaag tgagtttatg cttgaagctg ggaattccaa aactcggaat    780

tcgtgtaaaa ctagttcgat ttatcagagt tatgctaagg taacatagtc gattcatttc    840

aaatttacga actttatgtt catctgatct ctctctcttt ctcttctatt tttggtaacg    900

aatctcgaaa tttcttgtgt tgaattttgt agttagtgaa ggtgaatgaa aaagagttga    960

tttttgag                                                             968
```

```
<210> SEQ ID NO 75
<211> LENGTH: 2037
<212> TYPE: DNA
<213> ORGANISM: Arabidopsis thaliana
<220> FEATURE:
<221> NAME/KEY: promoter
<222> LOCATION: (1)..(2037)
<223> OTHER INFORMATION: promoter of gene At1g76580

<400> SEQUENCE: 75

tcaaatcaac tctttttcat tcaccttcac taactacaaa attcaacaca agaaatttcg     60

agattcgtta ccaaaaatag aagagaaaga gagagagatc agatgaacat aaagttcgta    120

aatttgaaat gaatcgacta tgttacctta gcataactct gataaatcga actagtttta    180
```

```
cacgaattcc gagttttgga attcccagct tcaagcataa actcactttt ttcgaatcga    240

atcaaaaagt ctgagacttt attaatcaag ggtgttttct tcttcttctt ctctcttcct    300

ctttttttgt ttccctctca aattttgatc tttctctttg ttggtcgtct tcgaaacttc    360

gtcttcaacg agcactcgta acatttaacg aaactttttc ttatttttatt cggtggtggt   420

acaaactgta aattcaaaaa gatttagggt catttctgta ataatccaag atacttttca    480

tttacttaaa gaaaacaatc ttggaagaaa taatgcaaat ttgtattatt atctcactac    540

atttttattt cttgtattca gtttgaattc tcaaaattcg tatatcaaca aacattgagg    600

ataattggac aaacataaac ttctgtttct ttcttatttc attattttgt aaaggataac    660

attaatctct ttattcgtca aaatgtgata cgtcattgat aaataaataa catatttgtt    720

tccatataga ccttaattag cttcatttca atataaggaa tacaacgtat tgtcgtgttg    780

actatcatat atgttcaagt tgagaattca accccaagtt ttcattttcc tcttttgatt    840

tgaccgtgca cttatcaaaa ttggtagaaa caaattttac gtaatgtcaa agaaataaaa    900

acaaagtcac aattagtata ccacaagtca aattacattc ggtaacgcga atcacgctat    960

attatgagct tattaattaa tttggaaaat tagtttttttg tttacatctt cttaattctt  1020

taatcgttga caattgagtt tcactttaga gatttttagc ctacttaaac acactaacca   1080

taaagcgcgt ccacgtttgg aggaagtcgg catcataaaa tacaaaaaac ctgtcgatac   1140

aaaaagacat aagtaccctt ttattttaca aaactactat atgaaatctc tcgcattgta   1200

cggattgatt tatgtagcta ttcaatttct cctttcttta ttttccggat gtgtataaaa   1260

aaaacttaaa ccctctcttc ttactctgtg tgcacttttt tttctaagga agtacaatac   1320

acgagattta gtgtgtgaat ctaactaata gtatgtatgt acttgtacat agaagtgggg   1380

aaaaaggttt gagaagaggg ggaaacagct gtatggtacg gaaagtagat gtcaatttga   1440

ttgggagaat actgacaccc attcattcgt ttctctgttt gtacttcctt catttcttgt   1500

actacaaaac tctcctttca ctttttttcta atcttttaaa ataattgtta ttcgtttctt  1560

tcaacctttt tgcttacatt cacgatgaat tggaaaatat tatgaaaata aaacgatttt   1620

tctcaattag tacgaccaaa aacaagatac taaaatgtag tgagcttctg aaatttctta   1680

ctatatagta tatcactcaa ttttacctat aaaaaactca taaaatagtt atttaatcac   1740

ggttatggct ttgatttgag atattggaag tgttgaccga agaacatgca cgttacgtta   1800

gtaatgggct ctgttggcaa tagttataca gcgatcataa agccaccaat tggcgagaaa   1860

aaaaaaaaaa ccaccaatca aacaactaat ggatatgagg aaattgtaca tgttcggttt   1920

tataatgccg aaaagaagct cttcgtgatt aattgtttta gaacgataag aaaaatatga   1980

tttgaaagct ttcaaatcat atttttctta tcgaatgaaa aagagttgat ttttgag      2037
```

```
<210> SEQ ID NO 76
<211> LENGTH: 1990
<212> TYPE: DNA
<213> ORGANISM: Arabidopsis thaliana
<220> FEATURE:
<221> NAME/KEY: promoter
<222> LOCATION: (1)..(1990)
<223> OTHER INFORMATION: promoter of gene At1g76580

<400> SEQUENCE: 76

ctcaaaaatc aactcttttt cattcacctt cactaactac aaaattcaac acaagaaatt     60

tcgagattcg ttaccaaaaa tagaagagaa agagagagag atcagatgaa cataaagttc    120

gtaaatttga aatgaatcga ctatgttacc ttagcataac tctgataaat cgaactagtt    180
```

```
ttacacgaat tccgagtttt ggaattccca gcttcaagca taaactcact tttttcgaat    240

cgaatcaaaa agtctgagac tttattaatc aagggtgttt tcttcttctt cttctctctt    300

cctctttttt tgtttccctc tcaaattttg atctttctct ttgttggtcg tcttcgaaac    360

ttcgtcttca acgagcactc gtaacattta acgaaacttt ttcttatttt attcggtggt    420

ggtacaaact gtaaattcaa aaagatttag ggtcatttct gtaataatcc aagatacttt    480

tcatttactt aaagaaaaca atcttggaag aaataatgca aatttgtatt attatctcac    540

tacattttta tttcttgtat tcagtttgaa ttctcaaaat tcgtatatca acaaacattg    600

aggataattg gacaaacata aacttctgtt tctttcttat ttcattattt tgtaaaggat    660

aacattaatc tctttattcg tcaaaatgtg atacgtcatt gataaataaa taacatattt    720

gtttccatat agaccttaat tagcttcatt tcaatataag gaatacaacg tattgtcgtg    780

ttgactatca tatatgttca agttgagaat tcaaccccaa gttttcattt tcctcttttg    840

atttgaccgt gcacttatca aaattggtag aaacaaattt tacgtaatgt caaagaaata    900

aaaacaaagt cacaattagt ataccacaag tcaaattaca ttcggtaacg cgaatcacgc    960

tatattatga gcttattaat taatttggaa aattagtttt ttttttacat cttcttaatt   1020

ctttaatcgt tgacaattga gtttcacttt agagattttt agcctactta aacacactaa   1080

ccataaagcg cgtccacgtt tggaggaagt cggcatcata aaatacaaaa aacctgtcga   1140

tacaaaaaga cataagtacc cttttatttt acaaaactac tatatgaaat ctctcgcatt   1200

gtacggattg atttatgtag ctattcaatt tctcctttct ttattttccg gatgtgtata   1260

aaaaaaactt aaaccctctc ttcttactct gtgtgcactt ttttttctaa ggaagtacaa   1320

tacacgagat ttagtgtgtg aatctaacta atagtatgta tgtacttgta catagaagtg   1380

gggaaaaagg tttgagaaga gggggaaaca gctgtatggt acggaaagta gatgtcaatt   1440

tgattgggag aatactgaca cccattcatt cgtttctctg tttgtacttc cttcatttct   1500

tgtactacaa aactctcttt tcactttttt ctaatctttt aaaataattg ttattcgttt   1560

ctttcaacct ttttgcttac attcacgatg aattggaaaa tattatgaaa ataaaacgat   1620

ttttctcaat tagtacgacc aaaaacaaga tactaaaatg tagtgagctt ctgaaatttc   1680

ttactatata gtatatcact caattttacc tataaaaaac tcataaaata gttatttaat   1740

cacggttatg gctttgattt gagatattgg aagtgttgac cgaagaacat gcacgttacg   1800

ttagtaatgg gctctgttga caatagttat acagcgatca taaagccacc aattggcgag   1860

aaaaaaaaaa aaaaaccacc aatcaaacaa ctaatggata tgaggaaatt gtacatgttc   1920

ggttttataa tgccgaaaag aagctcttcg tgattaattg ttttagaacg ataagaaaaa   1980

tatgatttga                                                          1990
```

<210> SEQ ID NO 77
<211> LENGTH: 3614
<212> TYPE: DNA
<213> ORGANISM: Arabidopsis thaliana
<220> FEATURE:
<221> NAME/KEY: CDS
<222> LOCATION: (798)..(2201)
<223> OTHER INFORMATION: coding for SPL1-Related3 protein (SPL1R3) (At1g76580)

<400> SEQUENCE: 77

```
gaagacgacc aacaaagaga aagatcaaaa tttgagaggg aaacaaaaaa agaggaagag     60

agaagaagaa gaagaaaaca cccttgatta ataaagtctc agactttttg attcgattcg    120
```

-continued

```
aaaaaagtga gtttatgctt gaagctggga attccaaaac tcggaattcg tgtaaaacta    180

gttcgattta tcagagttat gctaagttag tgaaggtgaa tgaaaaagag ttgatttttg    240

agagaggaga gaaatgggtg agttacccaa ggatgattgg cagatgaaca ggtggaagtg    300

ggatggtcag agatttgaag ctatagaact acaaggagag tctctccagc taagtaacaa    360

aaaaggtctt gatttgaatc taccttgtgg ttttaacgat gttgaaggca cgccggtgga    420

tttaaccaga ccgagtaaga aggttaggtc gggatctccg ggaagtggcg gcggaggagg    480

aggaaactat ccgaagtgtc aggttgataa ttgtaaggaa gatttatcaa ttgctaagga    540

ttatcataga agacataaag tttgtgaggt tcatagcaaa gctactaaag ctcttgttgg    600

gaaacagatg cagaggtttt gccaacagtg tagcagttgt taggtttcat ctgctttctg    660

agtttgatga ggggaagaga agttgtaggc gtagattgga tggtcataac aggcggagga    720

gaaaaacaca gcccgatgcg attacatctc aggttgtagc tctggagaat cgtgataata    780

cttctaataa cactaat atg gat gtt atg gct ttg tta aca gct tta gtt      830
                   Met Asp Val Met Ala Leu Leu Thr Ala Leu Val
                   1               5                   10

tgt gca caa ggt agg aac gag gct act act aat ggg tct ccg gga gtg      878
Cys Ala Gln Gly Arg Asn Glu Ala Thr Thr Asn Gly Ser Pro Gly Val
            15                  20                  25

cct caa aga gag caa ctt ctt cag ata ctt aac aag atc aag gct tta      926
Pro Gln Arg Glu Gln Leu Leu Gln Ile Leu Asn Lys Ile Lys Ala Leu
        30                  35                  40

cct ttg cct atg aat ctt acc tcg aag ttg aac aat atc gga att tta      974
Pro Leu Pro Met Asn Leu Thr Ser Lys Leu Asn Asn Ile Gly Ile Leu
    45                  50                  55

gcc agg aaa aat ccg gag caa ccc tcc ccg atg aat cct caa aat agt     1022
Ala Arg Lys Asn Pro Glu Gln Pro Ser Pro Met Asn Pro Gln Asn Ser
60                  65                  70                  75

atg aat ggg gct tct tct cca tct acg atg gac ttg ctt gct gct ctc     1070
Met Asn Gly Ala Ser Ser Pro Ser Thr Met Asp Leu Leu Ala Ala Leu
                80                  85                  90

tcg gca tct tta ggt tca tct gct cca gag gcc ata gct ttt tta tct     1118
Ser Ala Ser Leu Gly Ser Ser Ala Pro Glu Ala Ile Ala Phe Leu Ser
            95                  100                 105

caa gga ggg ttt ggt aac aaa gaa agc aat gat agg act aag tta act     1166
Gln Gly Gly Phe Gly Asn Lys Glu Ser Asn Asp Arg Thr Lys Leu Thr
        110                 115                 120

tct tct gac cac agc gcc aca acc agt tta gaa aag aaa act ttg gag     1214
Ser Ser Asp His Ser Ala Thr Thr Ser Leu Glu Lys Lys Thr Leu Glu
    125                 130                 135

ttt cct tct ttt ggg gga gga gag agg aca agt agc act aac cat tct     1262
Phe Pro Ser Phe Gly Gly Gly Glu Arg Thr Ser Ser Thr Asn His Ser
140                 145                 150                 155

cca tct cag tat tca gat tca cgc ggt caa gac act aga tcg agc tta     1310
Pro Ser Gln Tyr Ser Asp Ser Arg Gly Gln Asp Thr Arg Ser Ser Leu
                160                 165                 170

tct cta caa cta ttc acc tct tca cca gaa gag gag agt cga cca aaa     1358
Ser Leu Gln Leu Phe Thr Ser Ser Pro Glu Glu Glu Ser Arg Pro Lys
            175                 180                 185

gtt gca tct tca aca aag tat tat tct tct gcg agc agt aac cct gtt     1406
Val Ala Ser Ser Thr Lys Tyr Tyr Ser Ser Ala Ser Ser Asn Pro Val
        190                 195                 200

gag gat aga tca cca tca tca tct cca gtc atg caa gag tta ttc cct     1454
Glu Asp Arg Ser Pro Ser Ser Ser Pro Val Met Gln Glu Leu Phe Pro
    205                 210                 215
```

-continued

```
ttg cat act tct cct gaa acc agg agg tat aac aat tac aaa gac act      1502
Leu His Thr Ser Pro Glu Thr Arg Arg Tyr Asn Asn Tyr Lys Asp Thr
220                 225                 230                 235

agt acc agt ccc agg acc agt tgt ttg ccc cta gag ctc ttt ggt gca      1550
Ser Thr Ser Pro Arg Thr Ser Cys Leu Pro Leu Glu Leu Phe Gly Ala
                240                 245                 250

tca aat aga gga gct act gca aat cct aat tac aat gtt ttg agg cat      1598
Ser Asn Arg Gly Ala Thr Ala Asn Pro Asn Tyr Asn Val Leu Arg His
            255                 260                 265

caa tct ggt tat gct tca tct ggt tcg gat tat tct cct cct agc tta      1646
Gln Ser Gly Tyr Ala Ser Ser Gly Ser Asp Tyr Ser Pro Pro Ser Leu
        270                 275                 280

aac tct aat gct cag gag cgc aca gga aag ata tct ttc aaa cta ttt      1694
Asn Ser Asn Ala Gln Glu Arg Thr Gly Lys Ile Ser Phe Lys Leu Phe
    285                 290                 295

gaa aaa gat cct agt cag ctc cct aac aca ttg cga acc gag atc ttt      1742
Glu Lys Asp Pro Ser Gln Leu Pro Asn Thr Leu Arg Thr Glu Ile Phe
300                 305                 310                 315

aga tgg ctt tct agt ttt cca tca gat atg gag agt ttt atc agg cct      1790
Arg Trp Leu Ser Ser Phe Pro Ser Asp Met Glu Ser Phe Ile Arg Pro
                320                 325                 330

ggt tgt gtt att tta tct gtc tat gtg gca atg tca gct tct gct tgg      1838
Gly Cys Val Ile Leu Ser Val Tyr Val Ala Met Ser Ala Ser Ala Trp
            335                 340                 345

gaa caa ctt gag gaa aat tta ctg caa cga gtt aga tct ttg gtt caa      1886
Glu Gln Leu Glu Glu Asn Leu Leu Gln Arg Val Arg Ser Leu Val Gln
        350                 355                 360

gat tca gaa ttt tgg agt aat tca aga ttt ttg gtc aat gca ggc aga      1934
Asp Ser Glu Phe Trp Ser Asn Ser Arg Phe Leu Val Asn Ala Gly Arg
    365                 370                 375

cag ctc gcg tca cac aaa cat ggt aga att cgt ctg agc aaa tct tgg      1982
Gln Leu Ala Ser His Lys His Gly Arg Ile Arg Leu Ser Lys Ser Trp
380                 385                 390                 395

aga act ttg aat tta cca gag cta atc acg gtg tcg ccg ttg gct gtt      2030
Arg Thr Leu Asn Leu Pro Glu Leu Ile Thr Val Ser Pro Leu Ala Val
                400                 405                 410

gta gcc ggt gaa gaa aca gct tta ata gta agg ggt aga aac ttg act      2078
Val Ala Gly Glu Glu Thr Ala Leu Ile Val Arg Gly Arg Asn Leu Thr
            415                 420                 425

aat gac gga atg aga ctt cgt tgc gca cat atg ggt aac tac gcg tca      2126
Asn Asp Gly Met Arg Leu Arg Cys Ala His Met Gly Asn Tyr Ala Ser
        430                 435                 440

atg gag gta act gga aga gaa cat agg tta aca aaa gtt gat gag tta      2174
Met Glu Val Thr Gly Arg Glu His Arg Leu Thr Lys Val Asp Glu Leu
    445                 450                 455

aac gta agt agt ttc caa gtc cag agt gcaagctctg tttctctagg           2221
Asn Val Ser Ser Phe Gln Val Gln Ser
460                 465

acgatgtttc attgagccaa tgccacgatt tgcaaagagt tgaatcgcct tgaagaagag   2281

tttcatccaa aagacgtgat agaggaacaa atacagaact tagatcgtcc aagatcaaga   2341

gaagaagttc tttgcttctt gaatgagctt ggttggctat ttcagaggaa atggacatcc   2401

gatattcatg gagaacccga cttttctctt cctcgcttca aatttttgct cgtatgctct   2461

gttgaaagag attactgttc tctcataaga accgtcctgg atatgatggt agagagaaat   2521

ttgggaaaag acggtctgtt gaacaaggag tccttagata tgctggctga tattcagcta   2581

ctgaatcgcg ctatcaaaag gagaaacaca aaaatggctg aaactctgat ccattattcc   2641

gttaatccct ctactagaaa cttcatcttc ttgcctagta tcgctggacc tggcgatatc   2701
```

```
acacctttgc atttggctgc ttccacatct agttctgatg atatgattga tgccctgact   2761

aatgatccac aagagattgg attatcttgc tggaataccc tagtcgatgc aaccgggcaa   2821

actcccttta gctacgctgc aatgagagac aaccacagtt acaacacctt ggtggctcgt   2881

aaacttgcag ataaaagaaa cggtcaaata tctctgaaca ttgaaaatgg gatcgatcag   2941

attggcctga gtaagagact aagctcagag ctaaagagat cttgcaacac atgtgcaagt   3001

gtggctctaa agtatcagag gaaggtttcg ggttcacgtc gattgttccc aactccgatc   3061

attcactcga tgcttgcggt tgcgacagta tgtgtttgcg tctgcgtgtt tatgcatgct   3121

ttcccaatgg tcagacaagg ctctcacttc agttggggtg gtcttgatta tggctcaatc   3181

taaggtttgt tatataacta agtgttgtta attcttttgg ttcgatacca aaagggaaaa   3241

aaaaagtgcg atgaaggaaa ctgagaatga gaggcatagt gagaaaaccc aaagacatgt   3301

ggatcttgga cattgcagag atggaatcac tcactggtct ttggtgagcc agagagtaca   3361

gagaaactgg ttcaggtcag agcagacata gcttcaacac aacacccaag tttttatata   3421

tttggctaat tatgttttat tcttgcatat gttaatttcc cattctccct taattacagt   3481

ttttagttgc ttaacacaaa agctgttgct attttactga agctgttttc tcctgtgtgt   3541

ttattgtatc tctgtagagt tgtgaacgta gttgaacatt gttgtaaaat tgtaatgtaa   3601

taccttttg gtt                                                         3614
```

```
<210> SEQ ID NO 78
<211> LENGTH: 468
<212> TYPE: PRT
<213> ORGANISM: Arabidopsis thaliana

<400> SEQUENCE: 78

Met Asp Val Met Ala Leu Leu Thr Ala Leu Val Cys Ala Gln Gly Arg
1               5                   10                  15

Asn Glu Ala Thr Thr Asn Gly Ser Pro Gly Val Pro Gln Arg Glu Gln
            20                  25                  30

Leu Leu Gln Ile Leu Asn Lys Ile Lys Ala Leu Pro Leu Pro Met Asn
        35                  40                  45

Leu Thr Ser Lys Leu Asn Asn Ile Gly Ile Leu Ala Arg Lys Asn Pro
    50                  55                  60

Glu Gln Pro Ser Pro Met Asn Pro Gln Asn Ser Met Asn Gly Ala Ser
65                  70                  75                  80

Ser Pro Ser Thr Met Asp Leu Leu Ala Ala Leu Ser Ala Ser Leu Gly
                85                  90                  95

Ser Ser Ala Pro Glu Ala Ile Ala Phe Leu Ser Gln Gly Gly Phe Gly
            100                 105                 110

Asn Lys Glu Ser Asn Asp Arg Thr Lys Leu Thr Ser Ser Asp His Ser
        115                 120                 125

Ala Thr Thr Ser Leu Glu Lys Lys Thr Leu Glu Phe Pro Ser Phe Gly
    130                 135                 140

Gly Gly Glu Arg Thr Ser Ser Thr Asn His Ser Pro Ser Gln Tyr Ser
145                 150                 155                 160

Asp Ser Arg Gly Gln Asp Thr Arg Ser Ser Leu Ser Leu Gln Leu Phe
                165                 170                 175

Thr Ser Ser Pro Glu Glu Glu Ser Arg Pro Lys Val Ala Ser Ser Thr
            180                 185                 190

Lys Tyr Tyr Ser Ser Ala Ser Ser Asn Pro Val Glu Asp Arg Ser Pro
        195                 200                 205
```

```
Ser Ser Ser Pro Val Met Gln Glu Leu Phe Pro Leu His Thr Ser Pro
    210                 215                 220

Glu Thr Arg Arg Tyr Asn Asn Tyr Lys Asp Thr Ser Thr Ser Pro Arg
225                 230                 235                 240

Thr Ser Cys Leu Pro Leu Glu Leu Phe Gly Ala Ser Asn Arg Gly Ala
                245                 250                 255

Thr Ala Asn Pro Asn Tyr Asn Val Leu Arg His Gln Ser Gly Tyr Ala
            260                 265                 270

Ser Ser Gly Ser Asp Tyr Ser Pro Pro Ser Leu Asn Ser Asn Ala Gln
        275                 280                 285

Glu Arg Thr Gly Lys Ile Ser Phe Lys Leu Phe Glu Lys Asp Pro Ser
    290                 295                 300

Gln Leu Pro Asn Thr Leu Arg Thr Glu Ile Phe Arg Trp Leu Ser Ser
305                 310                 315                 320

Phe Pro Ser Asp Met Glu Ser Phe Ile Arg Pro Gly Cys Val Ile Leu
                325                 330                 335

Ser Val Tyr Val Ala Met Ser Ala Ser Ala Trp Glu Gln Leu Glu Glu
            340                 345                 350

Asn Leu Leu Gln Arg Val Arg Ser Leu Val Gln Asp Ser Glu Phe Trp
        355                 360                 365

Ser Asn Ser Arg Phe Leu Val Asn Ala Gly Arg Gln Leu Ala Ser His
    370                 375                 380

Lys His Gly Arg Ile Arg Leu Ser Lys Ser Trp Arg Thr Leu Asn Leu
385                 390                 395                 400

Pro Glu Leu Ile Thr Val Ser Pro Leu Ala Val Val Ala Gly Glu Glu
                405                 410                 415

Thr Ala Leu Ile Val Arg Gly Arg Asn Leu Thr Asn Asp Gly Met Arg
            420                 425                 430

Leu Arg Cys Ala His Met Gly Asn Tyr Ala Ser Met Glu Val Thr Gly
        435                 440                 445

Arg Glu His Arg Leu Thr Lys Val Asp Glu Leu Asn Val Ser Ser Phe
    450                 455                 460

Gln Val Gln Ser
465


<210> SEQ ID NO 79
<211> LENGTH: 2108
<212> TYPE: DNA
<213> ORGANISM: Arabidopsis thaliana
<220> FEATURE:
<221> NAME/KEY: promoter
<222> LOCATION: (1)..(2108)
<223> OTHER INFORMATION: promoter of gene At1g31930

<400> SEQUENCE: 79

tggtgtccga aaatgtcaaa ttctggaatc tatgattata taagaaagat ttgaaagttt      60

ttaatgaggg tttttgaatc tcatccctcg agattttcat ggaaaatatg agccacaagt     120

aaaagtattt gaaggttctg ataagtttgt gattagtgag agagaaaaga gagtggggtg     180

ctttggattt tctctccatg ctatgtgtca gttgttggga ccctccttaa aattgagatt     240

caaacacgat ttcaagtggt tcaatccggt tcggttcttc tgaaccgatc taatcgaaac     300

ataaattgga ggagtcacgg gcaagtagtc ggaaaccaaa acaggtttct tttgacaaat     360

gaagtcttct cacaaaacta tagaactgaa ataattgagg atataggaat tttgtgaaag     420

cgttttacga atagtgaaat agatatgttg gtgaatcatc atttttgaag tgagaataac     480
```

```
aagataccaa aattatggta tcctaatcac ggatatgttt ataagttgtt tttctttttg    540

ggttcaatag tcaacagata atagacaggg tgggtcgcca ttaattttta ctaattacaa    600

cttttcttat gatagtatgt tgtttaggtt tatctaaatt ggcgcataat ctttttggtt    660

tctgtcaaca tttgaactcc actaagaaca agtgaaacaa ataagacttt ttaaatcatc    720

ccatttatat aagtttagaa atcatcccaa aaaacctcat tacatatgtg aatgaatata    780

cggccaaaca acgtcacaac acaataataa tgtcattcct cacatgctta ctctgatttt    840

gaattttcaa atattaaaaa aattcgacaa ctcttatgcg catattagtt agcatataca    900

gttctttgta tatacgaatg ctaatttaat tctcaacggt tttcagacac aattggaaat    960

caatattaac tgtaattaag tttaatcaaa tataaaatca ttaaaacgtt gacgaaaaaa   1020

gaaaagtatt aattattaat aattattaat tccatatatg gtttttttaca tttcaagcgt   1080

gtgagtttgt agtgtagatt tgaaacacac gcgcatacag gcgcgtgggg gataaacgta   1140

actagtgtgt gtgtgtgtag gaaccaaatt attagattgg tcgtgacaat gtgaaccact   1200

cgctagaaaa cgagccgtga ttgccacgcg ctttcaccac ccgtctccat cgtcacgaac   1260

tatgtaagac tcgtgggtcc ttttttatcg attcatctct ctatagattt caccgtctct   1320

ctgccgtttc ctttctccag attctttttc tcagagaaat aaaacaaata tcacagctac   1380

caaaacagat tcctcttact tcttcttctt cttgttctgt gttcgtcttc tcagattcag   1440

cttcgacttt ttttggtttc tcacttttat acaaaaggta agattttttc atcttctttt   1500

acaaaagatt tattttgttc tgttgcttta attggtgtct tccttcagag acacagctca   1560

tttttttgt ttcattctat ttgaaatttt catgaatttg cttaatctat caacagtcat   1620

gatctgaaag tttgctgcat gtattcttag caaattcgat ttggtactgg atttagaata   1680

attaaccagt ttgtttgttt tttccttttt gttttcttct tctataggct gcgttcaaag   1740

ctggaaactt ttaagtgggt ttggttagat gttgaattaa tttttttcat ggacaattgt   1800

tttgaccaag aatttgtcaa aatgtcaatt taaaaagctt ttccttttta ggtttcaatg   1860

ctctctcgtg aaacgtccat atatgccggc tatttgactt tgatttttat tcatatgaca   1920

aaactaaagc caatttggta acacatatac ttatcctaat cccaactctt tcttgttgtt   1980

tttatcgtct ttgtgtctga accaggaacc ttgttttgtc ttaaatcaga ggaaatggtg   2040

atgtgatttg tggttgcatc ttgtaatttc tccattggtg gtgtggctct tttgattgtg   2100

taaaaaac                                                            2108
```

<210> SEQ ID NO 80
<211> LENGTH: 2113
<212> TYPE: DNA
<213> ORGANISM: Arabidopsis thaliana
<220> FEATURE:
<221> NAME/KEY: promoter
<222> LOCATION: (1)..(2113)
<223> OTHER INFORMATION: promoter of gene At1g31930

<400> SEQUENCE: 80

```
tggtgtccga aaatgtcaaa ttctggaatc tatgattata taagaaagat ttgaaagttt     60

ttaatgaggg tttttgaatc tcatccctcg agattttcat ggaaaatatg agccacaagt    120

aaaagtattt gaaggttctg ataagtttgt gattagtgag agagaaaaga gagtggggtg    180

ctttggattt tctctccatg ctatgtgtca gttgttggga ccctccttaa aattgagatt    240

caaacacgat ttcaagtggt tcaatccggt tcggttcttc taaaccgatc taatcgaaac    300
```

```
ataaattgga ggagtcacgg gcaagtagtc ggaaaccaaa acaggtttct tttgacaaat    360

gaagtcttct cacaaaacta tagaactgaa ataattgagg atataggaat tttgtgaaag    420

cgttttacaa atagtgaaat agatatgttg gtgaatcatc atttttgaag tgagaataac    480

aagataccaa aattatggta tcctaatcac ggatatgttt ataagttgtt tttctttttg    540

ggttcaatag tcaacagata atagacaggg tgggtcgcca ttaattttta ctaattacaa    600

cttttcttat gatagtatgt tgtttaggtt tatctaaatt ggcgcataat ctttttggtt    660

tctgtcaaca tttgaactcc actaagaaca agtgaaacaa ataagacttt ttaaatcatc    720

ccatttatat aagtttagaa atcatcccaa aaaacctcat tacatatgtg aatgaatata    780

cggccaaaca acgtcagaac acaataataa tgtcattcct cacatgctta ctctgatttt    840

gaattttcaa atattaaaaa aattcgacaa ctcttatgcg catattagtt agcatataca    900

gttctttgta tatacgaatg ctaatttaat tctcaacggt tttcagacac aattggaaat    960

caatattaac tgtaattaag tttaatcaaa tataaaatca ttaaaacgtt gacgaaaaaa   1020

agaaaagtat taattattaa taattattaa ttccatatat ggttttttac atttcaagcg   1080

tgtgagtatg tagtgtagat ttgaaacaca cacgcataca ggcgcgtggg ggataaacgt   1140

aactagtgtg tgtgtgtgta ggaaccaaat tattagattg gtcgtgacaa tgtgaaccac   1200

tcgctagaaa acgagccgtg attgccacgc gctttcacca cccgtctcca tcgtcacgaa   1260

ctatgtaaga ctcgtgggtc ctttttttatc gattcatctc tctatagatt tcaccgtctc   1320

tctgccgttt cctttctcca gattcttttt ctcagagaga taaaacaaat atcacagcta   1380

ccaaaacaga ttcctcttac ttcttcttct tcttgttctg tgttcgtctt ctcagattca   1440

gcttcgactt ttttttgtt tctcactttt atacaaaagg taagattttt tcatcttctt   1500

ttgcaaaaga tttattttgt tctgttgctt taattggtgt cttccttcag agacacagct   1560

catttttttt gtttcattct atttgaaatt ttcatgaatt tgcttaatct atcaacagtc   1620

atgatctgaa attttgctgc atgtattctt attagcaagt tcgattcggt agtggattta   1680

gaataattaa ccagtttagt ttttttttcc cttttagttt tttcttctat aggctgcgtt   1740

caaagctgga aacttttaag tgggtttggt tagatgttga attaattttt ttcatggaca   1800

attgatttga ccatgaattt gtcaaaatgt caatttaaaa agcttttcct ttttaggttt   1860

caatgctctc tcgtgaaacg tccatatatg ccggctattt gactttgatt tttattcata   1920

tgacaaaact aaagccaatt tggtaacaca tatacttatc ctaatcccaa ctctttcttt   1980

gtttttatcg tctttgtgtc tgaaccagga accttgtttt gtcttaaatc agaggaaatg   2040

gtgatgtgat ttgtggttgc atcttgtaat tttctctatt ggtggtgtgc ttcttttgat   2100

tgtgtaaaaa aac                                                       2113
```

<210> SEQ ID NO 81
<211> LENGTH: 1329
<212> TYPE: DNA
<213> ORGANISM: Arabidopsis thaliana
<220> FEATURE:
<221> NAME/KEY: promoter
<222> LOCATION: (1)..(1329)
<223> OTHER INFORMATION: promoter of gene At1g31930

<400> SEQUENCE: 81

```
tggtgtccga aaatgtcaaa ttctggaatc tatgattata taagaaagat ttgaaagttt     60

ttaatgaggg tttttgaatc tcatccctcg agattttcat ggaaaatatg agccacaagt    120

aaaagtattt gaaggttctg ataagtttgt gattagtgag agagaaaaga gagtggggtg    180
```

```
ctttggattt tctctccatg ctatgtgtca gttgttggga ccctccttaa aattgagatt    240

caaacacgat ttcaagtggt tcaatccggt tcggttcttc tgaaccgatc taatcgaaac    300

ataaattgga ggagtcacgg gcaagtagtc ggaaaccaaa acaggtttct tttgacaaat    360

gaagtcttct cacaaaacta tagaactgaa ataattgagg atataggaat tttgtgaaag    420

cgttttacga atagtgaaat agatatgttg gtgaatcatc atttttgaag tgagaataac    480

aagataccaa aattatggta tcctaatcac ggatatgttt ataagttgtt tttctttttg    540

ggttcaatag tcaacagata atagacaggg tgggtcgcca ttaattttta ctaattacaa    600

cttttcttat gatagtatgt tgtttaggtt tatctaaatt ggcgcataat ctttttggtt    660

tctgtcaaca tttgaactcc actaagaaca agtgaaacaa ataagacttt ttaaatcatc    720

ccatttatat aagtttagaa atcatcccaa aaaacctcat tacatatgtg aatgaatata    780

cggccaaaca acgtcacaac acaataataa tgtcattcct cacatgctta ctctgatttt    840

gaattttcaa atattaaaaa aattcgacaa ctcttatgcg catattagtt agcatataca    900

gttctttgta tatacgaatg ctaatttaat tctcaacggt tttcagacac aattggaaat    960

caatattaac tgtaattaag tttaatcaaa tataaaatca ttaaaacgtt gacgaaaaaa   1020

gaaaagtatt aattattaat aattattaat tccatatatg gttttttaca tttcaagcgt   1080

gtgagtttgt agtgtagatt tgaaacacac gcgcatacag gcgcgtgggg gataaacgta   1140

actagtgtgt gtgtgtgtag gaaccaaatt attagattgg tcgtgacaat gtgaaccact   1200

cgctagaaaa cgagccgtga ttgccacgcg ctttcaccac ccgtctccat cgtcacgaac   1260

tatgtaagac tcgtgggtcc ttttttatcg attcatctct ctatagattt caccgtctct   1320

ctgccgttt                                                           1329
```

```
<210> SEQ ID NO 82
<211> LENGTH: 1330
<212> TYPE: DNA
<213> ORGANISM: Arabidopsis thaliana
<220> FEATURE:
<221> NAME/KEY: promoter
<222> LOCATION: (1)..(1330)
<223> OTHER INFORMATION: promoter of gene At1g31930

<400> SEQUENCE: 82

tggtgtccga aaatgtcaaa ttctggaatc tatgattata taagaaagat ttgaaagttt     60

ttaatgaggg tttttgaatc tcatccctcg agattttcat ggaaaatatg agccacaagt    120

aaaagtattt gaaggttctg ataagtttgt gattagtgag agagaaaaga gagtggggtg    180

ctttggattt tctctccatg ctatgtgtca gttgttggga ccctccttaa aattgagatt    240

caaacacgat ttcaagtggt tcaatccggt tcggttcttc taaaccgatc taatcgaaac    300

ataaattgga ggagtcacgg gcaagtagtc ggaaaccaaa acaggtttct tttgacaaat    360

gaagtcttct cacaaaacta tagaactgaa ataattgagg atataggaat tttgtgaaag    420

cgttttacaa atagtgaaat agatatgttg gtgaatcatc atttttgaag tgagaataac    480

aagataccaa aattatggta tcctaatcac ggatatgttt ataagttgtt tttctttttg    540

ggttcaatag tcaacagata atagacaggg tgggtcgcca ttaattttta ctaattacaa    600

cttttcttat gatagtatgt tgtttaggtt tatctaaatt ggcgcataat ctttttggtt    660

tctgtcaaca tttgaactcc actaagaaca agtgaaacaa ataagacttt ttaaatcatc    720

ccatttatat aagtttagaa atcatcccaa aaaacctcat tacatatgtg aatgaatata    780
```

-continued

```
cggccaaaca acgtcagaac acaataataa tgtcattcct cacatgctta ctctgatttt    840

gaattttcaa atattaaaaa aattcgacaa ctcttatgcg catattagtt agcatataca    900

gttctttgta tatacgaatg ctaatttaat tctcaacggt tttcagacac aattggaaat    960

caatattaac tgtaattaag tttaatcaaa tataaaatca ttaaaacgtt gacgaaaaaa   1020

agaaaagtat taattattaa taattattaa ttccatatat ggttttttac atttcaagcg   1080

tgtgagtatg tagtgtagat ttgaaacaca cacgcataca ggcgcgtggg ggataaacgt   1140

aactagtgtg tgtgtgtgta ggaaccaaat tattagattg gtcgtgacaa tgtgaaccac   1200

tcgctagaaa acgagccgtg attgccacgc gctttcacca cccgtctcca tcgtcacgaa   1260

ctatgtaaga ctcgtgggtc ctttttatc gattcatctc tctatagatt tcaccgtctc   1320

tctgccgttt                                                          1330


<210> SEQ ID NO 83
<211> LENGTH: 3040
<212> TYPE: DNA
<213> ORGANISM: Arabidopsis thaliana
<220> FEATURE:
<221> NAME/KEY: CDS
<222> LOCATION: (290)..(2833)
<223> OTHER INFORMATION: coding for extra-large guanine
      nucleotidebinding protein, putative / G-protein, putative
      (At1g31930)

<400> SEQUENCE: 83

atctctctat agatttcacc gtctctctgc cgtttccttt ctccagattc tttttctcag     60

agagataaaa caaatatcac agctaccaaa acagattcct cttacttctt cttcttcttg    120

ttctgtgttc gtcttctcag attcagcttc gacttttttt ttgtttctca cttttataca    180

aaaggaacct tgttttgtct taaatcagag gaaatggtga tgtgatttgt ggttgcatct    240

tgtaattttc tctattggtg gtgtgcttct tttgattgtg taaaaaaac atg gag aag    298
                                                      Met Glu Lys
                                                      1

aaa gat gaa ggt gaa agc tgg aaa gaa atg gtg aga aag atg ctt cct      346
Lys Asp Glu Gly Glu Ser Trp Lys Glu Met Val Arg Lys Met Leu Pro
    5                   10                  15

cct gga gct cct tta cct gaa gat cca tcg gaa ttt gat tac tct ata      394
Pro Gly Ala Pro Leu Pro Glu Asp Pro Ser Glu Phe Asp Tyr Ser Ile
20                  25                  30                  35

gct tta gag tac act ggt cct cct cct gtt cat gat atc cct aga gtt      442
Ala Leu Glu Tyr Thr Gly Pro Pro Pro Val His Asp Ile Pro Arg Val
                40                  45                  50

tca cct gtt gat gtt aat cct cgt gtg aat aat ccg ata cca tta ccg      490
Ser Pro Val Asp Val Asn Pro Arg Val Asn Asn Pro Ile Pro Leu Pro
            55                  60                  65

gtc tct cgt ata gcg gga gga gtc aca agc tct tcg gga ggt tcg cca      538
Val Ser Arg Ile Ala Gly Gly Val Thr Ser Ser Ser Gly Gly Ser Pro
        70                  75                  80

gct agc tct gag tct gtg gtc tct gtg ttg cat aat aac cct gaa tca      586
Ala Ser Ser Glu Ser Val Val Ser Val Leu His Asn Asn Pro Glu Ser
    85                  90                  95

tca tct ggc tca gct tct gta tca cca gtt tct ggt cat aga caa aat      634
Ser Ser Gly Ser Ala Ser Val Ser Pro Val Ser Gly His Arg Gln Asn
100                 105                 110                 115

ggg aat cag gtt cgt aga ccg gtt gtg aaa ttc aaa cct gtc gat gat      682
Gly Asn Gln Val Arg Arg Pro Val Val Lys Phe Lys Pro Val Asp Asp
                120                 125                 130

cat gat cga att gaa ggt aga gaa gct gca gag gag gag gat aac aat      730
```

-continued

```
His Asp Arg Ile Glu Gly Arg Glu Ala Ala Glu Glu Glu Asp Asn Asn
            135                 140                 145

gtg gag gca gag aca gag agg gag agg aag gtt cat gag tgt act gca      778
Val Glu Ala Glu Thr Glu Arg Glu Arg Lys Val His Glu Cys Thr Ala
        150                 155                 160

agt acg aag aga cgg aag aag aag aag aaa agt gag tgt tat cga tgc      826
Ser Thr Lys Arg Arg Lys Lys Lys Lys Lys Ser Glu Cys Tyr Arg Cys
    165                 170                 175

gga aaa gcg aaa tgg gaa aat aag gag act tgc att gtg tgt gat gaa      874
Gly Lys Ala Lys Trp Glu Asn Lys Glu Thr Cys Ile Val Cys Asp Glu
180                 185                 190                 195

aag tat tgt gga aac tgt gtg ctt aga gca atg ggt tcg atg cct gaa      922
Lys Tyr Cys Gly Asn Cys Val Leu Arg Ala Met Gly Ser Met Pro Glu
                200                 205                 210

gga aga aag tgt gtg agt tgc atc ggt caa gct att gac gaa tcg aaa      970
Gly Arg Lys Cys Val Ser Cys Ile Gly Gln Ala Ile Asp Glu Ser Lys
            215                 220                 225

cgg tct aaa tta ggg aag cat tct cgg gta ttg tcg cgg ttg ctt agt     1018
Arg Ser Lys Leu Gly Lys His Ser Arg Val Leu Ser Arg Leu Leu Ser
        230                 235                 240

cca ttg gaa gtt aaa cag ata atg aag gcg gaa aag gag tgt act gct     1066
Pro Leu Glu Val Lys Gln Ile Met Lys Ala Glu Lys Glu Cys Thr Ala
    245                 250                 255

aat cag ctg aga cct gag cag ctg att gtg aat ggt tat cca tta aag     1114
Asn Gln Leu Arg Pro Glu Gln Leu Ile Val Asn Gly Tyr Pro Leu Lys
260                 265                 270                 275

cct gag gaa atg gct gac ttg ctc aac tgt ctt cta ccg cct cag aag     1162
Pro Glu Glu Met Ala Asp Leu Leu Asn Cys Leu Leu Pro Pro Gln Lys
                280                 285                 290

ttg aaa ccc ggt aga tat tgg tac gac aaa gaa tct ggt cta tgg ggc     1210
Leu Lys Pro Gly Arg Tyr Trp Tyr Asp Lys Glu Ser Gly Leu Trp Gly
            295                 300                 305

aag gaa gga gag aaa cca gat aga gtc att agc tcg aac ttg aac ttc     1258
Lys Glu Gly Glu Lys Pro Asp Arg Val Ile Ser Ser Asn Leu Asn Phe
        310                 315                 320

acc ggg aag ctg tcc ccg gac gcg agc aat ggg aac acg gaa gtt tat     1306
Thr Gly Lys Leu Ser Pro Asp Ala Ser Asn Gly Asn Thr Glu Val Tyr
    325                 330                 335

att aac ggt agg gag atc aca aag ctt gag ttg agg att tta aag cta     1354
Ile Asn Gly Arg Glu Ile Thr Lys Leu Glu Leu Arg Ile Leu Lys Leu
340                 345                 350                 355

gca aat gta cag tgt cca cgt gat act cat ttt tgg gta tat gac gat     1402
Ala Asn Val Gln Cys Pro Arg Asp Thr His Phe Trp Val Tyr Asp Asp
                360                 365                 370

gga cgt tat gag gaa gaa ggg cag aat aat atc cga gga aac att tgg     1450
Gly Arg Tyr Glu Glu Glu Gly Gln Asn Asn Ile Arg Gly Asn Ile Trp
            375                 380                 385

gag aag gca tct acg agg ttc atg tgt gcg ctg ttt tct tta cct gtt     1498
Glu Lys Ala Ser Thr Arg Phe Met Cys Ala Leu Phe Ser Leu Pro Val
        390                 395                 400

cct caa gga caa cct cgc gga acg gtg caa cca tcg agt aat tat gct     1546
Pro Gln Gly Gln Pro Arg Gly Thr Val Gln Pro Ser Ser Asn Tyr Ala
    405                 410                 415

act gtt ccg aat tat ata gag cat aag aag att cag aag ctt cta ctt     1594
Thr Val Pro Asn Tyr Ile Glu His Lys Lys Ile Gln Lys Leu Leu Leu
420                 425                 430                 435

ctt ggt att gaa ggt tct gga act agc act atc ttc aaa cag gcc aag     1642
Leu Gly Ile Glu Gly Ser Gly Thr Ser Thr Ile Phe Lys Gln Ala Lys
                440                 445                 450
```

-continued

```
ttt ttg tat gga aac aag ttt tca gtg gaa gag ctt caa gat att aag     1690
Phe Leu Tyr Gly Asn Lys Phe Ser Val Glu Glu Leu Gln Asp Ile Lys
            455                 460                 465

ctg atg gta caa agc aat atg tat aga tat ctc agt atc tta ctc gat     1738
Leu Met Val Gln Ser Asn Met Tyr Arg Tyr Leu Ser Ile Leu Leu Asp
        470                 475                 480

gga aga gaa cga ttt gaa gag gaa gct tta tcg cat acg aga ggt tta     1786
Gly Arg Glu Arg Phe Glu Glu Glu Ala Leu Ser His Thr Arg Gly Leu
    485                 490                 495

aac gcc gtt gaa gga gat tca gga ggg gaa gaa gca aac gac gag ggt     1834
Asn Ala Val Glu Gly Asp Ser Gly Gly Glu Glu Ala Asn Asp Glu Gly
500                 505                 510                 515

act gtc act aca cca caa agc gtc tat acc ttg aac ccg agg ttg aag     1882
Thr Val Thr Thr Pro Gln Ser Val Tyr Thr Leu Asn Pro Arg Leu Lys
                520                 525                 530

cat ttt tcg gat tgg ctt cta gat atc ata gca act ggt gat ctc gat     1930
His Phe Ser Asp Trp Leu Leu Asp Ile Ile Ala Thr Gly Asp Leu Asp
            535                 540                 545

gcg ttt ttc cca gct gca aca cgt gaa tat gct cca ttg gtt gaa gaa     1978
Ala Phe Phe Pro Ala Ala Thr Arg Glu Tyr Ala Pro Leu Val Glu Glu
        550                 555                 560

gtt tgg aaa gat ccg gct ata caa gca aca tat aga cga aaa gat gag     2026
Val Trp Lys Asp Pro Ala Ile Gln Ala Thr Tyr Arg Arg Lys Asp Glu
    565                 570                 575

ctg cat ttc ctt cct gat gtc gcg gaa tac ttc tta agc cgg gcc atg     2074
Leu His Phe Leu Pro Asp Val Ala Glu Tyr Phe Leu Ser Arg Ala Met
580                 585                 590                 595

gaa gta tcg agc aat gag tat gag cct tcg gag cga gat att gta tac     2122
Glu Val Ser Ser Asn Glu Tyr Glu Pro Ser Glu Arg Asp Ile Val Tyr
                600                 605                 610

gca gaa ggt gtt aca caa gga aat gga tta gct ttc atg gag ttt tct     2170
Ala Glu Gly Val Thr Gln Gly Asn Gly Leu Ala Phe Met Glu Phe Ser
            615                 620                 625

ctt agt gat cac agt cca atg tct gaa tct tac ccc gaa aac ccc gac     2218
Leu Ser Asp His Ser Pro Met Ser Glu Ser Tyr Pro Glu Asn Pro Asp
        630                 635                 640

gcc tta tca tct cct cag cca aag tac cag ctt atc cgc gta aac gca     2266
Ala Leu Ser Ser Pro Gln Pro Lys Tyr Gln Leu Ile Arg Val Asn Ala
    645                 650                 655

aag gga atg aac gat agc tgc aaa tgg gta gaa atg ttt gaa gat gta     2314
Lys Gly Met Asn Asp Ser Cys Lys Trp Val Glu Met Phe Glu Asp Val
660                 665                 670                 675

cga gca gtc atc ttc tgc atc agc tta agc gat tac gat caa atc aac     2362
Arg Ala Val Ile Phe Cys Ile Ser Leu Ser Asp Tyr Asp Gln Ile Asn
                680                 685                 690

atc aca ccc gaa agc agt gga aca gtc cag tat cag aac aag atg atc     2410
Ile Thr Pro Glu Ser Ser Gly Thr Val Gln Tyr Gln Asn Lys Met Ile
            695                 700                 705

caa agc aaa gaa ctt ttc gaa tca atg gtt aag cac ccc tgt ttc aaa     2458
Gln Ser Lys Glu Leu Phe Glu Ser Met Val Lys His Pro Cys Phe Lys
        710                 715                 720

gac aca cct ttt atc ttg atc cta aac aag tat gat cag ttc gaa gaa     2506
Asp Thr Pro Phe Ile Leu Ile Leu Asn Lys Tyr Asp Gln Phe Glu Glu
    725                 730                 735

aag cta aac cgt gca ccg tta aca tct tgt gac tgg ttc agc gat ttc     2554
Lys Leu Asn Arg Ala Pro Leu Thr Ser Cys Asp Trp Phe Ser Asp Phe
740                 745                 750                 755

tgc ccc gtg aga acg aac aac aac gta cag tca cta gct tac caa gct     2602
Cys Pro Val Arg Thr Asn Asn Asn Val Gln Ser Leu Ala Tyr Gln Ala
                760                 765                 770
```

-continued

```
tac ttc tat gta gca atg aag ttc aag ctt ctt tac ttt tct atc acg     2650
Tyr Phe Tyr Val Ala Met Lys Phe Lys Leu Leu Tyr Phe Ser Ile Thr
            775                 780                 785

ggt cag aaa ctg ttt gtg tgg caa gct cgg gct agg gac cgc gcg aat     2698
Gly Gln Lys Leu Phe Val Trp Gln Ala Arg Ala Arg Asp Arg Ala Asn
        790                 795                 800

gtg gat gaa ggg ttt aag tat gtg aga gag gtt ttg aaa tgg gat gaa     2746
Val Asp Glu Gly Phe Lys Tyr Val Arg Glu Val Leu Lys Trp Asp Glu
    805                 810                 815

gag aag gaa gag agt tac tta aat ggt ggt gga gaa gat tcg ttt tat     2794
Glu Lys Glu Glu Ser Tyr Leu Asn Gly Gly Gly Glu Asp Ser Phe Tyr
820                 825                 830                 835

agt acg gat atg agt tca tca cca tat aga ccg gag gag taaaatatta      2843
Ser Thr Asp Met Ser Ser Ser Pro Tyr Arg Pro Glu Glu
                840                 845

aatctccatg aggaaactct tgattaaatg atttgttgtt attttttaac ttttaagtag   2903

agagataatg tgggaagaag aaaaataaaa ttatttgtaa tcgcagaaat tttttatttg   2963

aatgccaagg ttttgtaagt tggtacacca aattgtttct ttgagatttt cttacacata   3023

atgtatatga aggtttt                                                  3040


<210> SEQ ID NO 84
<211> LENGTH: 848
<212> TYPE: PRT
<213> ORGANISM: Arabidopsis thaliana

<400> SEQUENCE: 84

Met Glu Lys Lys Asp Glu Gly Glu Ser Trp Lys Glu Met Val Arg Lys
1               5                   10                  15

Met Leu Pro Pro Gly Ala Pro Leu Pro Glu Asp Pro Ser Glu Phe Asp
            20                  25                  30

Tyr Ser Ile Ala Leu Glu Tyr Thr Gly Pro Pro Pro Val His Asp Ile
        35                  40                  45

Pro Arg Val Ser Pro Val Asp Val Asn Pro Arg Val Asn Asn Pro Ile
    50                  55                  60

Pro Leu Pro Val Ser Arg Ile Ala Gly Gly Val Thr Ser Ser Ser Gly
65                  70                  75                  80

Gly Ser Pro Ala Ser Ser Glu Ser Val Val Ser Val Leu His Asn Asn
                85                  90                  95

Pro Glu Ser Ser Ser Gly Ser Ala Ser Val Ser Pro Val Ser Gly His
            100                 105                 110

Arg Gln Asn Gly Asn Gln Val Arg Arg Pro Val Val Lys Phe Lys Pro
        115                 120                 125

Val Asp Asp His Asp Arg Ile Glu Gly Arg Glu Ala Ala Glu Glu Glu
    130                 135                 140

Asp Asn Asn Val Glu Ala Glu Thr Glu Arg Glu Arg Lys Val His Glu
145                 150                 155                 160

Cys Thr Ala Ser Thr Lys Arg Arg Lys Lys Lys Lys Lys Ser Glu Cys
                165                 170                 175

Tyr Arg Cys Gly Lys Ala Lys Trp Glu Asn Lys Glu Thr Cys Ile Val
            180                 185                 190

Cys Asp Glu Lys Tyr Cys Gly Asn Cys Val Leu Arg Ala Met Gly Ser
        195                 200                 205

Met Pro Glu Gly Arg Lys Cys Val Ser Cys Ile Gly Gln Ala Ile Asp
    210                 215                 220
```

-continued

```
Glu Ser Lys Arg Ser Lys Leu Gly Lys His Ser Arg Val Leu Ser Arg
225                 230                 235                 240

Leu Leu Ser Pro Leu Glu Val Lys Gln Ile Met Lys Ala Glu Lys Glu
                245                 250                 255

Cys Thr Ala Asn Gln Leu Arg Pro Glu Gln Leu Ile Val Asn Gly Tyr
            260                 265                 270

Pro Leu Lys Pro Glu Glu Met Ala Asp Leu Leu Asn Cys Leu Leu Pro
        275                 280                 285

Pro Gln Lys Leu Lys Pro Gly Arg Tyr Trp Tyr Asp Lys Glu Ser Gly
    290                 295                 300

Leu Trp Gly Lys Glu Gly Glu Lys Pro Asp Arg Val Ile Ser Ser Asn
305                 310                 315                 320

Leu Asn Phe Thr Gly Lys Leu Ser Pro Asp Ala Ser Asn Gly Asn Thr
                325                 330                 335

Glu Val Tyr Ile Asn Gly Arg Glu Ile Thr Lys Leu Glu Leu Arg Ile
            340                 345                 350

Leu Lys Leu Ala Asn Val Gln Cys Pro Arg Asp Thr His Phe Trp Val
        355                 360                 365

Tyr Asp Asp Gly Arg Tyr Glu Glu Glu Gly Gln Asn Asn Ile Arg Gly
    370                 375                 380

Asn Ile Trp Glu Lys Ala Ser Thr Arg Phe Met Cys Ala Leu Phe Ser
385                 390                 395                 400

Leu Pro Val Pro Gln Gly Gln Pro Arg Gly Thr Val Gln Pro Ser Ser
                405                 410                 415

Asn Tyr Ala Thr Val Pro Asn Tyr Ile Glu His Lys Lys Ile Gln Lys
            420                 425                 430

Leu Leu Leu Leu Gly Ile Glu Gly Ser Gly Thr Ser Thr Ile Phe Lys
        435                 440                 445

Gln Ala Lys Phe Leu Tyr Gly Asn Lys Phe Ser Val Glu Glu Leu Gln
    450                 455                 460

Asp Ile Lys Leu Met Val Gln Ser Asn Met Tyr Arg Tyr Leu Ser Ile
465                 470                 475                 480

Leu Leu Asp Gly Arg Glu Arg Phe Glu Glu Glu Ala Leu Ser His Thr
                485                 490                 495

Arg Gly Leu Asn Ala Val Glu Gly Asp Ser Gly Gly Glu Glu Ala Asn
            500                 505                 510

Asp Glu Gly Thr Val Thr Thr Pro Gln Ser Val Tyr Thr Leu Asn Pro
        515                 520                 525

Arg Leu Lys His Phe Ser Asp Trp Leu Leu Asp Ile Ile Ala Thr Gly
    530                 535                 540

Asp Leu Asp Ala Phe Phe Pro Ala Ala Thr Arg Glu Tyr Ala Pro Leu
545                 550                 555                 560

Val Glu Glu Val Trp Lys Asp Pro Ala Ile Gln Ala Thr Tyr Arg Arg
                565                 570                 575

Lys Asp Glu Leu His Phe Leu Pro Asp Val Ala Glu Tyr Phe Leu Ser
            580                 585                 590

Arg Ala Met Glu Val Ser Ser Asn Glu Tyr Glu Pro Ser Glu Arg Asp
        595                 600                 605

Ile Val Tyr Ala Glu Gly Val Thr Gln Gly Asn Gly Leu Ala Phe Met
    610                 615                 620

Glu Phe Ser Leu Ser Asp His Ser Pro Met Ser Glu Ser Tyr Pro Glu
625                 630                 635                 640

Asn Pro Asp Ala Leu Ser Ser Pro Gln Pro Lys Tyr Gln Leu Ile Arg
```

-continued

```
                645                 650                 655

Val Asn Ala Lys Gly Met Asn Asp Ser Cys Lys Trp Val Glu Met Phe
            660                 665                 670

Glu Asp Val Arg Ala Val Ile Phe Cys Ile Ser Leu Ser Asp Tyr Asp
        675                 680                 685

Gln Ile Asn Ile Thr Pro Glu Ser Ser Gly Thr Val Gln Tyr Gln Asn
    690                 695                 700

Lys Met Ile Gln Ser Lys Glu Leu Phe Glu Ser Met Val Lys His Pro
705                 710                 715                 720

Cys Phe Lys Asp Thr Pro Phe Ile Leu Ile Leu Asn Lys Tyr Asp Gln
                725                 730                 735

Phe Glu Glu Lys Leu Asn Arg Ala Pro Leu Thr Ser Cys Asp Trp Phe
            740                 745                 750

Ser Asp Phe Cys Pro Val Arg Thr Asn Asn Asn Val Gln Ser Leu Ala
        755                 760                 765

Tyr Gln Ala Tyr Phe Tyr Val Ala Met Lys Phe Lys Leu Leu Tyr Phe
    770                 775                 780

Ser Ile Thr Gly Gln Lys Leu Phe Val Trp Gln Ala Arg Ala Arg Asp
785                 790                 795                 800

Arg Ala Asn Val Asp Glu Gly Phe Lys Tyr Val Arg Glu Val Leu Lys
                805                 810                 815

Trp Asp Glu Glu Lys Glu Glu Ser Tyr Leu Asn Gly Gly Gly Glu Asp
            820                 825                 830

Ser Phe Tyr Ser Thr Asp Met Ser Ser Ser Pro Tyr Arg Pro Glu Glu
        835                 840                 845
```

<210> SEQ ID NO 85
<211> LENGTH: 1569
<212> TYPE: DNA
<213> ORGANISM: Arabidopsis thaliana
<220> FEATURE:
<221> NAME/KEY: promoter
<222> LOCATION: (1)..(1569)
<223> OTHER INFORMATION: promoter of gene At5g18230

<400> SEQUENCE: 85

```
aataagcttt agaagagtgc aacaaccttt ttatgataat cacacaggaa atgaaaagcc      60

tttgatttcc tttgttagct tgagggattc gtctaaaaat tgaattatta gtcgaactca     120

aaagagacat cttgtgcaac aatgtacaac actattaatt tgcgtagtta tgatctcatc     180

atataaatac agataaattt actaacttca tggaagatac tgaaattctt gagagaagga     240

cgtaaagctc cgtgcttttt aacaaagcaa gaacataccc atagatgtgt aagcattcac     300

aacgttgcaa atcgaagaaa aaccggaaag tgagaaacga atggccccgt cgaacgacga     360

gagattgggg attgtccgac gccttttttc aaaccgggtc ggttcgcata gatctgggtc     420

gggttaaact ggttttatcc gaattcgggc aagaggaccc catctgttac ctcaaagagt     480

gacaatgtca tgtttcgtcc ctgaaatttt agtaggcgct tattttcacc cattatagtt     540

ttctttggac cacttaacca aacattgcaa ttttgtttat tttatcgtta aatacacatc     600

tccagttttt tttttctttt tttttttgta gaaaaaaact tttgatttca tataattaag     660

tttaatactg tagaaaaaaa caaaaaaaaa ccattaaact aattaattac aatttactga     720

taaattttta aagtaaaaat ataatcgttt tattttataa aaatagtcgg ttaactacat     780

ttgcgtgtac taaaatgctg ataaatttat ataaaattaa aatatatctc gtatacatct     840

ataatgtatg acatacatat aggtgatata tctaatttta gtaaaataag tcaaactgtt     900
```

```
atatattaat aaggtatatt taagtttaga tttactaaac gatgtcaaca tataaaaatc     960

attgagtacg agattttaaa tttatttttc taaaaaataa aaaaaaactt taacaaataa    1020

taatacaaag gatatttaat ttgtccggta taaaattacc gttataataa aaaataacca    1080

gaatgcgtct cgcgccataa attcaaatat tctttaaatt gttttacatt actttccatt    1140

tttgtgtttt ctttttatac ttgaaatatc tacttcaata actttaattt aattttgata    1200

accaaattat tatagacctt cacatttggg aaaaacgagt aaaaataggg ggtaagaatc    1260

agaaagtagt aaaagtatga ggggcaaatc ggcgaataaa aagcccggta actcttttac    1320

tatgggccgt caatgtcaaa ctcgaaactc tcgttctgat ttctgtaatc aaatccacaa    1380

aagatccaat caaaattcat tcacccatca tcgttagtta cacatcatcg tcttcttcct    1440

ctcgctccct ctgatagcga aaccctaaaa tactctcagc tgctactttc cgtaaccaaa    1500

tcccgacgaa ttaacccttt ttttttgggg ggggataaaa tcatcggagt ctcttctctg    1560

gttcggctg                                                            1569
```

```
<210> SEQ ID NO 86
<211> LENGTH: 1575
<212> TYPE: DNA
<213> ORGANISM: Arabidopsis thaliana
<220> FEATURE:
<221> NAME/KEY: promoter
<222> LOCATION: (1)..(1575)
<223> OTHER INFORMATION: promoter of gene At5g18230

<400> SEQUENCE: 86

aataagcttt agaagagtgc aacaaccttt ttatgataat cacacaggaa atgaaaagcc      60

tttgatttcc tttgttagct tgagggattc gtctaaaaat tgaattatta gtcgaactca     120

aaagagacat cttgtgcaac aatgtacaac actattaatt tgcgtagtta tgatctcatc     180

atataaatac agataaattt actaacttca tggaagatac tgaaattctt gagagaagga     240

cgtaaagctc cgtgcttttt aacaaagcaa gaacataccc atagatgtgt aagcattcac     300

aacgttgcaa atcgaagaaa aaccggaaag tgagaaacga atggccccgt cgaacgacga     360

gagattgggg attgtccgac gcctttttc aaaccgggtc ggttcgcata gatctgggtc     420

gggttaaact ggttttatcc gaattcgggc aagaggaccc catctgttac ctcaaagagt     480

gacaatgtca tgtttcgtcc ctgaaatttt agtaggcgct tattttcacc cattatagtt     540

ttctttggac cacttaacca aacattgcaa ttttgtttat tttatcgtta aatacacatc     600

tcaaattttt ttttcttttt tttttataga aaaaaacttt tgatttcata taattaagtt     660

taatactgta gaaaaaaaca aaaaaaaacc attaaactaa ttaattacaa tctactgata     720

aatttttaaa gtaaaaatat aatcgtttta ttttatatga atgaaaaata gtcggttaac     780

tacatttgcg tgtactaaaa tgctgataaa tttatataaa attaaaatat atctcgtata     840

tatttataat gtatgacata catataggtg atatatctaa tttcagtaaa ataagtcaaa     900

ctgttatata ttaataaggt atatttaagt ttagatttac taaacgatgt caacatataa     960

aaatcattga gtacgagatt ttaaatttat ttttctataa aaataaaaaa aaactttaac    1020

aaataataat ataaagtata tttaatttgt ccggtataaa attaccgtta taataaaaaa    1080

taaccagaat gcgtctcgcg ccataaattc aaatattctt taaattgttt tacattactt    1140

tccatttttg tgttttcttt ttatacttga aatatctact tcaataactt taatttaatt    1200

ttgataacca aattattata gaccttcaca tttgggaaaa aggagtaaaa ataggggggta    1260
```

-continued

```
agaatcagaa agtagtaaaa gtatgagggg caaatcggcg aataaaaagc ccggtaactc   1320

ttttactatg ggccgtcaat gtcaaactcg aaactctcgt tctgatttct gtaatcaaat   1380

ccacaaaaga tccaatcaaa attcattcac ccatcatcgt tagttacaca tcatcgtctt   1440

cttcctctcg ctccctctga tagcgaaacc ctaaaatact ctcagctgct actttccgta   1500

accaaatccc gacgaattaa cccttttttt ttttgggggg ataaaatcat cggagtctct   1560

tctctggttc ggctg                                                      1575


<210> SEQ ID NO 87
<211> LENGTH: 2876
<212> TYPE: DNA
<213> ORGANISM: Arabidopsis thaliana
<220> FEATURE:
<221> NAME/KEY: CDS
<222> LOCATION: (138)..(2711)
<223> OTHER INFORMATION: coding for transcription regulator
      NOT2/NOT3/NOT5 family protein (At5g18230)

<400> SEQUENCE: 87

tcaaaattca ttcacccatc atcgttagtt acacatcatc gtcttcttcc tctcgctccc     60

tctgatagcg aaaccctaaa atactctcag ctgctacttt ccgtaaccaa atcccgacga    120

attaaccctt ttttttt ttg ggg gga taa aat cat cgg agt ctc ttc tct       170
                   Leu Gly Gly     Asn His Arg Ser Leu Phe Ser
                   1               5                   10

ggt tcg gct gtg atg ggt gcg agc cgg aaa tta caa ggc gag ata gat      218
Gly Ser Ala Val Met Gly Ala Ser Arg Lys Leu Gln Gly Glu Ile Asp
                15                  20                  25

cgg gtg ctg aag aag gtt caa gaa ggt gtt gat gtt ttc gac agc atc      266
Arg Val Leu Lys Lys Val Gln Glu Gly Val Asp Val Phe Asp Ser Ile
            30                  35                  40

tgg aac aag gta tat gat aca gac aat gtt aat caa aag gaa aag ttt      314
Trp Asn Lys Val Tyr Asp Thr Asp Asn Val Asn Gln Lys Glu Lys Phe
        45                  50                  55

gag gcg gac ttg aag aag gaa atc aag aag ctg cag cgg tat aga gac      362
Glu Ala Asp Leu Lys Lys Glu Ile Lys Lys Leu Gln Arg Tyr Arg Asp
    60                  65                  70

cag atc aag aca tgg att cag tct agt gag atc aaa gat aag aaa gtc      410
Gln Ile Lys Thr Trp Ile Gln Ser Ser Glu Ile Lys Asp Lys Lys Val
75                  80                  85                  90

agt gca tct tat gag caa tcc ctg gtg gat gct cgg aag ctt att gag      458
Ser Ala Ser Tyr Glu Gln Ser Leu Val Asp Ala Arg Lys Leu Ile Glu
                95                  100                 105

aaa gag atg gag agg ttt aag ata tgt gaa aaa gag acc aag aca aaa      506
Lys Glu Met Glu Arg Phe Lys Ile Cys Glu Lys Glu Thr Lys Thr Lys
            110                 115                 120

gcc ttc tcc aag gaa gga ctg ggt cag caa cct aaa act gac cca aaa      554
Ala Phe Ser Lys Glu Gly Leu Gly Gln Gln Pro Lys Thr Asp Pro Lys
        125                 130                 135

gag aaa gca aag tca gag aca agg gat tgg ttg aac aat gtg gtg agt      602
Glu Lys Ala Lys Ser Glu Thr Arg Asp Trp Leu Asn Asn Val Val Ser
    140                 145                 150

gaa ctg gag tcg cag att gat agc ttt gaa gct gag ttg gaa gga ctg      650
Glu Leu Glu Ser Gln Ile Asp Ser Phe Glu Ala Glu Leu Glu Gly Leu
155                 160                 165                 170

tct gtc aaa aaa gga aag aca aga ccg ccc aga ttg act cat ctt gag      698
Ser Val Lys Lys Gly Lys Thr Arg Pro Pro Arg Leu Thr His Leu Glu
                175                 180                 185

aca tct att aca aga cac aag gat cac ata ata aag ttg gaa ctg atc      746
Thr Ser Ile Thr Arg His Lys Asp His Ile Ile Lys Leu Glu Leu Ile
```

-continued

```
            190                 195                 200

ttg agg ctt ctg gac aat gat gaa tta agt cca gaa caa gta aat gac      794
Leu Arg Leu Leu Asp Asn Asp Glu Leu Ser Pro Glu Gln Val Asn Asp
        205                 210                 215

gtc aaa gat ttt ctg gat gat tat gtt gaa cga aat cag gat gat ttt      842
Val Lys Asp Phe Leu Asp Asp Tyr Val Glu Arg Asn Gln Asp Asp Phe
    220                 225                 230

gat gaa ttc agt gat gtc gat gag ctc tat agc acg ttg cca cta gat      890
Asp Glu Phe Ser Asp Val Asp Glu Leu Tyr Ser Thr Leu Pro Leu Asp
235                 240                 245                 250

gag gtg gag ggt ctt gaa gat cta gtt acc gct ggc cca ctt gtc aag      938
Glu Val Glu Gly Leu Glu Asp Leu Val Thr Ala Gly Pro Leu Val Lys
                255                 260                 265

ggt act cct tta agc atg aag agt tct ttg gca gcg tca gca tct caa      986
Gly Thr Pro Leu Ser Met Lys Ser Ser Leu Ala Ala Ser Ala Ser Gln
            270                 275                 280

gtt cgg agc ata agt ttg cca act cac cat caa gag aaa aca gag gat     1034
Val Arg Ser Ile Ser Leu Pro Thr His His Gln Glu Lys Thr Glu Asp
        285                 290                 295

aca tct tta ccg gat agc agt gct gag atg gtt cca aaa acc cct ccg     1082
Thr Ser Leu Pro Asp Ser Ser Ala Glu Met Val Pro Lys Thr Pro Pro
    300                 305                 310

cca aag aat ggt gca ggc ctt cac tca gca cca tca aca cct gcc gga     1130
Pro Lys Asn Gly Ala Gly Leu His Ser Ala Pro Ser Thr Pro Ala Gly
315                 320                 325                 330

gga cgt cca agt ttg aac gtg cct gcc ggt aat gtt tca aat aca tca     1178
Gly Arg Pro Ser Leu Asn Val Pro Ala Gly Asn Val Ser Asn Thr Ser
                335                 340                 345

gtt acc tta tca act tct att cct act caa act tcc ata gaa agc atg     1226
Val Thr Leu Ser Thr Ser Ile Pro Thr Gln Thr Ser Ile Glu Ser Met
            350                 355                 360

ggg agt ttg tct ccc gtg gct gcc aag gaa gaa gac gca aca acc ttg     1274
Gly Ser Leu Ser Pro Val Ala Ala Lys Glu Glu Asp Ala Thr Thr Leu
        365                 370                 375

cct tct cgt aaa cca ccc tca tct gtt gcg gat act cca ttg agg ggc     1322
Pro Ser Arg Lys Pro Pro Ser Ser Val Ala Asp Thr Pro Leu Arg Gly
    380                 385                 390

att ggt aga gtt ggt atc ccc aac caa ccc caa cca agc cag cct ccg     1370
Ile Gly Arg Val Gly Ile Pro Asn Gln Pro Gln Pro Ser Gln Pro Pro
395                 400                 405                 410

tct cct att cca gct aac ggg tct cgc att agt gca act tca gct gct     1418
Ser Pro Ile Pro Ala Asn Gly Ser Arg Ile Ser Ala Thr Ser Ala Ala
                415                 420                 425

gaa gtt gca aag aga aat ata atg gga gtt gag agc aac gtc caa cct     1466
Glu Val Ala Lys Arg Asn Ile Met Gly Val Glu Ser Asn Val Gln Pro
            430                 435                 440

ctt act tct cca ctg agc aaa atg gtg ttg cca cca act gca aag ggt     1514
Leu Thr Ser Pro Leu Ser Lys Met Val Leu Pro Pro Thr Ala Lys Gly
        445                 450                 455

aat gat gga act gcc tct gat agc aac cct ggt gat gtt gcg gct agt     1562
Asn Asp Gly Thr Ala Ser Asp Ser Asn Pro Gly Asp Val Ala Ala Ser
    460                 465                 470

att ggt aga gct ttt tca cca tct att gta tct ggt tcg cag tgg agg     1610
Ile Gly Arg Ala Phe Ser Pro Ser Ile Val Ser Gly Ser Gln Trp Arg
475                 480                 485                 490

cct ggt agt ccc ttt cag agt cag aat gaa acg gtt cgt ggg aga act     1658
Pro Gly Ser Pro Phe Gln Ser Gln Asn Glu Thr Val Arg Gly Arg Thr
                495                 500                 505

gaa ata gca cca gac caa aga gag aaa ttc tta cag aga tta cag caa     1706
```

-continued

```
Glu Ile Ala Pro Asp Gln Arg Glu Lys Phe Leu Gln Arg Leu Gln Gln
            510                 515                 520

gta cag caa ggc cat ggt aac ctc tta ggc ata cct tct tta tct gga     1754
Val Gln Gln Gly His Gly Asn Leu Leu Gly Ile Pro Ser Leu Ser Gly
        525                 530                 535

gga aac gag aag cag ttt tct tca caa cag caa aat cct ctt tta cag     1802
Gly Asn Glu Lys Gln Phe Ser Ser Gln Gln Gln Asn Pro Leu Leu Gln
    540                 545                 550

cag agc tct tcc atc tct cct cat gga agc ttg gga atc gga gtt cag     1850
Gln Ser Ser Ser Ile Ser Pro His Gly Ser Leu Gly Ile Gly Val Gln
555                 560                 565                 570

gca cca ggt ttt aat gtc atg agt tct gcc tcc tta cag cag caa tca     1898
Ala Pro Gly Phe Asn Val Met Ser Ser Ala Ser Leu Gln Gln Gln Ser
            575                 580                 585

aat gcc atg agt caa caa ttg ggt cag caa cct tct gtt gca gat gta     1946
Asn Ala Met Ser Gln Gln Leu Gly Gln Gln Pro Ser Val Ala Asp Val
            590                 595                 600

gac cat gtc aga aat gat gat caa tcc cag caa aac tta cct gat gat     1994
Asp His Val Arg Asn Asp Asp Gln Ser Gln Gln Asn Leu Pro Asp Asp
        605                 610                 615

tca gct tcc ata gca gct tca aaa gct att caa agt gag gat gac tct     2042
Ser Ala Ser Ile Ala Ala Ser Lys Ala Ile Gln Ser Glu Asp Asp Ser
    620                 625                 630

aaa gtt cta ttt gat act ccg tcg gga atg ccc agc tac atg ttg gat     2090
Lys Val Leu Phe Asp Thr Pro Ser Gly Met Pro Ser Tyr Met Leu Asp
635                 640                 645                 650

cca gta caa gta tct agc ggt cct gat ttc tct cct gga caa cct ata     2138
Pro Val Gln Val Ser Ser Gly Pro Asp Phe Ser Pro Gly Gln Pro Ile
            655                 660                 665

caa ccg ggt caa tct tca agt agc ctc ggg gtc att gga cgg aga agt     2186
Gln Pro Gly Gln Ser Ser Ser Ser Leu Gly Val Ile Gly Arg Arg Ser
            670                 675                 680

aac tct gag tta gga gcc att ggt gac cct tca gct gta ggg cca atg     2234
Asn Ser Glu Leu Gly Ala Ile Gly Asp Pro Ser Ala Val Gly Pro Met
        685                 690                 695

cat gat caa atg cac aat ctc cag atg ctt gaa gct gct ttt tac aaa     2282
His Asp Gln Met His Asn Leu Gln Met Leu Glu Ala Ala Phe Tyr Lys
    700                 705                 710

cgt cct caa ccc tca gat tca gaa cgt cct aga ccc tat tct ccg agg     2330
Arg Pro Gln Pro Ser Asp Ser Glu Arg Pro Arg Pro Tyr Ser Pro Arg
715                 720                 725                 730

aac cca gca atc aca cct caa aca ttt ccc caa aca caa gca cca atc     2378
Asn Pro Ala Ile Thr Pro Gln Thr Phe Pro Gln Thr Gln Ala Pro Ile
            735                 740                 745

ata aac aac cct ttg ctc tgg gaa cgg tta ggc agc gat gct tat gga     2426
Ile Asn Asn Pro Leu Leu Trp Glu Arg Leu Gly Ser Asp Ala Tyr Gly
            750                 755                 760

acc gat act ttg ttc ttt gcg ttc tac tat cag cag aac tca tac cag     2474
Thr Asp Thr Leu Phe Phe Ala Phe Tyr Tyr Gln Gln Asn Ser Tyr Gln
        765                 770                 775

caa tat ctt gct gca aaa gag ctg aag aaa cag tca tgg aga tac cac     2522
Gln Tyr Leu Ala Ala Lys Glu Leu Lys Lys Gln Ser Trp Arg Tyr His
    780                 785                 790

agg aag ttc aac act tgg ttt cag aga cat aaa gag cca aag att gca     2570
Arg Lys Phe Asn Thr Trp Phe Gln Arg His Lys Glu Pro Lys Ile Ala
795                 800                 805                 810

acc gat gaa tat gaa caa gga gcc tac gtt tac ttc gat ttc caa acc     2618
Thr Asp Glu Tyr Glu Gln Gly Ala Tyr Val Tyr Phe Asp Phe Gln Thr
            815                 820                 825
```

-continued

```
ccg aaa gac gag aat caa gaa gga gga tgg tgc caa agg atc aaa aac     2666
Pro Lys Asp Glu Asn Gln Glu Gly Gly Trp Cys Gln Arg Ile Lys Asn
            830                 835                 840

gag ttc aca ttt gaa tac agt tat ctt gaa gat gaa ctc gtc gta         2711
Glu Phe Thr Phe Glu Tyr Ser Tyr Leu Glu Asp Glu Leu Val Val
        845                 850                 855

tagaatagag agagatgcat gtttgtatat actctcgagc aagtgtgtta ttatttcctg   2771

cgactatttg tactcttctt ttcaataaac taattacttt tagtttcaac aagttgaaat   2831

tcttcgttaa cgactcttaa agacaataaa agccagagta tcatc                   2876


<210> SEQ ID NO 88
<211> LENGTH: 854
<212> TYPE: PRT
<213> ORGANISM: Arabidopsis thaliana

<400> SEQUENCE: 88

Asn His Arg Ser Leu Phe Ser Gly Ser Ala Val Met Gly Ala Ser Arg
1               5                   10                  15

Lys Leu Gln Gly Glu Ile Asp Arg Val Leu Lys Lys Val Gln Glu Gly
            20                  25                  30

Val Asp Val Phe Asp Ser Ile Trp Asn Lys Val Tyr Asp Thr Asp Asn
        35                  40                  45

Val Asn Gln Lys Glu Lys Phe Glu Ala Asp Leu Lys Lys Glu Ile Lys
    50                  55                  60

Lys Leu Gln Arg Tyr Arg Asp Gln Ile Lys Thr Trp Ile Gln Ser Ser
65                  70                  75                  80

Glu Ile Lys Asp Lys Lys Val Ser Ala Ser Tyr Glu Gln Ser Leu Val
                85                  90                  95

Asp Ala Arg Lys Leu Ile Glu Lys Glu Met Glu Arg Phe Lys Ile Cys
            100                 105                 110

Glu Lys Glu Thr Lys Thr Lys Ala Phe Ser Lys Glu Gly Leu Gly Gln
        115                 120                 125

Gln Pro Lys Thr Asp Pro Lys Glu Lys Ala Lys Ser Glu Thr Arg Asp
    130                 135                 140

Trp Leu Asn Asn Val Val Ser Glu Leu Glu Ser Gln Ile Asp Ser Phe
145                 150                 155                 160

Glu Ala Glu Leu Glu Gly Leu Ser Val Lys Lys Gly Lys Thr Arg Pro
                165                 170                 175

Pro Arg Leu Thr His Leu Glu Thr Ser Ile Thr Arg His Lys Asp His
            180                 185                 190

Ile Ile Lys Leu Glu Leu Ile Leu Arg Leu Leu Asp Asn Asp Glu Leu
        195                 200                 205

Ser Pro Glu Gln Val Asn Asp Val Lys Asp Phe Leu Asp Asp Tyr Val
    210                 215                 220

Glu Arg Asn Gln Asp Asp Phe Asp Glu Phe Ser Asp Val Asp Glu Leu
225                 230                 235                 240

Tyr Ser Thr Leu Pro Leu Asp Glu Val Glu Gly Leu Glu Asp Leu Val
                245                 250                 255

Thr Ala Gly Pro Leu Val Lys Gly Thr Pro Leu Ser Met Lys Ser Ser
            260                 265                 270

Leu Ala Ala Ser Ala Ser Gln Val Arg Ser Ile Ser Leu Pro Thr His
        275                 280                 285

His Gln Glu Lys Thr Glu Asp Thr Ser Leu Pro Asp Ser Ser Ala Glu
    290                 295                 300
```

-continued

```
Met Val Pro Lys Thr Pro Pro Pro Lys Asn Gly Ala Gly Leu His Ser
305                 310                 315                 320

Ala Pro Ser Thr Pro Ala Gly Gly Arg Pro Ser Leu Asn Val Pro Ala
                325                 330                 335

Gly Asn Val Ser Asn Thr Ser Val Thr Leu Ser Thr Ser Ile Pro Thr
            340                 345                 350

Gln Thr Ser Ile Glu Ser Met Gly Ser Leu Ser Pro Val Ala Ala Lys
        355                 360                 365

Glu Glu Asp Ala Thr Thr Leu Pro Ser Arg Lys Pro Pro Ser Ser Val
    370                 375                 380

Ala Asp Thr Pro Leu Arg Gly Ile Gly Arg Val Gly Ile Pro Asn Gln
385                 390                 395                 400

Pro Gln Pro Ser Gln Pro Pro Ser Pro Ile Pro Ala Asn Gly Ser Arg
                405                 410                 415

Ile Ser Ala Thr Ser Ala Ala Glu Val Ala Lys Arg Asn Ile Met Gly
            420                 425                 430

Val Glu Ser Asn Val Gln Pro Leu Thr Ser Pro Leu Ser Lys Met Val
        435                 440                 445

Leu Pro Pro Thr Ala Lys Gly Asn Asp Gly Thr Ala Ser Asp Ser Asn
    450                 455                 460

Pro Gly Asp Val Ala Ala Ser Ile Gly Arg Ala Phe Ser Pro Ser Ile
465                 470                 475                 480

Val Ser Gly Ser Gln Trp Arg Pro Gly Ser Pro Phe Gln Ser Gln Asn
                485                 490                 495

Glu Thr Val Arg Gly Arg Thr Glu Ile Ala Pro Asp Gln Arg Glu Lys
            500                 505                 510

Phe Leu Gln Arg Leu Gln Gln Val Gln Gln Gly His Gly Asn Leu Leu
        515                 520                 525

Gly Ile Pro Ser Leu Ser Gly Gly Asn Glu Lys Gln Phe Ser Ser Gln
    530                 535                 540

Gln Gln Asn Pro Leu Leu Gln Gln Ser Ser Ser Ile Ser Pro His Gly
545                 550                 555                 560

Ser Leu Gly Ile Gly Val Gln Ala Pro Gly Phe Asn Val Met Ser Ser
                565                 570                 575

Ala Ser Leu Gln Gln Gln Ser Asn Ala Met Ser Gln Gln Leu Gly Gln
            580                 585                 590

Gln Pro Ser Val Ala Asp Val Asp His Val Arg Asn Asp Asp Gln Ser
        595                 600                 605

Gln Gln Asn Leu Pro Asp Asp Ser Ala Ser Ile Ala Ala Ser Lys Ala
    610                 615                 620

Ile Gln Ser Glu Asp Asp Ser Lys Val Leu Phe Asp Thr Pro Ser Gly
625                 630                 635                 640

Met Pro Ser Tyr Met Leu Asp Pro Val Gln Val Ser Ser Gly Pro Asp
                645                 650                 655

Phe Ser Pro Gly Gln Pro Ile Gln Pro Gly Gln Ser Ser Ser Ser Leu
            660                 665                 670

Gly Val Ile Gly Arg Arg Ser Asn Ser Glu Leu Gly Ala Ile Gly Asp
        675                 680                 685

Pro Ser Ala Val Gly Pro Met His Asp Gln Met His Asn Leu Gln Met
    690                 695                 700

Leu Glu Ala Ala Phe Tyr Lys Arg Pro Gln Pro Ser Asp Ser Glu Arg
705                 710                 715                 720

Pro Arg Pro Tyr Ser Pro Arg Asn Pro Ala Ile Thr Pro Gln Thr Phe
```

-continued

```
                725                 730                 735

Pro Gln Thr Gln Ala Pro Ile Ile Asn Asn Pro Leu Leu Trp Glu Arg
            740                 745                 750

Leu Gly Ser Asp Ala Tyr Gly Thr Asp Thr Leu Phe Phe Ala Phe Tyr
        755                 760                 765

Tyr Gln Gln Asn Ser Tyr Gln Gln Tyr Leu Ala Ala Lys Glu Leu Lys
    770                 775                 780

Lys Gln Ser Trp Arg Tyr His Arg Lys Phe Asn Thr Trp Phe Gln Arg
785                 790                 795                 800

His Lys Glu Pro Lys Ile Ala Thr Asp Glu Tyr Glu Gln Gly Ala Tyr
                805                 810                 815

Val Tyr Phe Asp Phe Gln Thr Pro Lys Asp Glu Asn Gln Glu Gly Gly
            820                 825                 830

Trp Cys Gln Arg Ile Lys Asn Glu Phe Thr Phe Glu Tyr Ser Tyr Leu
        835                 840                 845

Glu Asp Glu Leu Val Val
    850


<210> SEQ ID NO 89
<211> LENGTH: 997
<212> TYPE: DNA
<213> ORGANISM: Arabidopsis thaliana
<220> FEATURE:
<221> NAME/KEY: promoter
<222> LOCATION: (1)..(997)
<223> OTHER INFORMATION: promoter of gene At1g20970

<400> SEQUENCE: 89

attacaaaat gtgatctttt tacctataat catggatgat aatttttcaa tatattagta     60

tttttaaaca tattttgaaa aattattaat tcttatctca aacaccactt taatcattaa    120

gaagcttctt taattttccc ttcggagtta aattatcctt ttcactttaa aaagtagaaa    180

gtcttgcaaa ataagaaaat ttctaaaact tatagataat tgatttgtca ttttcaacaa    240

aagttctatt aatcctcctt tcataaatat aaaaagatga aatccttttc ttcatggata    300

aaagtatatt tggatatgat attaatgttt aatgacgtca ttaaatagta gcaattagta    360

ataatgaata atgatgacaa tcataaacag aacttgaagt taacaatttt aacactgata    420

aaaacatttg gataaatctc tgtatccaag atttacatgt tccaacaata tacgctacta    480

tatatatatt tcttactaat taaaatgagt tttaatgcta atctatgcta atcaaaatat    540

gaaaaataca aagatattgg ttaatcgata aatacaataa atcagattaa cgaagccctc    600

tgttcaacaa agaggcttct cgatctcgtc cttaattcct tccttctcta agccagctgt    660

tttcttcttc ttcttcttca tctctctctc tctctctctc tcgtctccta ctctctcttt    720

gctcggacca aaatttcctc aaattcctcc tctgttaatc gccggcattg tctttcttac    780

cgatccgact atctcagcat tcgaaatctc cggcgacaaa gcctgatctc aaggttagtt    840

gcaaatcgct tttttatttt ccctgaaatt tctctgatct ccgtccatgt cggtttagtt    900

ttttatggtc gtgaattttc gttagagctg gctgcaattt cgtttgatct gatttattct    960

tacgcctttg attagcttat cgttcgtgaa gcggtga                             997


<210> SEQ ID NO 90
<211> LENGTH: 991
<212> TYPE: DNA
<213> ORGANISM: Arabidopsis thaliana
<220> FEATURE:
<221> NAME/KEY: promoter
```

```
<222> LOCATION: (1)..(991)
<223> OTHER INFORMATION: promoter of gene At1g20970

<400> SEQUENCE: 90

attacaaaat gtgatctttt tacctataat catggatgat aatttttcaa tatattagta     60

tttttaaaca tattttgaaa aattattaat tcttatctca aacaccactt taatcattaa    120

gaagctcctt taattttccc ttcggagtta aattatcctt ttcactttaa aaattagaaa    180

gtcttgcaaa ataagaaaat ttctgaaact tatagataat tgatttgtca ttttcaacaa    240

aagttctatt aatcctcctt tcataaatat aaaaagatga aatccttttc ttcatggata    300

aaagtatatt tggatatgat attaatgttt aatgacgtca ttaaatagta gcaattagta    360

ataatgaata atgatgacaa tcataaacag aacttgaagt taacaatttt aacactgata    420

aaaacatttg gataaatctc tgtatccaag atttacatgt tccaacaata tacgctacta    480

tatatatatt tcttactaat taaaatgagt tttaatgcta atctatgcta atcaaaatat    540

gaaaaataca aagatattgg ttaatcgata aatacaataa atcagattaa cgaagccctc    600

tgttcaacaa agaggcttct cgatctcgtc cttaattcct tccttctcta agccagctgt    660

tttcttcttc ttcttcttca tctctctctc tctctcgtct cctactctct ctttgctcgg    720

accaaaattt cctcaaattc ctcctctgtt aatcgccggc attgtctttc ttaccgatcc    780

gactatctca gcattcgaaa tctccggcga caaagcctga tctcaaggtt agttgcaaat    840

cgctttttta ttttccctga aatttctctg atctccgtcc atgtcggttt agttttttat    900

ggtcgtgaat tttcgttaga gctggctgca atttcgtttg atctgattta ttcttacgcc    960

tttgattagc ttatcgttcg tgaagcggtg a                                   991


<210> SEQ ID NO 91
<211> LENGTH: 2200
<212> TYPE: DNA
<213> ORGANISM: Arabidopsis thaliana
<220> FEATURE:
<221> NAME/KEY: promoter
<222> LOCATION: (1)..(2200)
<223> OTHER INFORMATION: promoter of gene At1g20970

<400> SEQUENCE: 91

tcaccgcttc acgcatgacc caaatatata caaaactaga agaaaaaaag cacaaaaaca     60

acgtgtagag gcgataatca taaaattgag ttcttatacc tatacatttg aaaagcttga    120

tataaagaaa aatatgtatc atagacggat atatatagct cgtgttgcgg catatattgt    180

cagttagttc atgcctattg attgatttat ttgtgtagct gtctctttga cgaattaact    240

caagttggta tattgttaat tagttttacc agctactcac tttattgtcg atctagtgct    300

taccaaacta atggcaacta caaattaaag tcgtctccgt atattaacgt atttttcaat    360

tctatttacg cgtataattt atcttcgtca actattatgg agtagatcta aataaacaaa    420

cagcggaaaa ctaaataaat gtcataatat gtaggcaaga aaacaaaaga gccattagat    480

aatgtgtgtc ttgtattgta tttattgaat cttaccaccg aaaccgacat atcattagag    540

ttttagtaag cacgtcattt tcagttagta ggttggaaaa gaaaaattct catcttcaat    600

atgaaaatat aggatgagta tctttttatg aacgttaatc gcttagttgt ggttaagtta    660

tttaaagtaa cttttaatca agttaggcag taaaaaataa ataatgaaga ataactatct    720

tctttacaat atgcaattta aatttctata gggaaatttt ttttcggtta tagtagtagc    780

acaattgaat cttattgatg tatttgaatt atactaaata ttttcattgt atcacccaat    840
```

-continued

```
aaaaagcttt aatgaaagag accaaaatta ggaggttaga tattacataa tcatcgttaa    900

tatgcaatca atataattta tgaaacgaga gagttaagaa tgagaacgta gttttctaat    960

gtggaacaga aatcgcatat ccgttttcgt aatagcaggg cccatccctc ctcacgcgct   1020

gctttatccg acccgatcca acctgatccg gataatataa cgaattatgg taaatctttg   1080

aattagtgtt aattaatatt gttggctaaa atctaactaa aatactacaa cttgctatgg   1140

tgatgtcaaa aactgcattt catcctatta aaggatgcca cgtgtattta tcttattaag   1200

tccattacaa aatgtgatct ttttacctat aatcatggat gataattttt caatatatta   1260

gtatttttaa acatattttg aaaaattatt aattcttatc tcaaacacca ctttaatcat   1320

taagaagctt ctttaatttt cccttcggag ttaaattatc cttttcactt taaaaagtag   1380

aaagtcttgc aaaataagaa aatttctaaa acttatagat aattgatttg tcattttcaa   1440

caaaagttct attaatcctc ctttcataaa tataaaaaga tgaaatcctt ttcttcatgg   1500

ataaaagtat atttggatat gatattaatg tttaatgacg tcattaaata gtagcaatta   1560

gtaataatga ataatgatga caatcataaa cagaacttga agttaacaat tttaacactg   1620

ataaaaacat ttggataaat ctctgtatcc aagatttaca tgttccaaca atatacgcta   1680

ctatatatat atttcttact aattaaaatg agttttaatg ctaatctatg ctaatcaaaa   1740

tatgaaaaat acaaagatat tggttaatcg ataaatacaa taaatcagat taacgaagcc   1800

ctctgttcaa caaagaggct tctcgatctc gtccttaatt ccttccttct ctaagccagc   1860

tgttttcttc ttcttcttct tcatctctct ctctctctct ctctcgtctc ctactctctc   1920

tttgctcgga ccaaaatttc ctcaaattcc tcctctgtta atcgccggca ttgtctttct   1980

taccgatccg actatctcag cattcgaaat ctccggcgac aaagcctgat ctcaaggtta   2040

gttgcaaatc gctttttat tttccctgaa atttctctga tctccgtcca tgtcggttta   2100

gtttttatg gtcgtgaatt ttcgttagag ctggctgcaa tttcgtttga tctgatttat   2160

tcttacgcct ttgattagct tatcgttcgt gaagcggtga                         2200
```

<210> SEQ ID NO 92
<211> LENGTH: 2194
<212> TYPE: DNA
<213> ORGANISM: Arabidopsis thaliana
<220> FEATURE:
<221> NAME/KEY: promoter
<222> LOCATION: (1)..(2194)
<223> OTHER INFORMATION: promoter of gene At1g20970

<400> SEQUENCE: 92

```
tcaccgcttc acgcatgacc caaatatata caaaagtaga aaaaaaaaag cacaaaaaca     60

acgtgtagag gcgataatca taaaattgag ttcttatacc tatacatttg aaaagcttga    120

tataaagaaa aatatgtatc atagacggat atatatagct cgtgttgcgg catatattgt    180

cagttagttc atgcctattg attgatttat ttgtgtagct gtctctttga cgaattaact    240

caagttggta tattgttaat tagttttacc agctactcac tttattgtcg atctagtgct    300

taccaaacta atggcaacta caaattaaag tcgtctccgt atattaacgt atttttcaat    360

tctatttacg cgtataatat atcttcgtca actattgtgg agtagatcta aataaacaaa    420

cagcggaaaa ctaaataaat gtcataatat gtaggcaaga aaacaaaaga gccattagat    480

aatgtgtgtc ttgtattgta tttattgaat cttaccaccg aaaccgacat atcattagag    540

ttttagtaag cacgtcattt tcagttagta ggttggaaaa gaaaaattct catcttcaat    600

atgaaaatat aggatgagta tctttttatg aacgttaatc gcttagttgt ggttaagtta    660
```

```
tttaaagtaa attttaatca agttaggcag taaaaaataa ataatgaaga ataactatct    720
tctttacaat atgcaattta aatttctata gggaaattat ttttcggtta tagtagtagc    780
acaattgaat cttattgatg tatttgaatt atactaaata ttttcattgt atcacccaat    840
aaaaagcttt aatgaaagag accaaaatta ggaggttaga tattacataa tcatcgttaa    900
tatgcaatca atataattca tgaaacgaga gagttaagaa tgagaacgtc gttttctaat    960
gtggaacaga aatcgcatat ccgttttcgt aatagcaagg cccatccctt ctcacgcgct   1020
actttatccg acccgatcca acctgatccg gataaatataa cgaattatgg taaatctttg  1080
aattagtgtt aattaatatt gttggctaaa atctaactaa aatactacaa cttgctatgg   1140
tgatgtcaaa aactgcattt catcctatta aaggatgcca cgtgtattta tcttattaag   1200
tccattacaa aatgtgatct ttttacctat aatcatggat gataattttt caatatatta   1260
gtatttttaa acatatttg aaaaattatt aattcttatc tcaaacacca ctttaatcat    1320
taagaagctc ctttaatttt cccttcggag ttaaattatc cttttcactt taaaaattag   1380
aaagtcttgc aaaataagaa aatttctgaa acttatagat aattgatttg tcattttcaa   1440
caaaagttct attaatcctc ctttcataaa tataaaaaga tgaaatcctt ttcttcatgg   1500
ataaaagtat atttggatat gatattaatg tttaatgacg tcattaaata gtagcaatta   1560
gtaataatga ataatgatga caatcataaa cagaacttga agttaacaat tttaacactg   1620
ataaaaacat ttggataaat ctctgtatcc aagatttaca tgttccaaca atatacgcta   1680
ctatatatat atttcttact aattaaaatg agttttaatg ctaatctatg ctaatcaaaa   1740
tatgaaaaat acaaagatat tggttaatcg ataaatacaa taaatcagat taacgaagcc   1800
ctctgttcaa caaagaggct tctcgatctc gtccttaatt ccttccttct ctaagccagc   1860
tgttttcttc ttcttcttct tcatctctct ctctctctcg tctcctactc tctctttgct   1920
cggaccaaaa tttcctcaaa ttcctcctct gttaatcgcc ggcattgtct ttcttaccga   1980
tccgactatc tcagcattcg aaatctccgg cgacaaagcc tgatctcaag gttagttgca   2040
aatcgctttt ttattttccc tgaaatttct ctgatctccg tccatgtcgg tttagttttt   2100
tatggtcgtg aattttcgtt agagctggct gcaatttcgt ttgatctgat ttattcttac   2160
gcctttgatt agcttatcgt tcgtgaagcg gtga                               2194
```

```
<210> SEQ ID NO 93
<211> LENGTH: 4497
<212> TYPE: DNA
<213> ORGANISM: Arabidopsis thaliana
<220> FEATURE:
<221> NAME/KEY: CDS
<222> LOCATION: (1)..(4497)
<223> OTHER INFORMATION: coding for adhesin-related protein (At1g20970)

<400> SEQUENCE: 93

atg ccg gtg gag gta gag aga gac caa gga gag gtg tcg gtg aag gtt       48
Met Pro Val Glu Val Glu Arg Asp Gln Gly Glu Val Ser Val Lys Val
1               5                   10                  15

gat ttt gag aat gcg act gag att aaa ccg gag gta gtt gtt tcg gcc       96
Asp Phe Glu Asn Ala Thr Glu Ile Lys Pro Glu Val Val Val Ser Ala
            20                  25                  30

acc aaa gag gac gtg gtg aat ggg atc agc cat ggt ggt agt aat aat      144
Thr Lys Glu Asp Val Val Asn Gly Ile Ser His Gly Gly Ser Asn Asn
        35                  40                  45

ggc aac ggg aac gat acc gat ggt tct tac gat ttc att acg gag aat      192
Gly Asn Gly Asn Asp Thr Asp Gly Ser Tyr Asp Phe Ile Thr Glu Asn
```

-continued

```
    50                  55                  60

gat acc gtt gga gat gat ttt gta gag tct gat tat gtt aag cct gtt      240
Asp Thr Val Gly Asp Asp Phe Val Glu Ser Asp Tyr Val Lys Pro Val
65                  70                  75                  80

gat gat gcc aat gtg gag aaa gat ctt aag gaa gga gag aat gtg aag      288
Asp Asp Ala Asn Val Glu Lys Asp Leu Lys Glu Gly Glu Asn Val Lys
                85                  90                  95

gta gat gct cca agt att gcc gat gat gat gtt ttg gga gtt tct caa      336
Val Asp Ala Pro Ser Ile Ala Asp Asp Asp Val Leu Gly Val Ser Gln
            100                 105                 110

gat agt caa acc ctg gaa aag tct gag cta gaa agt aca gat gat gga      384
Asp Ser Gln Thr Leu Glu Lys Ser Glu Leu Glu Ser Thr Asp Asp Gly
        115                 120                 125

cca gag gaa gtc gtt gag atc cca aag tcg gaa gtt gag gat tct ctt      432
Pro Glu Glu Val Val Glu Ile Pro Lys Ser Glu Val Glu Asp Ser Leu
    130                 135                 140

gaa aaa agt gtc gac cag cag cat cct ggt aat ggg cat cta gaa agt      480
Glu Lys Ser Val Asp Gln Gln His Pro Gly Asn Gly His Leu Glu Ser
145                 150                 155                 160

ggg ctt gag ggt aaa gtg gaa tct aaa gag gaa gtg gag caa ctt cat      528
Gly Leu Glu Gly Lys Val Glu Ser Lys Glu Glu Val Glu Gln Leu His
                165                 170                 175

gat tct gaa gtt gga tcc aag gat ctg aca aag aat aac gta gag gag      576
Asp Ser Glu Val Gly Ser Lys Asp Leu Thr Lys Asn Asn Val Glu Glu
            180                 185                 190

cct gaa gtt gaa atc gaa tct gat agt gaa aca gat gtc gag gga cat      624
Pro Glu Val Glu Ile Glu Ser Asp Ser Glu Thr Asp Val Glu Gly His
        195                 200                 205

caa ggg gac aag att gaa gcc caa gaa aaa tct gat cgg gat ttg gat      672
Gln Gly Asp Lys Ile Glu Ala Gln Glu Lys Ser Asp Arg Asp Leu Asp
    210                 215                 220

gtt tct caa gat cta aaa ctt aac gag aat gta gaa aag cac cct gtt      720
Val Ser Gln Asp Leu Lys Leu Asn Glu Asn Val Glu Lys His Pro Val
225                 230                 235                 240

gac tca gat gaa gta agg gag tct gag ttg gtg agc gct aag gtt tct      768
Asp Ser Asp Glu Val Arg Glu Ser Glu Leu Val Ser Ala Lys Val Ser
                245                 250                 255

cca act gag cct agt gat gga ggc atg gat ttg gga caa cct acg gta      816
Pro Thr Glu Pro Ser Asp Gly Gly Met Asp Leu Gly Gln Pro Thr Val
            260                 265                 270

aca gat cca gct gaa acc atc aat gga tct gaa tct gtg aat gat cac      864
Thr Asp Pro Ala Glu Thr Ile Asn Gly Ser Glu Ser Val Asn Asp His
        275                 280                 285

gtc gga tca gaa cct gta aca gtt ttg gaa cct gtt tct gtt gaa aac      912
Val Gly Ser Glu Pro Val Thr Val Leu Glu Pro Val Ser Val Glu Asn
    290                 295                 300

ggt cac cct cca gta gaa tca gag ttg gag aga agt agt gat gtt cca      960
Gly His Pro Pro Val Glu Ser Glu Leu Glu Arg Ser Ser Asp Val Pro
305                 310                 315                 320

ttc act tca gtg gcg gaa aaa gtc aat gct tcc gat ggt gaa gtg ttg     1008
Phe Thr Ser Val Ala Glu Lys Val Asn Ala Ser Asp Gly Glu Val Leu
                325                 330                 335

cca gac tct gga acc gtg gat gtt gtt gta tca gag gta agc agt gac     1056
Pro Asp Ser Gly Thr Val Asp Val Val Val Ser Glu Val Ser Ser Asp
            340                 345                 350

gtc cct gct gag act caa gct ctc aat gcc atc agc ttg gat tcc cag     1104
Val Pro Ala Glu Thr Gln Ala Leu Asn Ala Ile Ser Leu Asp Ser Gln
        355                 360                 365

cct tct ggc aaa gat agt gtt gtt gaa aat ggt aat agc aaa tca gaa     1152
```

-continued

```
Pro Ser Gly Lys Asp Ser Val Val Glu Asn Gly Asn Ser Lys Ser Glu
    370                 375                 380

tct gaa gac agc aag atg caa tcg gaa att gga gct gtt gat gat ggc      1200
Ser Glu Asp Ser Lys Met Gln Ser Glu Ile Gly Ala Val Asp Asp Gly
385                 390                 395                 400

tct gtg tct gat ggg agt ata aac act cat cca gaa tct caa gat gcc      1248
Ser Val Ser Asp Gly Ser Ile Asn Thr His Pro Glu Ser Gln Asp Ala
                405                 410                 415

agc gat cct act tgt gat caa ggt gga aaa caa cac ata tca tcc gaa      1296
Ser Asp Pro Thr Cys Asp Gln Gly Gly Lys Gln His Ile Ser Ser Glu
            420                 425                 430

gtt aag gaa gtt ctt gat gcc cct gct tca gaa gaa ata agt gat gct      1344
Val Lys Glu Val Leu Asp Ala Pro Ala Ser Glu Glu Ile Ser Asp Ala
        435                 440                 445

gtt att gtt gcc aaa gat aat ggt tca gaa gct gct att tct gat ggc      1392
Val Ile Val Ala Lys Asp Asn Gly Ser Glu Ala Ala Ile Ser Asp Gly
    450                 455                 460

tta tct tgt act aac cag cag gga tca gaa agt gat gag ata tct ggg      1440
Leu Ser Cys Thr Asn Gln Gln Gly Ser Glu Ser Asp Glu Ile Ser Gly
465                 470                 475                 480

cta gtt gaa aaa ctc cca tcc cat gcg cta cat gag gtt gtg tct tct      1488
Leu Val Glu Lys Leu Pro Ser His Ala Leu His Glu Val Val Ser Ser
                485                 490                 495

gcg aat gac acg agt gta att gta agc gat gac acc aaa agt caa ggt      1536
Ala Asn Asp Thr Ser Val Ile Val Ser Asp Asp Thr Lys Ser Gln Gly
            500                 505                 510

tta tca gag gat cat gga gtt gac act aac cag aca att caa gat gat      1584
Leu Ser Glu Asp His Gly Val Asp Thr Asn Gln Thr Ile Gln Asp Asp
        515                 520                 525

tgt agt gct gag ttg gaa gaa gtt acc gat gtg aat gta aaa cat gct      1632
Cys Ser Ala Glu Leu Glu Glu Val Thr Asp Val Asn Val Lys His Ala
    530                 535                 540

cca aat gag aaa gtt caa gga gac aat agc gag ggg aac tta aat gtt      1680
Pro Asn Glu Lys Val Gln Gly Asp Asn Ser Glu Gly Asn Leu Asn Val
545                 550                 555                 560

ggt ggt gat gtt tgt cta aat tct gct gaa gaa gcg aaa gaa tta cct      1728
Gly Gly Asp Val Cys Leu Asn Ser Ala Glu Glu Ala Lys Glu Leu Pro
                565                 570                 575

aca ggg gat ctt tct ggg aat gca tca cat gag agt gct gag act ctc      1776
Thr Gly Asp Leu Ser Gly Asn Ala Ser His Glu Ser Ala Glu Thr Leu
            580                 585                 590

tct aca aac atc gac gaa cca ttg agc ttg ttg gat acc aaa act gct      1824
Ser Thr Asn Ile Asp Glu Pro Leu Ser Leu Leu Asp Thr Lys Thr Ala
        595                 600                 605

gtc tct gac ttt gca gaa agc tca gca gga gtg gct ggc gaa ata gac      1872
Val Ser Asp Phe Ala Glu Ser Ser Ala Gly Val Ala Gly Glu Ile Asp
    610                 615                 620

gct gtt gcc atg gaa tct gaa gct gct caa tca att aaa caa tgc gct      1920
Ala Val Ala Met Glu Ser Glu Ala Ala Gln Ser Ile Lys Gln Cys Ala
625                 630                 635                 640

gaa gca cat gta gct cca tcc att att gaa gat ggt gaa ata gac aga      1968
Glu Ala His Val Ala Pro Ser Ile Ile Glu Asp Gly Glu Ile Asp Arg
                645                 650                 655

gaa gtc aat tgt ggt tca gaa gtg aac gtg aca aag act act cct gtt      2016
Glu Val Asn Cys Gly Ser Glu Val Asn Val Thr Lys Thr Thr Pro Val
            660                 665                 670

gct gtg cgc gag gat ata cca cct aaa gaa gtt tct gag atg gaa gaa      2064
Ala Val Arg Glu Asp Ile Pro Pro Lys Glu Val Ser Glu Met Glu Glu
        675                 680                 685
```

-continued

```
tcg gac gtc aaa gaa aga tct tcg ata aat aca gat gaa gaa gtc gct      2112
Ser Asp Val Lys Glu Arg Ser Ser Ile Asn Thr Asp Glu Glu Val Ala
    690                 695                 700

act gcc tca gtt gca tct gaa atc aag acc tgt gca cag gat ctt gaa      2160
Thr Ala Ser Val Ala Ser Glu Ile Lys Thr Cys Ala Gln Asp Leu Glu
705                 710                 715                 720

tct aaa gtg gtt aca tct act gat acc ata cat aca gga gct aaa gac      2208
Ser Lys Val Val Thr Ser Thr Asp Thr Ile His Thr Gly Ala Lys Asp
                725                 730                 735

tgt gtg gac agc caa cct gct gaa aac aaa gaa ggt aat aag tta att      2256
Cys Val Asp Ser Gln Pro Ala Glu Asn Lys Glu Gly Asn Lys Leu Ile
            740                 745                 750

aaa aat gaa att agg cta tgt act tct ctt gtt gag aat cag aag gat      2304
Lys Asn Glu Ile Arg Leu Cys Thr Ser Leu Val Glu Asn Gln Lys Asp
        755                 760                 765

gga gtt gac agt ata tat aaa ttg ttg tgt tca gga aat gtt gtt gat      2352
Gly Val Asp Ser Ile Tyr Lys Leu Leu Cys Ser Gly Asn Val Val Asp
    770                 775                 780

aga aca gat gat aaa gta gcc tcg acc ggt gaa gtt tct gta ctt gat      2400
Arg Thr Asp Asp Lys Val Ala Ser Thr Gly Glu Val Ser Val Leu Asp
785                 790                 795                 800

gct tct gaa ggg ctt act gta gcg gca gag ata gag aaa aga cct ttt      2448
Ala Ser Glu Gly Leu Thr Val Ala Ala Glu Ile Glu Lys Arg Pro Phe
                805                 810                 815

tac ttt ctg cct aga gtt cct aga tat gat gat gaa aag tta gcc gag      2496
Tyr Phe Leu Pro Arg Val Pro Arg Tyr Asp Asp Glu Lys Leu Ala Glu
            820                 825                 830

caa ctg aag cat gct gaa gag cag gtt gat cag aaa aca caa aat cgg      2544
Gln Leu Lys His Ala Glu Glu Gln Val Asp Gln Lys Thr Gln Asn Arg
        835                 840                 845

gat gct ctt aga gcg gat atc cag aag ata cgc gca ata tgt aag gac      2592
Asp Ala Leu Arg Ala Asp Ile Gln Lys Ile Arg Ala Ile Cys Lys Asp
    850                 855                 860

tat gat atc agt tac aag gcg gtc atg gca gaa gag aga tct gca aga      2640
Tyr Asp Ile Ser Tyr Lys Ala Val Met Ala Glu Glu Arg Ser Ala Arg
865                 870                 875                 880

aaa gca atg cat tca aaa cgg cag gaa att gag gcc ctt cag tct atg      2688
Lys Ala Met His Ser Lys Arg Gln Glu Ile Glu Ala Leu Gln Ser Met
                885                 890                 895

att agc cgg gtt aaa agt gct gcg tct gtt gat gat att gat tca agg      2736
Ile Ser Arg Val Lys Ser Ala Ala Ser Val Asp Asp Ile Asp Ser Arg
            900                 905                 910

gtg cgt aat atg gaa cat acg atg cag cac aca act tta tct ctg aat      2784
Val Arg Asn Met Glu His Thr Met Gln His Thr Thr Leu Ser Leu Asn
        915                 920                 925

gaa gaa aaa ggt ttc atg cgt gaa ata aag cag ttg aag caa ctt cgc      2832
Glu Glu Lys Gly Phe Met Arg Glu Ile Lys Gln Leu Lys Gln Leu Arg
    930                 935                 940

gag cag ata tct tcg agt atg ggt acc aag gat gaa gta aag caa gca      2880
Glu Gln Ile Ser Ser Ser Met Gly Thr Lys Asp Glu Val Lys Gln Ala
945                 950                 955                 960

ttg gat gag aaa gag aaa aca gaa gaa cgt ttg aag gtg ttg agg aag      2928
Leu Asp Glu Lys Glu Lys Thr Glu Glu Arg Leu Lys Val Leu Arg Lys
                965                 970                 975

gaa cta gac gca ctc aga aac gat cta tca aaa gcc gaa gaa atc aca      2976
Glu Leu Asp Ala Leu Arg Asn Asp Leu Ser Lys Ala Glu Glu Ile Thr
            980                 985                 990

aaa gct gcg aaa aaa aag tgt gat  ggg gaa tgg gaa gca  cag agt aaa    3024
Lys Ala Ala Lys Lys Lys Cys Asp  Gly Glu Trp Glu Ala  Gln Ser Lys
        995                 1000                1005
```

-continued

```
ctg caa  gaa cag ttc aga gct  gct gat gct gtt cgc  cag gaa gca      3069
Leu Gln  Glu Gln Phe Arg Ala  Ala Asp Ala Val Arg  Gln Glu Ala
    1010                 1015                 1020

ttt gtg  cac cta cag gat ttg  aag aaa caa caa cga  gaa aag aac      3114
Phe Val  His Leu Gln Asp Leu  Lys Lys Gln Gln Arg  Glu Lys Asn
    1025                 1030                 1035

aaa tat  ttc ttc aag tac aga  gat aat tca agg gca  gca agt gaa      3159
Lys Tyr  Phe Phe Lys Tyr Arg  Asp Asn Ser Arg Ala  Ala Ser Glu
    1040                 1045                 1050

atg gct  ttg aag aaa gac aga  gca gca ctg caa agc  ctt tgt tct      3204
Met Ala  Leu Lys Lys Asp Arg  Ala Ala Leu Gln Ser  Leu Cys Ser
    1055                 1060                 1065

gac cag  gtg gag aat ttc atg  aat atg tgg aac aat  gac gac gag      3249
Asp Gln  Val Glu Asn Phe Met  Asn Met Trp Asn Asn  Asp Asp Glu
    1070                 1075                 1080

ttc cgt  aaa tac tat gta aaa  agc aac aca agg agt  acc ttt aga      3294
Phe Arg  Lys Tyr Tyr Val Lys  Ser Asn Thr Arg Ser  Thr Phe Arg
    1085                 1090                 1095

aga cta  gga acc cta gat gga  cga tct ctt ggc cct  gat gag gag      3339
Arg Leu  Gly Thr Leu Asp Gly  Arg Ser Leu Gly Pro  Asp Glu Glu
    1100                 1105                 1110

cca cct  cgg atc act tat gct  cca aga acg gac aaa  ctt aga act      3384
Pro Pro  Arg Ile Thr Tyr Ala  Pro Arg Thr Asp Lys  Leu Arg Thr
    1115                 1120                 1125

tct agt  gac aga gca gag aaa  cat gag gca gtt cca  gca cag aaa      3429
Ser Ser  Asp Arg Ala Glu Lys  His Glu Ala Val Pro  Ala Gln Lys
    1130                 1135                 1140

gag aaa  gtc gtt aaa ttt gaa  ggt tca aaa gtt gaa  aac aac ggt      3474
Glu Lys  Val Val Lys Phe Glu  Gly Ser Lys Val Glu  Asn Asn Gly
    1145                 1150                 1155

aag gag  gtt gct aaa ccc acc  gag caa aag agt cag  acc act aaa      3519
Lys Glu  Val Ala Lys Pro Thr  Glu Gln Lys Ser Gln  Thr Thr Lys
    1160                 1165                 1170

tct aaa  aag gcc gtc aag cca  gac cag cct cca tca  att gtc aca      3564
Ser Lys  Lys Ala Val Lys Pro  Asp Gln Pro Pro Ser  Ile Val Thr
    1175                 1180                 1185

gaa ttg  gtt tct gga aaa gag  gag ata gag aag tca  gca aca ccg      3609
Glu Leu  Val Ser Gly Lys Glu  Glu Ile Glu Lys Ser  Ala Thr Pro
    1190                 1195                 1200

gaa gaa  gaa gag ccg cct aag  tta aca aaa gag gaa  gag gag tta      3654
Glu Glu  Glu Glu Pro Pro Lys  Leu Thr Lys Glu Glu  Glu Glu Leu
    1205                 1210                 1215

att aag  aaa gaa gaa gag aag  aga aaa caa aag gaa  gct gca aag      3699
Ile Lys  Lys Glu Glu Glu Lys  Arg Lys Gln Lys Glu  Ala Ala Lys
    1220                 1225                 1230

atg aag  gag caa cat cgg tta  gag gaa ata gca aaa  gcg aaa gag      3744
Met Lys  Glu Gln His Arg Leu  Glu Glu Ile Ala Lys  Ala Lys Glu
    1235                 1240                 1245

gca atg  gag agg aag aag aag  aga gag gag aag gca  aaa gca aga      3789
Ala Met  Glu Arg Lys Lys Lys  Arg Glu Glu Lys Ala  Lys Ala Arg
    1250                 1255                 1260

gct gtt  ctc aag gct cag aag  gaa gcc gaa gaa agg  gag aag gta      3834
Ala Val  Leu Lys Ala Gln Lys  Glu Ala Glu Glu Arg  Glu Lys Val
    1265                 1270                 1275

aaa gca  tat ttt tgt cat tct  gtt atc caa att gga  ttt cga tca      3879
Lys Ala  Tyr Phe Cys His Ser  Val Ile Gln Ile Gly  Phe Arg Ser
    1280                 1285                 1290

gtc tct  cta gct aga acg aga  gaa gaa gct aag gaa  gaa gga gag      3924
Val Ser  Leu Ala Arg Thr Arg  Glu Glu Ala Lys Glu  Glu Gly Glu
```

```
    1295                1300                1305

aag aaa  ggg gat ttt tac atc  aga aga gac agc aac  aga aaa ccc      3969
Lys Lys  Gly Asp Phe Tyr Ile  Arg Arg Asp Ser Asn  Arg Lys Pro
    1310                1315                1320

aat tcc  gac agc aga aac tgt  agt cga aac ccc aag  gga gat cga      4014
Asn Ser  Asp Ser Arg Asn Cys  Ser Arg Asn Pro Lys  Gly Asp Arg
    1325                1330                1335

aac tcc  aaa gaa aca aac cgt  aga gga gag tca aca  aat gaa gaa      4059
Asn Ser  Lys Glu Thr Asn Arg  Arg Gly Glu Ser Thr  Asn Glu Glu
    1340                1345                1350

atc tca  caa acc ttc atc aca  gtt tct gaa aca aaa  caa gtc aaa      4104
Ile Ser  Gln Thr Phe Ile Thr  Val Ser Glu Thr Lys  Gln Val Lys
    1355                1360                1365

atc ggt  tcc tct gcc ttt aag  aaa ccg agg aag caa  gag aaa act      4149
Ile Gly  Ser Ser Ala Phe Lys  Lys Pro Arg Lys Gln  Glu Lys Thr
    1370                1375                1380

gcg gca  atg gat gtg gat tgg  act cat agt tgt gat  cat cat cgc      4194
Ala Ala  Met Asp Val Asp Trp  Thr His Ser Cys Asp  His His Arg
    1385                1390                1395

att gtt  cct tct cga agt tct  acg att gtt cgt tct  tgt cac ata      4239
Ile Val  Pro Ser Arg Ser Ser  Thr Ile Val Arg Ser  Cys His Ile
    1400                1405                1410

agt cat  cca ggg gtg gtt cct  cat cag tgc caa gag  atc gtc cat      4284
Ser His  Pro Gly Val Val Pro  His Gln Cys Gln Glu  Ile Val His
    1415                1420                1425

cta gac  ttc cct agt ctt ttt  aag gac aga gca gag  aaa cat gag      4329
Leu Asp  Phe Pro Ser Leu Phe  Lys Asp Arg Ala Glu  Lys His Glu
    1430                1435                1440

act gtt  cca cca gtt tca gca  ctg gat tca gtc tta  tat ttg ccc      4374
Thr Val  Pro Pro Val Ser Ala  Leu Asp Ser Val Leu  Tyr Leu Pro
    1445                1450                1455

ctt cat  caa aat cat ctt cgg  gat caa att ttg gaa  cag tct atg      4419
Leu His  Gln Asn His Leu Arg  Asp Gln Ile Leu Glu  Gln Ser Met
    1460                1465                1470

agg cgc  acg aga act gct agt  cgc agt agc gct acg  ttt tgc ctt      4464
Arg Arg  Thr Arg Thr Ala Ser  Arg Ser Ser Ala Thr  Phe Cys Leu
    1475                1480                1485

gac aac  cgc agt agt ttg act  aga acg cca taa                       4497
Asp Asn  Arg Ser Ser Leu Thr  Arg Thr Pro
    1490                1495


<210> SEQ ID NO 94
<211> LENGTH: 1498
<212> TYPE: PRT
<213> ORGANISM: Arabidopsis thaliana

<400> SEQUENCE: 94

Met Pro Val Glu Val Glu Arg Asp Gln Gly Glu Val Ser Val Lys Val
1               5                   10                  15

Asp Phe Glu Asn Ala Thr Glu Ile Lys Pro Glu Val Val Val Ser Ala
            20                  25                  30

Thr Lys Glu Asp Val Val Asn Gly Ile Ser His Gly Gly Ser Asn Asn
        35                  40                  45

Gly Asn Gly Asn Asp Thr Asp Gly Ser Tyr Asp Phe Ile Thr Glu Asn
    50                  55                  60

Asp Thr Val Gly Asp Asp Phe Val Glu Ser Asp Tyr Val Lys Pro Val
65                  70                  75                  80

Asp Asp Ala Asn Val Glu Lys Asp Leu Lys Glu Gly Glu Asn Val Lys
                85                  90                  95
```

```
Val Asp Ala Pro Ser Ile Ala Asp Asp Asp Val Leu Gly Val Ser Gln
            100                 105                 110

Asp Ser Gln Thr Leu Glu Lys Ser Glu Leu Glu Ser Thr Asp Asp Gly
        115                 120                 125

Pro Glu Glu Val Val Glu Ile Pro Lys Ser Glu Val Glu Asp Ser Leu
    130                 135                 140

Glu Lys Ser Val Asp Gln Gln His Pro Gly Asn Gly His Leu Glu Ser
145                 150                 155                 160

Gly Leu Glu Gly Lys Val Glu Ser Lys Glu Glu Val Glu Gln Leu His
                165                 170                 175

Asp Ser Glu Val Gly Ser Lys Asp Leu Thr Lys Asn Asn Val Glu Glu
            180                 185                 190

Pro Glu Val Glu Ile Glu Ser Asp Ser Glu Thr Asp Val Glu Gly His
        195                 200                 205

Gln Gly Asp Lys Ile Glu Ala Gln Glu Lys Ser Asp Arg Asp Leu Asp
    210                 215                 220

Val Ser Gln Asp Leu Lys Leu Asn Glu Asn Val Glu Lys His Pro Val
225                 230                 235                 240

Asp Ser Asp Glu Val Arg Glu Ser Glu Leu Val Ser Ala Lys Val Ser
                245                 250                 255

Pro Thr Glu Pro Ser Asp Gly Gly Met Asp Leu Gly Gln Pro Thr Val
            260                 265                 270

Thr Asp Pro Ala Glu Thr Ile Asn Gly Ser Glu Ser Val Asn Asp His
        275                 280                 285

Val Gly Ser Glu Pro Val Thr Val Leu Glu Pro Val Ser Val Glu Asn
    290                 295                 300

Gly His Pro Pro Val Glu Ser Glu Leu Glu Arg Ser Ser Asp Val Pro
305                 310                 315                 320

Phe Thr Ser Val Ala Glu Lys Val Asn Ala Ser Asp Gly Glu Val Leu
                325                 330                 335

Pro Asp Ser Gly Thr Val Asp Val Val Val Ser Glu Val Ser Ser Asp
            340                 345                 350

Val Pro Ala Glu Thr Gln Ala Leu Asn Ala Ile Ser Leu Asp Ser Gln
        355                 360                 365

Pro Ser Gly Lys Asp Ser Val Val Glu Asn Gly Asn Ser Lys Ser Glu
    370                 375                 380

Ser Glu Asp Ser Lys Met Gln Ser Glu Ile Gly Ala Val Asp Asp Gly
385                 390                 395                 400

Ser Val Ser Asp Gly Ser Ile Asn Thr His Pro Glu Ser Gln Asp Ala
                405                 410                 415

Ser Asp Pro Thr Cys Asp Gln Gly Gly Lys Gln His Ile Ser Ser Glu
            420                 425                 430

Val Lys Glu Val Leu Asp Ala Pro Ala Ser Glu Glu Ile Ser Asp Ala
        435                 440                 445

Val Ile Val Ala Lys Asp Asn Gly Ser Glu Ala Ala Ile Ser Asp Gly
    450                 455                 460

Leu Ser Cys Thr Asn Gln Gly Ser Glu Ser Asp Glu Ile Ser Gly
465                 470                 475                 480

Leu Val Glu Lys Leu Pro Ser His Ala Leu His Glu Val Val Ser Ser
                485                 490                 495

Ala Asn Asp Thr Ser Val Ile Val Ser Asp Asp Thr Lys Ser Gln Gly
            500                 505                 510
```

-continued

```
Leu Ser Glu Asp His Gly Val Asp Thr Asn Gln Thr Ile Gln Asp Asp
        515                 520                 525

Cys Ser Ala Glu Leu Glu Glu Val Thr Asp Val Asn Val Lys His Ala
    530                 535                 540

Pro Asn Glu Lys Val Gln Gly Asp Asn Ser Glu Gly Asn Leu Asn Val
545                 550                 555                 560

Gly Gly Asp Val Cys Leu Asn Ser Ala Glu Glu Ala Lys Glu Leu Pro
                565                 570                 575

Thr Gly Asp Leu Ser Gly Asn Ala Ser His Glu Ser Ala Glu Thr Leu
            580                 585                 590

Ser Thr Asn Ile Asp Glu Pro Leu Ser Leu Leu Asp Thr Lys Thr Ala
        595                 600                 605

Val Ser Asp Phe Ala Glu Ser Ser Ala Gly Val Ala Gly Glu Ile Asp
    610                 615                 620

Ala Val Ala Met Glu Ser Glu Ala Ala Gln Ser Ile Lys Gln Cys Ala
625                 630                 635                 640

Glu Ala His Val Ala Pro Ser Ile Ile Glu Asp Gly Glu Ile Asp Arg
                645                 650                 655

Glu Val Asn Cys Gly Ser Glu Val Asn Val Thr Lys Thr Thr Pro Val
            660                 665                 670

Ala Val Arg Glu Asp Ile Pro Pro Lys Glu Val Ser Glu Met Glu Glu
        675                 680                 685

Ser Asp Val Lys Glu Arg Ser Ser Ile Asn Thr Asp Glu Glu Val Ala
    690                 695                 700

Thr Ala Ser Val Ala Ser Glu Ile Lys Thr Cys Ala Gln Asp Leu Glu
705                 710                 715                 720

Ser Lys Val Val Thr Ser Thr Asp Thr Ile His Thr Gly Ala Lys Asp
                725                 730                 735

Cys Val Asp Ser Gln Pro Ala Glu Asn Lys Glu Gly Asn Lys Leu Ile
            740                 745                 750

Lys Asn Glu Ile Arg Leu Cys Thr Ser Leu Val Glu Asn Gln Lys Asp
        755                 760                 765

Gly Val Asp Ser Ile Tyr Lys Leu Leu Cys Ser Gly Asn Val Val Asp
    770                 775                 780

Arg Thr Asp Asp Lys Val Ala Ser Thr Gly Glu Val Ser Val Leu Asp
785                 790                 795                 800

Ala Ser Glu Gly Leu Thr Val Ala Ala Glu Ile Glu Lys Arg Pro Phe
                805                 810                 815

Tyr Phe Leu Pro Arg Val Pro Arg Tyr Asp Asp Glu Lys Leu Ala Glu
            820                 825                 830

Gln Leu Lys His Ala Glu Glu Gln Val Asp Gln Lys Thr Gln Asn Arg
        835                 840                 845

Asp Ala Leu Arg Ala Asp Ile Gln Lys Ile Arg Ala Ile Cys Lys Asp
    850                 855                 860

Tyr Asp Ile Ser Tyr Lys Ala Val Met Ala Glu Glu Arg Ser Ala Arg
865                 870                 875                 880

Lys Ala Met His Ser Lys Arg Gln Glu Ile Glu Ala Leu Gln Ser Met
                885                 890                 895

Ile Ser Arg Val Lys Ser Ala Ala Ser Val Asp Asp Ile Asp Ser Arg
            900                 905                 910

Val Arg Asn Met Glu His Thr Met Gln His Thr Thr Leu Ser Leu Asn
        915                 920                 925

Glu Glu Lys Gly Phe Met Arg Glu Ile Lys Gln Leu Lys Gln Leu Arg
```

-continued

```
    930                 935                 940

Glu Gln Ile Ser Ser Ser Met Gly Thr Lys Asp Glu Val Lys Gln Ala
945                 950                 955                 960

Leu Asp Glu Lys Glu Lys Thr Glu Glu Arg Leu Lys Val Leu Arg Lys
                965                 970                 975

Glu Leu Asp Ala Leu Arg Asn Asp Leu Ser Lys Ala Glu Glu Ile Thr
            980                 985                 990

Lys Ala Ala Lys Lys Lys Cys Asp  Gly Glu Trp Glu Ala  Gln Ser Lys
        995                 1000                1005

Leu Gln  Glu Gln Phe Arg Ala  Ala Asp Ala Val Arg  Gln Glu Ala
    1010                1015                1020

Phe Val  His Leu Gln Asp Leu  Lys Lys Gln Gln Arg  Glu Lys Asn
    1025                1030                1035

Lys Tyr  Phe Phe Lys Tyr Arg  Asp Asn Ser Arg Ala  Ala Ser Glu
    1040                1045                1050

Met Ala  Leu Lys Lys Asp Arg  Ala Ala Leu Gln Ser  Leu Cys Ser
    1055                1060                1065

Asp Gln  Val Glu Asn Phe Met  Asn Met Trp Asn Asn  Asp Asp Glu
    1070                1075                1080

Phe Arg  Lys Tyr Tyr Val Lys  Ser Asn Thr Arg Ser  Thr Phe Arg
    1085                1090                1095

Arg Leu  Gly Thr Leu Asp Gly  Arg Ser Leu Gly Pro  Asp Glu Glu
    1100                1105                1110

Pro Pro  Arg Ile Thr Tyr Ala  Pro Arg Thr Asp Lys  Leu Arg Thr
    1115                1120                1125

Ser Ser  Asp Arg Ala Glu Lys  His Glu Ala Val Pro  Ala Gln Lys
    1130                1135                1140

Glu Lys  Val Val Lys Phe Glu  Gly Ser Lys Val Glu  Asn Asn Gly
    1145                1150                1155

Lys Glu  Val Ala Lys Pro Thr  Glu Gln Lys Ser Gln  Thr Thr Lys
    1160                1165                1170

Ser Lys  Lys Ala Val Lys Pro  Asp Gln Pro Pro Ser  Ile Val Thr
    1175                1180                1185

Glu Leu  Val Ser Gly Lys Glu  Glu Ile Glu Lys Ser  Ala Thr Pro
    1190                1195                1200

Glu Glu  Glu Glu Pro Pro Lys  Leu Thr Lys Glu Glu  Glu Glu Leu
    1205                1210                1215

Ile Lys  Lys Glu Glu Glu Lys  Arg Lys Gln Lys Glu  Ala Ala Lys
    1220                1225                1230

Met Lys  Glu Gln His Arg Leu  Glu Glu Ile Ala Lys  Ala Lys Glu
    1235                1240                1245

Ala Met  Glu Arg Lys Lys Lys  Arg Glu Glu Lys Ala  Lys Ala Arg
    1250                1255                1260

Ala Val  Leu Lys Ala Gln Lys  Glu Ala Glu Glu Arg  Glu Lys Val
    1265                1270                1275

Lys Ala  Tyr Phe Cys His Ser  Val Ile Gln Ile Gly  Phe Arg Ser
    1280                1285                1290

Val Ser  Leu Ala Arg Thr Arg  Glu Glu Ala Lys Glu  Glu Gly Glu
    1295                1300                1305

Lys Lys  Gly Asp Phe Tyr Ile  Arg Arg Asp Ser Asn  Arg Lys Pro
    1310                1315                1320

Asn Ser  Asp Ser Arg Asn Cys  Ser Arg Asn Pro Lys  Gly Asp Arg
    1325                1330                1335
```

```
Asn Ser  Lys Glu Thr Asn Arg  Arg Gly Glu Ser Thr  Asn Glu Glu
    1340                 1345                 1350

Ile Ser  Gln Thr Phe Ile Thr  Val Ser Glu Thr Lys  Gln Val Lys
    1355                 1360                 1365

Ile Gly  Ser Ser Ala Phe Lys  Lys Pro Arg Lys Gln  Glu Lys Thr
    1370                 1375                 1380

Ala Ala  Met Asp Val Asp Trp  Thr His Ser Cys Asp  His His Arg
    1385                 1390                 1395

Ile Val  Pro Ser Arg Ser Ser  Thr Ile Val Arg Ser  Cys His Ile
    1400                 1405                 1410

Ser His  Pro Gly Val Val Pro  His Gln Cys Gln Glu  Ile Val His
    1415                 1420                 1425

Leu Asp  Phe Pro Ser Leu Phe  Lys Asp Arg Ala Glu  Lys His Glu
    1430                 1435                 1440

Thr Val  Pro Pro Val Ser Ala  Leu Asp Ser Val Leu  Tyr Leu Pro
    1445                 1450                 1455

Leu His  Gln Asn His Leu Arg  Asp Gln Ile Leu Glu  Gln Ser Met
    1460                 1465                 1470

Arg Arg  Thr Arg Thr Ala Ser  Arg Ser Ser Ala Thr  Phe Cys Leu
    1475                 1480                 1485

Asp Asn  Arg Ser Ser Leu Thr  Arg Thr Pro
    1490                 1495
```

<210> SEQ ID NO 95
<211> LENGTH: 962
<212> TYPE: DNA
<213> ORGANISM: Arabidopsis thaliana
<220> FEATURE:
<221> NAME/KEY: promoter
<222> LOCATION: (1)..(962)
<223> OTHER INFORMATION: promoter of gene At4g35620

<400> SEQUENCE: 95

```
tcttgaagct atgtaataaa tcacaaatac aacaaattgc aacaccaaaa aaaactaatg     60

taaccattga tgtgtgatat atgatatagc gaagccgcaa ctgtcttaaa tattattttg    120

aataatatct agacactaga ctctaactaa acgtttaaca gttttctaaa aatgcagata    180

taaaaagtta tctaaaatat ttcacatatt tgaataacaa attagaaaca caatcacctt    240

ttgaccattc taaggaaatt caattacaat aactatgacc agaatcatct agcctaattt    300

ttgatattct ctaaattaaa tattttaaaa aagcttgacc aaaaaaaaag aaatggcaag    360

aacacttact acagagtcag cataattctc ggtaacaata attcttagga aagagagcaa    420

ttcttagctc tgtagtaaaa cacagattaa taagctaaga ttaagattaa ataatcaata    480

tgttgacttt aagatcttag agccgcgcct tacggaggct ctggctagtg gtaacgagcc    540

ttctttgtct gaaaaaggca acaaaaaaaa cacaaaaaag gaataataaa tttgaaatga    600

gaaagagaga gagccaccac acacaccaca tggccaaaaa agttaccgtt gggtttagac    660

agacttagaa acaaatcgtt tccttcatga tccaacggtc atcttaatca cctagccgtt    720

gctatttcct tcaataataa aaaaaataaa ataaaaaaag gtagcaactt taattttaat    780

tgatttgatt taatttctct ctctcgctta tttcatcccc ttctctgact cctcctgatt    840

cattcaattg catcagacgt atacacagag tcacagagag aagagagatc cttcttcgtt    900

tgatgctctt cttcttcttc tagattcttc tccaggagca ctatcaaatc gagtaaaata    960

aa                                                                   962
```

```
<210> SEQ ID NO 96
<211> LENGTH: 961
<212> TYPE: DNA
<213> ORGANISM: Arabidopsis thaliana
<220> FEATURE:
<221> NAME/KEY: promoter
<222> LOCATION: (1)..(961)
<223> OTHER INFORMATION: promoter of gene At4g35620

<400> SEQUENCE: 96

tcttgaagct atgtaataaa tcacaaatac aacaaattgc aacaccaaaa aaaactaatg      60

taaccattga tgtgtgatat atgatatagc gaagccgcaa ctgtcttaaa tattattttg     120

aataatatct acacactaga ctctaactaa acgtttaaca gttttctaaa aatgcagata     180

taaaaagtta tctaaaatat ttcacatatt tgaataagaa attagaaaca caatcacctt     240

ttgaccattc taaggaaatt caattacaat aactatgacc agaatcatct agcctaattt     300

ttgatattct ctaaattaaa tatttttaaa aagcttgacc aaaaaaaaag aaatggcaag     360

aacacttact acagagtcag cataattctc ggtaacaata attcttagga aagagagcaa     420

ttcttagctc tgtagtaaaa cacagattaa taagctaaga ttaagattaa agaatcaata     480

tgttgacttt aagatcttag agccgcgcct tacggaggct ctggctagtg gtaacgagcc     540

ttctttgtct gaaaaaggca acaaaaaaaa cacaaaaaag gaataataaa tttgaaatga     600

gaaagagaga gccaccacac acaccacatg gccaaaaaag ttaccgttgg gtttagacag     660

acttagaaac aaatcgtttc cttcatgatc caacggtcat cttaatcacc tagccgttgc     720

tatttccttc aataataaaa aaaaataaaa taaaaaaagg tagcaacttt aattttaatt     780

gatttgattt aatttctctc tctcgcttat ttcatcccct tctctgactc ctactgattc     840

attcaattgc atcagacgta tacacagagt cacagagaga agagagatcc ttcttcgttt     900

gatgctcttc ttcttcttct agattcttct ccaggagcac tatcaaatcg agtaaaataa     960

a                                                                     961


<210> SEQ ID NO 97
<211> LENGTH: 1537
<212> TYPE: DNA
<213> ORGANISM: Arabidopsis thaliana
<220> FEATURE:
<221> NAME/KEY: CDS
<222> LOCATION: (103)..(1389)
<223> OTHER INFORMATION: coding for cyclin 2b (CYC2b) (At4g35620)

<400> SEQUENCE: 97

acacagagtc acagagagaa gagagatcct tcttcgtttg atgctcttct tcttcttcta      60

gattcttctc caggagcact atcaaatcga gtaaaataaa ca atg gtt aat cca        114
                                               Met Val Asn Pro
                                               1

gag gag aac aat cgt aat ctc gtt gtc aaa ccc att aca gag att ctt       162
Glu Glu Asn Asn Arg Asn Leu Val Val Lys Pro Ile Thr Glu Ile Leu
5                   10                  15                  20

caa gat gat gat aag aga agc aga aaa ttc ggt gta gag atg aag aga       210
Gln Asp Asp Asp Lys Arg Ser Arg Lys Phe Gly Val Glu Met Lys Arg
                25                  30                  35

cag aac agg aga gca ttg ggt gtg att aat cac aat ctc gtt ggt gca       258
Gln Asn Arg Arg Ala Leu Gly Val Ile Asn His Asn Leu Val Gly Ala
            40                  45                  50

aaa gct tat cct tgt gtt gtt aac aag aga aga ggc tta tct cag aga       306
Lys Ala Tyr Pro Cys Val Val Asn Lys Arg Arg Gly Leu Ser Gln Arg
```

-continued

```
        55                  60                  65

aaa caa gaa agc tgt gac aag aag aag ctt gat tca ttg cat ccg tca      354
Lys Gln Glu Ser Cys Asp Lys Lys Lys Leu Asp Ser Leu His Pro Ser
    70                  75                  80

att tca aga tct cag gaa gag act aag aag ctg aaa cca agt gga aac      402
Ile Ser Arg Ser Gln Glu Glu Thr Lys Lys Leu Lys Pro Ser Gly Asn
85                  90                  95                  100

gag ttt ggt gat tgc ata ttc att gat gaa gaa gag gag aag aat gaa      450
Glu Phe Gly Asp Cys Ile Phe Ile Asp Glu Glu Glu Glu Lys Asn Glu
                105                 110                 115

gaa gtt aca ttg gac caa cct atg cca atg tca ttg gag gaa cca tac      498
Glu Val Thr Leu Asp Gln Pro Met Pro Met Ser Leu Glu Glu Pro Tyr
            120                 125                 130

att gaa ttt gat cca atg gag gaa gaa gtt gag atg gag gat atg gaa      546
Ile Glu Phe Asp Pro Met Glu Glu Glu Val Glu Met Glu Asp Met Glu
        135                 140                 145

gaa gaa caa gaa gaa cca gtt ttg gat ata gac gaa tac gat gca aac      594
Glu Glu Gln Glu Glu Pro Val Leu Asp Ile Asp Glu Tyr Asp Ala Asn
    150                 155                 160

aac tct ctt gca gct gtt gaa tac gtc caa gat ctt tac gat ttc tac      642
Asn Ser Leu Ala Ala Val Glu Tyr Val Gln Asp Leu Tyr Asp Phe Tyr
165                 170                 175                 180

cgt aaa acc gag aga ttt agc tgt gtt cct cta gat tac atg gcg caa      690
Arg Lys Thr Glu Arg Phe Ser Cys Val Pro Leu Asp Tyr Met Ala Gln
                185                 190                 195

cag ttt gat ata tct gac aaa atg aga gca ata ctt att gac tgg ctc      738
Gln Phe Asp Ile Ser Asp Lys Met Arg Ala Ile Leu Ile Asp Trp Leu
            200                 205                 210

atc gag gta cat gat aag ttt gag ctg atg aac gag aca ttg ttt cta      786
Ile Glu Val His Asp Lys Phe Glu Leu Met Asn Glu Thr Leu Phe Leu
        215                 220                 225

aca gtc aat ctg ata gat aga ttc ttg tcc aag caa gct gtt gca aga      834
Thr Val Asn Leu Ile Asp Arg Phe Leu Ser Lys Gln Ala Val Ala Arg
    230                 235                 240

aag aag ctt cag ctt gtt ggt tta gtt gca ttg ctc tta gct tgc aag      882
Lys Lys Leu Gln Leu Val Gly Leu Val Ala Leu Leu Leu Ala Cys Lys
245                 250                 255                 260

tac gaa gag gtt tca gta cct att gtt gaa gat ttg gta gtc att tcg      930
Tyr Glu Glu Val Ser Val Pro Ile Val Glu Asp Leu Val Val Ile Ser
                265                 270                 275

gac aaa gct tat acg agg acc gat gtt tta gaa atg gag aag att atg      978
Asp Lys Ala Tyr Thr Arg Thr Asp Val Leu Glu Met Glu Lys Ile Met
            280                 285                 290

ctt agt act ttg caa ttc aat atg tcg tta cca acg caa tac cct ttc     1026
Leu Ser Thr Leu Gln Phe Asn Met Ser Leu Pro Thr Gln Tyr Pro Phe
        295                 300                 305

ttg aag agg ttc ctc aag gca gct caa tca gac aag aag ctt gag atc     1074
Leu Lys Arg Phe Leu Lys Ala Ala Gln Ser Asp Lys Lys Leu Glu Ile
    310                 315                 320

ttg gcg tcg ttc ttg att gag ctt gct ctt gtg gac tac gaa atg gtt     1122
Leu Ala Ser Phe Leu Ile Glu Leu Ala Leu Val Asp Tyr Glu Met Val
325                 330                 335                 340

cgg tat cca cca tcg tta ctc gcc gcc act gcc gtg tac aca gct caa     1170
Arg Tyr Pro Pro Ser Leu Leu Ala Ala Thr Ala Val Tyr Thr Ala Gln
                345                 350                 355

tgt aca atc cat ggc ttc agt gaa tgg aac agc act tgt gaa ttc cat     1218
Cys Thr Ile His Gly Phe Ser Glu Trp Asn Ser Thr Cys Glu Phe His
            360                 365                 370

tgt cac tac tct gag aat caa ctc cta gaa tgt tgt aga aga atg gtg     1266
```

```
Cys His Tyr Ser Glu Asn Gln Leu Leu Glu Cys Cys Arg Arg Met Val
        375                 380                 385

aga cta cat cag aaa gct ggg act gat aaa cta aca gga gta cat aga      1314
Arg Leu His Gln Lys Ala Gly Thr Asp Lys Leu Thr Gly Val His Arg
    390                 395                 400

aaa tac agc tcc tcc aaa ttc gga tac ata gca aca aag tat gaa gct      1362
Lys Tyr Ser Ser Ser Lys Phe Gly Tyr Ile Ala Thr Lys Tyr Glu Ala
405                 410                 415                 420

gca cac ttt ctt gtg tca gat tct cac taaagagtgg aaaatagtag            1409
Ala His Phe Leu Val Ser Asp Ser His
                425

tttgtgtata gctcgctgct aacattttcc ctctcaattt ttaattacaa acgaaataag   1469

ttcaaaacat tcctctgatt tgatctgtaa caagtctttc ttttattgat atctcagcaa   1529

taaaattc                                                            1537


<210> SEQ ID NO 98
<211> LENGTH: 429
<212> TYPE: PRT
<213> ORGANISM: Arabidopsis thaliana

<400> SEQUENCE: 98

Met Val Asn Pro Glu Glu Asn Asn Arg Asn Leu Val Val Lys Pro Ile
1               5                   10                  15

Thr Glu Ile Leu Gln Asp Asp Asp Lys Arg Ser Arg Lys Phe Gly Val
            20                  25                  30

Glu Met Lys Arg Gln Asn Arg Arg Ala Leu Gly Val Ile Asn His Asn
        35                  40                  45

Leu Val Gly Ala Lys Ala Tyr Pro Cys Val Val Asn Lys Arg Arg Gly
    50                  55                  60

Leu Ser Gln Arg Lys Gln Glu Ser Cys Asp Lys Lys Lys Leu Asp Ser
65                  70                  75                  80

Leu His Pro Ser Ile Ser Arg Ser Gln Glu Glu Thr Lys Lys Leu Lys
                85                  90                  95

Pro Ser Gly Asn Glu Phe Gly Asp Cys Ile Phe Ile Asp Glu Glu Glu
            100                 105                 110

Glu Lys Asn Glu Glu Val Thr Leu Asp Gln Pro Met Pro Met Ser Leu
        115                 120                 125

Glu Glu Pro Tyr Ile Glu Phe Asp Pro Met Glu Glu Glu Val Glu Met
    130                 135                 140

Glu Asp Met Glu Glu Glu Gln Glu Glu Pro Val Leu Asp Ile Asp Glu
145                 150                 155                 160

Tyr Asp Ala Asn Asn Ser Leu Ala Ala Val Glu Tyr Val Gln Asp Leu
                165                 170                 175

Tyr Asp Phe Tyr Arg Lys Thr Glu Arg Phe Ser Cys Val Pro Leu Asp
            180                 185                 190

Tyr Met Ala Gln Gln Phe Asp Ile Ser Asp Lys Met Arg Ala Ile Leu
        195                 200                 205

Ile Asp Trp Leu Ile Glu Val His Asp Lys Phe Glu Leu Met Asn Glu
    210                 215                 220

Thr Leu Phe Leu Thr Val Asn Leu Ile Asp Arg Phe Leu Ser Lys Gln
225                 230                 235                 240

Ala Val Ala Arg Lys Lys Leu Gln Leu Val Gly Leu Val Ala Leu Leu
                245                 250                 255

Leu Ala Cys Lys Tyr Glu Glu Val Ser Val Pro Ile Val Glu Asp Leu
            260                 265                 270
```

```
Val Val Ile Ser Asp Lys Ala Tyr Thr Arg Thr Asp Val Leu Glu Met
        275                 280                 285

Glu Lys Ile Met Leu Ser Thr Leu Gln Phe Asn Met Ser Leu Pro Thr
    290                 295                 300

Gln Tyr Pro Phe Leu Lys Arg Phe Leu Lys Ala Ala Gln Ser Asp Lys
305                 310                 315                 320

Lys Leu Glu Ile Leu Ala Ser Phe Leu Ile Glu Leu Ala Leu Val Asp
                325                 330                 335

Tyr Glu Met Val Arg Tyr Pro Pro Ser Leu Leu Ala Ala Thr Ala Val
            340                 345                 350

Tyr Thr Ala Gln Cys Thr Ile His Gly Phe Ser Glu Trp Asn Ser Thr
        355                 360                 365

Cys Glu Phe His Cys His Tyr Ser Glu Asn Gln Leu Leu Glu Cys Cys
    370                 375                 380

Arg Arg Met Val Arg Leu His Gln Lys Ala Gly Thr Asp Lys Leu Thr
385                 390                 395                 400

Gly Val His Arg Lys Tyr Ser Ser Ser Lys Phe Gly Tyr Ile Ala Thr
                405                 410                 415

Lys Tyr Glu Ala Ala His Phe Leu Val Ser Asp Ser His
            420                 425
```

<210> SEQ ID NO 99
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer SUK3for

<400> SEQUENCE: 99
ataagcttat aatatagcgt gattcgcgtt 30

<210> SEQ ID NO 100
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer SUK3rev

<400> SEQUENCE: 100
tccccgggct caaaaatcaa ctctttttca 30

<210> SEQ ID NO 101
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer SUK4for

<400> SEQUENCE: 101
tgaagctttc aaatcaactc tttttcattc 30

<210> SEQ ID NO 102
<211> LENGTH: 29
<212> TYPE: DNA
<213> ORGANISM: Artificial
<220> FEATURE:

```
<221> NAME/KEY: misc_feature
<222> LOCATION: (1)..(29)
<223> OTHER INFORMATION: oligonucleotide primer SUK4rev

<400> SEQUENCE: 102

tacccgggct caaaaatcaa ctctttttc                                        29


<210> SEQ ID NO 103
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: oligonucleotide primer SUK88Sfor

<400> SEQUENCE: 103

aactagggat cctggtgtcc gaaaatg                                          27


<210> SEQ ID NO 104
<211> LENGTH: 29
<212> TYPE: DNA
<213> ORGANISM: Artificial
<220> FEATURE:
<221> NAME/KEY: misc_feature
<222> LOCATION: (1)..(29)
<223> OTHER INFORMATION: oligonucleotide primer SUK88Srev

<400> SEQUENCE: 104

tctggaccat ggaaacggca gagagacgg                                        29


<210> SEQ ID NO 105
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: oligonucleotide primer SUK88Lfor

<400> SEQUENCE: 105

aactagggat cctggtgtcc gaaaatg                                          27


<210> SEQ ID NO 106
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: oligonucleotide primer SUK88Lrev

<400> SEQUENCE: 106

tcttctccat ggttttttac acaatc                                           26


<210> SEQ ID NO 107
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: oligonucleotide primer SUK90for

<400> SEQUENCE: 107

ttgagaggat ccaataagct ttagaag                                          27
```

-continued

<210> SEQ ID NO 108
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: oligonucleotide primer SUK90rev

<400> SEQUENCE: 108
tcgcacccat ggcagccgaa ccagag 26

<210> SEQ ID NO 109
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: oligonucleotide primer SUK92Sfor

<400> SEQUENCE: 109
agtgtgggat ccctgttttt ctg 23

<210> SEQ ID NO 110
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer SUK92Srev

<400> SEQUENCE: 110
atttgcccat gggttctgaa gacttgtaat 30

<210> SEQ ID NO 111
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: oligonucleotide primer SUK92Lfor

<400> SEQUENCE: 111
agtgtgggat ccctgttttt ctg 23

<210> SEQ ID NO 112
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK92Lrev

<400> SEQUENCE: 112
tgcagtccat ggggatagaa aaagc 25

<210> SEQ ID NO 113
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK276for

<400> SEQUENCE: 113
cttattggat ccattacaaa atgtg 25

<210> SEQ ID NO 114
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK276rev

<400> SEQUENCE: 114
ccaccgccat ggtcaccgct tcacg 25

<210> SEQ ID NO 115
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK278for

<400> SEQUENCE: 115
ccaccgccat ggtcaccgct tcacg 25

<210> SEQ ID NO 116
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK278rev

<400> SEQUENCE: 116
ccaccgccat ggtcaccgct tcacg 25

<210> SEQ ID NO 117
<211> LENGTH: 27
<212> TYPE: DNA
<213> ORGANISM: Artificial
<220> FEATURE:
<221> NAME/KEY: misc_feature
<222> LOCATION: (1)..(27)
<223> OTHER INFORMATION: oligonucleotide primer SUK284for

<400> SEQUENCE: 117
tcagaaggat cctcttgaag ctatgta 27

<210> SEQ ID NO 118
<211> LENGTH: 25
<212> TYPE: DNA
<213> ORGANISM: Artificial
<220> FEATURE:
<221> NAME/KEY: misc_feature
<222> LOCATION: (1)..(25)
<223> OTHER INFORMATION: oligonucleotide primer SUK284rev

<400> SEQUENCE: 118
gattaaccat ggtttatttt actcg 25

<210> SEQ ID NO 119
<211> LENGTH: 32
<212> TYPE: DNA
<213> ORGANISM: Artificial

```
<220> FEATURE:
<221> NAME/KEY: misc_feature
<222> LOCATION: (1)..(32)
<223> OTHER INFORMATION: oligonucleotide primer UH301for

<400> SEQUENCE: 119

gcggatcctt gttcaagtaa aattgtgtta cc                                   32


<210> SEQ ID NO 120
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH301rev

<400> SEQUENCE: 120

cgccatggtt tgattttctt ttactgcatt aaa                                  33


<210> SEQ ID NO 121
<211> LENGTH: 46
<212> TYPE: DNA
<213> ORGANISM: Artificial
<220> FEATURE:
<221> NAME/KEY: misc_feature
<222> LOCATION: (1)..(46)
<223> OTHER INFORMATION: oligonucleotide primer UH303for

<400> SEQUENCE: 121

gcggatcctg tattggacct gagaaatggg aaaggtactg ccgttt                    46


<210> SEQ ID NO 122
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH303rev

<400> SEQUENCE: 122

cgccatggtt tgattttctt ttactgcatt aaa                                  33


<210> SEQ ID NO 123
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH303Srev

<400> SEQUENCE: 123

cgccatggtg ggctgtgtga gtttatttat agc                                  33


<210> SEQ ID NO 124
<211> LENGTH: 32
<212> TYPE: DNA
<213> ORGANISM: Artificial
<220> FEATURE:
<221> NAME/KEY: misc_feature
<222> LOCATION: (1)..(32)
<223> OTHER INFORMATION: oligonucleotide primer UH309for

<400> SEQUENCE: 124

gcggatccta ctgcaaacca taactaacac gg                                   32
```

<210> SEQ ID NO 125
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: oligonucleotide primer UH309rev

<400> SEQUENCE: 125
cgccatggtg gatagaaaaa gcaactgaaa atctcg 36

<210> SEQ ID NO 126
<211> LENGTH: 29
<212> TYPE: DNA
<213> ORGANISM: Artificial
<220> FEATURE:
<221> NAME/KEY: misc_feature
<222> LOCATION: (1)..(29)
<223> OTHER INFORMATION: oligonucleotide primer UH332rev

<400> SEQUENCE: 126
ccatggaaga gagaatcgcc gagattgtg 29

<210> SEQ ID NO 127
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH333for

<400> SEQUENCE: 127
ggatccatag ggaaaggaga gctataagaa tcg 33

<210> SEQ ID NO 128
<211> LENGTH: 31
<212> TYPE: DNA
<213> ORGANISM: Artificial
<220> FEATURE:
<221> NAME/KEY: misc_feature
<222> LOCATION: (1)..(31)
<223> OTHER INFORMATION: oligonucleotide primer UH333rev

<400> SEQUENCE: 128
ccatggtttg cagacctttt actgattttg a 31

<210> SEQ ID NO 129
<211> LENGTH: 28
<212> TYPE: DNA
<213> ORGANISM: Artificial
<220> FEATURE:
<221> NAME/KEY: misc_feature
<222> LOCATION: (1)..(28)
<223> OTHER INFORMATION: oligonucleotide primer UH337for

<400> SEQUENCE: 129
gcctcgaggt cgatcatgaa actcacat 28

<210> SEQ ID NO 130
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: oligonucleotide primer UH337rev

<400> SEQUENCE: 130
gcggatcctt ttgtttgttt tttgtttttt tactac 36

<210> SEQ ID NO 131
<211> LENGTH: 31
<212> TYPE: DNA
<213> ORGANISM: Artificial
<220> FEATURE:
<221> NAME/KEY: misc_feature
<222> LOCATION: (1)..(31)
<223> OTHER INFORMATION: oligonucleotide primer UH337Srev

<400> SEQUENCE: 131
gcggatccga tggagagtgt tctgtgttaa g 31

<210> SEQ ID NO 132
<211> LENGTH: 32
<212> TYPE: DNA
<213> ORGANISM: Artificial
<220> FEATURE:
<221> NAME/KEY: misc_feature
<222> LOCATION: (1)..(32)
<223> OTHER INFORMATION: oligonucleotide primer UH339Srev

<400> SEQUENCE: 132
cgccatggga agacactcct tacccactcg tg 32

<210> SEQ ID NO 133
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH339for

<400> SEQUENCE: 133
gcggatccat ctttgagatt ggtgtgtaat ttt 33

<210> SEQ ID NO 134
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH339rev

<400> SEQUENCE: 134
cgccatggct ggtctaccaa taaccatact ctt 33

<210> SEQ ID NO 135
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH340for

<400> SEQUENCE: 135
gcggatccaa aaattacaat cggttctatc aat 33

<210> SEQ ID NO 136
<211> LENGTH: 44
<212> TYPE: DNA

<213> ORGANISM: Artificial
<220> FEATURE:
<221> NAME/KEY: misc_feature
<222> LOCATION: (1)..(44)
<223> OTHER INFORMATION: oligonucleotide primer UH340rev

<400> SEQUENCE: 136
cgccatggca gggttttgtt gaaactatag agagattttt gaag 44

<210> SEQ ID NO 137
<211> LENGTH: 34
<212> TYPE: DNA
<213> ORGANISM: Artificial
<220> FEATURE:
<221> NAME/KEY: misc_feature
<222> LOCATION: (1)..(34)
<223> OTHER INFORMATION: oligonucleotide primer UH344for

<400> SEQUENCE: 137
gcggatccct gcgattgctt tgttttcgta ctga 34

<210> SEQ ID NO 138
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH344rev

<400> SEQUENCE: 138
cgccatggat agaaaaagca actgaaaatc tgc 33

<210> SEQ ID NO 139
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH345for

<400> SEQUENCE: 139
gcggatccag tcttcttcca tacatgttat gtc 33

<210> SEQ ID NO 140
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: oligonucleotide primer UH345rev

<400> SEQUENCE: 140
cgccatggct cactcaaatc aatgaagcca catctg 36

<210> SEQ ID NO 141
<211> LENGTH: 35
<212> TYPE: DNA
<213> ORGANISM: Artificial
<220> FEATURE:
<221> NAME/KEY: misc_feature
<222> LOCATION: (1)..(35)
<223> OTHER INFORMATION: oligonucleotide primer UH346for

<400> SEQUENCE: 141
cgccatggca ccggaatatt cctcctcctc acgga 35

<210> SEQ ID NO 142
<211> LENGTH: 29
<212> TYPE: DNA
<213> ORGANISM: Artificial
<220> FEATURE:
<221> NAME/KEY: misc_feature
<222> LOCATION: (1)..(29)
<223> OTHER INFORMATION: oligonucleotide primer UH346rev

<400> SEQUENCE: 142
ggccatggtt tcacctctag acctgacaa 29

<210> SEQ ID NO 143
<211> LENGTH: 26
<212> TYPE: DNA
<213> ORGANISM: Artificial
<220> FEATURE:
<221> NAME/KEY: misc_feature
<222> LOCATION: (1)..(26)
<223> OTHER INFORMATION: oligonucleotide primer UH373for

<400> SEQUENCE: 143
tatgggtttg ggatccatgt atcatg 26

<210> SEQ ID NO 144
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: oligonucleotide primer UH373rev

<400> SEQUENCE: 144
gcggatccac ccagatagca tccctcatct catccg 36

<210> SEQ ID NO 145
<211> LENGTH: 34
<212> TYPE: DNA
<213> ORGANISM: Artificial
<220> FEATURE:
<221> NAME/KEY: misc_feature
<222> LOCATION: (1)..(34)
<223> OTHER INFORMATION: oligonucleotide primer UH373Srev

<400> SEQUENCE: 145
gcggatccgt aaaagagaga gagagagagg tcaa 34

<210> SEQ ID NO 146
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer UH375for

<400> SEQUENCE: 146
gcggatccgg aagtgaaaaa tggtgggatg 30

<210> SEQ ID NO 147
<211> LENGTH: 35
<212> TYPE: DNA
<213> ORGANISM: Artificial
<220> FEATURE:
<221> NAME/KEY: misc_feature
<222> LOCATION: (1)..(35)

<223> OTHER INFORMATION: oligonucleotide primer UH375rev

<400> SEQUENCE: 147
cgccatggtc cggttggcga tggatggtta cttac 35

<210> SEQ ID NO 148
<211> LENGTH: 30
<212> TYPE: DNA
<213> ORGANISM: Artificial
<220> FEATURE:
<221> NAME/KEY: misc_feature
<222> LOCATION: (1)..(30)
<223> OTHER INFORMATION: oligonucleotide primer UH376for

<400> SEQUENCE: 148
actaaatttc gttttctcga gataattgag 30

<210> SEQ ID NO 149
<211> LENGTH: 37
<212> TYPE: DNA
<213> ORGANISM: Artificial
<220> FEATURE:
<221> NAME/KEY: misc_feature
<222> LOCATION: (1)..(37)
<223> OTHER INFORMATION: oligonucleotide primer UH376rev

<400> SEQUENCE: 149
cgccatggtt tgatcaagcc tgttcacaaa acagagt 37

<210> SEQ ID NO 150
<211> LENGTH: 23
<212> TYPE: DNA
<213> ORGANISM: Artificial
<220> FEATURE:
<221> NAME/KEY: misc_feature
<222> LOCATION: (1)..(23)
<223> OTHER INFORMATION: oligonucleotide primer UH376Srev

<400> SEQUENCE: 150
gagacacaaa aaatctctac tta 23

<210> SEQ ID NO 151
<211> LENGTH: 33
<212> TYPE: DNA
<213> ORGANISM: Artificial
<220> FEATURE:
<221> NAME/KEY: misc_feature
<222> LOCATION: (1)..(33)
<223> OTHER INFORMATION: oligonucleotide primer UH381for

<400> SEQUENCE: 151
gcggatcccg ttttacaaac aaagctatgg ctg 33

<210> SEQ ID NO 152
<211> LENGTH: 35
<212> TYPE: DNA
<213> ORGANISM: Artificial
<220> FEATURE:
<221> NAME/KEY: misc_feature
<222> LOCATION: (1)..(35)
<223> OTHER INFORMATION: oligonucleotide primer UH381rev

<400> SEQUENCE: 152
cgccatggtt aactttgaaa cctccgcaaa aaccc 35

<210> SEQ ID NO 153
<211> LENGTH: 24

-continued

<212> TYPE: DNA
<213> ORGANISM: Artificial
<220> FEATURE:
<221> NAME/KEY: misc_feature
<222> LOCATION: (1)..(24)
<223> OTHER INFORMATION: oligonucleotide primer UH381Srev

<400> SEQUENCE: 153
gaaaagtctc tttcagtcat acct 24

<210> SEQ ID NO 154
<211> LENGTH: 36
<212> TYPE: DNA
<213> ORGANISM: Artificial
<220> FEATURE:
<221> NAME/KEY: misc_feature
<222> LOCATION: (1)..(36)
<223> OTHER INFORMATION: oligonucleotide primer UH408for

<400> SEQUENCE: 154
cgccatggga gcaaccatct tcctttgtaa atttga 36

<210> SEQ ID NO 155
<211> LENGTH: 39
<212> TYPE: DNA
<213> ORGANISM: Artificial
<220> FEATURE:
<221> NAME/KEY: misc_feature
<222> LOCATION: (1)..(39)
<223> OTHER INFORMATION: oligonucleotide primer UH408rev

<400> SEQUENCE: 155
cgccatggtt tagctcgacc ctcaaaaaaa gtctcaaac 39

<210> SEQ ID NO 156
<211> LENGTH: 8986
<212> TYPE: DNA
<213> ORGANISM: Artificial
<220> FEATURE:
<221> NAME/KEY: misc_feature
<222> LOCATION: (1)..(8986)
<223> OTHER INFORMATION: binary vector pSUN0301

<400> SEQUENCE: 156
cgttgtaaaa cgacggccag tgaattcgag ctcggtacct cgagcccggg cgatatcgga 60
tccactagtc tagagtcgat cgaccatggt acgtcctgta gaaaccccaa cccgtgaaat 120
caaaaaactc gacggcctgt gggcattcag tctggatcgc gaaaactgtg gaattggtca 180
gcgttggtgg gaaagcgcgt tacaagaaag ccgggcaatt gctgtgccag gcagttttaa 240
cgatcagttc gccgatgcag atattcgtaa ttatgcgggc aacgtctggt atcagcgcga 300
agtctttata ccgaaaggtt gggcaggcca gcgtatcgtg ctgcgtttcg atgcggtcac 360
tcattacggc aaagtgtggg tcaataatca ggaagtgatg gagcatcagg gcggctatac 420
gccatttgaa gccgatgtca cgccgtatgt tattgccggg aaaagtgtac gtaagtttct 480
gcttctacct ttgatatata tataataatt atcattaatt agtagtaata taatatttca 540
aatatttttt tcaaaataaa agaatgtagt atatagcaat tgcttttctg tagtttataa 600
gtgtgtatat tttaatttat aacttttcta atatatgacc aaaatttgtt gatgtgcagg 660
tatcaccgtt tgtgtgaaca acgaactgaa ctggcagact atcccgccgg gaatggtgat 720
taccgacgaa aacggcaaga aaaagcagtc ttacttccat gatttcttta actatgccgg 780
aatccatcgc agcgtaatgc tctacaccac gccgaacacc tgggtggacg atatcaccgt 840

-continued

```
ggtgacgcat gtcgcgcaag actgtaacca cgcgtctgtt gactggcagg tggtggccaa    900
tggtgatgtc agcgttgaac tgcgtgatgc ggatcaacag gtggttgcaa ctggacaagg    960
cactagcggg actttgcaag tggtgaatcc gcacctctgg caaccgggtg aaggttatct   1020
ctatgaactg tgcgtcacag ccaaaagcca gacagagtgt gatatctacc cgcttcgcgt   1080
cggcatccgg tcagtggcag tgaagggcga acagttcctg attaaccaca aaccgttcta   1140
ctttactggc tttggtcgtc atgaagatgc ggacttacgt ggcaaaggat tcgataacgt   1200
gctgatggtg cacgaccacg cattaatgga ctggattggg gccaactcct accgtacctc   1260
gcattaccct tacgctgaag agatgctcga ctgggcagat gaacatggca tcgtggtgat   1320
tgatgaaact gctgctgtcg gctttaacct ctctttaggc attggtttcg aagcgggcaa   1380
caagccgaaa gaactgtaca gcgaagaggc agtcaacggg gaaactcagc aagcgcactt   1440
acaggcgatt aaagagctga tagcgcgtga caaaaaccac ccaagcgtgg tgatgtggag   1500
tattgccaac gaaccggata cccgtccgca agtgcacggg aatatttcgc cactggcgga   1560
agcaacgcgt aaactcgacc cgacgcgtcc gatcacctgc gtcaatgtaa tgttctgcga   1620
cgctcacacc gataccatca gcgatctctt tgatgtgctg tgcctgaacc gttattacgg   1680
atggtatgtc caaagcggcg atttggaaac ggcagagaag gtactggaaa aagaacttct   1740
ggcctggcag gagaaactgc atcagccgat tatcatcacc gaatacggcg tggatacgtt   1800
agccgggctg cactcaatgt acaccgacat gtggagtgaa gagtatcagt gtgcatggct   1860
ggatatgtat caccgcgtct ttgatcgcgt cagcgccgtc gtcggtgaac aggtatggaa   1920
tttcgccgat tttgcgacct cgcaaggcat attgcgcgtt ggcggtaaca agaaagggat   1980
cttcactcgc gaccgcaaac cgaagtcggc ggcttttctg ctgcaaaaac gctggactgg   2040
catgaacttc ggtgaaaaac cgcagcaggg aggcaaacaa tgaatcaaca actctcctgg   2100
cgcaccatcg tcggctacag cctcgggaat tgctaccgag ctcggtaccc ggcgcaaaaa   2160
tcaccagtct ctctctacaa atctatctct ctctattttt ctccagaata atgtgtgagt   2220
agttcccaga taagggaatt agggttctta tagggtttcg ctcatgtgtt gagcatataa   2280
gaaaccctta gtatgtattt gtatttgtaa aatacttcta tcaataaaat ttctaattcc   2340
taaaaccaaa atccagtgac cgggtaccga gctcgaattt cgacctgcag gcatgcaagc   2400
ttggcgtaat catggtcata gctgtttcct actagatctg attgtcgttt cccgccttca   2460
gtttaaacta tcagtgtttg acaggatata ttggcgggta aacctaagag aaaagagcgt   2520
ttattagaat aatcggatat ttaaaagggc gtgaaaaggt ttatccgttc gtccatttgt   2580
atgtccatga taagtcgcgc tgtatgtgtt tgtttgaata ttcatggaac gcagtggcgg   2640
ttttcatggc ttgttatgac tgttttttg gggtacagtc tatgcctcgg gcatccaagc   2700
agcaagcgcg ttacgccgtg ggtcgatgtt tgatgttatg gagcagcaac gatgttacgc   2760
agcagggcag tcgccctaaa acaaagttaa acatcatggg ggaagcggtg atcgccgaag   2820
tatcgactca actatcagag gtagttggcg tcatcgagcg ccatctcgaa ccgacgttgc   2880
tggccgtaca tttgtacggc tccgcagtgg atggcggcct gaagccacac agtgatattg   2940
atttgctggt tacggtgacc gtaaggcttg atgaaacaac gcggcgagct ttgatcaacg   3000
accttttgga aacttcggct tcccctggag agagcgagat tctccgcgct gtagaagtca   3060
ccattgttgt gcacgacgac atcattccgt ggcgttatcc agctaagcgc gaactgcaat   3120
ttggagaatg gcagcgcaat gacattcttg caggtatctt cgagccagcc acgatcgaca   3180
ttgatctggc tatcttgctg acaaaagcaa gagaacatag cgttgccttg gtaggtccag   3240
```

-continued

```
cggcggagga actctttgat ccggttcctg aacaggatct atttgaggcg ctaaatgaaa   3300
ccttaacgct atggaactcg ccgcccgact gggctggcga tgagcgaaat gtagtgctta   3360
cgttgtcccg catttggtac agcgcagtaa ccggcaaaat cgcgccgaag gatgtcgctg   3420
ccgactgggc aatggagcgc ctgccggccc agtatcagcc cgtcatactt gaagctagac   3480
aggcttatct tggacaagaa gaagatcgct tggcctcgcg cgcagatcag ttggaagaat   3540
ttgtccacta cgtgaaaggc gagatcacca aggtagtcgg caaataatgt ctagctagaa   3600
attcgttcaa gccgacgccg cttcgcggcg cggcttaact caagcgttag atgcactaag   3660
cacataattg ctcacagcca aactatcagg tcaagtctgc ttttattatt tttaagcgtg   3720
cataataagc cctacacaaa ttgggagata tatcatgcat gaccaaaatc ccttaacgtg   3780
agttttcgtt ccactgagcg tcagaccccg tagaaaagat caaaggatct tcttgagatc   3840
ctttttttct gcgcgtaatc tgctgcttgc aaacaaaaaa accaccgcta ccagcggtgg   3900
tttgtttgcc ggatcaagag ctaccaactc tttttccgaa ggtaactggc ttcagcagag   3960
cgcagatacc aaatactgtc cttctagtgt agccgtagtt aggccaccac ttcaagaact   4020
ctgtagcacc gcctacatac ctcgctctgc taatcctgtt accagtggct gctgccagtg   4080
gcgataagtc gtgtcttacc gggttggact caagacgata gttaccggat aaggcgcagc   4140
ggtcgggctg aacggggggt tcgtgcacac agcccagctt ggagcgaacg acctacaccg   4200
aactgagata cctacagcgt gagctatgag aaagcgccac gcttcccgaa gggagaaagg   4260
cggacaggta tccggtaagc ggcagggtcg gaacaggaga gcgcacgagg gagcttccag   4320
ggggaaacgc ctggtatctt tatagtcctg tcgggtttcg ccacctctga cttgagcgtc   4380
gatttttgtg atgctcgtca ggggggcgga gcctatggaa aaacgccagc aacgcggcct   4440
ttttacggtt cctggccttt tgctggcctt ttgctcacat gttctttcct gcgttatccc   4500
ctgattctgt ggataaccgt attaccgcct ttgagtgagc tgataccgct cgccgcagcc   4560
gaacgaccga gcgcagcgag tcagtgagcg aggaagcgga agagcgcctg atgcggtatt   4620
ttctccttac gcatctgtgc ggtatttcac accgcatagg ccgcgatagg ccgacgcgaa   4680
gcggcggggc gtagggagcg cagcgaccga agggtaggcg ctttttgcag ctcttcggct   4740
gtgcgctggc cagacagtta tgcacaggcc aggcgggttt taagagtttt aataagtttt   4800
aaagagtttt aggcggaaaa atcgcctttt ttctctttta tatcagtcac ttacatgtgt   4860
gaccggttcc caatgtacgg ctttgggttc ccaatgtacg ggttccggtt cccaatgtac   4920
ggctttgggt tcccaatgta cgtgctatcc acaggaaaga gaccttttcg accttttttcc  4980
cctgctaggg caatttgccc tagcatctgc tccgtacatt aggaaccggc ggatgcttcg   5040
ccctcgatca ggttgcggta gcgcatgact aggatcgggc cagcctgccc cgcctcctcc   5100
ttcaaatcgt actccggcag gtcatttgac ccgatcagct tgcgcacggt gaaacagaac   5160
ttcttgaact ctccggcgct gccactgcgt tcgtagatcg tcttgaacaa ccatctggct   5220
tctgccttgc ctgcggcgcg gcgtgccagg cggtagagaa aacggccgat gccgggatcg   5280
atcaaaaagt aatcggggtg aaccgtcagc acgtccgggt tcttgccttc tgtgatctcg   5340
cggtacatcc aatcagctag ctcgatctcg atgtactccg gccgcccggt ttcgctcttt   5400
acgatcttgt agcggctaat caaggcttca ccctcggata ccgtcaccag gcggccgttc   5460
ttggccttct tcgtacgctg catggcaacg tgcgtggtgt ttaaccgaat gcaggtttct   5520
accaggtcgt ctttctgctt tccgccatcg gctcgccggc agaacttgag tacgtccgca   5580
```

-continued

```
acgtgtggac ggaacacgcg gccgggcttg tctcccttcc cttcccggta tcggttcatg   5640
gattcggtta gatgggaaac cgccatcagt accaggtcgt aatcccacac actggccatg   5700
ccggccggcc ctgcggaaac ctctacgtgc ccgtctggaa gctcgtagcg gatcacctcg   5760
ccagctcgtc ggtcacgctt cgacagacgg aaaacggcca cgtccatgat gctgcgacta   5820
tcgcgggtgc ccacgtcata gagcatcgga acgaaaaaat ctggttgctc gtcgcccttg   5880
ggcggcttcc taatcgacgg cgcaccggct gccggcggtt gccgggattc tttgcggatt   5940
cgatcagcgg ccccttgcca cgattcaccg gggcgtgctt ctgcctcgat gcgttgccgc   6000
tgggcggcct gcgcggcctt caacttctcc accaggtcat cacccagcgc cgcgccgatt   6060
tgtaccgggc cggatggttt gcgaccgctc acgccgattc ctcgggcttg ggggttccag   6120
tgccattgca gggccggcag acaacccagc cgcttacgcc tggccaaccg cccgttcctc   6180
cacacatggg gcattccacg gcgtcggtgc ctggttgttc ttgattttcc atgccgcctc   6240
ctttagccgc taaaattcat ctactcattt attcatttgc tcatttactc tggtagctgc   6300
gcgatgtatt cagatagcag ctcggtaatg gtcttgcctt ggcgtaccgc gtacatcttc   6360
agcttggtgt gatcctccgc cggcaactga aagttgaccc gcttcatggc tggcgtgtct   6420
gccaggctgg ccaacgttgc agccttgctg ctgcgtgcgc tcggacggcc ggcacttagc   6480
gtgtttgtgc ttttgctcat tttctcttta cctcattaac tcaaatgagt tttgatttaa   6540
tttcagcggc cagcgcctgg acctcgcggg cagcgtcgcc ctcgggttct gattcaagaa   6600
cggttgtgcc ggcggcggca gtgcctgggt agctcacgcg ctgcgtgata cgggactcaa   6660
gaatgggcag ctcgtacccg gccagcgcct cggcaacctc accgccgatg cgcgtgcctt   6720
tgatcgcccg cgacacgaca aaggccgctt gtagccttcc atccgtgacc tcaatgcgct   6780
gcttaaccag ctccaccagg tcggcggtgg cccatatgtc gtaagggctt ggctgcaccg   6840
gaatcagcac gaagtcggct gccttgatcg cggacacagc caagtccgcc gcctggggcg   6900
ctccgtcgat cactacgaag tcgcgccggc cgatggcctt cacgtcgcgg tcaatcgtcg   6960
ggcggtcgat gccgacaacg gttagcggtt gatcttcccg cacggccgcc caatcgcggg   7020
cactgccctg gggatcggaa tcgactaaca gaacatcggc cccggcgagt tgcagggcgc   7080
gggctagatg ggttgcgatg gtcgtcttgc ctgacccgcc tttctggtta agtacagcga   7140
taaccttcat gcgttcccct tgcgtatttg tttatttact catcgcatca tatacgcagc   7200
gaccgcatga cgcaagctgt tttactcaaa tacacatcac ctttttagac gcgtggtgat   7260
tttgtgccga gctgccggtc ggggagctgt tggctggctg gtggcaggat atattgtggt   7320
gtaaacaaat tgacgcttag acaacttaat aacacattgc ggacgtcttt aatgtactga   7380
attaacatcc gtttgatact tgtctaaaat tggctgattt cgagtgcatc tatgcataaa   7440
aacaatctaa tgacaattat taccaagcag tgatcctgtc aaacactgat agtttaaact   7500
gaaggcggga aacgacaatc tgatcatgag cggagaatta agggagtcac gttatgaccc   7560
ccgccgatga cgcgggacaa gccgttttac gtttggaact gacagaaccg caacgttgaa   7620
ggagccactc agccgcgggt ttctggagtt taatgagcta agcacatacg tcagaaacca   7680
ttattgcgcg ttcaaaagtc gcctaaggtc actatcagct agcaaatatt tcttgtcaaa   7740
aatgctccac tgacgttcca taaattcccc tcggtatcca attagagtct catattcact   7800
ctcaatccaa ataatctgca ccggatctgg atcgtttcgc atgattgaac aagatggatt   7860
gcacgcaggt tctccggccg cttgggtgga gaggctattc ggctatgact gggcacaaca   7920
gacaatcggc tgctctgatg ccgccgtgtt ccggctgtca gcgcaggggc gcccggttct   7980
```

-continued

```
ttttgtcaag accgacctgt ccggtgccct gaatgaactg caggacgagg cagcgcggct   8040
atcgtggctg gccacgacgg gcgttccttg cgcagctgtg ctcgacgttg tcactgaagc   8100
gggaagggac tggctgctat tgggcgaagt gccggggcag gatctcctgt catctcacct   8160
tgctcctgcc gagaaagtat ccatcatggc tgatgcaatg cggcggctgc atacgcttga   8220
tccggctacc tgcccattcg accaccaagc gaaacatcgc atcgagcgag cacgtactcg   8280
gatggaagcc ggtcttgtcg atcaggatga tctggacgaa gagcatcagg ggctcgcgcc   8340
agccgaactg ttcgccaggc tcaaggcgcg catgcccgac ggcgaggatc tcgtcgtgac   8400
acatggcgat gcctgcttgc cgaatatcat ggtggaaaat ggccgctttt ctggattcat   8460
cgactgtggc cggctgggtg tggcggaccg ctatcaggac atagcgttgg ctacccgtga   8520
tattgctgaa gagcttggcg gcgaatgggc tgaccgcttc ctcgtgcttt acggtatcgc   8580
cgctcccgat tcgcagcgca tcgccttcta tcgccttctt gacgagttct tctgagcggg   8640
acccaagctc tagatcttgc tgcgttcgga tattttcgtg gagttcccgc cacagacccg   8700
gatgatcccc gatcgttcaa acatttggca ataaagtttc ttaagattga atcctgttgc   8760
cggtcttgcg atgattatca tataatttct gttgaattac gttaagcatg taataattaa   8820
catgtaatgc atgacgttat ttatgagatg ggtttttatg attagagtcc cgcaattata   8880
catttaatac gcgatagaaa acaaaatata gcgcgcaaac taggataaat tatcgcgcgc   8940
ggtgtcatct atgttactag atcgggcctc ctgtcaagct ctgagt                  8986
```

EXPRESSION CASSETTES FOR SEED-PREFERENTIAL EXPRESSION IN PLANTS

RELATED APPLICATIONS

This application claims benefit to European Application 04026295.8 filed Nov. 5, 2004, to European Application 04029024.9 filed Dec. 8, 2004, to European Application 05002262.3 filed Feb. 3, 2005, and to European Application 05002850.5 filed Feb. 11, 2005.

FIELD OF THE INVENTION

The present invention relates to expression cassettes comprising transcription regulating nucleotide sequences with seed-preferential or seed-specific expression profiles in plants obtainable from *Arabidopsis thaliana* genes At4g12910, At1g66250, At4g00820, At2g36640, At2g34200, At3g11180, At4g00360, At2g48030, At2g38590, At1g23000, At3g15510, At3g50870, At4g00220, or At4g26320.

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

The seed-preferential or seed-specific promoters are useful for expressing genes as well as for producing large quantities of protein, for expressing oils or proteins of interest, e.g., antibodies, genes for increasing the nutritional value of the seed and the like. It is advantageous to have the choice of a variety of different promoters so that the most suitable promoter may be selected for a particular gene, construct, cell, tissue, plant or environment. Moreover, the increasing interest in cotransforming plants with multiple plant transcription units (PTU) and the potential problems associated with using common regulatory sequences for these purposes merit having a variety of promoter sequences available.

There is, therefore, a great need in the art for the identification of novel sequences that can be used for expression of selected transgenes in economically important plants. It is thus an objective of the present invention to provide new and alternative expression cassettes for seed-preferential or seed-specific expression of transgenes in plants. The objective is solved by the present invention.

SUMMARY OF THE INVENTION

Accordingly, a first embodiment of the invention relates to an expression cassette for seed-specific or seed-preferential transcription (e.g., of an operatively linked nucleic acid sequence) in plants comprising i) at least one transcription regulating nucleotide sequence of a plant gene, said plant gene selected from the group of genes described by the GenBank *Arabidopsis thaliana* genome loci At4g12910, At1g66250, At4g00820, At2g36640, At2g34200, At3g11180, At4g00360, At2g48030, At2g38590, At1g23000, At3g15510, At3g50870, At4g00220, or At4g26320, or a functional equivalent thereof, and functionally linked thereto ii) at least one nucleic acid sequence which is heterologous in relation to said transcription regulating nucleotide sequence.

Preferably, the transcription regulating nucleotide sequence (or the functional equivalent thereof) is selected from the group of sequences consisting of i) the sequences described by SEQ ID NOs: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, ii) a fragment of at least 50 consecutive bases of a sequence under i) which has substantially the same promoter activity as the corresponding transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99%) to a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185;

iv) a nucleotide sequence capable of hybridizing under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185, or the complement thereof;

v) a nucleotide sequence capable of hybridizing under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, or the complement thereof;

vi) a nucleotide sequence which is the complement or reverse complement of any of the previously mentioned nucleotide sequences under i) to v).

The functional equivalent of the transcription regulating nucleotide sequence is obtained or obtainable from plant genomic DNA from a gene encoding a polypeptide which has at least 70% amino acid sequence identity to a polypeptide selected from the group described by SEQ ID NO: 14, 22, 30, 35, 49, 59, 73, 79, 83, 89, 157, 167, 177, and 187, respectively.

The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

Other embodiments of the invention relate to vectors comprising an expression cassette of the invention, and transgenic host cell or non-human organism comprising an expression cassette or a vector of the invention. Preferably the organism is a plant.

Another embodiment of the invention relates to a method for identifying and/or isolating a sequence with seed-specific or seed-preferential transcription regulating activity characterized that said identification and/or isolation utilizes a nucleic acid sequence encoding a amino acid sequence as described by SEQ ID NO: 14, 22, 30, 35, 49, 59, 73, 79, 83, 89, 157, 167, 177, or 187 or a part of at least 15 bases thereof. Preferably the nucleic acid sequences is described by SEQ ID NO: 13, 21, 29, 34, 48, 58, 72, 78, 82, 88, 156, 166, 176, or 186 or a part of at least 15 bases thereof. More preferably, identification and/or isolation is realized by a method selected from polymerase chain reaction, hybridization, and database screening.

Another embodiment of the invention relates to a method for providing a transgenic expression cassette for seed-specific or seed-preferential expression comprising the steps of:

I. isolating of a seed-preferential or seed-specific transcription regulating nucleotide sequence utilizing at least one nucleic acid sequence or a part thereof, wherein said sequence is encoding a polypeptide described by SEQ ID NO: 14, 22, 30, 35, 49, 59, 73, 79, 83, 89, 157, 167, 177, or 187, or a part of at least 15 bases thereof, and II. functionally linking said seed-preferential or seed-specific transcription regulating nucleotide sequence to another nucleotide sequence of interest, which is heterologous in relation to said seed-preferential or seed-specific transcription regulating nucleotide sequence.

DEFINITIONS

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 per-cent up or down (higher or lower). As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains

1) DNA sequences, including regulatory and coding sequences, that are not found together in nature, or 2) sequences encoding parts of proteins not naturally adjoined, or 3) parts of promoters that are not naturally adjoined.

Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein. The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters, most preferred are the seed-specific or seed-preferential promoters of the invention. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such, as the octopine synthase and nopaline synthase termination regions (see also, Guerineau 1991; Proudfoot 1991; Sanfacon 1991; Mogen 1990; Munroe 1990; Ballas 1989; Joshi 1987).

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of a expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from Aequora victoria. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is an *Arabidopsis* polypeptide encoded by a gene with a promoter having any one of SEQ ID NOs: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185, a nucleotide sequence comprising an open reading frame having any one of SEQ ID NOs: 13, 21, 29, 34, 48, 58, 72, 78, 82, 88, 156, 166, 176, or 186, which encodes one of SEQ ID NOs: 14, 22, 30, 35, 49, 59, 73, 79, 83, 89, 157, 167, 177, or 187. One indication that two polypeptides are substantially similar to each other, besides having substantially the same function, is that an agent, e.g., an antibody, which specifically binds to one of the polypeptides, also specifically binds to the other.

Sequence comparisons maybe carried out using a Smith-Waterman sequence alignment algorithm (see e.g., Waterman (1995)). The localS program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as *Agrobacterium*-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,793 and 5,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred. Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., the seed-specific or seed-preferential promoters of the invention).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra.

Software for performing BLAST analyses is publicly available though the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et at, supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" or "substantial similarity" of polynucleotide sequences for a protein encoding sequence means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. The term "substantial identity" or "substantial similarity" of polynucleotide sequences for promoter sequence means (as described above for variants) that a polynucleotide comprises a sequence that has at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m=81.5^\circ\ \mathrm{C.}+16.6(\log_{10} M)+0.41(\%\ \mathrm{GC})-0.61(\%\ \mathrm{form})-500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule' is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom.

Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others.

The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, sequoia, cedar, oak, etc. Especially preferred are *Arabidopsis thaliana, Nicotiana tabacum*, oilseed rape, soybean, corn (maize), wheat, *Linum usitatissimum* (linseed and fax), *Camelina sativa, Brassica juncea*, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs seed-preferential or seed-specific transcription of an operably linked nucleic acid fragment in a plant cell.

Specifically, the present invention provides transgenic expression cassettes for regulating seed-preferential or seed-specific expression (or transcription) in plants comprising i) at least one transcription regulating nucleotide sequence of a plant gene, said plant gene selected from the group of genes described by the GenBank *Arabidopsis thaliana* genome locii At4g12910, At1g66250, At4g00820, At2g36640, At2g34200, At3g11180, At4g00360, At2g48030, At2g38590, At1g23000, At3g15510, At3g50870, At4g00220, or At4g26320, or a functional equivalent thereof, and functionally linked thereto ii) at least one nucleic acid sequence which is heterologous in relation to said transcription regulating nucleotide sequence.

The seed-preferential or seed-specific promoters may be useful for expressing genes as well as for producing large quantities of protein, for expressing oils or proteins of interest, e.g., antibodies, genes for increasing the nutritional value of the seed and the like.

The term "seed" in the context of the inventions means a seed of a plant in any stage of its development i.e. starting from the fusion of pollen and oocyte, continuing over the embryo stage and the stage of the dormant seed, until the germinating seed, ending with early seedling organs, as e.g. cotyledons and hypocotyl.

"Seed-specific transcription" in the context of this invention means the transcription of a nucleic acid sequence by a transcription regulating element in a way that transcription of said nucleic acid sequence in seeds contribute to more than 90%, preferably more than 95%, more preferably more than 99% of the entire quantity of the RNA transcribed from said nucleic acid sequence in the entire plant during any of its developmental stage. The transcription regulating nucleotide sequences designated pSUK19, pSUK29, pSUK298, pSUK352 and their respective shorter and longer variants are considered to be seed-specific transcription regulating nucleotide sequences.

"Seed-preferential transcription" in the context of this invention means the transcription of a nucleic acid sequence by a transcription regulating element in a way that transcription of said nucleic acid sequence in seeds contribute to more than 50%, preferably more than 70%, more preferably more than 80% of the entire quantity of the RNA transcribed from said nucleic acid sequence in the entire plant during any of its developmental stage. The transcription regulating nucleotide sequences designated (pSUK222, pSUK224, pSUK226), (pSUK322, pSUK324), (pSUK250, pSUK252), (pSUK28, pSUK30), pSUK300, (pSUK292, pSUK294, pSUK296), pSUK164, (pSUK40, pSUK42), (pSUK48, pSUK50), (pSUK96, pSUK98), (pSUK152, pSUK154) and their respective shorter and longer variants are considered to be seed-preferential transcription regulating nucleotide sequences (transcription regulating nucleotide sequences in brackets are variants from one specific gene locus).

Preferably a transcription regulating nucleotide sequence of the invention comprises at least one promoter sequence of the respective gene (e.g., a sequence localized upstream of the transcription start of the respective gene capable to induce transcription of the downstream sequences). Said transcription regulating nucleotide sequence may comprise the promoter sequence of said genes but may further comprise other elements such as the 5'-untranslated sequence, enhancer, introns etc. Preferably, said promoter sequence directs seed-preferential or seed-specific transcription of an operably linked nucleic acid segment in a plant or plant cell e.g., a linked plant DNA comprising an open reading frame for a structural or regulatory gene.

The following Table 1 illustrates the genes from which the promoters of the invention are preferably isolated, the function of said genes, the cDNA encoded by said genes, and the protein (ORF) encoded by said genes.

TABLE 1

Genes from which the promoters of the invention are preferably isolated, putative function of said genes, cDNA and the protein encoded by said genes.

| Gene Locus | Putative function | Promotor SEQ ID | mRNA locus ID cDNA SEQ ID | Proteine ID Protein SEQ ID |
|---|---|---|---|---|
| At4g12910 | serine carboxypeptidase I precursor-like protein | SEQ ID NO: 1, 2, 3, 4, 5, 6, 7, 8, 9, 10, 11, 12 | NM_117360 SEQ ID NO: 13 | NP_193027.2 SEQ ID NO: 14 |
| At1g66250 | glycosyl hydrolase family 17 protein | SEQ ID NO: 15, 16, 17, 18, 19, 20 | NM_105296 SEQ ID NO: 21 | NP_176799.2 SEQ ID NO: 22 |
| At4g00820 | calmodulin-binding protein-related protein | SEQ ID NO: 23, 24, 25, 26, 27, 28 | NM_116308 SEQ ID NO: 29 | NP_567191.2 SEQ ID NO: 30 |
| At2g36640 | late embryogenesis abundant protein (ECP63)/ LEA protein | SEQ ID NO: 31, 32, 33 | NM_129219 SEQ ID NO: 34 | NP_181202.1 SEQ ID NO: 35 |
| At2g34200 | Zinc finger (C3HC4-type RING finger) family protein | SEQ ID NO: 36, 37, 38, 39, 40, 41, 42, 43, 44, 45, 46, 47 | NM_128971 SEQ ID NO: 48 | NP_180967.2 SEQ ID NO: 49 |
| At3g11180 | oxidoreductase, 2OG-Fe(II) oxygenase family protein | SEQ ID NO: 50, 51, 52, 53, 54, 55, 56, 57 | NM_111954 SEQ ID NO: 58 | NP_187728.1 SEQ ID NO: 59 |
| At4g00360 | putative cytochrome P450 | SEQ ID NO: 60, 61, 62, 63, 64, 65, 66, 67, 68, 69 70, 71 | NM_116260 SEQ ID NO: 72 | NP_191946.1 SEQ ID NO: 73 |
| At2g48030 | endonuclease/exonuclease/ phosphatase family protein | SEQ ID NO: 74, 75, 76, 77 | NM_130370 SEQ ID NO: 78 | NP_566121.1 SEQ ID NO: 79 |
| At2g38590 | F-box family protein | SEQ ID NO: 80, 81 | NM_129416 SEQ ID NO: 82 | NP_181393.1 SEQ ID NO: 83 |
| At1g23000 | heavy-metal-associated domain-containing protein | SEQ ID NO: 84, 85, 86, 87 | NM_102148 SEQ ID NO: 88 | NP_173713.1 SEQ ID NO: 89 |
| At3g15510 | encoding *Arabidopsis thaliana* no apical meristem (NAM) family protein (NAC2) | SEQ ID NO: 148, 149, 150, 151, 152, 153, 154, 155 | NM_112419 SEQ ID NO: 156 | NP_188170.1 SEQ ID NO: 157 |
| At3g50870 | encoding *Arabidopsis thaliana* zinc finger (GATA type) family protein | SEQ ID NO: 158, 159, 160, 161, 162, 163, 164, 165 | NM_114947 SEQ ID NO: 166 | NP_566939.1 SEQ ID NO: 167 |
| At4g00220 | encoding *Arabidopsis thaliana* LOB domain protein 30/lateral organ boundaries domain protein 30 (LBD30) | SEQ ID NO: 168, 169, 170, 171, 172, 173, 174, 175 | NM_116239 SEQ ID NO: 176 | NP_191933.1 SEQ ID NO: 177 |

TABLE 1-continued

Genes from which the promoters of the invention are preferably isolated, putative function of said genes, cDNA and the protein encoded by said genes.

| Gene Locus | Putative function | Promotor SEQ ID | mRNA locus ID cDNA SEQ ID | Proteine ID Protein SEQ ID |
|---|---|---|---|---|
| At4g26320 | encoding *Arabidopsis thaliana* arabinogalactan-protein (AGP13) | SEQ ID NO: 178, 179, 180, 181, 182, 183, 184, 185 | NM_118765 SEQ ID NO: 186 | NP_194362.1 SEQ ID NO: 187 |

Preferably the transcription regulating nucleotide sequence (or the functional equivalent thereof) is selected from the group of sequences consisting of i) the sequences described by SEQ ID NOs: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, ii) a fragment of at least 50 consecutive bases of a sequence under i) which has substantially the same promoter activity as the corresponding transcription regulating nucleotide sequence described by 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98%, and 99%) to a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185;

iv) a nucleotide sequence capable of hybridizing under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185, or the complement thereof;

v) a nucleotide sequence capable of hybridizing under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides (preferably at least 100, 200, or 300, more preferably 400, 500, or 600, most preferably at least 700, 800, or 900 consecutive nucleotides) of a transcription regulating nucleotide sequence described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185, or the complement thereof;

vi) a nucleotide sequence which is the complement or reverse complement of any of the previously mentioned nucleotide sequences under i) to v).

A functional equivalent of the transcription regulating nucleotide sequence can also be obtained or is obtainable from plant genomic DNA from a gene encoding a polypeptide which is substantially similar and preferably has at least 70%, preferably 80%, more preferably 90%, most preferably 95% amino acid sequence identity to a polypeptide encoded by an *Arabidopsis thaliana* gene comprising any one of SEQ ID NOs: 14, 22, 30, 35, 49, 59, 73, 79, 83, 89, 157, 167, 177, or 187, respectively, or a fragment of said transcription regulating nucleotide sequence which exhibits promoter activity in a seed-preferential or seed-specific fashion.

The activity of a transcription regulating nucleotide sequence is considered equivalent if transcription is initiated in a seed-preferential or seed-specific fashion (as defined above). Such expression profile is preferably demonstrated using reporter genes operably linked to said transcription regulating nucleotide sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987).

Beside this the transcription regulating activity of a function equivalent may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences, which—in comparison with its parent sequence—does, not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Preferably functional equivalent of the transcription regulating nucleotide sequence can be obtained or is obtainable from plant genomic DNA from a gene expressing a mRNA described by a cDNA which is substantially similar and preferably has at least 70%, preferably 80%, more preferably 90%, most preferably 95% sequence identity to a sequence described by any one of SEQ ID NOs: 13, 21, 29, 34, 48, 58, 72, 78, 82, 88, 156, 166, 176, or 186, respectively, or a fragment of said transcription regulating nucleotide sequence which exhibits promoter activity in a seed-preferential or seed-specific fashion.

Such functional equivalent of the transcription regulating nucleotide sequence may be obtained from other plant species by using the seed-preferential or seed-specific *Arabidopsis* promoter sequences described herein as probes to screen for homologous structural genes in other plants by hybridization under low, moderate or stringent hybridization conditions. Regions of the seed-preferential or seed-specific promoter sequences of the present invention which are conserved among species could also be used as PCR primers to amplify a segment from a species other than *Arabidopsis*, and that segment used as a hybridization probe (the latter approach permitting higher stringency screening) or in a transcription assay to determine promoter activity. Moreover, the seed-preferential or seed-specific promoter sequences could be employed to identify structurally related sequences in a database using computer algorithms.

More specifically, based on the *Arabidopsis* nucleic acid sequences of the present invention, orthologs may be identified or isolated from the genome of any desired organism, preferably from another plant, according to well known techniques based on their sequence similarity to the *Arabidopsis* nucleic acid sequences, e.g., hybridization, PCR or computer generated sequence comparisons. For example, all or a portion of a particular *Arabidopsis* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis* sequences disclosed herein, i.e., the corresponding nucleotide sequences in organisms other than *Arabidopsis*, including, but not limited to, plants other than *Arabidopsis*, preferably dicotyledonous plants, e.g., *Brassica napus*, alfalfa, sunflower, soybean, cotton, peanut, tobacco or sugar beet, but also cereal plants such as corn, wheat, rye, turfgrass, sorghum, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 65% amino acid sequence identity, but which ortholog encodes a polypeptide having the same or similar function. Databases such GenBank may be employed to identify sequences related to the *Arabidopsis* sequences, e.g., orthologs in other dicotyledonous plants such as *Brassica napus* and others. Alternatively, recombinant DNA techniques such as hybridization or PCR may be employed to identify sequences related to the *Arabidopsis* sequences or to clone the equivalent sequences from different *Arabidopsis* DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another embodiment of the invention relates to a method for identifying and/or isolating a sequence with seed-preferential or seed-specific transcription regulating activity utilizing a nucleic acid sequence encoding a amino acid sequence as described by SEQ ID NO: 14, 22, 30, 35, 49, 59, 73, 79, 83, 89, 157, 167, 177, or 187 or a part thereof. Preferred are nucleic acid sequences described by SEQ ID NO: 13, 21, 29, 34, 48, 58, 72, 78, 82, 88, 156, 166, 176, or 186 or parts thereof. "Part" in this context means a nucleic acid sequence of at least 15 bases preferably at least 25 bases, more preferably at least 50 bases. The method can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Another embodiment of the invention is related to a method for providing a transgenic expression cassette for seed-preferential or seed-specific expression comprising the steps of:

I. isolating of a seed-preferential or seed-specific transcription regulating nucleotide sequence utilizing at least one nucleic acid sequence or a part thereof, wherein said sequence is encoding a polypeptide described by SEQ ID NO: 14, 22, 30, 35, 49, 59, 73, 79, 83, 89, 157, 167, 177, or 187, or a part of at least 15 bases thereof, and II. functionally linking said seed-preferential or seed-specific transcription regulating nucleotide sequence to another nucleotide sequence of interest, which is heterologous in relation to said seed-preferential or seed-specific transcription regulating nucleotide sequence.

Preferably, the nucleic acid sequence employed for the isolation comprises at least 15 base, preferably at least 25 bases, more preferably at least 50 bases of a sequence described by SEQ ID NO: 13, 21, 29, 34, 48, 58, 72, 78, 82, 88, 156, 166, 176, or 186. Preferably, the isolation of the seed-preferential or seed-specific transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, or the promoter orthologs thereof, which include the minimal promoter region.

In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95%, nucleic acid sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, or the promoter orthologs thereof, which include the minimal promoter region. The above-defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving seed-preferential or seed-specific expression of a coding sequence in a target cell, particularly in a plant cell. The promoter sequences and methods disclosed herein are useful in regulating seed-preferential or seed-specific expression, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. The term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185) into the plant genome. Such insertion will result in an operable linkage to a nucleic acid sequence of interest which as such already existed in the genome. By the insertion the nucleic acid of interest is expressed in a seed-preferential or seed-specific way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide sequence in its natural genomic environment (i.e. linked to its natural gene) in a way that the inserted sequence becomes operably linked to the transcription regulating nucleotide sequence, thereby forming an expression cassette of the invention.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant, which exhibits substantially no phenotypic changes as a consequence of agent administration, infection with a pathogen, or exposure to stress. By "tolerant" is meant a plant, which, although it may exhibit some phenotypic changes as a consequence of infection, does not have a substantially decreased reproductive capacity or substantially altered metabolism.

Seed-preferential or seed-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Seed-preferential or seed-specific transcription regulating nucleotide sequences (e.g., promoters) may be modified so as to be regulatable, e.g., inducible. The genes and transcription regulating nucleotide sequences (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

The expression regulating nucleotide sequences specified above may be optionally operably linked to other suitable regulatory sequences, e.g., a transcription terminator sequence, operator, repressor-binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating nucleotide sequences of the invention further comprise sequences which are complementary to one (hereinafter "test" sequence) which hybridizes under stringent conditions with a nucleic acid molecule as described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185 as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors, which may be employed in conjunction with the present invention, will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as *E. coli*, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating nucleotide sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses.

The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences, which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof, which is introduced into the plant genome, is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods, which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector, which exists in both a single stranded and double stranded form. Typical vectors useful in site-directed mutagenesis include vectors such as the M13 phage. These phages are readily commercially available and their use is generally well known to those skilled in the art.

Double stranded plasmids also are routinely employed in site directed mutagenesis, which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Ramstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template-dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences, which are shared among promoters with similar expression patterns, are likely candidates for the binding of transcription factors and are thus likely elements that confer expression patterns. Confirmation of these putative regulatory elements can be achieved by deletion analysis of each putative regulatory region followed by functional analysis of each deletion construct by assay of a reporter gene, which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002).

Preferably, functional equivalent fragments of one of the transcription regulating nucleotide sequences of the invention comprises at least 100 base pairs, preferably, at least 200 base pairs, more preferably at least 500 base pairs of a transcription regulating nucleotide sequence as described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, or 185. More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences (see Table 2 below).

TABLE 2

Relationship of transcription regulating nucleotide sequences of the invention

| Transcription regulating sequence | Equivalent sequence | Equivalent fragment |
|---|---|---|
| SEQ ID NO: 9 (3954 bp) | SEQ ID NO: 10 (3962 bp) | SEQ ID NO: 1 (980 bp) |
| | | SEQ ID NO: 2 (994 bp) |
| | | SEQ ID NO: 3 (686 bp) |
| | | SEQ ID NO: 4 (698 bp) |
| | | SEQ ID NO: 5 (2051 bp) |
| | | SEQ ID NO: 6 (2066 bp) |
| | | SEQ ID NO: 7 (1757 bp) |
| | | SEQ ID NO: 8 (1770 bp) |
| | | SEQ ID NO: 11 (3660 bp) |
| | | SEQ ID NO: 12 (3666 bp) |
| SEQ ID NO: 19 (3892 bp) | SEQ ID NO: 20 (3083 bp) | SEQ ID NO: 15 (2254 bp) |
| | | SEQ ID NO: 16 (2259 bp) |
| | | SEQ ID NO: 17 (1446 bp) |
| | | SEQ ID NO: 18 (1450 bp) |
| SEQ ID NO: 27 (2352 bp) | SEQ ID NO: 28 (2168 bp) | SEQ ID NO: 23 (1026 bp) |
| | | SEQ ID NO: 24 (1030 bp) |
| | | SEQ ID NO: 25 (844 bp) |
| | | SEQ ID NO: 26 (846 bp) |
| SEQ ID NO: 33 (1441 bp) | — | SEQ ID NO: 31 (1201 bp) |
| | | SEQ ID NO: 32 (1216 bp) |
| SEQ ID NO: 36 (1587 bp) | SEQ ID NO: 37 (1602 bp) | SEQ ID NO: 38 (1130 bp) |
| | | SEQ ID NO: 39 (1145 bp) |
| | | SEQ ID NO: 40 (1169 bp) |
| | | SEQ ID NO: 41 (1191 bp) |
| | | SEQ ID NO: 42 (1130 bp) |
| | | SEQ ID NO: 43 (1145 bp) |
| | | SEQ ID NO: 44 (1120 bp) |
| | | SEQ ID NO: 45 (1135 bp) |
| | | SEQ ID NO: 46 (663 bp) |
| | | SEQ ID NO: 47 (678 bp) |
| SEQ ID NO: 54 (2012 bp) | SEQ ID NO: 55 (2033 bp) | SEQ ID NO: 50 (1069 bp) |
| | | SEQ ID NO: 51 (1088 bp) |
| | | SEQ ID NO: 52 (1034 bp) |
| | | SEQ ID NO: 53 (1053 bp) |
| | | SEQ ID NO: 56 (1977 bp) |
| | | SEQ ID NO: 57 (1998 bp) |
| SEQ ID NO: 68 (2996 bp) | SEQ ID NO: 69 (3008 bp) | SEQ ID NO: 60 (949 bp) |
| | | SEQ ID NO: 61 (962 bp) |
| | | SEQ ID NO: 62 (768 bp) |
| | | SEQ ID NO: 63 (779 bp) |
| | | SEQ ID NO: 64 (2040 bp) |
| | | SEQ ID NO: 65 (2053 bp) |
| | | SEQ ID NO: 66 (1859 bp) |
| | | SEQ ID NO: 67 (1870 bp) |
| | | SEQ ID NO: 70 (2815 bp) |
| | | SEQ ID NO: 71 (2825 bp) |
| SEQ ID NO: 74 (1564 bp) | SEQ ID NO: 75 (1578 bp) | SEQ ID NO: 76 (1404 bp) |
| | | SEQ ID NO: 77 (1418 bp) |
| SEQ ID NO: 80 (524 bp) | SEQ ID NO: 81(539 bp) | — |
| SEQ ID NO: 84 (1988 bp) | SEQ ID NO: 85 (2010 bp) | SEQ ID NO: 86 (1776 bp) |
| | | SEQ ID NO: 87 (1800 bp) |
| SEQ ID NO: 152 (1845 bp) | SEQ ID NO: 153 (1854 bp) | SEQ ID NO: 148 (1106 bp) |
| | | SEQ ID NO: 149 (1115 bp) |
| | | SEQ ID NO: 150 (923 bp) |
| | | SEQ ID NO: 151 (930 bp) |
| | | SEQ ID NO: 154 (1662 bp) |
| | | SEQ ID NO: 155 (1669 bp) |
| SEQ ID NO: 162 (2017 bp) | SEQ ID NO: 163 (2004 bp) | SEQ ID NO: 158 (1017 bp) |
| | | SEQ ID NO: 159 (1008 bp) |
| | | SEQ ID NO: 160 (894 bp) |
| | | SEQ ID NO: 161 (886 bp) |
| | | SEQ ID NO: 164 (1894 bp) |
| | | SEQ ID NO: 165 (1882 bp) |
| SEQ ID NO: 172 (3232 bp) | SEQ ID NO: 173 (3269 bp) | SEQ ID NO: 168 (1300 bp) |
| | | SEQ ID NO: 169 (1337 bp) |
| | | SEQ ID NO: 170 (1190 bp) |
| | | SEQ ID NO: 171 (1226 bp) |
| | | SEQ ID NO: 174 (3123 bp) |
| | | SEQ ID NO: 175 (3158 bp) |

TABLE 2-continued

Relationship of transcription regulating nucleotide sequences of the invention

| Transcription regulating sequence | Equivalent sequence | Equivalent fragment |
| --- | --- | --- |
| SEQ ID NO: 182 (3019 bp) | SEQ ID NO: 183 (3006 bp) | SEQ ID NO: 178 (1504 bp) |
| | | SEQ ID NO: 179 (1492 bp) |
| | | SEQ ID NO: 180 (1450 bp) |
| | | SEQ ID NO: 181 (1436 bp) |
| | | SEQ ID NO: 184 (2965 bp) |
| | | SEQ ID NO: 185 (2950 bp) |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct, which contains a deleted segment to a selectable or screenable marker, and to isolate only those cells expressing the marker gene. In this way, a number of different, deleted promoter constructs are identified which still retain the desired, or even enhanced, activity. The smallest segment, which is required for activity, is thereby identified through comparison of the selected constructs. This segment may then be used for the construction of vectors for the expression of exogenous genes.

An expression cassette of the invention may comprise further regulatory elements. The term in this context is to be understood in the a broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realize expression in other organisms (such as *E. coli* or *Agrobacterium*). Such regulatory elements can be found in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters, which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those, which include sequences, predicted to direct optimum expression of the attached gene, i.e., to include a preferred consensus leader sequence, which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, New York (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired. Especially preferred are the 5'-untranslated region, introns and the 3+-untranslated region from the genes described by the GenBank *Arabidopsis thaliana* genome locii At4g12910, At1g66250, At4g00820, At2g36640, At2g34200, At3g1180, At4g00360, At2g48030, At2g38590, At1g23000, At3g15510, At3g50870, At4g00220, or At4g26320, or of functional equivalent thereof.

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis el al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a seed-preferential or seed-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789, 538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences, which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest, which encodes a polypeptide, are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used, for examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be nonexpressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Exemplary Transgenes 1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes, which can be introduced, include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CrylA(b) and CrylA(c) genes. Endotoxin genes from other species of *B. thuringiensis*, which affect insect growth or development, may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes, which encode inhibitors of the insects' digestive system, or those that encode enzymes or co-factors that facilitate the production of inhibitors, may also be useful. Cystatin and amylase inhibitors, such as those from wheat and barley, may exemplify this group.

Also, genes encoding lectins may confer additional or alternative insecticide properties. Lectins (originally termed phytohemagglutinins) are multivalent carbohydrate-binding proteins, which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes, which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn rootworm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes, which are not sugars, include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or tissue-specific of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences, which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the Trichoderma harzianum chit42 endochitinase (GenBank Acc. No.: S78423) or the N-hydroxylating, multi-functional cytochrome P-450 (CYP79) protein from Sorghum bicolor (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77).The expression of synthetic crylA(b) and crylA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene, which encodes an enzyme capable of rendering the mycotoxin nontoxic, would be useful in order to achieve reduced mycotoxin contamination of grain. The result of any of the above mechanisms would be a reduced presence of mycotoxins on grain.

1.6 Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes, which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other wellknown fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA, which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase, which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level.

Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups, which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping, quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

1.7 Tuber or Seed Composition or Quality

Various traits can be advantegously expressed especially in seeds or tubers to improve composition or quality. Such traits include but are not limited to:

- Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.
- Expression of genes which bring about an accumulation of fine chemicals such as of tocopherols, tocotrienols or carotenoids. An example which may be mentioned is phytoene desaturase. Preferred are nucleic acids which encode the Narcissus pseudonarcissus photoene desaturase (GenBank Acc. No.: X78815) or functional equivalents thereof.
- Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the *Bertholletia excelsa* high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella alpina* Δ6-desaturase (Sakuradani et al. 1999 Gene 238:445-453), the *Caenorhabditis elegans* Δ5-desaturase (Michaelson et al. 1998, FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273: 19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.
- Production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial b-glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those which encode the Medicago sativa acetyl-CoA carboxylase (ACCase) (GenBank Acc. No.: L25042), or functional equivalents thereof.

Reducing levels of $\alpha$-glucan L-type tuber phosphorylase (GLTP) or .$\alpha$-glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an $\alpha$-glucan phosphorylase selected from the group consisting of $\alpha$-glucan L-type tuber phosphorylase (GLTP) and $\alpha$-glucan H-type phosphorylase (GHTP).

Further examples of advantageous genes are mentioned for example in Dunwell J M, Transgenic approaches to crop improvement, J Exp Bot. 2000; 51 Spec No; pages 487-96.

1.8 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plants of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes, which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilates into the grain and thus increase yield. Overexpression of genes within plants that are associated with “stay green” or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.9 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.10 Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani 1990). For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

1.11. Non-Protein-Expressing Sequences 1.11.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a nontranslatable RNA. Gene regulation by double-stranded RNA ("double-stranded RNA interference"; dsRNAi) is well known in the arte and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants, which possess them. The transgenic plants may possess reduced levels of polypeptides including but not limited to the polypeptides cited above that may be affected by antisense RNA.

It is also possible that genes may be introduced to produce novel transgenic plants, which have reduced expression of a native gene product, by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.11.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element, which may be introduced, is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., seed-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers, which encode a secretable antigen that can be identified by antibody interaction, or even secretable enzymes, which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98145456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide), which suppresses growth of an untransformed wild type tissue. Especially preferred negative selection markers are those, which confer resistance to herbicides. Examples, which may be mentioned, are:

- Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.
- altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A 10 218 571).
- Glyphosate® degrading enzymes (Glyphosate® oxidoreductase; gox),
- Dalapon® inactivating dehalogenases (deh)
- sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)
- Bromoxynil® degrading nitrilases (bxn; Stalker 1988)
- Kanamycin- or geneticin (G418) resistance genes (NPTII; NPT or neo; Potrykus 1985) coding e.g., for neomycin phosphotransferases (Fraley 1983; Nehra 1994)
- 2-Desoxyglucose-6-phosphate phosphatase ($DOG^R$1-Gene product; WO 98/45456; EP 0 807 836) conferring resistance against 2-desoxyglucose (Randez-Gil 1995).
- hygromycin phosphotransferase (HPT), which mediates resistance to hygromycin (Vanden Elzen 1985).
- altered dihydrofolate reductase (Eichholtz 1987) conferring resistance against methotrexat (Thillet 1988);
- mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the dao1 gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive Selection Marker

Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a nontransformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schiaman & Hooykaas 1997), tms2 gene products (Fedoroff & Smith 1993), or α-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transfomation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue, i.e., in seeds, roots, green tissue (leaf and stem), panicles or pollen, or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the transacting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and airborne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within the seeds of a plant to achieve a desired phenotype. In this case, such inhibition might be accomplished with transformation of the plant to comprise a promoter operably linked to an antisense nucleotide sequence, such that seed-preferential or seed-specific expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter, an actin cl promoter, a sucrose synthetase promoter, an INOPS promoter, an EXM5 promoter, a globulin2 promoter, a b-32, ADPG-pyrophosphorylase promoter, an Ltpl promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapeturn-specific gene promoter, tapeturn-specific gene RAB24 promoter, a anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, *Brassica*, canola, soybean, barley, soybean, sugarbeet, cotton, safflower, peanut, sorghum, wheat, millet, tobacco, *Linum usitatissimum* (linseed and fax), *Camelina sativa, Brassica juncea*, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to transgenic cells or non-human, transgenic organisms comprising an expression cassette of the invention. Preferred are prokaryotic and eukaryotic organisms. Both microorganism and higher organisms are comprised. Preferred microorganisms are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11).

Especially preferred are microorganisms capable to infect plants and to transfer DNA into their genome, especially bacteria of the genus *Agrobacterium*, preferably *Agrobacterium tumefaciens* and *rhizogenes*. Preferred yeasts are *Candida, Saccharomyces, Hansenula* and *Pichia*. Preferred Fungi are *Aspergillus, Trichoderma, Ashbya, Neurospora, Fusarium*, and *Beauveria*. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid-targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

Various *Agrobacterium* strains can be employed, preferably disarmed *Agrobacterium tumefaciens* or *rhizogenes* strains. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105[pEHA105] (Li 1992), LBA4404[pAL4404] (Hoekema 1983), C58C1[pMP90] (Koncz & Schell 1986), and C58C1[pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Klapwijk 1980). In another preferred embodiment the soil-borne bacterium is a disarmed variant of *Agrobacterium rhizogenes* strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the *Agrobacterium* strain used to transform the plant tissue precultured with the plant phenolic compound contains a L,L-succinamopine type Ti-plasmid, preferably disarmed, such as pEHA101. In another preferred embodiment, the *Agrobacterium* strain used to transform the plant tissue precultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with super-virulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo & Hooykaas 1991).

*Agrobacterium* is grown and used in a manner similar to that described in Ishida (1996). The vector comprising *Agrobacterium* strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C.

The transformation of the target tissue (e.g., an immature embryo) by the *Agrobacterium* may be carried out by merely contacting the target tissue with the *Agrobacterium*. The concentration of *Agrobacterium* used for infection and co-cultivation may need to be varied. For example, a cell suspension of the *Agrobacterium* having a population density of approximately from $10^5$-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the *Agrobacterium*.

Preferably, the bacterium is employed in concentration of $10^6$ to $10^{10}$ cfu/ml. In a preferred embodiment for the co-cultivation step about 1 to 10 μl of a suspension of the soil-borne bacterium (e.g., *Agrobacteria*) in the co-cultivation medium are directly applied to each target tissue explant and air-dried. This is saving labor and time and is reducing unintended *Agrobacterium*-mediated damage by excess *Agrobacterium* usage.

For *Agrobacterium* treatment, the bacteria are resuspended in a plant compatible cocultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defence responses (like phenolic oxidation) may further improve the efficiency of *Agrobacterium*-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 μM to about 10 μM of silver nitrate and from about 50 mg/L to about 1,000 mg/L of L-Cystein. This results in a highly reduced vulnerability of the target tissue against *Agrobacterium*-mediated damage (such as induced necrosis) and highly improves overall transformation efficiency.

Various vector systems can be used in combination with *Agrobacteria*. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or *Agrobacterium*-mediated transfer usually, but not necessarily, are undertaken with a selectable marker, which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells, which are then grown to callus. Shoots are grown from callus. Plantlets are generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA, which has been introduced. Components of DNA constructs including transcription cassettes of this invention may be prepared from sequences, which are native (endogenous) or foreign (exogenous) to the host. By “foreign” it is meant that the sequence is not found in the wild-type host into which the construct is introduced. Heterologous constructs will contain at least one region, which is not native to the gene from which the transcription-initiation-region is derived.

To confirm the presence of the transgenes in transgenic cells and plants, a variety of assays may be performed. Such assays include, for example, “molecular biological” assays well known to those of skill in the art, such as Southern and Northern blotting, in situ hybridization and nucleic acid-based amplification methods such as PCR or RT-PCR or TaqMan; “biochemical” assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using these technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant, which only differs in that the expression cassette is absent. The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding, which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross-pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, which for example increase the effectiveness of conventional methods such as herbicide or pesticide treatment or allow dispensing with said methods due to their modified genetic properties. Alternatively new crops with improved stress tolerance can be obtained which, due to their optimized genetic "equipment", yield harvested product of better quality than products, which were not able to tolerate comparable adverse developmental conditions.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Generation of Transgenic Plants 1.1 Generation of Transgenic *Arabidopsis thaliana* Plants For generating transgenic *Arabidopsis* plants *Agrobacterium tumefaciens* (strain C58C1[pMP90]) is transformed with the various promoter::GUS vector constructs (see below). Resulting *Agrobacterium* strains are subsequently employed to obtain transgenic plants. For this purpose a isolated transformed *Agrobacterium* colony is incubated in 4 ml culture (Medium: YEB medium with 50 μg/ml Kanamycin and 25 μg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (1/2 MS-Medium; 0.5 g/l MES, pH 5.8; 50 g/l sucrose). The suspension is placed in a plant box (Duchefa) and 100 ml SILVET L-77 (Osi Special-ties Inc., Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

1.2 Generation of Transgenic Linseed

Transgenic linseed plants can be generated for example by the method of Bell et al., 1999, In Vitro Cell. Dev. Biol.-Plant. 35(6):456-465 by means of particle bombardment. *Agrobacteria*-mediated transformations can be generated for example by the method of Mlynarova et al. (1994), Plant Cell Report 13: 282-285.

Example 2

Growth Conditions for Plants for Tissue-specific Expression Analysis

To obtain 4 and 7 days old seedlings, about 400 seeds (*Arabidopsis thaliana* ecotype Columbia) are sterilized with a 80% (v/v) ethanol:water solution for 2 minutes, treated with a sodium hypochlorite solution (0.5% v/v) for 5 minutes, washed three times with distillated water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cyklus (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stem, stem leaves, and flower buds are harvested in development stage 12 (Bowmann J (ed.), *Arabidopsis*, Atlas of Morphology, Springer New York, 1995) prior to stamen development. Open flowers are harvested in development stage 14 immediately after stamen development. Wilting flowers are harvested in stage 15 to 16. Green and yellow shoots used for the analysis have a length of 10 to 13 mm.

Example 3

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity plant tissue is dissected, embedded, stained and analyzed as described (e.g., Bäumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

Example 4

Cloning of the Promoter Fragments

To isolate the promoter fragments described by SEQ ID NO: 1, 2, 3, 4, 5, 6, 7, 8, 9, 10, 11, 12, 15, 16, 17, 18, 19, 20, 23, 24, 25, 26, 27, 28, 31, 32, 33, 36, 37, 38, 39, 40, 41, 42, 43, 44, 45, 46, 47, 50, 51, 52, 53, 54, 55, 56, 57, 60, 61, 62, 63, 64, 65, 66, 67, 68, 69, 70, 71, 74, 75, 76, 77, 80, 81, 84, 85, 86, 87, 148, 149, 150, 151, 152, 153, 154, 155, 158, 159, 160, 161, 162, 163, 164, 165, 168, 169, 170, 171, 172, 173, 174, 175, 178, 179, 180, 181, 182, 183, 184, and 185, genomic DNA is isolated from *Arabidopsis thaliana* (ecotype Columbia) as described (Galbiati 2000). The isolated genomic DNA is employed as matrix DNA for a polymerase chain reaction (PCR) mediated amplification using the oligonucleotide primers and protocols indicated below (Table 3).

TABLE 3

PCR oligonucleotide primers for amplification of the various transcription regulating nucleotide sequences and restriction enzymes for modifying the resulting PCR products

| SEQ ID | Promoter | Forward Primer | Reverse Primer | Restriction enzymes |
|---|---|---|---|---|
| SEQ ID NO: 1 | pSUK222L | SUK222for SEQ ID NO: 90 | SUK222Lrev SEQ ID NO: 91 | BamHI/NcoI |
| SEQ ID NO: 2 | pSUK222LGB | SUK222for SEQ ID NO: 90 | SUK222Lrev SEQ ID NO: 91 | BamHI/NcoI |
| SEQ ID NO: 3 | pSUK222S | SUK222for SEQ ID NO: 90 | SUK222Srev SEQ ID NO: 92 | BamHI/NcoI |
| SEQ ID NO: 4 | pSUK222SGB | SUK222for SEQ ID NO: 90 | SUK222Srev SEQ ID NO: 92 | BamHI/NcoI |
| SEQ ID NO: 5 | pSUK224L | SUK224for SEQ ID NO: 93 | SUK224Lrev SEQ ID NO: 94 | BamHI/NcoI |
| SEQ ID NO: 6 | pSUK224LGB | SUK224for SEQ ID NO: 93 | SUK224Lrev SEQ ID NO: 94 | BamHI/NcoI |
| SEQ ID NO: 7 | pSUK224S | SUK224for SEQ ID NO: 93 | SUK224Srev SEQ ID NO: 95 | BamHI/NcoI |
| SEQ ID NO: 8 | pSUK224SGB | SUK224for SEQ ID NO: 93 | SUK224Srev SEQ ID NO: 95 | BamHI/NcoI |
| SEQ ID NO: 9 | pSUK226L | SUK226for SEQ ID NO: 96 | SUK226Lrev SEQ ID NO: 97 | BamHI/NcoI |
| SEQ ID NO: 10 | pSUK226LGB | SUK226for SEQ ID NO: 96 | SUK226Lrev SEQ ID NO: 97 | BamHI/NcoI |
| SEQ ID NO: 11 | pSUK226S | SUK226for SEQ ID NO: 96 | SUK226Srev SEQ ID NO: 98 | BamHI/NcoI |
| SEQ ID NO: 12 | pSUK226SGB | SUK226for SEQ ID NO: 96 | SUK226Srev SEQ ID NO: 98 | BamHI/NcoI |
| SEQ ID NO: 15 | pSUK322L | SUK322for SEQ ID NO: 99 | SUK322Lrev SEQ ID NO: 100 | XhoI/BamHI |
| SEQ ID NO: 16 | pSUK322LGB | SUK322for SEQ ID NO: 99 | SUK322Lrev SEQ ID NO: 100 | XhoI/BamHI |
| SEQ ID NO: 17 | pSUK322S | SUK322for SEQ ID NO: 99 | SUK322Srev SEQ ID NO: 101 | XhoI/HindIII |
| SEQ ID NO: 18 | pSUK322SGB | SUK322for SEQ ID NO: 99 | SUK322Srev SEQ ID NO: 101 | XhoI/HindIII |
| SEQ ID NO: 19 | pSUK324LGB | SUK324for SEQ ID NO: 102 | SUK324Lrev SEQ ID NO: 103 | EcoRI/EcoRI |
| SEQ ID NO: 20 | pSUK324SGB | SUK324for SEQ ID NO: 102 | SUK324Srev SEQ ID NO: 104 | EcoRI/HindIII |
| SEQ ID NO: 23 | pSUK250L | SUK250for SEQ ID NO: 105 | SUK250Lrev SEQ ID NO: 106 | BamHI/NcoI |
| SEQ ID NO: 24 | pSUK250LGB | SUK250for SEQ ID NO: 105 | SUK250Lrev SEQ ID NO: 106 | BamHI/NcoI |
| SEQ ID NO: 25 | pSUK250S | SUK250for SEQ ID NO: 105 | SUK250Srev SEQ ID NO: 107 | BamHI/NcoI |
| SEQ ID NO: 26 | pSUK250SGB | SUK250for SEQ ID NO: 105 | SUK250Srev SEQ ID NO: 107 | BamHI/NcoI |
| SEQ ID NO: 27 | pSUK252LGB | SUK252for SEQ ID NO: 108 | SUK252Lrev SEQ ID NO: 109 | BamHI/NcoI |
| SEQ ID NO: 28 | pSUK252SGB | SUK252for SEQ ID NO: 108 | SUK252Srev SEQ ID NO: 110 | BamHI/NcoI |
| SEQ ID NO: 31 | pSUK19S | SUK19Sfor SEQ ID NO: 111 | SUK19Srev SEQ ID NO: 112 | HindIII/XbaI |
| SEQ ID NO: 32 | pSUK19SGB | SUK19Sfor SEQ ID NO: 111 | SUK19Srev SEQ ID NO: 112 | HindIII/XbaI |
| SEQ ID NO: 33 | pSUK19LGB | SUK19Lfor SEQ ID NO: 113 | SUK19Lrev SEQ ID NO: 114 | BamHI/NcoI |
| SEQ ID NO: 36 | pSUK28L | SUK28for SEQ ID NO: 115 | SUK28Lrev SEQ ID NO: 116 | SalI/SmaI |
| SEQ ID NO: 37 | pSUK28LGB | SUK28for SEQ ID NO: 115 | SUK28Lrev SEQ ID NO: 116 | SalI/SmaI |
| SEQ ID NO: 38 | pSUK28S | SUK28for SEQ ID NO: 115 | SUK28Srev SEQ ID NO: 117 | SalI/XhoI |
| SEQ ID NO: 39 | pSUK28SGB | SUK28for SEQ ID NO: 115 | SUK28Srev SEQ ID NO: 117 | SalI/XhoI |
| SEQ ID NO: 40 | pSUK29L | SUK29for SEQ ID NO: 118 | SUK29Lrev SEQ ID NO: 119 | SalI/SmaI |
| SEQ ID NO: 41 | pSUK29LGB | SUK29for SEQ ID NO: 118 | SUK29Lrev SEQ ID NO: 119 | SalI/SmaI |
| SEQ ID NO: 42 | pSUK29S | SUK29for SEQ ID NO: 118 | SUK29Srev SEQ ID NO: 120 | SalI/XhoI |
| SEQ ID NO: 43 | pSUK29SGB | SUK29for SEQ ID NO: 118 | SUK29Srev SEQ ID NO: 120 | SalI/XhoI |
| SEQ ID NO: 44 | pSUK30L | SUK30for SEQ ID NO: 121 | SUK30Lrev SEQ ID NO: 122 | BamHI/NcoI |

TABLE 3-continued

PCR oligonucleotide primers for amplification of the various transcription regulating nucleotide sequences and restriction enzymes for modifying the resulting PCR products

| SEQ ID | Promoter | Forward Primer | Reverse Primer | Restriction enzymes |
|---|---|---|---|---|
| SEQ ID NO: 45 | pSUK30LGB | SUK30for SEQ ID NO: 121 | SUK30Lrev SEQ ID NO: 122 | BamHI/NcoI |
| SEQ ID NO: 46 | pSUK30S | SUK30for SEQ ID NO: 121 | SUK30Srev SEQ ID NO: 123 | BamHI/XhoI |
| SEQ ID NO: 47 | pSUK30SGB | SUK30for SEQ ID NO: 121 | SUK30Srev SEQ ID NO: 123 | BamHI/XhoI |
| SEQ ID NO: 50 | pSUK298L | SUK298for SEQ ID NO: 124 | SUK298Lrev SEQ ID NO: 125 | BamHI/NcoI |
| SEQ ID NO: 51 | pSUK298LGB | SUK298for SEQ ID NO: 124 | SUK298Lrev SEQ ID NO: 125 | BamHI/NcoI |
| SEQ ID NO: 52 | pSUK298S | SUK298for SEQ ID NO: 124 | SUK298Srev SEQ ID NO: 126 | BamHI/NcoI |
| SEQ ID NO: 53 | pSUK298SGB | SUK298for SEQ ID NO: 124 | SUK298Srev SEQ ID NO: 126 | BamHI/NcoI |
| SEQ ID NO: 54 | pSUK300L | SUK300for SEQ ID NO: 127 | SUK300Lrev SEQ ID NO: 128 | BamHI/NcoI |
| SEQ ID NO: 55 | pSUK300LGB | SUK300for SEQ ID NO: 127 | SUK300Lrev SEQ ID NO: 128 | BamHI/NcoI |
| SEQ ID NO: 56 | pSUK300S | SUK300for SEQ ID NO: 127 | SUK300Srev SEQ ID NO: 129 | BamHI/NcoI |
| SEQ ID NO: 57 | pSUK300SGB | SUK300for SEQ ID NO: 127 | SUK300Srev SEQ ID NO: 129 | BamHI/NcoI |
| SEQ ID NO: 60 | pSUK292L | SUK292for SEQ ID NO: 130 | SUK292Lrev SEQ ID NO: 131 | BamHI/NcoI |
| SEQ ID NO: 61 | pSUK292LGB | SUK292for SEQ ID NO: 130 | SUK292Lrev SEQ ID NO: 131 | BamHI/NcoI |
| SEQ ID NO: 62 | pSUK292S | SUK292for SEQ ID NO: 130 | SUK292Srev SEQ ID NO: 132 | BamHI/NcoI |
| SEQ ID NO: 63 | pSUK292SGB | SUK292for SEQ ID NO: 130 | SUK292Srev SEQ ID NO: 132 | BamHI/NcoI |
| SEQ ID NO: 64 | pSUK294L | SUK294for SEQ ID NO: 133 | SUK294Lrev SEQ ID NO: 134 | BamHI/NcoI |
| SEQ ID NO: 65 | pSUK294LGB | SUK294for SEQ ID NO: 133 | SUK294Lrev SEQ ID NO: 134 | BamHI/NcoI |
| SEQ ID NO: 66 | pSUK294S | SUK294for SEQ ID NO: 133 | SUK294Srev SEQ ID NO: 135 | BamHI/NcoI |
| SEQ ID NO: 67 | pSUK294SGB | SUK294for SEQ ID NO: 133 | SUK294Srev SEQ ID NO: 135 | BamHI/NcoI |
| SEQ ID NO: 68 | pSUK296L | SUK296for SEQ ID NO: 136 | SUK296Lrev SEQ ID NO: 137 | BamHI/NcoI |
| SEQ ID NO: 69 | pSUK296LGB | SUK296for SEQ ID NO: 136 | SUK296Lrev SEQ ID NO: 137 | BamHI/NcoI |
| SEQ ID NO: 70 | pSUK296S | SUK296for SEQ ID NO: 136 | SUK296Srev SEQ ID NO: 138 | BamHI/NcoI |
| SEQ ID NO: 71 | pSUK296SGB | SUK296for SEQ ID NO: 136 | SUK296Srev SEQ ID NO: 138 | BamHI/NcoI |
| SEQ ID NO: 74 | pSUK262L | SUK262for SEQ ID NO: 139 | SUK262Lrev SEQ ID NO: 140 | BamHI/NcoI |
| SEQ ID NO: 75 | pSUK262LGB | SUK262for SEQ ID NO: 139 | SUK262Lrev SEQ ID NO: 140 | BamHI/NcoI |
| SEQ ID NO: 76 | pSUK262S | SUK262for SEQ ID NO: 139 | SUK262Srev SEQ ID NO: 141 | BamHI/NcoI |
| SEQ ID NO: 77 | pSUK262SGB | SUK262for SEQ ID NO: 139 | SUK262Srev SEQ ID NO: 141 | BamHI/NcoI |
| SEQ ID NO: 80 | pSUK164 | SUK164for SEQ ID NO: 142 | SUK164rev SEQ ID NO: 143 | BamHI/NcoI |
| SEQ ID NO: 81 | pSUK164GB | SUK164for SEQ ID NO: 142 | SUK164rev SEQ ID NO: 143 | BamHI/NcoI |
| SEQ ID NO: 84 | pSUK352L | SUK352for SEQ ID NO: 144 | SUK352Lrev SEQ ID NO: 145 | BamHI/NcoI |
| SEQ ID NO: 85 | pSUK352LGB | SUK352for SEQ ID NO: 144 | SUK352Lrev SEQ ID NO: 145 | BamHI/NcoI |
| SEQ ID NO: 86 | pSUK352S | SUK352for SEQ ID NO: 144 | SUK352Srev SEQ ID NO: 146 | BamHI/NcoI |
| SEQ ID NO: 87 | pSUK352SGB | SUK352for SEQ ID NO: 144 | SUK352Srev SEQ ID NO: 146 | BamHI/NcoI |
| SEQ ID NO: 148 | pSUK40L | SUK40for SEQ ID NO: 188 | SUK40Lrev SEQ ID NO: 189 | BamHI/NcoI |
| SEQ ID NO: 149 | pSUK40LGB | SUK40for SEQ ID NO: 188 | SUK40Lrev SEQ ID NO: 189 | BamHI/NcoI |
| SEQ ID NO: 150 | pSUK40S | SUK40for SEQ ID NO: 188 | SUK40Srev SEQ ID NO: 190 | BamHI/NcoI |

TABLE 3-continued

PCR oligonucleotide primers for amplification of the various transcription regulating nucleotide sequences and restriction enzymes for modifying the resulting PCR products

| SEQ ID | Promoter | Forward Primer | Reverse Primer | Restriction enzymes |
|---|---|---|---|---|
| SEQ ID NO: 151 | pSUK40SGB | SUK40for SEQ ID NO: 188 | SUK40Srev SEQ ID NO: 190 | BamHI/NcoI |
| SEQ ID NO: 152 | pSUK42L | SUK42for SEQ ID NO: 191 | SUK42Lrev SEQ ID NO: 192 | BamHI/NcoI |
| SEQ ID NO: 153 | pSUK42LGB | SUK42for SEQ ID NO: 191 | SUK42Lrev SEQ ID NO: 192 | BamHI/NcoI |
| SEQ ID NO: 154 | pSUK42S | SUK42for SEQ ID NO: 191 | SUK42Srev SEQ ID NO: 193 | BamHI/NcoI |
| SEQ ID NO: 155 | pSUK42SGB | SUK42for SEQ ID NO: 191 | SUK42Srev SEQ ID NO: 193 | BamHI/NcoI |
| SEQ ID NO: 158 | pSUK48L | SUK48for SEQ ID NO: 194 | SUK48Lrev SEQ ID NO: 195 | BamHI/NcoI |
| SEQ ID NO: 159 | pSUK48LGB | SUK48for SEQ ID NO: 194 | SUK48Lrev SEQ ID NO: 195 | BamHI/NcoI |
| SEQ ID NO: 160 | pSUK48S | SUK48for SEQ ID NO: 194 | SUK48Srev SEQ ID NO: 196 | BamHI/NcoI |
| SEQ ID NO: 161 | pSUK48SGB | SUK48for SEQ ID NO: 194 | SUK48Srev SEQ ID NO: 196 | BamHI/NcoI |
| SEQ ID NO: 162 | pSUK50L | SUK50for SEQ ID NO: 197 | SUK50Lrev SEQ ID NO: 198 | BamHI/NcoI |
| SEQ ID NO: 163 | pSUK50LGB | SUK50for SEQ ID NO: 197 | SUK50Lrev SEQ ID NO: 198 | BamHI/NcoI |
| SEQ ID NO: 164 | pSUK50S | SUK50for SEQ ID NO: 197 | SUK50Srev SEQ ID NO: 199 | BamHI/NcoI |
| SEQ ID NO: 165 | pSUK50SGB | SUK50for SEQ ID NO: 197 | SUK50Srev SEQ ID NO: 199 | BamHI/NcoI |
| SEQ ID NO: 168 | pSUK96L | SUK96for SEQ ID NO: 200 | SUK96Lrev SEQ ID NO: 201 | XhoI/NcoI |
| SEQ ID NO: 169 | pSUK96LGB | SUK96for SEQ ID NO: 200 | SUK96Lrev SEQ ID NO: 201 | XhoI/NcoI |
| SEQ ID NO: 170 | pSUK96S | SUK96for SEQ ID NO: 200 | SUK96Srev SEQ ID NO: 202 | XhoI/NcoI |
| SEQ ID NO: 171 | pSUK96SSGB | SUK96for SEQ ID NO: 200 | SUK96Srev SEQ ID NO: 202 | XhoI/NcoI |
| SEQ ID NO: 172 | pSUK98L | SUK98for SEQ ID NO: 203 | SUK98Lrev SEQ ID NO: 204 | XhoI/NcoI |
| SEQ ID NO: 173 | pSUK98LGB | SUK98for SEQ ID NO: 203 | SUK98rev SEQ ID NO: 204 | XhoI/NcoI |
| SEQ ID NO: 174 | pSUK98S | SUK98for SEQ ID NO: 203 | SUK98Srev SEQ ID NO: 205 | XhoI/NcoI |
| SEQ ID NO: 175 | pSUK98SGB | SUK98for SEQ ID NO: 203 | SUK98Srev SEQ ID NO: 205 | XhoI/NcoI |
| SEQ ID NO: 178 | pSUK152L | SUK152for SEQ ID NO: 206 | SUK152Lrev SEQ ID NO: 207 | BamHI/NcoI |
| SEQ ID NO: 179 | pSUK152LGB | SUK152for SEQ ID NO: 206 | SUK152Lrev SEQ ID NO: 207 | BamHI/NcoI |
| SEQ ID NO: 180 | pSUK152S | SUK152for SEQ ID NO: 206 | SUK152Srev SEQ ID NO: 208 | BamHI/NcoI |
| SEQ ID NO: 181 | pSUK152SGB | SUK152for SEQ ID NO: 206 | SUK152Srev SEQ ID NO: 208 | BamHI/NcoI |
| SEQ ID NO: 182 | pSUK154L | SUK154for SEQ ID NO: 209 | SUK154Lrev SEQ ID NO: 210 | BamHI/NcoI |
| SEQ ID NO: 183 | pSUK154LGB | SUK154for SEQ ID NO: 209 | SUK154Lrev SEQ ID NO: 210 | BamHI/NcoI |
| SEQ ID NO: 184 | pSUK154S | SUK154for SEQ ID NO: 209 | SUK154Srev SEQ ID NO: 211 | BamHI/NcoI |
| SEQ ID NO: 185 | pSUK154SGB | SUK154for SEQ ID NO: 209 | SUK154Srev SEQ ID NO: 211 | BamHI/NcoI |

Amplification is carried out as follows:

100 ng genomic DNA

1×PCR buffer 2.5 mM $MgCl_2$, 200 pM each of dATP, dCTP, dGTP und dTTP 10 pmol of each oligonucleotide primers 2.5 Units Pfu DNA Polymerase (Stratagene)

in a final volume of 50 μl

The following temperature program is employed for the various amplifications (BIORAD Thermocycler).

1. 95° C. for 5 min
2. 54° C. for 1 min, followed by 72° C. for 5 min and 95° C. for 30 sec. Repeated 25 times.
3. 54° C. for 1 min, followed by 72° C. for 10 min.
4. Storage at 4° C.

The resulting PCR-products are digested with the restriction endonucleases specified in the Table above (Table 3) and cloned into the vector pSUN0301 (SEQ ID NO: 147) (pre-digested with the same enzymes) upstream and in operable linkage to the glucuronidase (GUS) gene. Following stable transformation of each of these constructs into *Arabidopsis thaliana* tissue specificity and expression profile was analyzed by a histochemical and quantitative GUS-assay, respectively.

Example 5

Expression Profile of the Various Promoter::GUS Constructs in Stably Transformed *A. thaliana* Plants 5.1 pSUK222L, pSUK222LGB, pSUK222S, pSUK222SGB, pSUK224L, pSUK224LGB, pSUK224S, pSUK224SGB, pSUK226L, pSUK226LGB, pSUK226S, pSUK226SGB All promoter fragments conferred seed-preferred expression to the reporter gene construct tested. GUS expression was not limited to embryos but covered also seed coat and endosperm tissue. GUS expression was detected early in seed development and continued into maturing siliques. Promoter activity was also observed in various organs and tissues of adult plants at varying strength, e.g. in hydathodes of rosette and caudal leaves, vessels of stalks and rosette leaves, and also in sepals, petals and pollen. GUS expression in seedlings was detected in vasculature of rosette leaves as well as in the central cylinder of roots and also in root tips. These side activities were least apparent while expression in seeds was strongest for the longest promoter fragment analyzed.

5.2 pSUK322L, pSUK322LGB, pSUK322S, pSUK322SGB, pSUK324LGB, pSUK324SGB

These promoter fragments conferred seed-preferred GUS expression. GUS activity in seeds including expression in embryos became apparent early during silique development and continued well into later stages. GUS expression was also detected at strongly varying degrees in rosette leaves and lateral roots of seedlings, as well as rosette leaves, stalks, siliques and anthers (mainly pollen) of adult plants analyzed.

5.3 pSUK250L, pSUK250LGB, pSUK250S, pSUK250SGB, pSUK252LGB, pSUK252SGB

Seed-preferred GUS expression conferred by the promoters analyzed commenced early in seed development and continued well into mature siliques. The promoters were found to be active only partially in embryos but strongly in seed coat and endosperm. In seedlings, side activities were mainly detected in petioles and leaf tips as well as root tips while GUS expression in adult plants was highly specific for seeds.

5.4 pSUK19S, pSUK19SGB, pSUK19LGB

Rather strong and seed-specific GUS expression was detected late during seed development in maturing siliques. The promoters were predominantly active in embryos but side activities were also observed at cotyledons of seedlings as well as guard cells of stalks and siliques and (rarely) in midveins of rosette leaves and anthers.

5.5 pSUK28L, pSUK28LGB, pSUK28S, pSUK28SGB, pSUK29L, pSUK29LGB, pSUK29S, pSUK29SGB, pSUK30L, pSUK30LGB, pSUK30S, pSUK30SGB

Embryos as well as seed coat and endosperm in late developing to mature seeds revealed GUS expression driven by all promoters analyzed. While pSUK28L and pSUK30L were also characterized by promoter side activity in vascular tissue of stalks and leaves of adult plants as well as silique and flower bottoms and mainly vascular tissue of seedlings, pSUK29L was highly seed-specific in its expression pattern observed.

5.6 pSUK298L, pSUK298LGB, pSUK298S, pSUK298SGB, pSUK300L, pSUK300LGB, pSUK300S, pSUK300SGB

These promoter fragments drive expression in entire seeds, i.e. embryos and seed coats as well as endosperm are affected. However, promoter activity is confined to an intermediate developmental phase of the seeds, i.e. neither young nor completely mature seeds reveal GUS expression. Side activities occur in patchy styles in hypocotyl, petioles and vascular leaf tissue of seedlings as well as in stalks, siliques, rosette leaves and floral organs of full-grown plants. These side activities are less pronounced for the shorter promoter fragment pSUK298L compared with pSUK300L.

5.7 pSUK292L, pSUK292LGB, pSUK292S, pSUK292SGB, pSUK294L, pSUK294LGB, pSUK294S, pSUK294SGB, pSUK296L, pSUK296LGB, pSUK296S, pSUK296SGB

Reporter gene expression was driven by all promoter fragments in embryos, endosperm and seed coat. GUS activity commenced rather early in seed development and continued into mature seeds. However, multiple side activities were observed, in particular for the longer promoter fragments analyzed. The most prominent side activity was obvious in guard cells, but other organs of seedlings and adult plants transformed with reporter gene constructs harboring the longer promoter variants also clearly showed GUS expression (e.g. in styles, trichomes).

5.8 pSUK262L, pSUK262LGB, pSUK262S, pSUK262SGB

These weak to medium-strong promoters are active in maturing seeds while expression was not detected in very young and completely mature seeds. Reporter gene expression was observed in seed coat and endosperm but could not be proven for the embryo. Side activity is marginal compared to other promoters disclosed: Expression apart from the seeds became only apparent for sepals, midveins and hydathodes of adult plants and seedlings analyzed.

5.9 pSUK164, pSUK164GB

Promoter activity was detected in embryo, endosperm and seed coat of seeds starting early in development and continuing into the maturing phase. Side activities were observed in cotyledons and first rosette leaves of seedlings as well as in vascular tissue of rosette leaves of adult plants and in pollen.

5.10 pSUK352L, pSUK352LGB, pSUK352S, pSUK352SGB

Promoter activity commences early in seed development and ceases before full maturation. Expression is specific for embryos, i.e. no reporter gene activity was detected in seeds coat or endosperm. Weak to medium side activity was also observed in cotyledons and leaves of seedlings.

5.11 pSUK40L, pSUK40LGB, pSUK40S, pSUK40SGB, pSUK42L, pSUK42LGB, pSUK42S, pSUK42SGB

These promoters confer seed-preferential expression when tested in *Arabidopsis thaliana*. Expression is strongest in young seeds and covers the developing embryo as well as the seed coat. Side activities are observed in root tips, rarely in vascular tissue of pods and stalks and also in anthers. Longer promoter fragments confer stronger expression in seeds but are also accompanied by more pronounced side activities.

5.12 pSUK48L, pSUK48LGB, pSUK48S, pSUK48SGB, pSUK50L, pSUK50LGB, pSUK50S, pSUK50SGB

These promoters drive seed-preferential expression starting at rather early but maintained also in later stages of seed development of *Arabidopsis thaliana*. Endosperm and seed coat clearly revealed reporter gene activity while it could not been shown that these promoters are also active in embryos. Whereas the shorter promoter fragments (pSUK48 derivatives) are almost void of side activity apart from some expression observed in vascular tissue of stalks and rarely observed expression in root tips, pSUK50 derivatives are also characterized by varying degrees of reporter gene activity in various organs and tissues analyzed.

5.13 pSUK96L, pSUK96LGB, pSUK96S, pSUK96SGB, pSUK98L, pSUK98LGB, pSUK98S, pSUK98SGB

These promoters confer seed-preferential expression in *Arabidopsis thaliana*. Expression in seed coat is stronger than in any other seed tissue. Side activity of the promoters was observed mainly in vascular tissue of stalks, ovaries and siliques but also in roots (particularly root tips). Those side activity but also the expression detected in seeds was stronger with longer promoter fragments (pSUK98 derivatives) where expression of the marker gene was also visible in vascular tissue of flowers and leaves of a number of plants analyzed.

5.14 pSUK152L, pSUK152LGB, pSUK152S, pSU K152SGB, pSU K154L, pSUK154LGB, pSUK154S, pSUK154SGB

These promoters drive strong seed-preferential expression of the marker gene analyzed in *Arabidopsis thaliana*. However, expression is weaker or not detectable in very young and fully mature seeds. The promoters are active in endosperm and embryo but not in the seed coat. The strength and variation of side activity does not depend on the length of the promoter analyzed. Marker gene expression was (besides seeds) observed in roots, apical meristems and petioles of seedlings, axillary meristems and vascular tissue of stalks of adult plants as well as in various flower organs.

Example 6

Expression Profile of the Various Promoter::GUS Constructs in Stably Transformed Linseed Plants 6.1 pSUK40L pSUK40L is a seed-specific promoter in linseed. No GUS expression was detected in early and young embryos. Middle strong to strong GUS expression was found in middle, late and mature embryos.

6.2 pSUK48L, and pSUK50L pSUK48L is a seed-specific promoter in linseed. No GUS expression was detected in early and young embryos. Middle strong to strong GUS expression was found in middle, late and mature embryos.

pSUK50L is a seed-specific promoter in linseed. No GUS expression was detected in early and young embryos. Middle strong GUS expression was found mid-phase during embryo development. Middle strong to strong GUS expression was found in late and mature embryos.

6.3 pSUK96L pSUK96L is a seed-specific promoter in linseed. No GUS expression was detected in early and young embryos. Weak to medium-strong expression was found in medium, late and mature embryos.

6.4 pSUK152L pSUK152L is a seed-specific promoter in linseed. No to very weak GUS expression was detected in early and young embryos. Middle strong to strong GUS expression was found in middle, late and mature embryos. Often medium strong to strong GUS expression was also found in the seed capsula and in the flower.

Example 7

Vector Construction for Overexpression and Gene "Knockout" Experiments 7.1 Overexpression Vectors used for expression of full-length "candidate genes" of interest in plants (overexpression) are designed to overexpress the protein of interest and are of two general types, biolistic and binary, depending on the plant transformation method to be used.

For biolistic transformation (biolistic vectors), the requirements are as follows:

1. a backbone with a bacterial selectable marker (typically, an antibiotic resistance gene) and origin of replication functional in *Escherichia coli* (*E. coli*; e.g., ColE1), and
2. a plant-specific portion consisting of:
   a. a gene expression cassette consisting of a promoter (eg. ZmUBlint MOD), the gene of interest (typically, a full-length cDNA) and a transcriptional terminator (e.g., *Agrobacterium tumefaciens* nos terminator);
   b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:

1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by *A. tumefaciens* right and left border sequences which mediate transfer of the DNA flanked by these two sequences to the plant.

7.2 Gene Silencing Vectors

Vectors designed for reducing or abolishing expression of a single gene or of a family or related genes (gene silencing vectors) are also of two general types corresponding to the methodology used to downregulate gene expression: antisense or doublestranded RNA interference (dsRNAi).

(a) Anti-sense

For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter; thus, mRNA will be made from the non-coding (antisense) strand in planta.

(b) dsRNAi

For dsRNAi vectors, a partial gene fragment (typically, 300 to 500 basepairs long) is used in the gene expression cassette, and is expressed in both the sense and antisense orientations, separated by a spacer region (typically, a plant intron, eg. the OsSH1 intron 1, or a selectable marker, eg. conferring kanamycin resistance). Vectors of this type are designed to form a double-stranded mRNA stem, resulting from the basepairing of the two complementary gene fragments in planta.

Biolistic or binary vectors designed for overexpression or knockout can vary in a number of different ways, including eg. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinasebased cloning).

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzeret al., Nucleic Acid Res., 19:5081 (1991).
10. Bäumlein et al. Mol Gen Genet 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110(1989).
24. Bustos M M et al. (1989) Plant Gell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed. Ivermectin and Abamectin, Springer-Verlag, New York, 1989.
29. Chee et al. Plant Physiol., 91:1212 (1989).
30. Chen and Winans (1991) J. Bacteriol. 173: 1139-1144
31. Christou et al. Proc. Natl. Acad. Sci USA, 86:7500 (1989).
32. Christou et al., Biotechnology, 9:957 (1991).
33. Christou et al., Plant Physiol., 87:671 (1988).
34. Chui et al. (1996) Curr Biol 6:325-330
35. Coe et al., In: Corn and Corn Improvement, Sprague et al. (eds.) pp. 81-258 (1988).
36. Corpet et al. Nucleic Acids Res., 16:10881 (1988).
37. Coxson et al., Biotropica, 24:121 (1992).
38. Crameri et al., Nature Biotech., 15:436 (1997).
39. Crameri et al., Nature, 391:288 (1998).
40. Crossway et al., Bio/Techniques, 4:320 (1986).
41. Cuozzo et al., Bio/Technology, 6:549 (1988).
42. Cutler et al., J. Plant Physiol., 135:351 (1989).
43. Czapla and Lang, J. Econ. Entomol., 83:2480 (1990).
44. Datta et al., Bio/Technology, 8:736 (1990).
45. Davies et al., Plant Physiol., 93:588 (1990).
46. Dayhoff et al., Atlas of Protein Sequence and Structure, Natl. Biomed. Res. Found., Washington, C. D. (1978).
47. De Blaere et al., Meth. Enzymol., 143:277 (1987).
48. De Block et al. Plant Physiol., 91:694 (1989).
49. De Block et al., EMBO Journal, 6:2513 (1987).
50. Deblaere et al. Nucl Acids Res 13:4777-4788 (1985)
51. Della-Cioppa et al. Bio/Technology 5:579-584 (1987)
52. Della-Cioppa et al., Plant Physiology, 84:965-968 (1987).
53. Dellaporta et al., in Chromosome Structure and Function, Plenum Press, 263-282 (1988).
54. Depicker et al., Plant Cell Reports, 7:63 (1988).
55. Dunn et al., Can. J. Plant Sci., 61:583 (1981).
56. Dure et al., Plant Mol. Biol., 12:475 (1989).
57. Ebinuma et al. Proc Natl Acad Sci USA 94:2117-2121 (2000a)
58. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b)
59. Eichholtz et al. Somatic Cell and Molecular Genetics 13, 67-76 (1987)
60. Ellis et al., EMBO Journal, 6:3203 (1987).
61. Elroy-Stein et al., Proc. Natl. Acad. Sci. U.S.A., 86:6126 (1989).
62. English et al., Plant Cell, 8:179 (1996).
63. Erdmann et al., J. Gen. Microbiol., 138:363 (1992).
64. Erikson et al. Nat Biotechnol. 22(4):455-8 (2004)
65. Everett et al., Bio/Technology, 5:1201(1987).
66. Fedoroff N V & Smith D L Plant J 3:273-289 (1993)
67. Fire A et al Nature 391:806-811 (1998)
68. Fitzpatrick, Gen. Engineering News, 22:7 (1993).
69. Fraley et al. Proc Natl Acad Sci USA 80:4803 (1983)
70. Fromm et al., Bio/Technology, 8:833 (1990).
71. Fromm et al., Nature (London), 319:791 (1986).
72. Galbiati et al. Funct. Integr Genozides 2000, 20 1:25-34
73. Gallie et al. Nucl Acids Res 15:8693-8711 (1987)
74. Gallie et al., Nucleic Acids Res., 15:3257 (1987).
75. Gallie et al., The Plant Cell, 1:301 (1989).
76. Gan et al., Science, 270:1986 (1995).
77. Gatehouse et al., J. Sci. Food Agric., 35:373 (1984).
78. Gelfand, eds., PCR Strategies Academic Press, New York (1995).
79. Gelvin et al., Plant Molecular Biology Manual, (1990).
80. Gleave et al. Plant Mol Biol. 40(2):223-35 (1999)
81. Gordon-Kamm et al., Plant Cell, 2:603 (1990).
82. Goring et al, PNAS, 88:1770 (1991).
83. Gruber, et al., Vectors for Plant Transformation, in: Methods in Plant Molecular Biology & Biotechnology" in Glich et al., (Eds. pp. 89-119, CRC Press, 1993).
84. Guerineau et al., Mol. Gen. Genet., 262:141 (1991).
85. Guerrero et al., Plant Mol. Biol., 15:11 (1990).
86. Gupta et al., PNAS, 90:1629 (1993).
87. Haines and Higgins (eds.), Nucleic Acid Hybridization, IRL Press, Oxford, U.K.
88. Hajdukiewicz et al. Plant Mol Biol 25:989-994 (1994)
89. Hammock et al., Nature, 344:458 (1990).
90. Hansen et al. Proc. Natl. Acad. Sci. USA 91:7603-7607 (1994)
91. Hayford et al. Plant Physiol. 86:1216 (1988)
92. Hemenway et al., EMBO Journal, 7:1273 (1988).
93. Henikoff& Henikoff, Proc. Natl. Acad. Sci. USA, 89:10915 (1989).
94. Hiei et al. Plant J 6: 271-282 (1994)
95. Higgins et al., Gene, 73:237 (1988).
96. Higo et al. (1999) Nucl Acids Res 27(1): 297-300
97. Hilder et al., Nature, 330:160 (1987).
98. Hille et al. Plant Mol. Biol. 7:171 (1986)
99. Hinchee et al. Bio/Technology 6:915 (1988).
100. Hoekema et al. (1983) Nature 303:179-181
101. Hoekema, In: The Binary Plant Vector System. Offsetdrukkerij Kanters B. V.; Alblasserdam (1985).

102. Hood et al. J Bacteriol 168:1291-1301 (1986)

103. Huang et al., CABIOS, 8:155 (1992).

104. Ikeda et al., J. Bacteriol., 169:5612 (1987).

105. Ikuta et al., Biotech., 8:241 (1990).

106. Ingelbrecht et al., Plant Cell, 1:671 (1989).

107. Innis and Gelfand, eds., PCR Methods Manual (Academic Press, New York) (1999).

108. Innis et al., eds., PCR Protocols: A Guide to Methods and Applications (Academic Press, New York (1995).

109. Innis et al., PCR Protocols: A Guide to Methods and Applications, Academic Press, Inc., San Diego, Calif. (1990).

110. Ishida Y et al. Nature Biotech 745-750 (1996)

111. Jefferson et al. EMBO J 6:3901-3907 (1987)

112. Jefferson et al. Plant Mol Biol Rep 5:387-405 (1987)

113. Jenes B et al. Techniques for Gene Transfer, in: Recombinant Plants, Vol. 1, Engineering and Utilization, edited by S D Kung and R Wu, Academic Press, pp. 128-143 (1993)

114. Jobling et al., Nature, 325:622 (1987).

115. Johnson et al., PNAS USA, 86:9871 (1989)

116. Jones et al. Mol. Gen. Genet., 210:86 (1987)

117. Joshi et al., Nucleic Acid Res., 15:9627 (1987).

118. Kaasen et al., J. Bacteriol., 174:889 (1992).

119. Karlin and Altschul, Proc. Natl. Acad Sci. USA, 87:2264 (1990).

120. Karlin and Altschul, Proc. Natl. Acad. Sci. USA, 90:5873 (1993).

121. Karsten et al., Botanica Marina, 35:11 (1992).

122. Katz et al., J. Gen. Microbiol., 129:2703 (1983).

123. Keller et al., EMBO Journal, 8:1309 (1989).

124. Keller et al., Genes Dev., 3:1639 (1989). (Eine der beiden <<Keller>> Referenzen ist zuviel)

125. Klapwijk et al. J. Bacteriol., 141,128-136 (1980)

126. Klein et al., Bio/Technoloy, 6:559 (1988).

127. Klein et al., Plant Physiol., 91:440 (1988).

128. Klein et al., Proc. Natl. Acad. Sci. USA, 85:4305 (1988).

129. Knauf, et al., Genetic Analysis of Host Range Expression by *Agrobacterium* In: Molecular Genetics of the Bacteria-Plant Interaction, Puhler, A. ed., Springer-Verlag, New York, 1983.

130. Koncz & Schell Mol Gen Genet 204:383-396 (1986)

131. Koprek T et al. Plant J 19(6): 719-726 (1999)

132. Koster and Leopold, Plant Physiol., 88:829 (1988).

133. Koziel et al., Biotechnology, 11:194 (1993).

134. Kunkel et al., Methods in Enzymol., 154:367 (1987).

135. Kunkel, Proc. Natl. Acad. Sci. USA, 82:488 (1985).

136. Lam E und Chua N H, J Biol Chem; 266(26):17131-17135 (1991)

137. Laufs et al., PNAS, 87:7752 (1990).

138. Lawton et al., Mol. Cell Biol., 7:335 (1987).

139. Lee and Saier, J. Bacteriol., 153 (1982).

140. Leffel et al. Biotechniques 23(5):912-8 (1997)

141. Lescot et al. Nucleic Acids Res 30(1):325-7 (2002)

142. Levings, Science, 250:942 (1990).

143. Li et al. Plant Mol Biol 20:1037-1048 (1992)

144. Lindsey et al., Transgenic Research, 2:3347 (1993).

145. Liu et al.,. Plant J. 8, 457-463 (1995)

146. Lommel et al., Virology, 181:382 (1991).

147. Loomis et al., J. Expt. Zool., 252:9 (1989).

148. Lorz et al., Mol. Gen. Genet., 199:178 (1985).

149. Ma et al., Nature, 334 :631 (1988).

150. Macejak et al., Nature, 353:90 (1991).

151. Maki et al., Methods in Plant Molecular Biology & Biotechnology, Glich et al., 67-88 CRC Press, (1993).

152. Maniatis T, Fritsch E F, and Sambrook J Molecular Cloning: A Laboratory Manual, Cold Spring Harbor Laboratory, Cold Spring Harbor (N.Y.), (1989)

153. Mariani et al, Nature, 347:737 (1990).

154. Matzke et al. (2000) Plant Mol Biol 43:401-415;

155. McBride et al., PNAS USA, 91:7301 (1994).

156. McCabe et al., Bio/Technology, 6:923 (1988).

157. Meinkoth and Wahl, Anal. Biochem., 138:267 (1984).

158. Messing and Vierra, Gene, 19:259 (1982).

159. Michael et al., J. Mol. Biol., 26 :585 (1990). (im Text steht: Michael et al. 1994)

160. Millar et al. Plant Mol Biol Rep 10:324-414 (1992)

161. Mogen et al., Plant Cell, 2:1261 (1990).

162. Moore et al., J. Mol. Biol., 272:336 (1997).

163. Mozo & Hooykaas Plant Mol. Biol. 16:917-918 (1991)

164. Mundy and Chua, EMBO J., 7:2279 (1988).

165. Munroe et al., Gene, 91:151 (1990).

166. Murakami et al., Mol. Gen. Genet., 205:42 (1986).

167. Murata et al., FEBS Lett., 296:187 (1992).

168. Murdock et al., Phytochemistry, 29:85 (1990).

169. Murray et al., Nucleic Acids Res., 17:477 (1989).

170. Myers and Miller, CABIOS, 4:11 (1988).

171. Naested H Plant J 18:571-576 (1999)

172. Napoli et al., Plant Cell, 2:279 (1990).

173. Needleman and Wunsch, J. Mol. Biol., 48:443-453 (1970).

174. Nehra et al. Plant J. 5:285-297 (1994)

175. Niedz et al., Plant Cell Reports, 14:403 (1995).

176. Odell et al., Mol. Gen. Genet., 113:369 (1990).

177. Odell et al., Nature, 313:810 (1985).

178. Ohtsuka et al., J. Biol. Chem., 260:2605 (1985)

179. Olhoft et al. Plant Cell Rep 20: 706-711 (2001)

180. Ow et al., Science, 234:856 (1986).

181. Pacciotti et al., Bio/Technology, 3:241 (1985).

182. Park et al., J. Plant Biol., 38:365 (1985).

183. Paszkowski et al., EMBO J., 3:2717 (1984).

184. Pearson and Lipman, Proc. Natl. Acad. Sci., 85:2444 (1988).

185. Pearson et al., Meth. Mol. Biol., 24:307 (1994).

186. Perera R J et al. Plant Mol. Biol 23(4): 793-799 (1993)

187. Perlak et al., Proc. Natl. Acad. Sci. USA, 88:3324 (1991).

188. Phillips et al., In Corn & Corn Improvement, 3rd Edition 10 Sprague et al. (Eds. pp. 345-387)(1988).

189. Phi-Van et al., Mol. Cell. Biol., 10:2302 (1990).

190. Piatkowski et al., Plant Physiol., 94:1682 (1990).

191. Potrykus et al., Mol. Gen. Genet., 199:183 (1985).

192. Potrykus, Trends Biotech., 7:269 (1989).

193. Prasher et al., Biochem. Biophys. Res. Comm., 126: 1259 (1985).

194. Proudfoot, Cell, 64:671 (1991).

195. Reed et al., J. Gen. Microbiol., 130:1 (1984).

196. Riggs et al., Proc. Natl. Acad. Sci. USA, 83:5602 (1986).

197. Rossolini et al., Mol. Cell. Probes, 8:91 (1994).

198. Ruiz, Plant Cell, 10:937 (1998).

199. Sambrook et al., Molecular Cloning: A Laboratory Manual (2d ed., Cold Spring Harbor Laboratory Press, Plainview, N.Y.) (1989).

200. Sanfacon et al., Genes Dev., 5:141 (1991).

201. Sanford et al., Particulate Science and Technology, 5:27 (1987).

202. Scheeren-Groot et al. J. Bacteriol 176: 6418-6426 (1994)

203. Schenborn and Groskreutz Mol Biotechnol 13(1): 29-44 (1999)

204. Schlaman and Hooykaas Plant J 11:1377-1385 (1997)

205. Schoffl F et al. (1989) Mol Gen Genetics 217(2-3): 246-53
206. Shagan et al., Plant Physiol., 101:1397 (1993).
207. Shah et al. Science 233: 478 (1986)
208. Shapiro, Mobile Genetic Elements, Academic Press, N.Y. (1983).
209. Shimamoto et al., Nature, 338:274 (1989).
210. Silhavy T J, Berman M L, and Enquist L W Experiments with Gene Fusions, Cold Spring Harbor Laboratory Press, Cold Spring Harbor (N.Y.), (1984)
211. Skuzeski et al., Plant Molec. Biol. 15: 65-79 (1990).
212. Smith et al., Adv. Appl. Math., 2:482.(1981).
213. Smith et al., Mol. Gen. Genet., 224:447 (1990).
214. Spencer et al., Theor. Appl. Genet, 79:625 (1990). Spencer 1992 Referenz fehlt
215. Stalker et al., Science, 242:419 (1988).
216. Staub et al., EMBO J., 12:601 (1993).
217. Staub et al., Plant Cell, 4:39 (1992).
218. Steifel et al., The Plant Cell, 2:785 (1990).
219. Stemmer, Nature, 370:389 (1994).
220. Stemmer, Proc. Natl. Acad. Sci. USA, 91:10747 (1994).
221. Stief et al., Nature, 341:343 (1989).
222. Stougaard Plant J 3:755-761 (1993)
223. Sukhapinda et al., Plant Mol. Biol., 8:209 (1987).
224. Sundaresan et al. Gene Develop 9: 1797-1810 (1995)
225. Sutcliffe, PNAS USA, 75:3737 (1978).
226. Svab et al., Plant Mol. Biol. 14:197 (1990)
227. Svab et al., Proc. Natl. Acad. Sci. USA, 87:8526 (1990).
228. Svab et al., Proc. Natl. Acad. Sci. USA, 90:913 (1993).
229. Tarczynski et al., PNAS USA, 89:2600 (1992).
230. Thillet et al., J. Biol. Chem., 263:12500 (1988).
231. Tijssen, Laboratory Techniques in Biochemistry and Molecular Biology-Hybridization with Nucleic Acid Probes, Elsevier, N.Y. (1993).
232. Tomes et al., Plant Cell, Tissue and Organ Culture: Fundamental Methods, Springer Verlag, Berlin (1995).
233. Tomic et al., NAR, 12:1656 (1990).
234. Turner et al., Molecular Biotechnology, 3:225 (1995).
235. Twell et al., Plant Physiol., 91:1270 (1989).
236. Ugaki et al., Nucl. Acids Res., 19:371 (1991).
237. Ulmasov et al., Plant Mol. Biol., 35:417 (1997).
238. Upender et al., Biotechniques, 18:29 (1995).
239. van der Krol et al., Plant Cell, 2:291 (1990).
240. Vanden Elzen et al. Plant Mol Biol. 5:299 (1985)
241. Vasil et al. Bio/Technology, 10:667-674 (1992)
242. Vasil et al. Bio/Technology, 11:1153-1158 (1993)
243. Vasil et al., Mol. Microbiol., 3:371 (1989).
244. Vasil et al., Plant Physiol., 91:1575 (1989).
245. Vernon and Bohnert, EMBO J., 11:2077 (1992).
246. Walker and Gaastra, eds., Techniques in Molecular Biology, MacMillan Publishing Company, New York (1983).
247. Wan & Lemaux (1994) Plant Physiol., 104:3748
248. Wang et al., Mol. Cell. Biol., 12:3399 (1992).
249. Waterman, M. S. Introduction to Computational Biology: Maps, sequences and genomes. Chapman & Hall. London (1995).
250. Watrud et al., in Engineered Organisms and the Environment (1985).
251. Watson et al. J. Bacteriol 123, 255-264 (1975)
252. Watson et al., Corn: Chemistry and Technology (1987).
253. Weeks et al. Plant Physiol 102:1077-1084 (1993)
254. Weissinger et al., Annual Rev. Genet., 22:421 (1988).
255. White et al, Nucl Acids Res, 18, 1062 (1990).
256. Wingender E et al. Nucleic Acids Res 29(1):281-3 (2001)
257. Wolter et al., EMBO Journal, 11:4685 (1992).
258. Wyn-Jones and Storey, Physiology and Biochemistry of Drought Resistance in Plants, Paleg et al. (eds.), pp. 171-204 (1981).
259. Yamaguchi-Shinozaki et al., Plant Cell Physiol., 33:217 (1992).
260. Zhang et al., Proc. Natl. Acad. Sci. USA, 94:4504 (1997).
261. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An expression cassette for seed-specific or seed-preferential transcription in a plant comprising:

i) at least one transcription regulating nucleotide sequence of a plant gene, and ii) at least one nucleic acid sequence which is operably linked to and heterologous in relation to said transcription regulating nucleotide sequence;

wherein the plant gene comprises the nucleic acid sequence as set forth in SEQ ID NO: 48 and wherein the transcription regulating nucleotide sequence has seed-specific or seed-preferential transcription activity.

2. An expression cassette for seed-specific or seed-preferential transcription in a plant comprising:

i) at least one transcription regulating nucleotide sequence; and ii) at least one nucleic acid sequence which is operably linked to and heterologous in relation to said transcription regulating nucleotide sequence;

wherein the transcription regulating nucleotide sequence comprises the nucleotide sequence of SEQ ID NO: 36, 37, 38, 39, 40, 41, 42, 43, 44, 45, 46, or 47, or a nucleotide sequence having at least 99% identity to the nucleotide sequence of SEQ ID NO: 36, 37, 38, 39, 40, 41, 42, 43, 44, 45, 46, or 47, and wherein the transcription regulating nucleotide sequence has seed-specific or seed-preferential transcription activity.

3. The expression cassette of claim 1, wherein expression of the nucleic acid sequence results in expression of a protein, or expression of an antisense RNA, a sense RNA, or a double-stranded RNA.

4. The expression cassette of claim 1, wherein expression of the at least one nucleic acid sequence confers to the plant an agronomically valuable trait.

5. A vector comprising the expression cassette of claim 1.

6. A transgenic plant, plant cell or microorganism comprising the expression cassette of claim 1.

7. The expression cassette of claim 2, wherein the transcription regulating nucleotide sequence comprises a nucleotide sequence having at least 99% identity to the nucleotide sequence of SEQ ID NO: 36, 37, 38, 39, 40, 41, 42, 43, 44, 45, 46, or 47, and wherein the transcription regulating nucleotide sequence has seed-specific or seed-preferential transcription activity.

8. The expression cassette of claim 2, wherein expression of the nucleic acid sequence results in expression of a protein, or expression of an antisense RNA, a sense RNA, or a double-stranded RNA.

9. The expression cassette of claim 2, wherein expression of the at least one nucleic acid sequence confers to the plant an agronomically valuable trait.

10. A vector comprising the expression cassette of claim 2.

11. A transgenic plant, plant cell or microorganism comprising the expression cassette of claim 2.

12. An expression cassette for seed-specific or seed-preferential transcription in a plant comprising:

i) at least one transcription regulating nucleotide sequence; and ii) at least one nucleic acid sequence which is operably linked to and heterologous in relation to said transcription regulating nucleotide sequence;

wherein the transcription regulating nucleotide sequence comprises a fragment of SEQ ID NO: 36, 37, 38, 39, 40, 41, 42, 43, 44, 45, 46, or 47, and wherein the fragment has seed-specific or seed-preferential expression activity.

13. The expression cassette of claim 12, wherein expression of the nucleic acid sequence results in expression of a protein, or expression of an antisense RNA, a sense RNA, or a double-stranded RNA.

14. The expression cassette of claim 12, wherein expression of the at least one nucleic acid sequence confers to the plant an agronomically valuable trait.

15. A vector comprising the expression cassette of claim 12.

16. A transgenic plant, plant cell or microorganism comprising the expression cassette of claim 12.

17. A method for producing a transgenic plant cell, which comprises transforming a plant cell with the expression cassette of claim 12.

18. A method for producing a transgenic plant, which comprises transforming a plant cell with the expression cassette of claim 12, and generating from the plant cell the transgenic plant.

* * * * *